US012492194B2

(12) United States Patent
Mevellec et al.

(10) Patent No.: US 12,492,194 B2
(45) Date of Patent: Dec. 9, 2025

(54) HPK1 INHIBITORS

(71) Applicant: Janssen Pharmaceutica NV, Beerse (BE)

(72) Inventors: Laurence Anne Mevellec, Louviers (FR); Jorge Eduardo Vialard, Zurich (CH); Sophie Coupa, Belbeuf (FR); Christophe Denis Pascal Adelinet, Iville (FR); Berthold Wroblowski, Vosselaar (BE); James Patrick Edwards, Ambler, PA (US)

(73) Assignee: Janssen Pharmaceutica NV, Beerse (BE)

( * ) Notice: Subject to any disclaimer, the term of this patent is extended or adjusted under 35 U.S.C. 154(b) by 861 days.

(21) Appl. No.: 17/442,650

(22) PCT Filed: Mar. 24, 2020

(86) PCT No.: PCT/EP2020/058081

§ 371 (c)(1),
(2) Date: Sep. 24, 2021

(87) PCT Pub. No.: WO2020/193511

PCT Pub. Date: Oct. 1, 2020

(65) Prior Publication Data

US 2022/0177458 A1 Jun. 9, 2022

Related U.S. Application Data

(60) Provisional application No. 62/823,708, filed on Mar. 26, 2019.

(30) Foreign Application Priority Data

Apr. 8, 2019 (EP) .................................... 19167820

(51) Int. Cl.

| | |
|---|---|
| ***C07D 405/14*** | (2006.01) |
| ***C07D 401/14*** | (2006.01) |
| ***C07D 405/10*** | (2006.01) |
| ***C07D 409/04*** | (2006.01) |
| ***C07D 413/14*** | (2006.01) |
| ***C07D 417/14*** | (2006.01) |
| ***C07D 471/14*** | (2006.01) |
| ***C07D 491/048*** | (2006.01) |

(52) U.S. Cl.

CPC ......... *C07D 405/14* (2013.01); *C07D 401/14* (2013.01); *C07D 405/10* (2013.01); *C07D 409/04* (2013.01); *C07D 413/14* (2013.01); *C07D 417/14* (2013.01); *C07D 471/14* (2013.01); *C07D 491/048* (2013.01)

(58) Field of Classification Search

CPC .. C07D 405/14; C07D 401/14; C07D 405/10; C07D 409/04; C07D 413/14; C07D 417/14; C07D 471/14; C07D 491/048; C07D 471/04; A61P 35/00

See application file for complete search history.

(56) References Cited

U.S. PATENT DOCUMENTS

| | | | | |
|---|---|---|---|---|
| 2003/0139457 A1* | 7/2003 | Baxter | ................ | A61K 31/517 514/357 |
| 2019/0076401 A1 | 3/2019 | Vechorkin et al. | | |
| 2020/0000780 A1 | 1/2020 | Heffron et al. | | |

FOREIGN PATENT DOCUMENTS

| | | |
|---|---|---|
| WO | 2016/090300 A1 | 6/2016 |
| WO | 2016/205942 A1 | 12/2016 |
| WO | 2018/049152 A1 | 3/2018 |
| WO | 2018/049191 A1 | 3/2018 |
| WO | 2018/049200 A1 | 3/2018 |
| WO | 2018/049214 A1 | 3/2018 |
| WO | 2018/081531 A2 | 5/2018 |
| WO | 2018/102366 A1 | 6/2018 |
| WO | 2018/167147 A1 | 9/2018 |
| WO | 2018/183956 A1 | 10/2018 |
| WO | 2018/183964 A1 | 10/2018 |
| WO | 2018/215668 A1 | 11/2018 |
| WO | 2018/228920 A1 | 12/2018 |
| WO | 2018/228923 A1 | 12/2018 |
| WO | 2018/228925 A1 | 12/2018 |
| WO | 2019/051199 A1 | 3/2019 |

OTHER PUBLICATIONS

James w. Leahy et al., "Discovery of a Novel Series of Potent and Orally Bioavailable Phosphoinositide 3-Kinase [gamma] Inhibitors," Journal of Medicinal Chemistry, vol. 55, No. 11, Jun. 14, 2012, pp. 5467-5482.
Alzabin et al., "Hematopoietic progenitor kinase 1 is a critical component of prostaglandin E2-mediated suppression of the anti-tumor immune response", Cancer Immunol. Immunother., 2010, 59, 419-429.
Alzabin et al., "Hematopoietic progenitor kinase 1 is a negative regulator of dendritic cell activation", J. Immunol., 2009, 182, 6187-6194.
Arnold et al., "Activation of Hematopoietic Progenitor Kinase 1 Involves Relocation, Autophosphorylation, and Transphosphorylation by Protein Kinase D 1", Mol. Cell Biol, 2005, 25, 2364-2383.
Arnold et al., "Caspase-mediated cleavage of hematopoietic progenitor kinase 1 (HPK1) converts an activator of NFkappaB into an inhibitor of NFkappaB", J. Biol. Chem. 2001, 276, 14675-14684.
Batliwalla et al., "Microarray analyses of peripheral blood cells identifies unique gene expression signature in psoriatic arthritis", Mol Med., 2005, 11, 21-29.
Brenner et al., "Activation or suppression of NFkappaB by HPK1 determines sensitivity to activation-induced cell death", Embo J., 2005, 24, 4279-4290.

(Continued)

*Primary Examiner* — Rayna Rodriguez
(74) *Attorney, Agent, or Firm* — BakerHostetler

(57) ABSTRACT

The present invention relates to pharmaceutical agents useful for therapy and/or prophylaxis in a mammal, pharmaceutical composition comprising such compounds, and their use as HPK1 inhibitors, useful for treating diseases such as cancer.

15 Claims, No Drawings

(56) References Cited

OTHER PUBLICATIONS

Charron et al., Tetrahedron Letters, "Recent developments in radiolabelled peptides for PET imaging of cancer" 2016, 57(37), 4119-4127.

Di Bartolo et al., "A novel pathway down-modulating T cell activation involves HPK-1-dependent recruitment of 14-3-3 proteins on SLP-76", J. Exp. Med., 2007, 204, 681-691.

Gennaro et al., "Remington's Pharmaceutical Sciences (18th ed., Mack Publishing Company", 1990, see especially Part 8: Pharmaceutical preparations and their Manufacture).

Hernandez et al., "The kinase activity of Hematopoietic Progenitor Kinase 1 Is essential for the regulation of T cell function", Cell Rep., 2018, 25, 80-94.

Hu et al., "Human HPK1, a novel human hematopoietic progenitor kinase that activates the JNK/SAPK kinase cascade", Genes Dev., 1996, 10, 2251-2264.

Kiefer et al., "HPK1, a hematopoietic protein kinase activating the SAPK/JNK pathway", Embo J., 1996, 15, 7013-7025.

Königsberger et al., "HPK1 associates with SKAP-HOM to negatively regulate Rap1-mediated Blymphocyte adhesion", PLoS One, 2010, 5(9), e12468, 9pp.

Lasserre et al., "Release of serine/threoninephosphorylated adaptors from signaling microclusters down-regulates T cell activation", J Cell Biol., 2011, 195, 839-853.

Ling et al., "Involvement of hematopoietic progenitor kinase 1 in T cell receptor signaling", J Biol Chem., 2001, 276, 18908-18914.

Liou et al., "HPK1 is activated by lymphocyte antigen receptors and negatively regulates AP-1", Immunity, 2000, 12, 399-408.

Nagata et al., "Activation of hematopoietic progenitor kinase-1 by erythropoietin", Blood, 1999, 93, 3347-3354.

Pantel et al., Cancer Letters, "Molecular imaging to guide systemic cancer therapy: Illustrative examples of PET imaging cancer biomarkers", 2016, doi: 10.1016/j.canlet.2016.05.008, 25-31.

Patzak et al., "HPK1 competes with ADAP for SLP-76 binding and via Rap1 negatively affects T-cell adhesion", Eur. J. Immunol., 2010, 40, 3220-3225.

Ribas et al., "Cancer immunotherapy using checkpoint blockade", Science, 2018, 359, 1350-1355.

Sawasdikosol et al., "Prostaglandin E2 activates HPK1 kinase activity via a PKA-dependent pathway", J Biol Chem., 2007, 282, 34693-34699.

Shui et al., "Hematopoietic progenitor kinase 1 negatively regulates T cell receptor signaling and T cell-mediated immune responses", Nat Immunol., 2007, 8, 84-91.

Stoeckman et al., "A distinct inflammatory gene expression profile in patients with psoriatic arthritis", Genes Immun., 2006, 7, 583-591.

Wuts et al., Greene's Protective Groups in Organic Synthesis, 4th ed., Wiley, Hoboken, New Jersey, 2007, 1pp.

Zhang et al., "Inhibited expression of hematopoietic progenitor kinase 1 associated with loss of jumonji domain containing 3 promoter binding contributes to autoimmunity in systemic lupus erythematosus", J. Autoimmun., 2011, 37, 180-189.

Zhou et al., "Hematopoietic progenitor kinase 1 is a component of transforming growth factor beta-induced c-Jun N-terminal kinase signaling cascade", J. Biol. Chem., 1999, 274, 13133-13138.

Sawasdikosol et al., Hematopoietic progenitor kinase 1 (HPK1) negatively regulates prostaglandin E2-induced fos gene transcription. Blood, 2003, vol. 101, No. 9, 3687-3689.

* cited by examiner

HPK1 INHIBITORS

CROSS-REFERENCE TO RELATED APPLICATIONS

This application is the National Stage of International Patent Application No. PCT/EP2020/058081, "HPK1 Inhibitors" (filed Mar. 24, 2020), which claims priority to U.S. Patent Application No. 62/823,708 (filed Mar. 26, 2019) and European Patent Application No. 19167820.0 (filed Apr. 8, 2019). The foregoing applications are incorporated herein by reference in their entireties for any and all purposes.

FIELD OF THE INVENTION

The present invention relates to pharmaceutical agents useful for therapy and/or prophylaxis in a mammal, pharmaceutical composition comprising such compounds, and their use as HPK1 inhibitors, useful for treating diseases such as cancer.

BACKGROUND OF THE INVENTION

One of the hallmarks of cancer is its ability to evade the immune system by suppressing its ability to recognize malignant cells and mount an effective immune response against them. Therapeutic strategies designed to overcome these immunosuppressive effects include interfering with mechanisms that negatively regulate effector T cell function, such as the PD1/PDL1 immune checkpoint axis (Ribas and Wolchok, 2018). Antibodies that block PD1/PDL1 interaction and thereby eliminate the suppressive effect on T cells have demonstrated clinical benefit in several cancer types. Another example is the use of therapeutic antibodies that block the interaction between CD80/CD86 and the T-cell co-inhibitory receptor, CTLA-4, which facilitates T cell expansion in secondary lymphoid tissues. In addition to these cell-surface associated proteins, negative regulators of intracellular signalling required for an effective immune response have also been identified. One of these is Hematopoietic Progenitor Kinase 1 (HPK1), also known as MAP4K1, a serine/threonine kinase whose expression is restricted to hematopoietic cells (Hu et al., 1996; Kiefer et al., 1996).

HPK1 deficiency is associated with autoimmunity in humans and mice, suggesting a role in immune tolerance. HPK1 expression was down-regulated in PBMCs from patients with psoriatic arthritis (Batliwalla et al., 2005; Stoeckman et al., 2006) and in T cells from patients with systemic lupus erythematosus (Zhang et al., 2011), while HPK1-deficient mice displayed increased susceptibility to experimentally induced autoimmune encephalitis (Shui et al., 2007). T and B cells isolated from HPK1-deficient mice demonstrated enhanced antigen-dependent activation (Shui et al., 2007; Alzabin et al., 2010), highlighting its role as a negative regulator of T and B cell function. HPK1-deficient dendritic cells displayed enhanced antigen-presenting and T-cell activating properties, consistent with a negative regulatory role in these immune cells (Alzabin et al., 2009). HPK1 may also play a role in T and B cell adhesion by regulating integrin activation (Patzak et al., 2010; Konigsberger et al., 2010). Overexpression studies suggested a role in activation-induced cell death through JNK pathway activation (Arnold et al., 2001; Brenner et al., 2005).

The HPK1 kinase is activated by T cell receptor and B cell receptor engagement. Upon TCR activation in T cells, Hpk1 is recruited to the TCR foci where it is phosphorylated and activated by Lck and Zap70 kinases (Arnold et al., 2005; Ling et al., 2001; Liou et al; 2000). Activated Hpk1 phosphorylates the adaptor proteins SLP76 and LAT, components of the TCR signalling complex that also includes GADS (Di Bartolo et al., 2007). Hpk1-dependent SLP76 phosphorylation on 5376 creates a docking site for 14-3-3 proteins, which target SLP76 for degradation, thereby causing disruption of the TCR signalling complex and preventing further downstream signalling required for T cell activation (Lasserre et al., 2011). Hpk1 can also be activated by PGE2 in a PKA-dependent manner (Sawasdikosol et al., 2003, 2007; Alzabin et al., 2010) and possibly other immunosuppressive factors produced by tumors (Nagata et al., 1999; Zhou et al., 1999).

Growth of syngeneic Lewis Lung carcinoma tumors was reduced in HPK1$^{-/-}$ compared to wild-type mice (Alzabin et al., 2010). Adoptive T cell transfer studies into T cell deficient mice demonstrated that the anti-tumor immune response in HPK1−/− mice was at least partially T-cell dependent (Alzabin et al., 2010). A potential contribution from dendritic cells to the anti-tumor effect in HPK1$^{-/-}$ mice was demonstrated by reconstitution of irradiated mice with HPK1-deficent bone marrow derived dendritic cells (Alzabin et al., 2009). In more recent studies using mutant mice expressing a catalytically inactive form of HPK1, reduced GL261 glioblastoma tumor growth was observed and the anti-tumoral effect of anti-PD1 treatment on MC38 tumors was enhanced in mutant compared to wild-type mice (Hernanadez et al., 2018). These studies suggest that small molecule HPK1 kinase inhibitors could provide anti-tumoral effects as single agents, but also in combination with other immune modulators.

REFERENCES REFERRED TO HEREABOVE

Alzabin S, Bhardwaj N, Kiefer F, Sawasdikosol S, Burakoff S. (2009). Hematopoietic progenitor kinase 1 is a negative regulator of dendritic cell activation. J. Immunol. 182: 6187-94.

Alzabin S, Pyarajan S, Yee H, Kiefer F, Suzuki A, Burakoff S, Sawasdikosol S. (2010). Hematopoietic progenitor kinase 1 is a critical component of prostaglandin E2-mediated suppression of the anti-tumor immune response. Cancer Immunol. Immunother. 59:419-29.

Arnold R, Liou J, Drexler H C, Weiss A, Kiefer F. (2001). Caspase-mediated cleavage of hematopoietic progenitor kinase 1 (HPK1) converts an activator of NFkappaB into an inhibitor of NFkappaB. J Biol Chem. 276:14675-84.

Arnold R, Patzak I M, Neuhaus B, Vancauwenbergh S, Veillette A, Van Lint J, Kiefer F. (2005). Mol Cell Biol. 25:2364-83.

Batliwalla F M, Li W, Ritchlin C T, Xiao X, Brenner M, Laragione T, Shao T, Durham R, Kemshetti S, Schwarz E, Coe R, Kern M, Baechler E C, Behrens T W, Gregersen P K, Gulko P S. (2005). Microarray analyses of peripheral blood cells identifies unique gene expression signature in psoriatic arthritis. Mol Med. 11:21-9.

Brenner D, Golks A, Kiefer F, Krammer P H, Arnold R. (2005). Activation or suppression of NFkappaB by HPK1 determines sensitivity to activation-induced cell death. EMBO J. 24:4279-90.

Di Bartolo V, Montagne B, Salek M, Jungwirth B, Carrette F, Fourtane J, Sol-Foulon N, Michel F, Schwartz O, Lehmann W D, Acuto O. (2007). A novel pathway down-modulating T cell activation involves HPK-1-dependent recruitment of 14-3-3 proteins on SLP-76. J Exp Med. 204:681-91.

Hernandez S, Qing J, Thibodeau R H, et al. (2018). The kinase activity of Hematopoietic Progenitor Kinase 1 Is essential for the regulation of T cell function. Cell Rep. 25:80-94. Hu M C, Qiu W R, Wang X, Meyer C F, Tan T H. (1996). Human HPK1, a novel human hematopoietic progenitor kinase that activates the JNK/SAPK kinase cascade. Genes Dev. 10:2251-64.

Kiefer F, Tibbles L A, Anafi M, Janssen A, Zanke B W, Lassam N, Pawson T, Woodgett J R, Iscove N N. (1996). HPK1, a hematopoietic protein kinase activating the SAPK/JNK pathway. EMBO J. 15:7013-25.

Konigsberger S, Peckl-Schmid D, Zaborsky N, Patzak I, Kiefer F, Achatz G. (2010). HPK1 associates with SKAP-HOM to negatively regulate Rapl-mediated B-lymphocyte adhesion. PLoS One. 5(9): e12468.

Lasserre R, Cuche C, Blecher-Gonen R, Libman E, Biquand E, Danckaert A, Yablonski D, Alcover A, Di Bartolo V. (2011). Release of serine/threonine-phosphorylated adaptors from signaling microclusters down-regulates T cell activation. J Cell Biol. 195:839-53.

Ling P, Meyer C F, Redmond L P, Shui J W, Davis B, Rich R R, Hu M C, Wange R L, Tan T H. (2001). Involvement of hematopoietic progenitor kinase 1 in T cell receptor signaling. J Biol Chem. 276:18908-14.

Liou J, Kiefer F, Dang A, Hashimoto A, Cobb M H, Kurosaki T, Weiss A. (2000). HPK1 is activated by lymphocyte antigen receptors and negatively regulates AP-1. Immunity. 12:399-408.

Nagata Y, Kiefer F, Watanabe T, Todokoro K. (1999). Activation of hematopoietic progenitor kinase-1 by erythropoietin. Blood 93:3347-54. Patzak I M, Konigsberger S, Suzuki A, Mak T W, Kiefer F. (2010). HPK1 competes with ADAP for SLP-76 binding and via Rapl negatively affects T-cell adhesion. Eur J Immunol. 40:3220-5.

Ribas A, Wolchok J D. (2018). Cancer immunotherapy using checkpoint blockade. Science 359:1350-1355.

Sawasdikosol S, Russo K M, and Burakoff S J. (2003). Hematopoietic progenitor kinase 1 (HPK1) negatively regulates prostaglandin E2-induced fos gene transcription. Blood 101:3687-9.

Sawasdikosol S, Pyaraj an S, Alzabin S, Matejovic G, and Burakoff S J. (2007). Prostaglandin E2 activates HPK1 kinase activity via a PKA-dependent pathway. J Biol Chem. 282:34693-9.

Shui J W, Boomer J S, Han J, Xu J, Dement G A, Zhou G, Tan T H. (2007). Hematopoietic progenitor kinase 1 negatively regulates T cell receptor signaling and T cell-mediated immune responses. Nat Immunol. 8:84-91.

Stoeckman A K, Baechler E C, Ortmann W A, Behrens T W, Michet C J, Peterson E J. (2006). A distinct inflammatory gene expression profile in patients with psoriatic arthritis. Genes Immun. 7:583-91.

Zhang Q, Long H, Liao J, Zhao M, Liang G, Wu X, Zhang P, Ding S, Luo S, Lu Q. (2011). Inhibited expression of hematopoietic progenitor kinase 1 associated with loss of jumonji domain containing 3 promoter binding contributes to autoimmunity in systemic lupus erythematosus. J Autoimmun. 37:180-9.

Zhou G, Lee S C, Yao Z, Tan T H. (1999). Hematopoietic progenitor kinase 1 is a component of transforming growth factor beta-induced c-Jun N-terminal kinase signaling cascade. J Biol Chem. 274:13133-8.

WO2018049152, WO2018049214, WO2018049200, WO2018049191 and WO2019051199 describe derivatives as HPK1 modulators and uses thereof for the treatment of cancer.

WO2018081531 describes methods for human T-cell activation.

WO2018102366 describes anilinopyrimidines as HPK1 inhibitors.

WO2016090300 describes methods and compositions for treating cancer using PD-1 axis antagonists and HPK1 antagonists.

WO2018167147, WO2018183956 and WO2018183964 describe compounds as inhibitors of HPK1.

WO2018215668 describes inhibitors of MAP4K1.

WO2018228920, WO2018228923 and WO2018228925 describe compounds useful in the treatment or prophylaxis of a disease, where the disease is cancer or conditions with dysregulated immune responses or other disorders associated with aberrant MAP4K1 signaling.

WO2016205942 describes HPK1 inhibitors.

DESCRIPTION OF THE INVENTION

The present invention concerns novel compounds of Formula (I), (I)

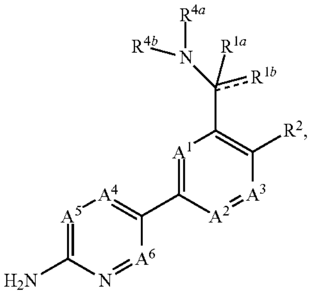

and the tautomers and stereoisomeric forms thereof, wherein the dotted bond towards $R^{1b}$ is an optional bond that may be present when $R^{1b}$ and $R^{4b}$ are taken together to form a monocyclic or bicyclic aromatic heterocyclyl as defined herein;

$A^1$ represents CH or N; $A^2$ represents CH; $A^3$ represents CH or N;

provided that only one of $A^1$ and $A^3$ represents N;

$A^4$ represents CH or N; $A^5$ represents $CR^3$a; $A^6$ represents CH;

$R^{1a}$ represents hydrogen;

$R^{1b}$ represents hydrogen or $CH_3$;

$R^{4a}$ represents hydrogen, $C_{1-4}$alkyl, or $C_{3-6}$ cycloalkyl;

$R^{4b}$ represents hydrogen, $C_{1-4}$alkyl, $C_{3-6}$ cycloalkyl, or a carbon linked monocyclic 4-, 5-, 6- or 7-membered non-aromatic heterocyclyl containing 1, 2 or 3 heteroatoms each independently selected from the group consisting of N, O, and S; wherein said S-atom might be substituted to form S(=O), $S(=O)_2$, or S(=O)(=$NR^x$); or $R^{1b}$ and $R^{4b}$ are taken together to form together with the atoms to which they are attached a monocyclic 5-membered aromatic heterocyclyl or a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(=O), $S(=O)_2$, or S(=O)(=$NR^x$); or a bicyclic 6- to 12-membered aromatic or fully saturated heterocyclyl containing 1 N-atom and optionally 1 or 2 additional heteroatoms each independently selected from the group consisting of N, O, S; wherein said optional S-atom might be substituted to form S(=O), $S(=O)_2$, or S(=O)(=$NR^x$);

wherein said monocyclic or bicyclic, aromatic or fully saturated heterocyclyl might be substituted on one or more of the carbon atoms with in total 1, 2 or 3 substituents each independently selected from the group consisting of —OH, CN, halo, $R^7$, —O—$R^7$, —$S(=O)_2$—$R^7$, —C(=O)—$R^7$, —$NR^{6c}R^{6d}$, —C(=O)—$NR^{6a}R^{6b}$, and $Het^c$;

wherein said monocyclic or bicyclic, aromatic or fully saturated heterocyclyl might be substituted on the optional additional nitrogen atoms with in total 1 or 2 substituents each independently selected from the group consisting of $R^7$, —$S(=O)_2$—$R^7$, —C(=O)—$R^7$, —C(=O)—$NR^{6a}R^{6b}$, and $Het^d$;

provided that in case $R^{1b}$ and $R^{4b}$ are taken together, R' represents hydrogen; and $R^{1a}$ represents hydrogen or $R^{1a}$ is absent when the dotted bond towards $R^{1b}$ is a bond; or $R^{4a}$ and $R^{4b}$ are taken together to form together with the N-atom to which they are attached a monocyclic 5-membered aromatic heterocyclyl or a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(=O), $S(=O)_2$, or S(=O)(=$NR^x$); or a bicyclic 6- to 12-membered aromatic or fully saturated heterocyclyl containing 1 N-atom and optionally 1 or 2 additional heteroatoms each independently selected from the group consisting of N, O, S; wherein said optional S-atom might be substituted to form S(=O), $S(=O)_2$, or S(=O)(=$NR^x$);

wherein said monocyclic or bicyclic, aromatic or fully saturated heterocyclyl might be substituted on one or more of the carbon atoms with in total 1, 2 or 3 substituents each independently selected from the group consisting of —OH, CN, halo, $R^7$, —O—$R^7$, —$S(=O)_2$—$R^7$, —C(=O)—$R^7$, —$NR^{6c}R^{6d}$, —C(=O)—$NR^{6a}R^{6b}$, and $Het^c$;

wherein said monocyclic or bicyclic, aromatic or fully saturated heterocyclyl might be substituted on the nitrogen atoms with in total 1 or 2 substituents each independently selected from the group consisting of $R^7$, —$S(=O)_2$—$R^7$, —C(=O)—$R^7$, —C(=O)—$NR^{6a}R^{6b}$, and $Het^d$;

in case $R^{4a}$ and $R^{4b}$ are taken together, $R^{1a}$ represents hydrogen, and $R^{1b}$ represents hydrogen;

$R^2$ is selected from the group consisting of cyano; halo; —C(=O)—$NR^{8a}R^{8b}$;

—$CH_2$—$NR^{8c}R^{8d}$; $Het^b$; —P(=O)—($C_{1-4}$alkyl)$_2$; —$S(=O)_2$—$C_{1-4}$alkyl; —S(=O)(=$NR^x$)—$C_{1-4}$alkyl;

$C_{1-6}$alkyl optionally substituted with 1 or 2 substituents each independently selected from the group consisting of halo, —OH, cyano, and —O—$C_{1-4}$ alkyl;

$C_{3-6}$ cycloalkyl optionally substituted with 1 or 2 substituents each independently selected from the group consisting of halo, —OH, cyano and —O—$C_{1-4}$ alkyl; and $C_{3-6}$ cycloalkenyl optionally substituted with 1 or 2 substituents each independently selected from the group consisting of halo, —OH, cyano and —O—$C_{1-4}$ alkyl;

$R^{3a}$ represents hydrogen, halo, $R^7$, —O—$R^7$, cyano, —C(=O)—$NR^{6e}R^{6f}$, $Het^a$, or phenyl optionally substituted with 1, 2 or 3 substituents each independently selected from the group consisting of halo, cyano, $C_{1-4}$ alkyl, $C_{1-4}$ alkyl substituted with one cyano, and $C_{1-4}$ alkyl substituted with 1, 2 or 3 halo atoms;

$Het^a$ represents a carbon linked monocyclic 5-, 6- or 7-membered aromatic heterocyclyl or carbon linked monocyclic 4-, 5-, 6- or 7-membered non-aromatic heterocyclyl, each containing 1, 2 or 3 heteroatoms each independently selected from the group consisting of N, O or S; wherein said S-atom might be substituted to form S(=O), $S(=O)_2$, or S(=O)(=$NR^x$); or a carbon linked bicyclic 6- to 12-membered aromatic or non-aromatic heterocyclyl containing 1, 2 or 3 heteroatoms each independently selected from the group consisting of N, O or S; wherein said S-atom might be substituted to form S(=O), $S(=O)_2$, or S(=O)(=$NR^x$);

wherein said monocyclic or bicyclic, aromatic or non-aromatic heterocyclyl might be substituted on one or more of the carbon atoms with in total 1, 2 or 3 substituents each independently selected from the group consisting of —OH, CN, halo, $R^7$, —O—$R^7$, —$S(=O)_2$—$R^7$, —C(=O)—$R^7$, —$NR^{6c}R^{6d}$, —C(=O)—$NR^{6a}R^{6b}$, and $Het^c$;

wherein said monocyclic or bicyclic, aromatic or non-aromatic heterocyclyl might be substituted on the nitrogen atoms with in total 1 or 2 substituents each independently selected from the group consisting of $R^7$, —$S(=O)_2$—$R^7$, —C(=O)—$R^7$, —C(=O)—$NR^{6a}R^{6b}$ and $Het^d$;

$R^{6a}$, $R^{6b}$, $R^{6c}$, $R^{6d}$, $R^{6e}$, and $R^{6f}$ are each independently selected from the group consisting of hydrogen; $C_{3-6}$ cycloalkyl optionally substituted with one —$OR^5$; and $C_{1-4}$ alkyl optionally substituted with one —$OR^5$, wherein two hydrogen atoms on the same carbon atom of said $C_{1-4}$ alkyl might be taken together to form $C_{3-6}$ cycloalkyl;

$R^5$ represents hydrogen or $C_{1-4}$ alkyl;

$R^{8a}$, $R^{8c}$, and $R^{8d}$ are each independently selected from the group consisting of hydrogen;

$C_{1-4}$ alkyl optionally substituted with one —OH or —O—$C_{1-4}$ alkyl; and $C_{3-6}$ cycloalkyl optionally substituted with one —OH or —O—$C_{1-4}$ alkyl;

$R^{8b}$ is selected from the group consisting $C_{1-4}$alkyl optionally substituted with one —OH or —O—$C_{1-4}$ alkyl; and $C_{3-6}$ cycloalkyl optionally substituted with one —OH or —O—$C_{1-4}$ alkyl; or $R^{8a}$ and $R^{8b}$, or $R^{8c}$ and $R^{8d}$ are taken together to form together with the N-atom to which they are attached a monocyclic fully saturated heterocyclyl containing 1 N-atom and optionally 1 or 2 additional heteroatoms each independently selected from the group consisting of N, O, S; wherein said optional S-atom might be substituted to form S(=O), $S(=O)_2$, or S(=O)(=$NR^x$); wherein said monocyclic 4-, 5-, 6- or 7-membered fully saturated heterocyclyl might be substituted on one or more of the carbon atoms with in total 1, 2 or 3 substituents each independently selected from the group consisting of —OH, CN, halo, $R^7$, —O—$R^7$, —S(═O)$_2$—$R^7$, —C(═O)—$R^7$, —$NR^{6c}R^{6d}$, and —C(═O)—$NR^{6a}R^{6b}$;

wherein said monocyclic fully saturated heterocyclyl might be substituted on the nitrogen atoms with in total 1 or 2 substituents each independently selected from the group consisting of $R^7$, —S(═O)$_2$—$R^7$, —C(═O)—$R^7$, and —C(═O)—$NR^{6a}R^{6b}$;

each $Het^c$ independently represents a monocyclic 4-, 5-, 6- or 7-membered fully saturated heterocyclyl containing 1, 2 or 3 heteroatoms each independently selected from the group consisting of N, O or S; wherein said S-atom might be substituted to form S(═O), S(═O)$_2$, or S(═O)(═$NR^x$);

each $Het^d$ independently represents a carbon linked monocyclic 4-, 5-, 6- or 7-membered fully saturated heterocyclyl containing 1, 2 or 3 heteroatoms each independently selected from the group consisting of N, O or S; wherein said S-atom might be substituted to form S(═O), S(═O)$_2$, or S(═O)(═$NR^x$);

$Het^b$ represents a monocyclic 4-, 5-, 6- or 7-membered non-aromatic heterocyclyl containing 1, 2 or 3 heteroatoms each independently selected from the group consisting of N, O, S; wherein said S-atom might be substituted to form S(═O), S(═O)$_2$, or S(═O)(═$NR^x$); or a bicyclic 6- to 12-membered non-aromatic heterocyclyl containing 1, 2 or 3 heteroatoms each independently selected from the group consisting of N, O, S; wherein said S-atom might be substituted to form S(═O), S(═O)$_2$, or S(═O)(═$NR^x$);

wherein said monocyclic or bicyclic non-aromatic heterocyclyl might be substituted on one or more of the carbon atoms with in total 1, 2 or 3 substituents each independently selected from the group consisting of —OH, CN, halo, $R^7$, —O—$R^7$, —S(═O)$_2$—$R^7$, —C(═O)—$R^7$, —$NR^{6c}R^{6d}$, and —C(═O)—$NR^{6a}R^{6b}$;

wherein said monocyclic or bicyclic non-aromatic heterocyclyl might be substituted on the nitrogen atoms with in total 1 or 2 substituents each independently selected from the group consisting of $R^7$, —S(═O)$_2$—$R^7$, —C(═O)—$R^7$, and —C(═O)—$NR^{6a}R^{6b}$;

each $R^7$ independently represents $C_{3-6}$ cycloalkyl optionally substituted with 1, 2 or 3 substituents each independently selected from the group consisting of halo, —OH, —O—$C_{1-4}$ alkyl and cyano; or $C_{1-4}$alkyl optionally substituted with 1, 2 or 3 substituents each independently selected from the group consisting of halo, —OH, —O—$C_{1-4}$ alkyl and cyano;

each $R^x$ independently represents hydrogen or $C_{1-4}$alkyl;

and the pharmaceutically acceptable addition salts, the N-oxides, and the solvates thereof.

The present invention also relates to a pharmaceutical composition comprising a therapeutically effective amount of a compound of Formula (I), a pharmaceutically acceptable addition salt, an N-oxide, or a solvate thereof, and a pharmaceutically acceptable carrier or excipient.

Additionally, the invention relates to a compound of Formula (I), a pharmaceutically acceptable addition salt, an N-oxide, or a solvate thereof, for use as a medicament, and to a compound of Formula (I), a pharmaceutically acceptable addition salt, an N-oxide or a solvate thereof, for use in the treatment or in the prevention of cancer.

In a particular embodiment, the invention relates to a compound of Formula (I), a pharmaceutically acceptable addition salt, an N-oxide, or a solvate thereof, for use in the treatment or in the prevention of cancer.

The invention also relates to the use of a compound of Formula (I), a pharmaceutically acceptable addition salt, an N-oxide, or a solvate thereof, in combination with an additional pharmaceutical agent for use in the treatment or prevention of cancer.

Furthermore, the invention relates to a process for preparing a pharmaceutical composition according to the invention, characterized in that a pharmaceutically acceptable carrier is intimately mixed with a therapeutically effective amount of a compound of Formula (I), a pharmaceutically acceptable addition salt, an N-oxide, or a solvate thereof.

The invention also relates to a product comprising a compound of Formula (I), a pharmaceutically acceptable addition salt, an N-oxide, or a solvate thereof, and an additional pharmaceutical agent, as a combined preparation for simultaneous, separate or sequential use in the treatment or prevention of cancer.

Additionally, the invention relates to a method of treating or preventing a cell proliferative disease in a warm-blooded animal which comprises administering to the said animal an effective amount of a compound of Formula (I), a pharmaceutically acceptable addition salt, an N-oxide, or a solvate thereof, as defined herein, or a pharmaceutical composition or combination as defined herein.

DETAILED DESCRIPTION OF THE INVENTION

The term 'halo' or 'halogen' as used herein represents fluoro, chloro, bromo and iodo.

The prefix '$C_{x-y}$' (where x and y are integers) as used herein refers to the number of carbon atoms in a given group. Thus, a $C_{1-6}$alkyl group contains from 1 to 6 carbon atoms, and so on.

The term '$C_{1-4}$ alkyl' as used herein as a group or part of a group represents a straight or branched chain fully saturated hydrocarbon radical having from 1 to 4 carbon atoms, such as methyl, ethyl, n-propyl, isopropyl, n-butyl, s-butyl, t-butyl and the like.

The term '$C_{3-6}$ cycloalkyl' as used herein as a group or part of a group defines a fully saturated, cyclic hydrocarbon radical having from 3 to 6 carbon atoms, such as cyclopropyl, cyclobutyl, cyclopentyl and cyclohexyl.

It will be clear for the skilled person that S(═O)$_2$ or $SO_2$ represents a sulfonyl moiety.

It will be clear for the skilled person that CO or C(═O) represents a carbonyl moiety.

In general, whenever the term 'substituted' is used in the present invention, it is meant, unless otherwise indicated or clear from the context, to indicate that one or more hydrogens, in particular from 1 to 4 hydrogens, more in particular from 1 to 3 hydrogens, preferably 1 or 2 hydrogens, more preferably 1 hydrogen, on the atom or radical indicated in the expression using 'substituted' are replaced with a selection from the indicated group, provided that the normal valency is not exceeded, and that the substitution results in a chemically stable compound, i.e. a compound that is sufficiently robust to survive isolation to a useful degree of purity from a reaction mixture.

Combinations of substituents and/or variables are permissible only if such combinations result in chemically stable compounds. 'Stable compound' is meant to indicate a compound that is sufficiently robust to survive isolation to a useful degree of purity from a reaction mixture.

The skilled person will understand that the term 'optionally substituted' means that the atom or radical indicated in the expression using 'optionally substituted' may or may not be substituted (this means substituted or unsubstituted respectively).

When two or more substituents are present on a moiety they may, where possible and unless otherwise indicated or clear from the context, replace hydrogens on the same atom or they may replace hydrogen atoms on different atoms in the moiety.

It will be clear for the skilled person that, unless otherwise is indicated or is clear from the context, a substituent on a heterocyclyl group may replace any hydrogen atom on a ring carbon atom or on a ring heteroatom (e.g. a hydrogen on a nitrogen atom may be replaced by a substituent).

A 'non-aromatic' group (e.g. a 'monocyclic non-aromatic heterocyclyl') embraces unsaturated ring systems without aromatic character, partially saturated and fully saturated carbocyclic and heterocyclic ring systems. The term 'partially saturated' refers to rings wherein the ring structure(s) contain(s) at least one multiple bond e.g. a C═C, N═C bond. The term 'fully saturated' refers to rings where there are no multiple bonds between ring atoms.

Unless otherwise specified or clear from the context, aromatic, non-aromatic or fully saturated heterocyclyl groups, can be attached to the remainder of the molecule of Formula (I) through any available ring carbon atom (carbon linked) or nitrogen atom (nitrogen linked).

Unless otherwise specified or clear from the context, aromatic, non-aromatic or fully saturated heterocyclyl groups, may optionally be substituted, where possible, on carbon and/or nitrogen atoms according to the embodiments.

The term 'monocyclic 4-, 5-, 6- or 7-membered non-aromatic heterocyclyl containing 1, 2 or 3 hetereoatoms each independently selected from the group consisting of N, O and S' as used herein alone or as part of another group, defines a monocyclic non-aromatic, cyclic hydrocarbon radical containing at least one nitrogen, oxygen or sulphur atom having from 4 to 7 ring members, as defined above. Non-limiting examples are:

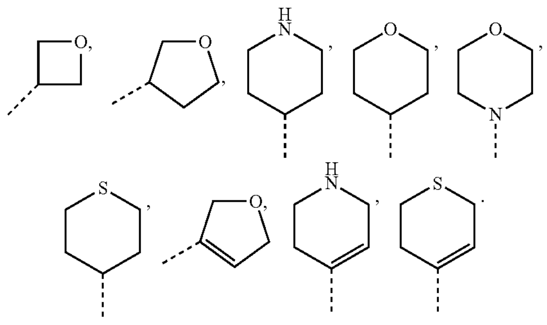

Within the context of this invention, bicyclic fully saturated heterocyclyl groups include fused, spiro and bridged saturated heterocycles.

Fused bicyclic groups are two cycles that share two atoms and the bond between these atoms.

Spiro bicyclic groups are two cycles that are joined at a single atom.

Bridged bicyclic groups are two cycles that share more than two atoms.

As defined in the scope, when $R^{1b}$ and $R^{4b}$ are taken together, $R^{4a}$ represents hydrogen. This means that the nitrogen atom to which $R^{4a}$ is attached, always has a hydrogen atom and is not substituted, nor is a double bond attached to said nitrogen atom.

Therefore, non-limiting examples of $R^{1b}$ and $R^{4b}$ taken together to form a monocyclic 5-membered aromatic heterocyclyl containing 1 N-atom and optionally 1 or 2 additional heteroatoms each independently selected from the group consisting of N, O, S, include, but are not limited to

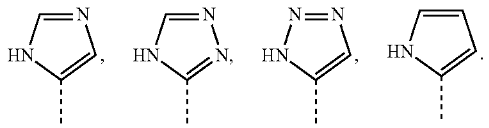

Therefore, non-limiting examples of $R^{1b}$ and $R^{4b}$ taken together to form a monocyclic 4-, 5-, 6- or 7-membered fully saturated heterocyclyl containing 1 N-atom and optionally 1 or 2 additional heteroatoms each independently selected from the group consisting of N, O, S, include, but are not limited to:

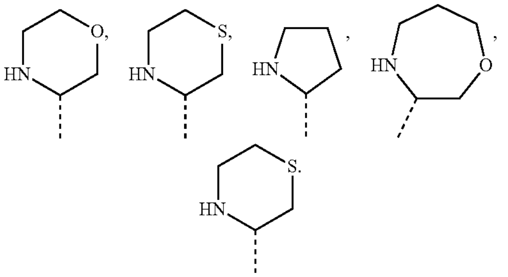

Therefore, non-limiting examples of $R^{1b}$ and $R^{4b}$ taken together to form a bicyclic 6- to 12-membered aromatic heterocyclyl containing 1 N-atom and optionally 1 or 2 additional heteroatoms each independently selected from the group consisting of N, O, S, include, but are not limited to

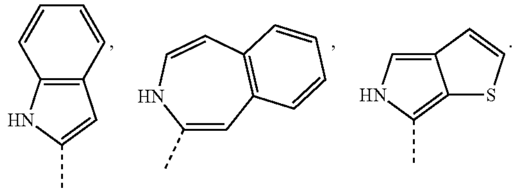

Therefore, non-limiting examples of $R^{1b}$ and $R^{4b}$ taken together to form a bicyclic 6- to 12-membered fully saturated heterocyclyl containing 1 N-atom and optionally 1 or 2 additional heteroatoms each independently selected from the group consisting of N, O, S, include, but are not limited to

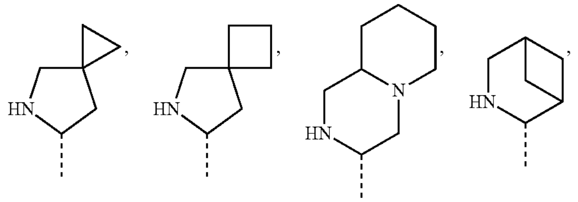

-continued

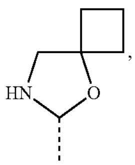,
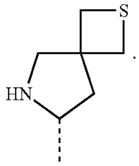.

Non-limiting examples of $R^{4a}$ and $R^{4b}$ taken together to form together with the N-atom to which they are attached a monocyclic 5-membered aromatic heterocyclyl containing 1 N-atom and optionally 1 or 2 additional heteroatoms each independently selected from the group consisting of N, O, S, include, but are not limited to

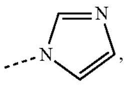,
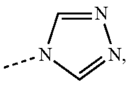,
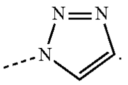.

Non-limiting examples of $R^{4a}$ and $R^{4b}$ taken together to form together with the N-atom to which they are attached a monocyclic 4-, 5-, 6- or 7-membered fully saturated heterocyclyl containing 1 N-atom and optionally 1 or 2 additional heteroatoms each independently selected from the group consisting of N, O, S, include, but are not limited to:

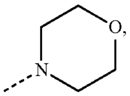,
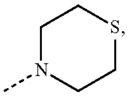,
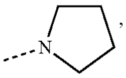,
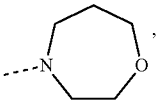,
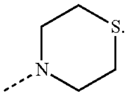.

Non-limiting examples of $R^{4a}$ and $R^{4b}$ taken together to form together with the N-atom to which they are attached a bicyclic 6- to 12-membered aromatic heterocyclyl containing 1 N-atom and optionally 1 or 2 additional heteroatoms each independently selected from the group consisting of N, O, S, include, but are not limited to

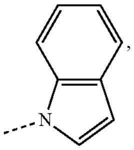,
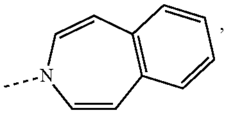,
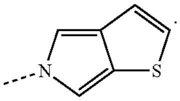.

Non-limiting examples of $R^{4a}$ and $R^{4b}$ taken together to form together with the N-atom to which they are attached a bicyclic 6- to 12-membered fully saturated heterocyclyl containing 1 N-atom and optionally 1 or 2 additional heteroatoms each independently selected from the group consisting of N, O, S, include, but are not limited to

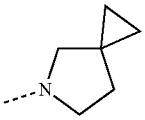,
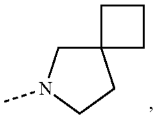,
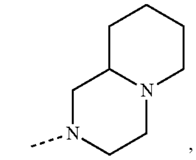,

-continued

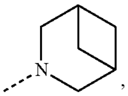,
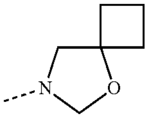,
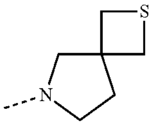.

Non-limiting examples of carbon linked monocyclic 5-, 6- or 7-membered aromatic heterocyclyl containing 1, 2 or 3 hetereoatoms each independently selected from the group consisting of N, O and S, include, but are not limited to

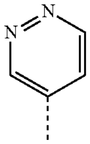,
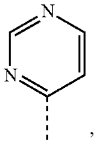,
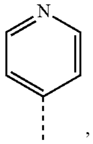,
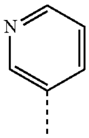,
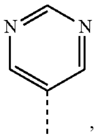,
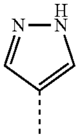,
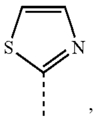,
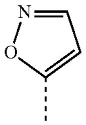.

Non-limiting examples of carbon linked bicyclic 6- to 12-membered aromatic heterocyclyl containing 1, 2 or 3 hetereoatoms each independently selected from the group consisting of N, O and S, include, but are not limited to

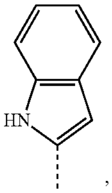,
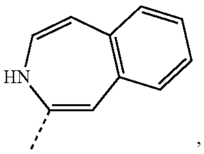,
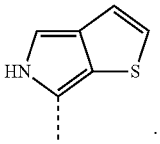.

The term 'bicyclic 6- to 12-membered non-aromatic heterocyclyl containing 1, 2 or 3 hetereoatoms each independently selected from the group consisting of N, O and S' as used herein alone or as part of another group, defines a bicyclic non-aromatic, cyclic hydrocarbon radical containing at least one nitrogen, oxygen or sulphur atom having from 6 to 12 ring members, as defined above. Non-limiting examples are:

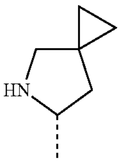,
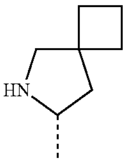,
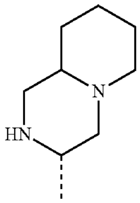,
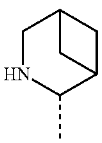,
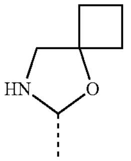,
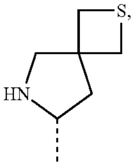,
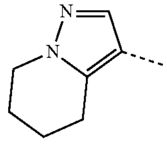, -continued

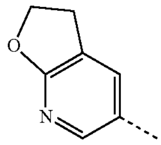
,
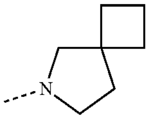
,
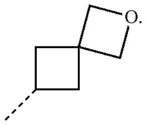

Non-limiting examples of monocyclic 4-, 5-, 6- or 7-membered fully saturated heterocyclyl containing 1, 2 or 3 heteroatoms each independently selected from the group consisting of N, O, S, include, but are not limited to:

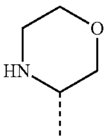
,
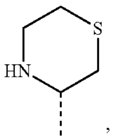
,
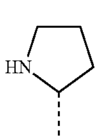
,
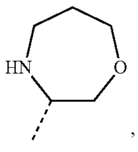
,
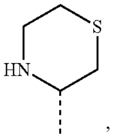
,
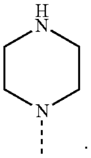
.

When any variable occurs more than one time in any constituent, each definition is independent.

When any variable occurs more than one time in any formula (e.g. Formula (I)), each definition is independent.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compound(s) of the (present) invention" or "compound(s) according to the (present) invention" as used herein, is meant to include the compounds of Formula (I) and the pharmaceutically acceptable addition salts, the N-oxides, and the solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound(s) of Formula (I)" is meant to include the tautomers thereof and the stereoisomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic saturated or partially saturated radicals may have either the cis- or trans-configuration; for example if a compound contains a disubstituted cycloalkyl group, the substituents may be in the cis or trans configuration.

Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (5) isomer; when a compound of Formula (I) is for instance specified as E, this means that the compound is substantially free of the Z isomer; when a compound of Formula (I) is for instance specified as cis, this means that the compound is substantially free of the trans isomer.

The stereochemical configuration for centers in some compounds may be designated "R" or "S" when the mixture(s) was separated; for some compounds, the stereochemical configuration at indicated centers has been designated as "R*" or "S*" when the absolute stereochemistry is undetermined (even if the bonds are drawn stereo specifically) although the compound itself has been isolated as a single stereoisomer and is enantiomerically pure.

For example, it will be clear that Compound 5b

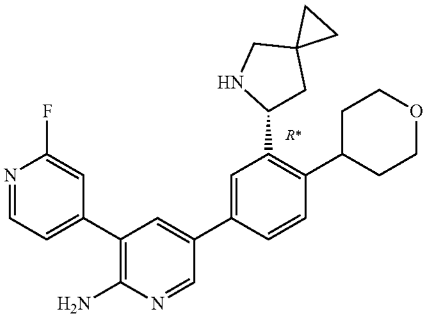

is

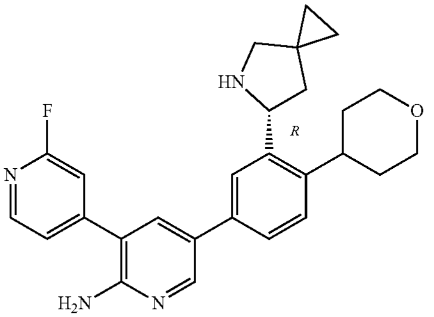

or

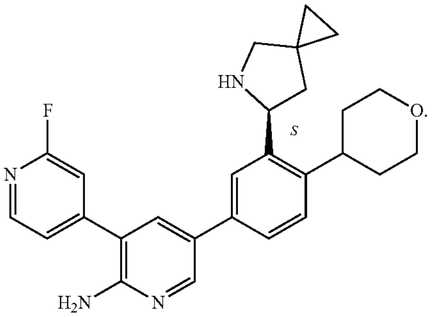

For compounds wherein the stereochemical configuration of two stereocentres is indicated by * (e.g. "R*" or "S*"), the absolute stereochemistry of the stereocentres is undetermined (even if the bonds are drawn stereospecifically), although the compound itself has been isolated as a single stereoisomer and is enantiomerically pure. In this case, the configuration of the first stereocentre is independent of the configuration of the second stereocentre in the same compound.

For example, for Compound 15a

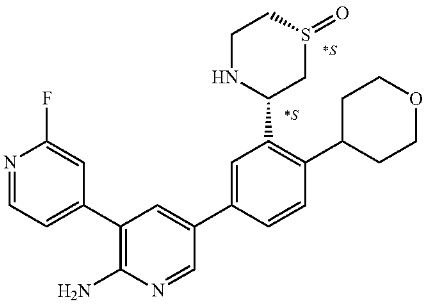 [SMILES: Nc1ncc(-c2ccc(C3CCOCC3)c([C@H]3C[S@@](=O)CCN3)c2)cc1-c1ccnc(F)c1]

this means that the compound is

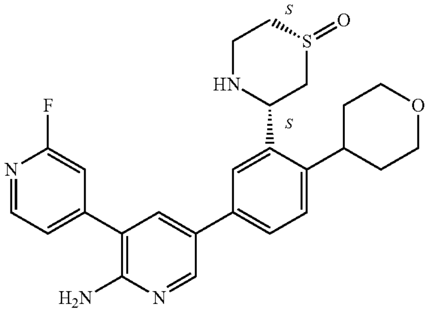

or

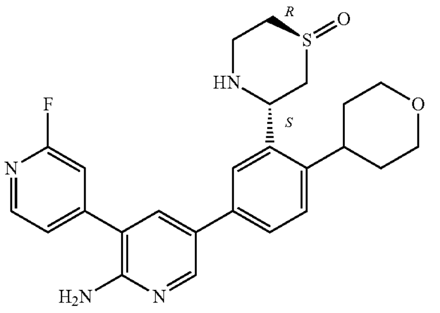

or

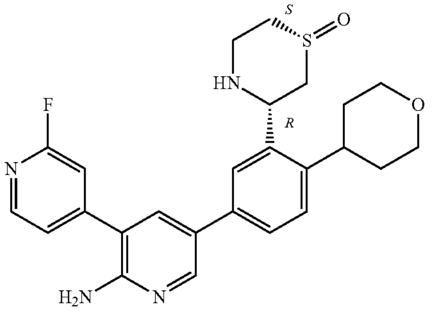

or

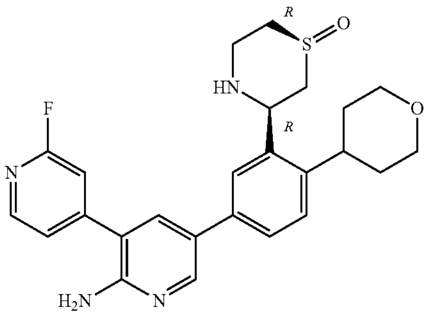

Some of the compounds according to Formula (I) may also exist in their tautomeric form. Such forms in so far as they may exist, although not explicitly indicated in the above Formula (I) are intended to be included within the scope of the present invention. It follows that a single compound may exist in both stereoisomeric and tautomeric form.

For example Co. 56

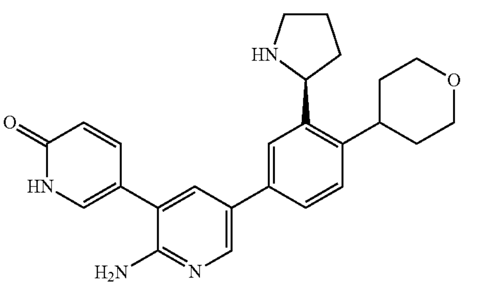 [SMILES: Nc1ncc(-c2ccc(C3CCOCC3)c([C@@H]3CCCN3)c2)cc1-c1ccc(=O)[nH]c1]

also covers the other tautomeric form

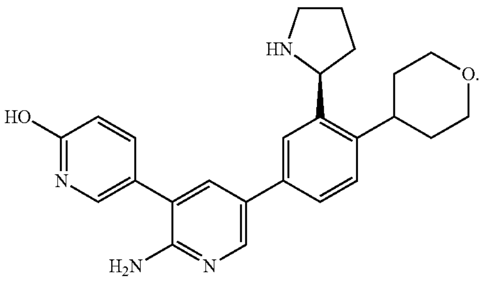 [SMILES: Nc1ncc(-c2ccc(C3CCOCC3)c([C@@H]3CCCN3)c2)cc1-c1ccc(O)nc1]

Pharmaceutically acceptable addition salts include acid addition salts and base addition salts. Such salts may be formed by conventional means, for example by reaction of a free acid or a free base form with one or more equivalents of an appropriate base or acid, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable addition salts as mentioned hereinabove or hereinafter are meant to comprise the therapeutically active non-toxic acid and base salt forms which the compounds of Formula (I), N-oxides and solvates thereof, are able to form.

Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine salt forms by treatment with appropriate organic and inorganic bases.

Appropriate base salt forms comprise, for example, the ammonium salts, the alkali and earth alkaline metal salts, e.g. the lithium, sodium, potassium, cesium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and pharmaceutically acceptable addition salts, N-oxides and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The term "enantiomerically pure" as used herein means that the product contains at least 80% by weight of one enantiomer and 20% by weight or less of the other enantiomer. Preferably the product contains at least 90% by weight of one enantiomer and 10% by weight or less of the other enantiomer. In the most preferred embodiment the term "enantiomerically pure" means that the composition contains at least 99% by weight of one enantiomer and 1% or less of the other enantiomer.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature).

All isotopes and isotopic mixtures of any particular atom or element as specified herein are contemplated within the scope of the compounds of the invention, either naturally occurring or synthetically produced, either with natural abundance or in an isotopically enriched form. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{2}H$, $^{3}H$, $^{11}C$ and $^{18}F$. More preferably, the radioactive isotope is $^{2}H$. In particular, deuterated compounds are intended to be included within the scope of the present invention.

Certain isotopically-labeled compounds of the present invention (e.g., those labeled with $^{3}H$ and $^{14}C$) may be useful for example in substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies. PET imaging in cancer finds utility in helping locate and identify tumours, stage the disease and determine suitable treatment. Human cancer cells overexpress many receptors or proteins that are potential disease-specific molecular targets. Radiolabelled tracers that bind with high affinity and specificity to such receptors or proteins on tumour cells have great potential for diagnostic imaging and targeted radionuclide therapy (Charron, Carlie L. et al. Tetrahedron Lett. 2016, 57(37), 4119-4127). Additionally, target-specific PET radiotracers may be used as biomarkers to examine and evaluate pathology, by for example, measuring target expression and treatment response (Austin R. et al. Cancer Letters (2016), doi: 10.1016/j.canlet.2016.05.008).

The present invention relates in particular to compounds of Formula (I) as defined herein, and the tautomers and the stereoisomeric forms thereof, wherein the dotted bond towards $R^{1b}$ is an optional bond that may be present when $R^{1b}$ and $R^{4b}$ are taken together to form a monocyclic aromatic heterocyclyl as defined herein;

$A^1$ represents CH or N; $A^2$ represents CH; $A^3$ represents CH or N;

provided that only one of $A^1$ and $A^3$ represents N;

$A^4$ represents CH; $A^5$ represents $CR^3$a; $A^6$ represents CH;

$R^{1a}$ represents hydrogen;

$R^{1b}$ represents hydrogen;

$R^{4a}$ represents hydrogen, or $C_{1-4}$alkyl;

$R^{4b}$ represents $C_{1-4}$ alkyl, $C_{3-6}$ cycloalkyl, or a carbon linked monocyclic 4-, 5-, 6- or 7-membered non-aromatic heterocyclyl containing 1, 2 or 3 oxygen atoms;

or $R^{1b}$ and $R^{4b}$ are taken together to form together with the atoms to which they are attached a monocyclic 5-membered aromatic heterocyclyl or a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(═O); or a bicyclic 6- to 12-membered fully saturated heterocyclyl containing 1 N-atom and optionally 1 or 2 additional heteroatoms each independently selected from the group consisting of N, O, S; wherein said optional S-atom might be substituted to form S(═O); wherein said monocyclic or bicyclic, aromatic or fully saturated heterocyclyl might be substituted on one or more of the carbon atoms with in total 1, 2 or 3 substituents each independently selected from the group consisting of halo and $R^7$;

provided that in case $R^{1b}$ and $R^{4b}$ are taken together, $R^{4a}$ represents hydrogen; and $R^{1a}$ represents hydrogen or $R^{1a}$ is absent when the dotted bond towards $R^{1b}$ is a bond;

or $R^{4a}$ and $R^{4b}$ are taken together to form together with the N-atom to which they are attached a monocyclic 4-, 5-, 6- or 7-membered fully saturated heterocyclyl containing 1 N-atom; wherein said monocyclic fully saturated heterocyclyl might be substituted on one or more of the carbon atoms with in total 1, 2 or 3 halo substituents;

in case $R^{4a}$ and $R^{4b}$ are taken together, $R^{1a}$ represents hydrogen, and $R^{1b}$ represents hydrogen;

$R^2$ is selected from the group consisting of cyano; $Het^b$; and $C_{3-6}$ cycloalkyl optionally substituted with 1 or 2 substituents each independently selected from the group consisting of halo and —O—$C_{1-4}$ alkyl;

$R^{3a}$ represents halo, $R^7$, —O—$R^7$, cyano, —C(═O)—$NR^{6e}R^{6f}$, $Het^a$, or phenyl optionally substituted with 1, 2 or 3 substituents each independently selected from the group consisting of halo and cyano;

$Het^a$ represents a carbon linked monocyclic 5-, 6- or 7-membered aromatic heterocyclyl or carbon linked monocyclic 4-, 5-, 6- or 7-membered non-aromatic heterocyclyl, each containing 1, 2 or 3 heteroatoms each independently selected from the group consisting of N, O or S; wherein said S-atom might be substituted to form S(═O) or $S(═O)_2$; or a carbon linked bicyclic 6- to 12-membered non-aromatic heterocyclyl containing containing 1, 2 or 3 heteroatoms each independently selected from the group consisting of N or O;

wherein said monocyclic or bicyclic, aromatic or non-aromatic heterocyclyl might be substituted on one or more of the carbon atoms with in total 1, 2 or 3 substituents each independently selected from the group consisting of —OH, CN, halo, $R^7$, —$NR^{6c}R^{6d}$, and $Het^c$;

wherein said monocyclic or bicyclic, aromatic or non-aromatic heterocyclyl might be substituted on the nitrogen atoms with in total 1 or 2 substituents each independently selected from the group consisting of $R^7$, —$S(═O)_2$—$R^7$, and —C(═O)—$R^7$;

$R^{6c}$, $R^{6d}$, $R^{6e}$, and $R^{6f}$ are each independently selected from the group consisting of hydrogen; and $C_{1-4}$alkyl optionally substituted with one —$OR^5$;

$R^5$ represents hydrogen;

each $Het^c$ independently represents a monocyclic 4-, 5-, 6- or 7-membered fully saturated heterocyclyl containing 1, 2 or 3 nitrogen atoms;

$Het^b$ represents a monocyclic 4-, 5-, 6- or 7-membered non-aromatic heterocyclyl containing 1, 2 or 3 heteroatoms each independently selected from the group consisting of N, O, S; wherein said S-atom might be substituted to form S(═O) or $S(═O)_2$; or a bicyclic 6- to 12-membered non-aromatic heterocyclyl containing 1, 2 or 3 heteroatoms each independently selected from the group consisting of N, O, S; wherein said S-atom might be substituted to form S(═O) or $S(═O)_2$;

wherein said monocyclic or bicyclic non-aromatic heterocyclyl might be substituted on the nitrogen atoms with in total 1 or 2 substituents each independently selected from the group consisting of —$S(═O)_2$—$R^7$, and —C(═O)—$R^7$;

each $R^7$ independently represents $C_{1-4}$ alkyl optionally substituted with 1, 2 or 3 substituents each independently selected from the group consisting of halo, —OH, and cyano;

and the pharmaceutically acceptable addition salts, the N-oxides, and the solvates thereof.

The present invention relates in particular to compounds of Formula (I) as defined herein, and the tautomers and the stereoisomeric forms thereof, wherein the dotted bond towards $R^{1b}$ is absent;

$A^1$ represents CH or N; $A^2$ represents CH; $A^3$ represents CH;

$A^4$ represents CH; $A^5$ represents $CR^3$a; $A^6$ represents CH;

$R^{1b}$ and $R^{4b}$ are taken together to form together with the atoms to which they are attached a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(═O);

wherein said monocyclic fully saturated heterocyclyl might be substituted on one of the carbon atoms with 1 substituent selected from the group consisting of halo and $R^7$;

provided that $R^{4a}$ represents hydrogen; and $R^{1a}$ represents hydrogen;

$R^2$ represents $Het^b$;

$R^{3a}$ represents halo, cyano, or $Het^a$;

$Het^a$ represents a carbon linked monocyclic 5-, 6- or 7-membered aromatic heterocyclyl containing 1, 2 or 3 heteroatoms each independently selected from the group consisting of N, O or S; wherein said S-atom might be substituted to form S(═O) or $S(═O)_2$;

wherein said monocyclic aromatic heterocyclyl might be substituted on one of the carbon atoms with a halo substituent;

wherein said monocyclic aromatic heterocyclyl might be substituted on one nitrogen atom with $R^7$;

$Het^b$ represents a monocyclic 4-, 5-, 6- or 7-membered non-aromatic heterocyclyl containing 1 oxygen atom;

each $R^7$ represents $C_{1-4}$ alkyl;

and the pharmaceutically acceptable addition salts, the N-oxides, and the solvates thereof.

The present invention relates in particular to compounds of Formula (I) as defined herein, and the tautomers and the stereoisomeric forms thereof, wherein the dotted bond towards $R^{1b}$ is absent;

$A^1$ represents CH or N; $A^2$ represents CH; $A^3$ represents CH;

$A^4$ represents CH; $A^5$ represents $CR^3$a; $A^6$ represents CH;

$R^{1b}$ and $R^{4b}$ are taken together to form together with the atoms to which they are attached

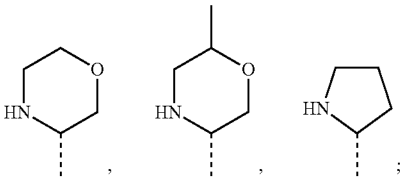

$R^{4a}$ represents hydrogen; and $R^{1a}$ represents hydrogen;

$R^2$ represents $Het^b$;

$R^{3a}$ represents halo, cyano, or $Het^a$;

$Het^a$ represents

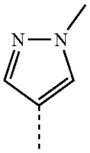

or

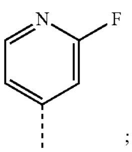

;

$Het^b$ represents tetrahydropyranyl; in particular 4-tetrahydropyranyl;

and the pharmaceutically acceptable addition salts, the N-oxides, and the solvates thereof.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^2$ represents $Het^b$.

In an embodiment, the present invention relates to those compounds of Formula (I) and the pharmaceutically acceptable addition salts, the N-oxides, and the solvates thereof, or any subgroup thereof as mentioned in any of the other embodiments, wherein $Het^b$ is attached the remainder of the molecule via a carbon atom (carbon linked).

In an embodiment, the present invention relates to those compounds of Formula (I) and the pharmaceutically acceptable addition salts, the N-oxides, and the solvates thereof, or any subgroup thereof as mentioned in any of the other embodiments, wherein $Het^b$ represents a carbon linked monocyclic 4-, 5-, 6- or 7-membered non-aromatic heterocyclyl containing 1, 2 or 3 heteroatoms each independently selected from the group consisting of N, O, S; wherein said S-atom might be substituted to form S(═O), $S(═O)_2$, or $S(═O)(═NR^x)$; or a carbon linked bicyclic 6- to 12-membered non-aromatic heterocyclyl containing 1, 2 or 3 heteroatoms each independently selected from the group consisting of N, O, S; wherein said S-atom might be substituted to form S(═O), $S(═O)_2$, or $S(═O)(═NR^x)$;

wherein said monocyclic or bicyclic non-aromatic heterocyclyl might be substituted on one or more of the carbon atoms with in total 1, 2 or 3 substituents each independently selected from the group consisting of —OH, CN, halo, $R^7$, —O—$R^7$, —$S(═O)_2$—$R^7$, —C(═O)—$R^7$, —$NR^{6c}R^{6d}$, and —C(═O)—$NR^{6a}R^{6b}$;

wherein said monocyclic or bicyclic non-aromatic heterocyclyl might be substituted on the nitrogen atoms with in total 1 or 2 substituents each independently selected from the group consisting of $R^7$, —$S(═O)_2$—$R^7$, —C(═O)—$R^7$, and —C(═O)—$NR^{6a}R^{6b}$.

In an embodiment, the present invention relates to those compounds of Formula (I) and the pharmaceutically acceptable addition salts, the N-oxides, and the solvates thereof, or any subgroup thereof as mentioned in any of the other embodiments, wherein In an embodiment, the present invention relates to those compounds of Formula (I) and the pharmaceutically acceptable addition salts, the N-oxides, and the solvates thereof, or any subgroup thereof as mentioned in any of the other embodiments, wherein $R^2$ represents $Het^b$;

$Het^b$ represents a carbon linked monocyclic 4-, 5-, 6- or 7-membered non-aromatic heterocyclyl containing 1, 2 or 3 heteroatoms each independently selected from the group consisting of N, O, S; wherein said S-atom might be substituted to form S(═O), $S(═O)_2$, or $S(═O)(═NR^x)$; or a carbon linked bicyclic 6- to 12-membered non-aromatic heterocyclyl containing 1, 2 or 3 heteroatoms each independently selected from the group consisting of N, O, S; wherein said S-atom might be substituted to form S(═O), $S(═O)_2$, or $S(═O)(═NR^x)$;

wherein said monocyclic or bicyclic non-aromatic heterocyclyl might be substituted on one or more of the carbon atoms with in total 1, 2 or 3 substituents each independently selected from the group consisting of —OH, CN, halo, $R^7$, —O—$R^7$, —$S(═O)_2$—$R^7$, —C(═O)—$R^7$, —$NR^{6c}R^{6d}$, and —C(═O)—$NR^{6a}R^{6b}$.

In an embodiment, the present invention relates to those compounds of Formula (I) and the pharmaceutically acceptable addition salts, the N-oxides, and the solvates thereof, or any subgroup thereof as mentioned in any of the other embodiments, wherein $Het^b$ represents a carbon linked monocyclic 4-, 5-, 6- or 7-membered non-aromatic heterocyclyl containing 1, 2 or 3 heteroatoms each independently selected from the group consisting of N, O, S; wherein said S-atom might be substituted to form S(=O), $S(=O)_2$, or $S(=O)(=NR^x)$;

wherein said monocyclic non-aromatic heterocyclyl might be substituted on the nitrogen atoms with in total 1 or 2 substituents each independently selected from the group consisting of $R^7$, $—S(=O)_2—R^7$, $—C(=O)—R^7$, and $—C(=O)—NR^{6a}R^{6b}$.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^2$ represents $Het^b$;

$Het^b$ represents a carbon linked monocyclic 4-, 5-, 6- or 7-membered non-aromatic heterocyclyl containing 1, 2 or 3 heteroatoms each independently selected from the group consisting of N, O, S; wherein said S-atom might be substituted to form S(=O), $S(=O)_2$, or $S(=O)(=NR^x)$;

wherein said monocyclic non-aromatic heterocyclyl might be substituted on the nitrogen atoms with in total 1 or 2 substituents each independently selected from the group consisting of $R^7$, $—S(=O)_2—R^7$, $—C(=O)—R^7$, and $—C(=O)—NR^{6a}R^{6b}$.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^2$ represents

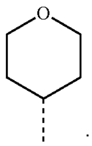
.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^2$ represents

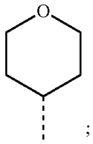
;

$R^{1b}$ and $R^{4b}$ are taken together to form together with the atoms to which they are attached

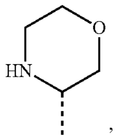
,
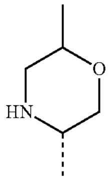
,
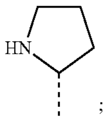
;

$R^{4a}$ represents hydrogen; and $R^{1a}$ represents hydrogen.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^{1b}$ and $R^{4b}$ are taken together to form together with the atoms to which they are attached

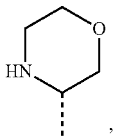
,
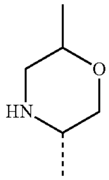
,
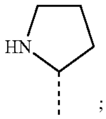
;

$R^{4a}$ represents hydrogen; and $R^{1a}$ represents hydrogen.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^{1b}$ and $R^{4b}$ are taken together to form together with the atoms to which they are attached

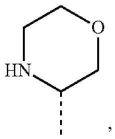
,
R stereochemistry

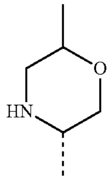
,
R stereochemistry

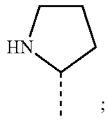
;
S stereochemistry $R^{4a}$ represents hydrogen; and $R^{1a}$ represents hydrogen.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^{1b}$ and $R^{4b}$ are taken together to form together with the atoms to which they are attached

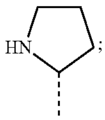
;

$R^{4a}$ represents hydrogen; and $R^{1a}$ represents hydrogen.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^{1b}$ and $R^{4b}$ are taken together to form together with the atoms to which they are attached

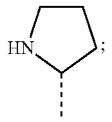

S stereochemistry $R^{4a}$ represents hydrogen; and $R^{1a}$ represents hydrogen.

In an embodiment, the present invention relates to those compounds of Formula (I) and the pharmaceutically acceptable addition salts, the N-oxides, and the solvates thereof, or any subgroup thereof as mentioned in any of the other embodiments, wherein $A^1$ represents CH or N; $A^2$ represents CH; $A^3$ represents CH;

$A^4$ represents CH; $A^5$ represents $CR^{3a}$; $A^6$ represents CH.

In an embodiment, the present invention relates to those compounds of Formula (I) and the pharmaceutically acceptable addition salts, the N-oxides, and the solvates thereof, or any subgroup thereof as mentioned in any of the other embodiments, wherein $A^1$ represents CH or N; $A^2$ represents CH; $A^3$ represents CH;

$A^4$ represents CH; $A^5$ represents $CR^3$a; $A^6$ represents CH;

$R^2$ represents $Het^b$;

$R^{3a}$ represents halo, cyano, or $Het^a$.

In an embodiment, the present invention relates to those compounds of Formula (I) and the pharmaceutically acceptable addition salts, the N-oxides, and the solvates thereof, or any subgroup thereof as mentioned in any of the other embodiments, wherein $A^1$ represents CH or N; $A^2$ represents CH; $A^3$ represents CH;

$A^4$ represents CH; $A^5$ represents $CR^{3a}$; $A^6$ represents CH;

$R^2$ represents $Het^b$;

$R^{3a}$ represents halo, cyano, or $Het^a$;

$Het^a$ represents a carbon linked monocyclic 5-, 6- or 7-membered aromatic heterocyclyl containing 1, 2 or 3 heteroatoms each independently selected from the group consisting of N, O or S; wherein said S-atom might be substituted to form S(═O) or $S(=O)_2$;

wherein said monocyclic aromatic heterocyclyl might be substituted on one of the carbon atoms with a halo substituent;

wherein said monocyclic aromatic heterocyclyl might be substituted on one nitrogen atom with $R^7$;

$Het^b$ represents a monocyclic 4-, 5-, 6- or 7-membered non-aromatic heterocyclyl containing 1 oxygen atom;

each $R^7$ represents $C_{1-4}$alkyl.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^{1a}$ represents hydrogen;

$R^{1b}$ represents hydrogen or $CH_3$;

$R^{4a}$ represents hydrogen, $C_{1-4}$alkyl, or $C_{3-6}$ cycloalkyl;

$R^{4b}$ represents hydrogen, $C_{1-4}$alkyl, $C_{3-6}$ cycloalkyl, or a carbon linked monocyclic 4-, 5-, 6- or 7-membered non-aromatic heterocyclyl containing 1, 2 or 3 heteroatoms each independently selected from the group consisting of N, O, and S; wherein said S-atom might be substituted to form S(═O), $S(=O)_2$, or S(═O)(═$NR^x$).

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^{1b}$ and $R^{4b}$ are taken together to form together with the atoms to which they are attached a monocyclic 5-membered aromatic heterocyclyl or a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(═O), $S(=O)_2$, or S(═O)(═$NR^x$); or a bicyclic 6- to 12-membered aromatic or fully saturated heterocyclyl containing 1 N-atom and optionally 1 or 2 additional heteroatoms each independently selected from the group consisting of N, O, S; wherein said optional S-atom might be substituted to form S(═O), $S(=O)_2$, or S(═O)(═$NR^x$);

wherein said monocyclic or bicyclic, aromatic or fully saturated heterocyclyl might be substituted on one or more of the carbon atoms with in total 1, 2 or 3 substituents each independently selected from the group consisting of —OH, CN, halo, $R^7$, —O—$R^7$, —$S(=O)_2$—$R^7$, —C(═O)—$R^7$, —$NR^{6c}R^{6d}$, —C(═O)—$NR^{6a}R^{6b}$, and $Het^c$;

wherein said monocyclic or bicyclic, aromatic or fully saturated heterocyclyl might be substituted on the optional additional nitrogen atoms with in total 1 or 2 substituents each independently selected from the group consisting of $R^7$, —$S(=O)_2$—$R^7$, —C(═O)—$R^7$, —C(═O)—$NR^{6a}R^{6b}$, and $Het^d$;

provided that $R^{4a}$ represents hydrogen; and $R^{1a}$ represents hydrogen or $R^{1a}$ is absent when the dotted bond towards $R^{1b}$ is a bond.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^{1b}$ and $R^{4b}$ are taken together to form together with the atoms to which they are attached a monocyclic 5-membered aromatic heterocyclyl or a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(═O), $S(=O)_2$, or S(═O)(═$NR^x$);

wherein said monocyclic aromatic or fully saturated heterocyclyl might be substituted on one or more of the carbon atoms with in total 1, 2 or 3 substituents each independently selected from the group consisting of —OH, CN, halo, $R^7$, —O—$R^7$, —$S(=O)_2$—$R^7$, —C(═O)—$R^7$, —$NR^{6c}R^{6d}$, —C(═O)—$NR^{6a}R^{6b}$, and $Het^c$;

wherein said monocyclic aromatic or fully saturated heterocyclyl might be substituted on the optional additional nitrogen atoms with in total 1 or 2 substituents each independently selected from the group consisting of $R^7$, —$S(=O)_2$—$R^7$, —C(═O)—$R^7$, —C(═O)—$NR^{6a}R^{6b}$, and $Het^d$;

provided that $R^{4a}$ represents hydrogen; and $R^{1a}$ represents hydrogen or $R^{1a}$ is absent when the dotted bond towards $R^{1b}$ is a bond.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^{1b}$ and $R^{4b}$ are taken together to form together with the atoms to which they are attached a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(=O), $S(=O)_2$, or $S(=O)(=NR^x)$;

wherein said monocyclic fully saturated heterocyclyl might be substituted on one or more of the carbon atoms with in total 1, 2 or 3 substituents each independently selected from the group consisting of —OH, CN, halo, $R^7$, —O—$R^7$, —$S(=O)_2$—$R^7$, —C(=O)—$R^7$, —$NR^{6c}R^{6d}$, —C(=O)—$NR^{6a}R^{6b}$, and $Het^c$;

wherein said monocyclic fully saturated heterocyclyl might be substituted on the optional additional nitrogen atoms with in total 1 or 2 substituents each independently selected from the group consisting of $R^7$, —$S(=O)_2$—$R^7$, —C(=O)—$R^7$, —C(=O)—$NR^{6a}R^{6b}$, and $Het^d$;

provided that $R^{4a}$ represents hydrogen; and $R^{1a}$ represents hydrogen or $R^{1a}$ is absent when the dotted bond towards $R^{1b}$ is a bond.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^{1b}$ and $R^{4b}$ are taken together;

provided that $R^{4a}$ represents hydrogen; and $R^{1a}$ represents hydrogen or $R^{1a}$ is absent when the dotted bond towards $R^{1b}$ is a bond.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^{4a}$ and $R^{4b}$ are taken together to form together with the N-atom to which they are attached a monocyclic 5-membered aromatic heterocyclyl or a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(=O), $S(=O)_2$, or $S(=O)(=NR^x)$; or a bicyclic 6- to 12-membered aromatic or fully saturated heterocyclyl containing 1 N-atom and optionally 1 or 2 additional heteroatoms each independently selected from the group consisting of N, O, S; wherein said optional S-atom might be substituted to form S(=O), $S(=O)_2$, or $S(=O)(=NR^x)$;

wherein said monocyclic or bicyclic, aromatic or fully saturated heterocyclyl might be substituted on one or more of the carbon atoms with in total 1, 2 or 3 substituents each independently selected from the group consisting of —OH, CN, halo, $R^7$, —O—$R^7$, —$S(=O)_2$—$R^7$, —C(=O)—$R^7$, —$NR^{6c}R^{6d}$, —C(=O)—$NR^{6a}R^{6b}$, and $Het^c$;

wherein said monocyclic or bicyclic, aromatic or fully saturated heterocyclyl might be substituted on the nitrogen atoms with in total 1 or 2 substituents each independently selected from the group consisting of $R^7$, —$S(=O)_2$—$R^7$, —C(=O)—$R^7$, —C(=O)—$NR^{6a}R^{6b}$, and $Het^d$.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^{1a}$ represents hydrogen;

$R^{1b}$ represents hydrogen or $CH_3$;

$R^{4a}$ represents hydrogen, $C_{1-4}$alkyl, or $C_{3-6}$ cycloalkyl;

$R^{4b}$ represents hydrogen, $C_{1-4}$alkyl, $C_{3-6}$ cycloalkyl, or a carbon linked monocyclic 4-, 5-, 6- or 7-membered non-aromatic heterocyclyl containing 1, 2 or 3 heteroatoms each independently selected from the group consisting of N, O, and S; wherein said S-atom might be substituted to form S(=O), $S(=O)_2$, or S(=O)(=$NR^x$); or $R^{1b}$ and $R^{4b}$ are taken together to form together with the atoms to which they are attached a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(=O), $S(=O)_2$, or $S(=O)(=NR^x)$; or a bicyclic 6- to 12-membered fully saturated heterocyclyl containing 1 N-atom and optionally 1 or 2 additional heteroatoms each independently selected from the group consisting of N, O, S; wherein said optional S-atom might be substituted to form S(=O), $S(=O)_2$, or $S(=O)(=NR^x)$;

wherein said monocyclic or bicyclic, fully saturated heterocyclyl might be substituted on one or more of the carbon atoms with in total 1, 2 or 3 substituents each independently selected from the group consisting of —OH, CN, halo, $R^7$, —O—$R^7$, —$S(=O)_2$—$R^7$, —C(=O)—$R^7$, —$NR^{6c}R^{6d}$, —C(=O)—$NR^{6a}R^{6b}$, and $Het^c$;

wherein said monocyclic or bicyclic, fully saturated heterocyclyl might be substituted on the optional additional nitrogen atoms with in total 1 or 2 substituents each independently selected from the group consisting of $R^7$, —$S(=O)_2$—$R^7$, —C(=O)—$R^7$, —C(=O)—$NR^{6a}R^{6b}$, and $Het^d$;

provided that in case $R^{1b}$ and $R^{4b}$ are taken together, $R^{4a}$ represents hydrogen; and $R^{1a}$ represents hydrogen or $R^{1a}$ is absent when the dotted bond towards $R^{1b}$ is a bond;

or $R^{4a}$ and $R^{4b}$ are taken together to form together with the N-atom to which they are attached a monocyclic 5-, 6- or 7-membered aromatic heterocyclyl or a monocyclic 4-, 5-, 6- or 7-membered fully saturated heterocyclyl, each containing 1 N-atom and optionally 1 or 2 additional heteroatoms each independently selected from the group consisting of N, O, S;

wherein said optional S-atom might be substituted to form S(=O), $S(=O)_2$, or $S(=O)(=NR^x)$; or a bicyclic 6- to 12-membered aromatic or fully saturated heterocyclyl containing 1 N-atom and optionally 1 or 2 additional heteroatoms each independently selected from the group consisting of N, O, S; wherein said optional S-atom might be substituted to form S(═O), $S(═O)_2$, or S(═O)(═$NR^x$);

wherein said monocyclic or bicyclic, aromatic or fully saturated heterocyclyl might be substituted on one or more of the carbon atoms with in total 1, 2 or 3 substituents each independently selected from the group consisting of —OH, CN, halo, $R^7$, —O—$R^7$, —$S(═O)_2$—$R^7$, —C(═O)—$R^7$, —$NR^{6c}R^{6d}$, —C(═O)—$NR^{6a}R^{6b}$, and $Het^c$;

wherein said monocyclic or bicyclic, aromatic or fully saturated heterocyclyl might be substituted on the nitrogen atoms with in total 1 or 2 substituents each independently selected from the group consisting of $R^7$, —$S(═O)_2$—$R^7$, —C(═O)—$R^7$, —C(═O)—$NR^{6a}R^{6b}$, and $Het^d$;

in case $R^{4a}$ and $R^{4b}$ are taken together, $R^{1a}$ represents hydrogen, and $R^{1b}$ represents hydrogen.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^{1a}$ represents hydrogen;

$R^{1b}$ represents hydrogen or $CH_3$;

$R^{4a}$ represents hydrogen, $C_{1-4}$ alkyl, or $C_{3-6}$ cycloalkyl;

$R^{4b}$ represents hydrogen, $C_{1-4}$ alkyl, $C_{3-6}$ cycloalkyl, or a carbon linked monocyclic 4-, 5-, 6- or 7-membered non-aromatic heterocyclyl containing 1, 2 or 3 heteroatoms each independently selected from the group consisting of N, O, and S; wherein said S-atom might be substituted to form S(═O), $S(═O)_2$, or S(═O)(═$NR^x$); or $R^{1b}$ and $R^{4b}$ are taken together to form together with the atoms to which they are attached a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(═O), $S(═O)_2$, or S(═O)(═$NR^x$); or a bicyclic 6- to 12-membered fully saturated heterocyclyl containing 1 N-atom and optionally 1 or 2 additional heteroatoms each independently selected from the group consisting of N, O, S; wherein said optional S-atom might be substituted to form S(═O), $S(═O)_2$, or S(═O)(═$NR^x$);

wherein said monocyclic or bicyclic, fully saturated heterocyclyl might be substituted on one or more of the carbon atoms with in total 1, 2 or 3 substituents each independently selected from the group consisting of —OH, CN, halo, $R^7$, —O—$R^7$, —$S(═O)_2$—$R^7$, —C(═O)—$R^7$, —$NR^{6c}R^{6d}$, —C(═O)—$NR^{6a}R^{6b}$, and $Het^c$;

wherein said monocyclic or bicyclic, fully saturated heterocyclyl might be substituted on the optional additional nitrogen atoms with in total 1 or 2 substituents each independently selected from the group consisting of $R^7$, —$S(═O)_2$—$R^7$, —C(═O)—$R^7$, —C(═O)—$NR^{6a}R^{6b}$, and $Het^d$;

provided that in case $R^{1b}$ and $R^{4b}$ are taken together, R' represents hydrogen; and $R^{1a}$ represents hydrogen or $R^{1a}$ is absent when the dotted bond towards $R^{1b}$ is a bond.

In an embodiment, the present invention relates to those compounds of Formula (I) and the pharmaceutically acceptable addition salts, the N-oxides, and the solvates thereof, or any subgroup thereof as mentioned in any of the other embodiments, wherein $R^{1b}$ and $R^{4b}$ are taken together to form together with the atoms to which they are attached a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(═O), $S(═O)_2$, or S(═O)(═$NR^x$); or a bicyclic 6- to 12-membered fully saturated heterocyclyl containing 1 N-atom and optionally 1 or 2 additional heteroatoms each independently selected from the group consisting of N, O, S; wherein said optional S-atom might be substituted to form S(═O), $S(═O)_2$, or S(═O)(═$NR^x$);

wherein said monocyclic or bicyclic, fully saturated heterocyclyl might be substituted on one or more of the carbon atoms with in total 1, 2 or 3 substituents each independently selected from the group consisting of —OH, CN, halo, $R^7$, —O—$R^7$, —$S(═O)_2$—$R^7$, —C(═O)—$R^7$, —$NR^{6c}R^{6d}$, —C(═O)—$NR^{6a}R^{6b}$, and $Het^c$;

wherein said monocyclic or bicyclic, fully saturated heterocyclyl might be substituted on the optional additional nitrogen atoms with in total 1 or 2 substituents each independently selected from the group consisting of $R^7$, —$S(═O)_2$—$R^7$, —C(═O)—$R^7$, —C(═O)—$NR^{6a}R^{6b}$, and $Het^d$;

provided that $R^{4a}$ represents hydrogen; and $R^{1a}$ represents hydrogen or $R^{1a}$ is absent when the dotted bond towards $R^{1b}$ is a bond.

In an embodiment, the present invention relates to those compounds of Formula (I) and the pharmaceutically acceptable addition salts, the N-oxides, and the solvates thereof, or any subgroup thereof as mentioned in any of the other embodiments, wherein $Het^c$ represents oxetanyl.

In an embodiment, the present invention relates to those compounds of Formula (I) and the pharmaceutically acceptable addition salts, the N-oxides, and the solvates thereof, or any subgroup thereof as mentioned in any of the other embodiments, wherein the compounds of Formula (I) are restricted to compounds of Formula (I-a1):

(I-a1)

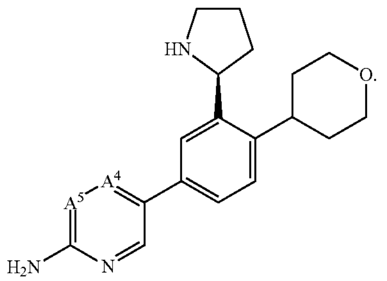

In an embodiment, the present invention relates to those compounds of Formula (I) and the pharmaceutically acceptable addition salts, the N-oxides, and the solvates thereof, or any subgroup thereof as mentioned in any of the other embodiments, wherein the compounds of Formula (I) are restricted to compounds of Formula (I-a2):

(I-a2)

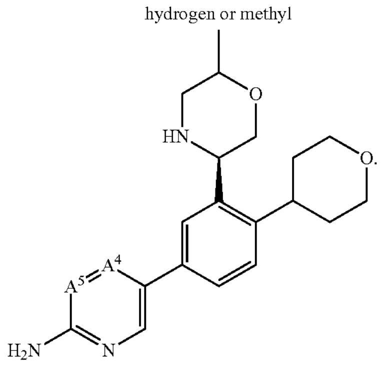

In an embodiment, the present invention relates to a subgroup of Formula (I) as defined in the general reaction schemes.

In an embodiment the compound of Formula (I) is selected from the group consisting of any of the exemplified compounds, tautomers and stereoisomeric forms thereof, any pharmaceutically acceptable addition salts, the N-oxides, and the solvates thereof.

All possible combinations of the above indicated embodiments are considered to be embraced within the scope of the invention.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples and are generally prepared from starting materials which are either commercially available or prepared by standard synthetic processes commonly used by those skilled in the art of organic chemistry. The following schemes are only meant to represent examples of the invention and are in no way meant to be a limit of the invention.

Alternatively, compounds of the present invention may also be prepared by analogous reaction protocols as described in the general schemes below and the specific examples, combined with standard synthetic processes commonly used by those skilled in the art.

The skilled person will realize that in the reactions described in the Schemes, although this is not always explicitly shown, it may be necessary to protect reactive functional groups (for example hydroxy, amino, or carboxy groups) where these are desired in the final product, to avoid their unwanted participation in the reactions. In general, conventional protecting groups can be used in accordance with standard practice. The protecting groups may be removed at a convenient subsequent stage using methods known from the art.

The skilled person will realize that in the reactions described in the Schemes, it may be advisable or necessary to perform the reaction under an inert atmosphere, such as for example under $N_2$-gas atmosphere.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of Formula (I).

The skilled person will realize that intermediates and final compounds shown in the Schemes below may be further functionalized according to methods well-known by the person skilled in the art. The intermediates and compounds described herein can be isolated in free form or as a salt, or a solvate thereof. The intermediates and compounds described herein may be synthesized in the form of mixtures of tautomers and stereoisomeric forms that can be separated from one another following art-known resolution procedures.

Hereinafter, "DCM" means dichloromethane; "LAH" means lithium aluminium hydride; "r.t." means room temperature; "Boc" means tert-butoxycarbonyl; "MeCN" means acetonitrile; "MeOH" means methanol; "TFA" means trifluoroacetic acid; "THF" means tetrahydrofuran; "$Ti(OEt)_4$" means titanium ethoxide; "$Pd(PPh_3)_4$" means tetrakis(triphenylphosphine)palladium; "$[Ir(dtbbpy)(ppy)_2]PF_6$" means (4,4'-Di-t-butyl-2, 2'-bipyridine)bis[2-(2-pyridinyl-kN)phenyl-kC]iridium(III) hexafluorophosphate; "SnAP" means tin amine protocol; "SLAP" means silicon amine protocol; "h" means hours; "$PdCl_2(dppf)$" means [1,1'-bis(diphenylphosphino-κP)ferrocene]dichloropalladium; "SFC" means Supercritical fluid chromatography; "LiHMDS" means Lithium bis(trimethylsilyl)amide; "$SnBu_3$" means tributyltin; "$SiMe_3$" means trimethylsilyl; "$Cu(OTf)_2$ means Copper (II) triflate; "PhBox" means 2,2'-Isopropylidenebis[(4R)-4-phenyl-2-oxazoline; "$Bi(OTO_3$" means Bismuth(III) trifluoromethanesulfonate; "$BF_3$·2 MeOH means boron trifluoride in methanol; "TMSOTf" means trimethylsilyltriflate; "Me-THF" means methyltetrahydrofuran; "$NiCl_2$" means Nickel (II) chloride.

Scheme 1

In general, compounds of Formula (I) wherein all variables are defined according to the scope of the present invention, can be prepared according to the following reaction Scheme 1.

In the scheme 1, the following definitions apply: X represents an halo. The following a)

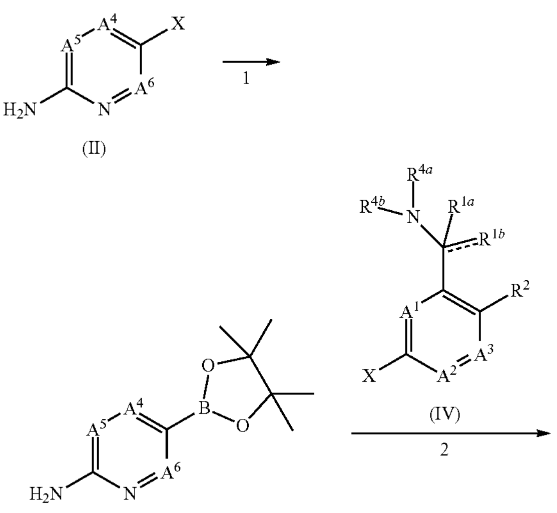

(II)

(IV)

(III)

-continued

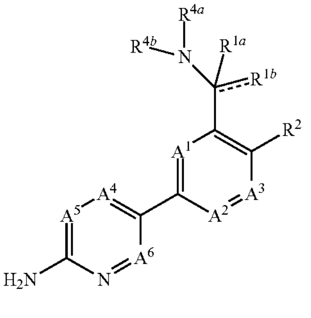

(I)

b)

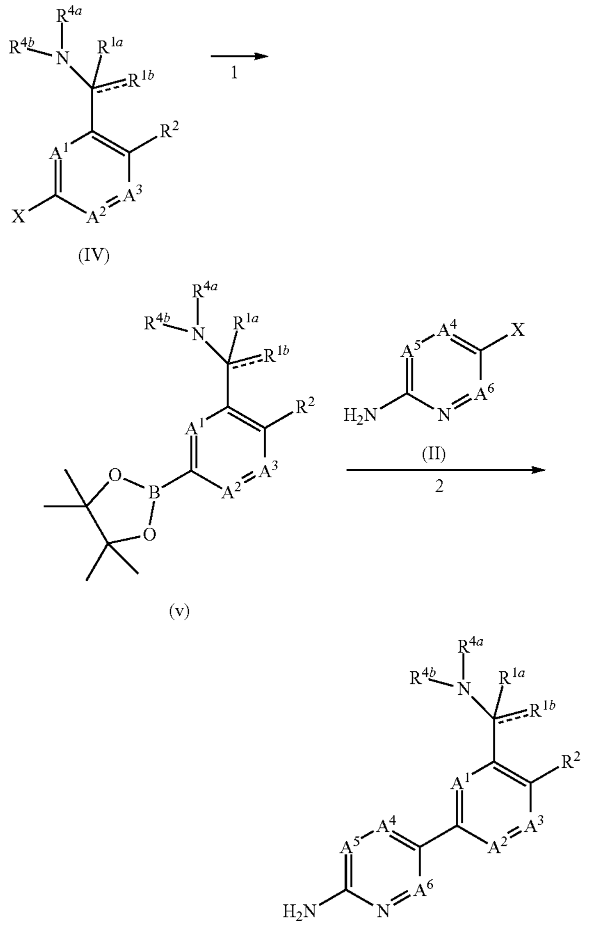

(IV)

(v)

(II)

(I)

reaction conditions apply:
1: at a suitable temperature such as for example at 80° C., in the presence of bis(pinacolatodiboron), a suitable catalyst as for example $PdCl_2$(dppf), a suitable basis such as potassium acetate, in a suitable solvent such 1,4-dioxane
2: at a suitable temperature such as for example at 80° C., in the presence of a suitable catalyst as for example $PdCl_2$(dppf), a suitable basis such as sodium carbonate, in a suitable solvent or mixture of solvents such 1,4-dioxane and water In the preparation of compounds of the present invention, protection of remote functionality (e.g., primary or secondary amine) of intermediates may be necessary. The need for such protection will vary depending on the nature of the remote functionality and the conditions of the preparations methods. Suitable amino-protecting groups (NH-Pg) include t-butoxycarbonyl (Boc), acetyl, benzyl . . . . The need for such protection is readily determined by one skilled in the art.

Scheme 2

Intermediates of Formula (IV) wherein $R^{1a}$ and $R^{1b}$ represent hydrogen, and X represent halo can be prepared according to the following reaction Scheme 2. All other variables in Scheme 2 are defined according to the scope of the present invention.

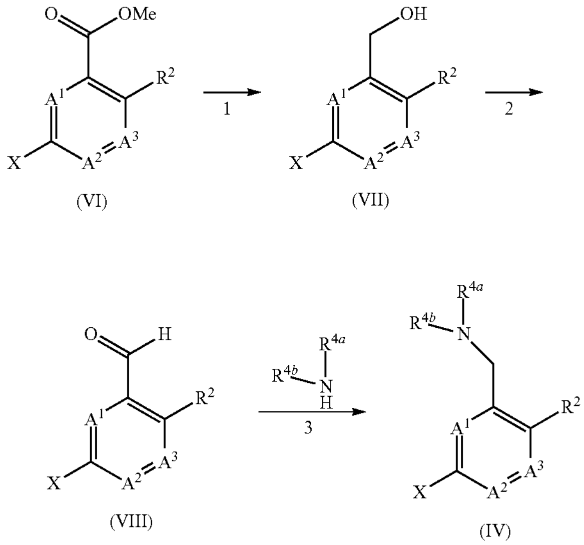

(VI) (VII) (VIII) (IV)

1: at a suitable temperature such as for example from 0° C. to rt, in the presence of a suitable reducing agent such as LAH in a suitable solvent such as for example THF
2: at a suitable temperature such as rt, in the presence of an oxidizing agent such as for example manganese oxide or Dess-Martin periodinane, in a suitable solvent such as for example DCM
3: at a suitable temperature such as for example rt, in the presence of a suitable reducing agent such as for example sodium triacetoxyborohydride in a suitable solvent such as for example DCM or THF.

Scheme 3

Intermediates of Formula (IV) wherein $R^{1a}$ represents hydrogen, $R^{1b}$ and $R^{4b}$ are taken together to form together with the atoms to which they attached a monocyclic 5-membered fully saturated heterocyclyl containing 1N-atom as for example intermediates of Formula (XII) can be prepared according to the following reaction Scheme 3. X represents halo, PG means protective group, all other variables in Scheme 3 are defined according to the scope of the present invention.

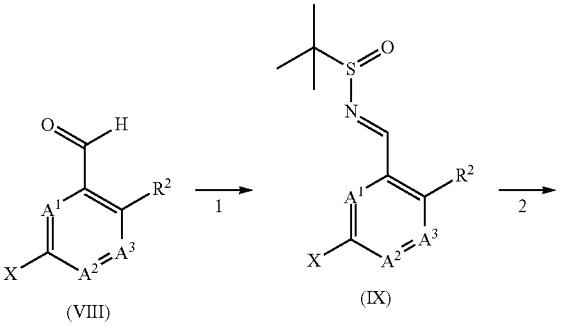

(VIII) (IX)

-continued

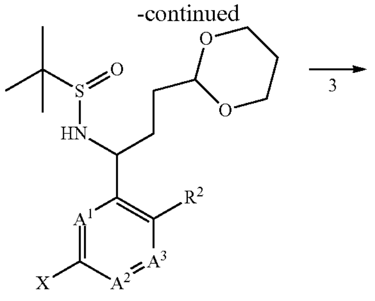

(X)

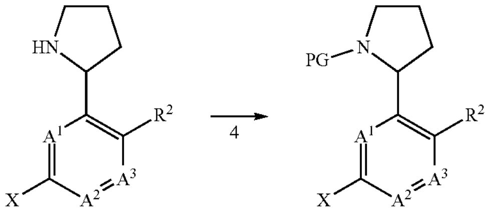

(XI) (XII)

1: an intermediate of Formula (VIII) can react with t-Butylsulfinamide in the presence of $Ti(OEt)_4$ in a suitable solvent such as for example THF 2: Reaction with (1,3-dioxan-2-ylethyl) magnesium bromide in a suitable solvent, such as for example THF 3: in the presence of a suitable acid, such as for example TFA and a reductant triethylsilane in a suitable solvent as for example water 4: an intermediate for Formula (XI) can be protected into a compound of Formula (XII) by reaction for example with di-tert-butyl dicarbonate in a suitable solvent such as for example DCM The intermediates of Formula (XII) may be synthesized in the form of racemic mixtures of enantiomers which can be separated from one another such as liquid chromatography using a chiral stationary phase or SFC.

A skilled person will realize that similar chemistry can be used to prepare compounds wherein $R^{1b}$ and $R^{4b}$ are taken together to form together with the atoms to which they attached a monocyclic 4-, 6- or 7-membered fully saturated heterocyclyl containing 1N-atom.

Scheme 4

Intermediates of Formula (IV) wherein $R^{1a}$ represents hydrogen, $R^{1b}$ and $R^{4b}$ are taken together to form together with the atoms to which they attached a monocyclic 5-membered fully saturated heterocyclyl containing at least 1N-atom and substituted as for example in intermediates of Formula (XV) and (XVIII), can be prepared according to the following reaction Scheme 4. X represents halo and n and p=1, 2, Y represents O or $CH_2$, PG means protective group. All other variables in Scheme 4 are defined according to the scope of the present invention.

A skilled person will realize that similar chemistry can be used to prepare compounds wherein $R^{1b}$ and $R^{4b}$ are taken together to form together with the atoms to which they attached other sizes of fully saturated heterocyclyls containing at least 1N-atom.

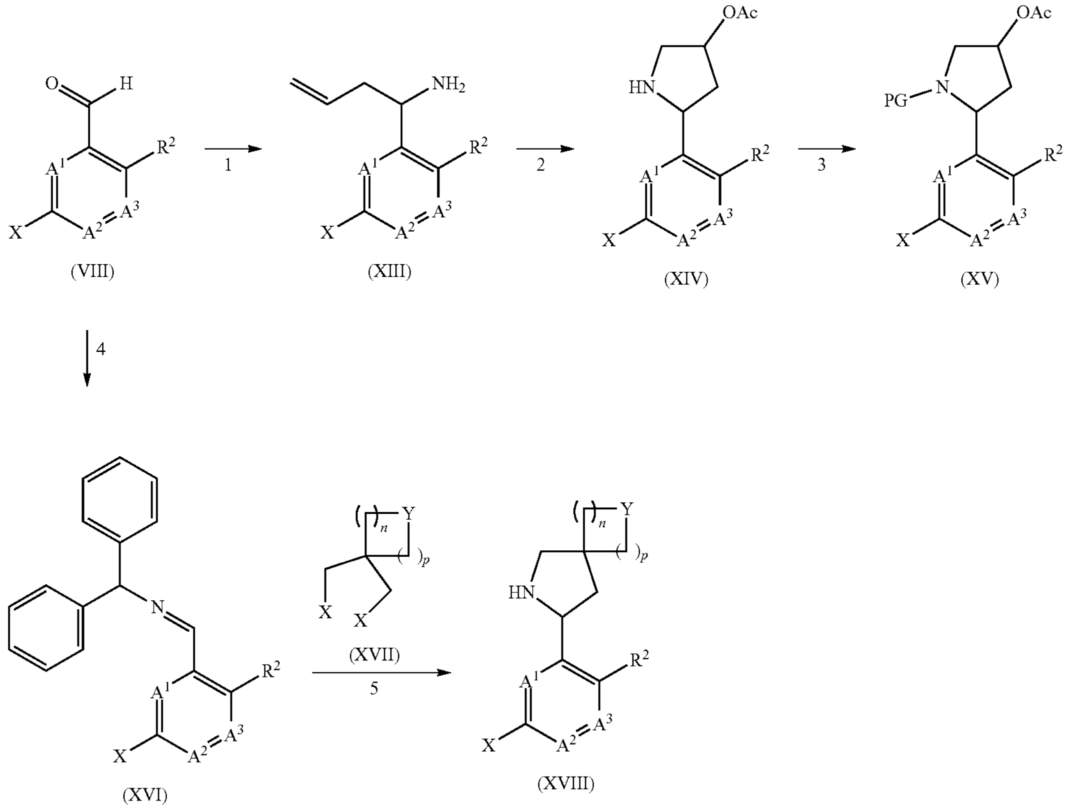

(VIII) (XIII) (XIV) (XV)

(XVII)

(XVI) (XVIII)

-continued 1 and 2: an intermediate of Formula (VIII) can be converted into a compound of formula (XIII) by reaction with Allylmagnesium chloride and LiHMDS in a suitable solvent, such as for example THF, followed by reaction with acetic anhydride in presence of a suitable basic such as triethylamine in a suitable solvent such as DCM.
3: an intermediate of Formula (XIV) can be protected into a compound of Formula (XV) by for example reaction with di-tert-butyl dicarbonate in a suitable solvent such as for example DCM
4. an intermediate of Formula (VIII) can react with Benzhydrylamine with magnesium sulfate in a suitable solvent such as DCM to give an intermediate of Formula (XVI)
5. an intermediate of Formula (XVI) can react with a compound of Formula (XVII) in presence of a suitable basis such as potassium tert-butoxide in a suitable solvent such as THF Intermediates of Formula (XV) can be further functionalized by a person skilled in the art. The stereoisomers of intermediates of Formula (XV) and (XVIII) can be separated from one another such as liquid chromatography using a chiral stationary phase or SFC.

Scheme 5

Intermediates of Formula (IV) wherein $R^{1a}$ represents hydrogen, $R^{1b}$ and $R^{4b}$ are taken together to form together with the atoms to which they attached a monocyclic 6- or 7-membered fully saturated heterocyclyl containing at least 1 N-atom and substituted as for example intermediates of Formula (XX), can be prepared according to the following reaction Scheme 5. X represents halo, n and p represent 1 or 2 (but only one of n and p can represent 2), Y represents O, S, or N, Z represents $SnBu_3$ or $SiMe_3$. A skilled person will understand that $R^q$ and $R^z$ can be selected from the list of substituents as defined in the scope of the present invention and do also include bicyclic spiro moieties formed together with the N-containing heterocyclyls to which they are attached. A skilled person will understand that $R^q$ and $R^z$ for example will not represent cyano or a directly attached amine substituent.

All other variables in Scheme 5 are defined according to the scope of the present invention.

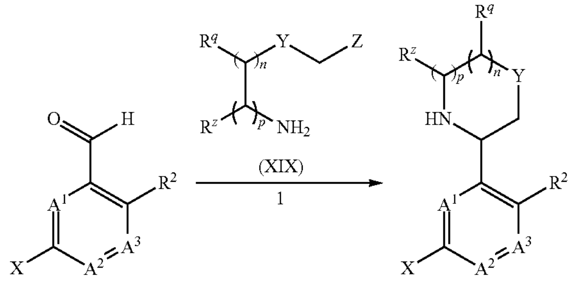

(VIII) (XX)

1: an intermediate of Formula (VIII) can react with a compound of formula (XIX, Y represents O, S, N, Z = $SnBu_3$) in the presence of an oxidant, such as for example $Cu(OTf)_2$, a suitable ligand, such as for example Lutidine or PhBox, and a suitable solvent or solvent mixture, such as hexafluoroisopropanol (HFIP) and DCM or an intermediate of Formula (VIII) can react with a compound of Formula (XIX, Y = N, Z = $SiMe_3$) in the presence of a photocatalyst, such as for example $Ir[ppy]_2(dtbbpy)PF_6$, and a suitable solvent or solvent mixture, such as trifluoroethanol (TFE) and $CH_3CN$ under blue light irradiation resulting or an intermediate of Formula (VIII) can react with a compound of Formula (XIX, Y = S, Z = $SiMe_3$) in the presence of a photocatalyst, such as for example $Ir[ppy]_2(dtbbpy)PF_6$, a suitable acid or an acid mixture such as for example $Bi(OTF)_3$, $Cu(OTf)_2$, $BF_3$•2MeOH in a suitable solvent $CH_3CN$ under blue light irradiation resulting or an intermediate of Formula (VIII) can react with a compound of Formula (XIX, Y = S, Z = $SiMe_3$) in the presence of a photocatalyst, such as for example $Ir[ppy]_2(dtbbpy)PF_6$, a suitable acid or an acid mixture such as for example $Bi(OTf)_3$, $BF_3$•2MeOh in a suitable solvent $CH_3CN$ under blue light irradiation. or an intermediate of Formula (VIII) can react with a compound of Formula (XIX, Y = O, Z = $SiMe_3$) in the presence of a photocatalyst, such as for example triphenylpyrilium (TPP), a suitable acid such as for example TMSOTf, and a suitable solvent or solvent mixture, such as hexafluoroisopropanol (HFIP) and $CH_3CN$ under blue light irradiation.

Scheme 6

Intermediates of Formula (IV) wherein $R^{1a}$ is absent when the dotted towards $R^{1b}$ is a bond as for example intermediates of Formula (XXIV) and (XXVI) can be prepared according to the following reaction Scheme 6. All other variables in Scheme 6 are defined according to the scope of the present invention.

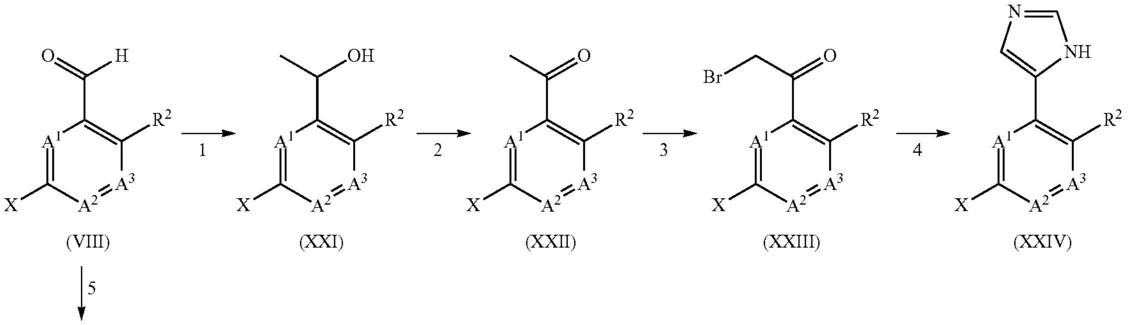

-continued

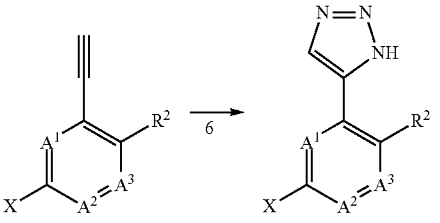

(XXV) (XXVI)

1: an intermediate of Formula (VIII) can be converted into an intermediate of Formula (XXI) by reaction for example with methylmagnesium bromide in a suitable solvent, such as for example THF 2: an intermediate of Formula (XXI) can be converted into an intermediate of Formula (XXII) by reaction for example with an oxident such as for example manganese oxide in a suitable solvent, such as for example DCM 3: an intermediate of Formula (XXII) can be converted into an intermediate of Fomula (XXIII) by reaction for example with a bromination agent such as for example tetra-n-butylammonium tribromide in a suitable solvent, such as for example acetonitrile 4: an intermediate of Formula (XXIII) can be converted into an intermediate of Formula (XXIV) by reaction for example with formamide as a suitable solvent 5: an intermediate of Formula (VIII) can be converted into an intermediate of Formula (XXV) by reaction for example with dimethyl(1-diazo-2-oxopropyl)phosphonate in presence of a suitable basis such as potassium carbonate in a suitable solvent, such as for example MeOH 6: an intermediate of Formula (XXV) can be converted into an intermediate of Formula (XXVI) by reaction for example with trimethylsilyl azide in the presence of a catalyst as for example copper iodide in a suitable solvent or mixture of solvents as for example DMF and MeOH.

Scheme 7

Intermediates of Formula (II) wherein $R^{1a}$ represents $Het^a$ (or can also be used for Ria represents phenyl optionally substituted) and X=Br can be prepared according to the following reaction Scheme 7. All other variables in Scheme 7 are defined according to the scope of the present invention.

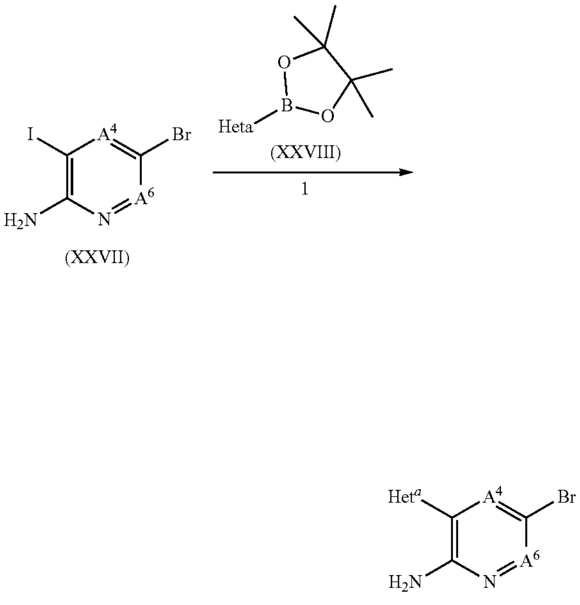

(XXVII) (XXVIII) (XXIX)

1. an intermediate of Formula (XXVII) can react with an intermediate of Formula (XXVIII) in the presence of a suitable catalyst, such as for example $Pd(PPh_3)_4$, a suitable base, such as sodium bicarbonate ($Na_2CO_3$), and a suitable solvent or solvent mixture, such as for example Me—THF or 1-4 dioxane and water.

Scheme 8

An alternative to synthesis of compounds of Formula (I) wherein $A^5$ represents $Het^a$ and $R^2$ different from Br (compounds of Formula (XXXIII)): can be prepared according to the following reaction Scheme 8. All other variables are defined according to the scope of the present invention

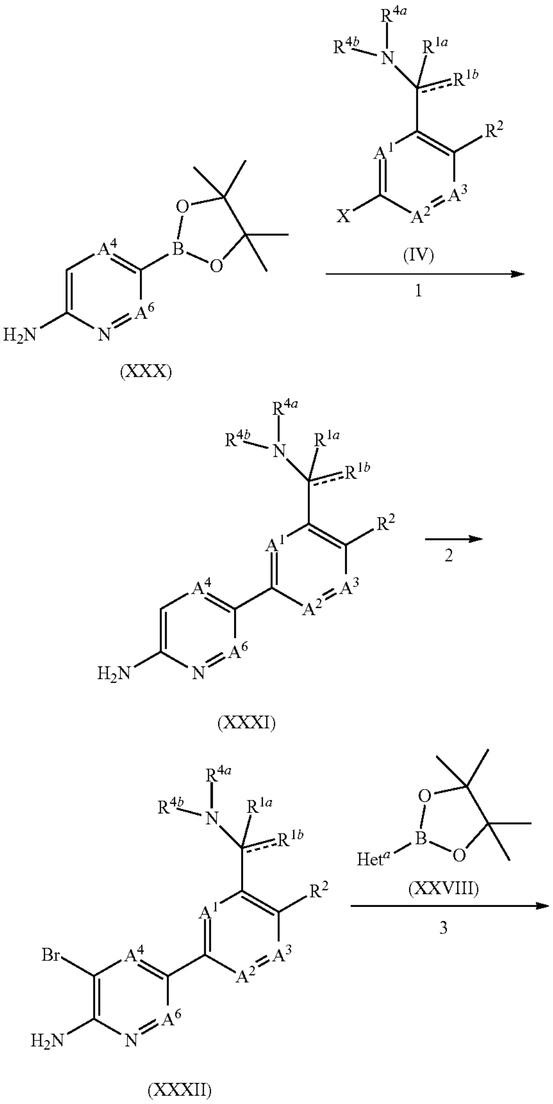

(XXX) (IV) (XXXI) (XXXII) (XXVIII)

-continued

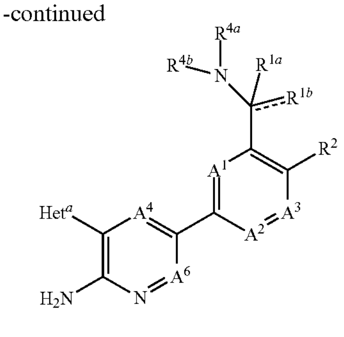

(XXXIII)

1. an intermediate of Formula (XXX) can react with an intermediate of Formula (IV) in the presence of suitable catalyst, such as for example $Pd(PPh_3)_4$, a suitable base, such as sodium bicarbonate ($Na_2CO_3$), in a suitable solvent or solvent mixutre, such as for example Me—THF and water
2. an intermediate of Formula (XXXI) can be converted into an intermediate of Formula (XXXII) by reaction with bromine ($Br_2$) in the presence of a suitable solvent, such as for example acetic acid (AcOH)
3. an intermediate of Formula (XXXII) can react with an intermediate of Formula (XXVIII) in the presence of a suitable catalyst, such as for example $Pd(PPh_3)_4$, in the presence of a suitable base, such as sodium bicarbonate ($Na_2CO_3$), in a suitable solvent or solvent mixture, such as for example Me—THF and water.

Scheme 9

An alternative to synthesis of compounds of Formula (I) wherein $R^{3a}$ is different from halo, can be prepared according to the following reaction in Scheme 9, as for example, compounds of Formula (XXXV) wherein $R^2$ represents Het$^b$. All other variables are defined according to the scope of the present invention

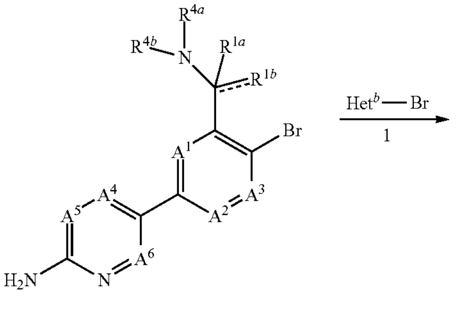

(XXXIV)

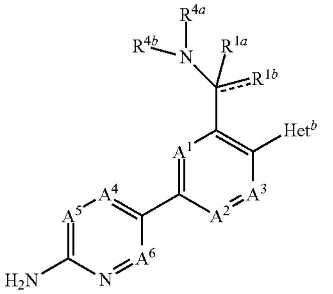

(XXXV)

1: an intermediate of Formula (XXXIV) can react with Het$^b$ bromides in the presence of a suitable photocatalyst, such as for example $Ir[ppy]_2(dtbbpy)PF_6$, a suitable Nickel source, such as for example $NiCl_2$, a suitable ligand, such as for example di-tert-butylbispyridine (dtbbp), a suitable reductant, such as for example tris(trimethylsilyl)silane (TTMSS), a suitable base, such as sodium bicarbonate ($Na_2CO_3$), and a suitable solvent, such as DME, under blue light irradiation Scheme 10

An alternative to synthesis of compounds of Formula (I), can be prepared according to the following reaction in Scheme 10, as for example, compounds of Formula (XXXVII) wherein $R^{1a}$ represents hydrogen, $R^{1b}$ and $R^{4b}$ are taken together to form together with the atoms to which they attached a monocyclic 6- or 7-membered fully saturated heterocyclyl containing at least 1N-atom and substituted; n and p represent 1 or 2 (but only one of n and p can represent 2), Y represents O, S, or N, and Z represents $SnBu_3$ or $SiMe_3$. A skilled person will understand that $R^q$ and $R^z$ can be selected from the list of substituents as defined in the scope of the present invention and do also include bicyclic spiro moieties formed together with the N-containing heterocyclyls to which they are attached. A skilled person will understand that $R^q$ and $R^z$ for example will not represent cyano or a directly attached amine substituent.

All other variables are defined according to the scope of the present invention

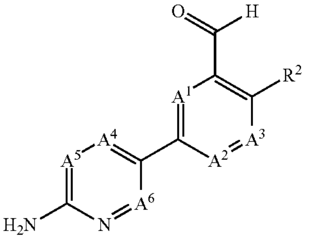

(XXXVI)

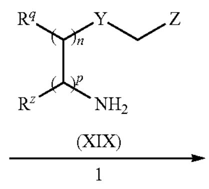

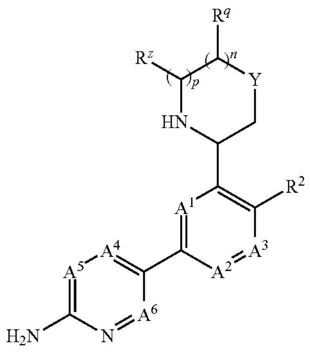

(XXXV)

1: an intermediate of Formula (XXXVI) can react with a compound of Formula (XIX, Y represents O, S or N, Z = $SnBu_3$) in the presence of an oxidant, such as for example $Cu(OTf)_2$, a suitable ligand, such as for example Lutidine or PhBox, and a suitable solvent or solvent mixture, such as hexafluoroisopropanol (HFIP) and DCM or an intermediate of Formula (XXXVI) can react with a compound of Formula (XIX, Y = N, Z = $SiMe_3$) in the presence of a photocatalyst, such as for example $Ir[ppy]_2(dtbbpy)PF_6$, and a suitable solvent or solvent mixture, such as trifluoroethanol (TFE) and $CH_3CN$ under blue light irradiation or an intermediate of Formula (XXXVI) can react with a compound of Formula (XIX, Y = S, Z = $SiMe_3$) in the presence of a photocatalyst, such as for example $Ir[ppy]_2(dtbbpy)PF_6$, a suitable acid or an acid mixture such as for example $Bi(OTf)_3$, $Cu(OTf)_2$, $BF_3$•2MeOH in a suitable solvent $CH_3CN$ under blue light irradiation or an intermediate of Formula (XXXVI) can react with a compound of Formula (XIX, Y = O, Z = $SiMe_3$) in the presence of a photocatalyst, such as for example triphenylpyrilium (TPP), a suitable acid such as for example TMSOTf, and a suitable solvent or solvent mixture, such as hexafluoroisopropanol (HFIP) and $CH_3CN$ under blue light irradiation.

In the preparation of compounds of the present invention, protection of remote functionality (e.g., primary amine) of intermediates may be necessary. The need for such protection will vary depending on the nature of the remote functionality and the conditions of the preparations methods. Suitable amino-protecting groups (NH-Pg) include t-butoxycarbonyl (Boc), acetyl . . . . The need for such protection is readily determined by one skilled in the art.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

The compounds of Formula (I) may be synthesized in the form of racemic mixtures of enantiomers which can be separated from one another following art-known resolution procedures. The racemic compounds of Formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (Boc), benzyloxycarbonyl (CBz) and 9-fluorenylmethyleneoxycarbonyl (Fmoc). The need for such protection is readily determined by one skilled in the art. For a general description of protecting groups and their use, see T. W. Greene and P. G. M. Wuts, Protective Groups in Organic Synthesis, 4th ed., Wiley, Hoboken, New Jersey, 2007.

Pharmacology

It has been found that the compounds of the present invention inhibit Hpk1 activity.

An Hpk1 inhibitor is a compound that reduces Hpk1 functions, such as the ability to recruit proteins to the TCR and phosphorylate proteins like SLP76 and GADS.

The compounds of the present invention inhibit the Hpk1 kinase. Therefore, the compounds may be useful in the treatment or prevention, in particular in the treatment, of diseases that are susceptible to the effects of the immune system, such as cancer and viral infection.

The compounds of the present invention may enhance an immune response.

The compounds of the present invention may increase T cell activity.

The compounds of the present invention may have antitumoral properties through immune modulation.

In particular the compounds according to the present invention or pharmaceutical compositions thereof may be useful for treating or preventing, in particular treating, of diseases such as lung cancer, melanoma, head and neck cancer, esophageal cancer, bladder and urothelial cancer, liver cancer, kidney cancer, prostate cancer and hematopoietic cancer.

In some embodiments, the inhibition of HPK1 by a provided compound may be useful in treating or preventing, in particular treating, the following non-limiting list of cancers: breast cancer, lung cancer, esophageal cancer, bladder cancer, hematopoietic cancer, lymphoma, medulloblastoma, rectum adenocarcinoma, colon adenocarcinoma, gastric cancer, pancreatic cancer, liver cancer, adenoid cystic carcinoma, lung adenocarcinoma, head and neck squamous cell carcinoma, brain tumors, hepatocellular carcinoma, renal cell carcinoma, melanoma, oligodendroglioma, ovarian clear cell carcinoma, and ovarian serous cystadenoma.

Examples of cancers which may be treated or prevented, in particular treated, include, but are not limited to, acoustic neuroma, adenocarcinoma, adrenal gland cancer, anal cancer, angiosarcoma (e.g., lymphangio sarcoma, lymphangioendothelio sarcoma, hemangio sarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), chordoma, choriocarcinoma, craniopharyngioma, colorectal cancer (e.g., colon cancer, rectal cancer, colorectal adenocarcinoma), epithelial carcinoma, ependymoma, endothelio sarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., pharyngeal cancer, laryngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macro globulinemia"), immunoblastic large cell lymphoma, hairy cell leukemia (HCL), precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, non-small cell lung cancer (NSCLC), squamous lung cancer (SLC), adenocarcinoma of the lung, Lewis lung carcinoma, lung neuroendocrine tumors: typical carcinoid, atypical carcinoid, small cell lung cancer (SCLC), and large cell neuroendocrine carcinoma), leiomyosarcoma (LMS), mastocytosis (e.g., systemic mastocytosis), myelodysplastic syndromes (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (FEES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer, and vulvar cancer (e.g., Paget's disease of the vulva).

The compounds according to the present invention or pharmaceutical compositions thereof, may also have therapeutic applications in combination with immune modulatory agents, such as inhibitors of the PD1/PDL1 immune checkpoint axis, for example antibodies (or peptides) that bind to and/or inhibit the activity of PD-1 or the activity of PD-L1.

The compounds according to the present invention or pharmaceutical compositions thereof, may also be combined with radiotherapy or chemotherapeutic agents.

The compounds according to the present invention or pharmaceutical compositions thereof, may also be combined with other agents that stimulate or enhance the immune response, such as vaccines.

The compounds according to the present invention or pharmaceutical compositions thereof, may also be used to enhance the antigen presenting properties of dendritic cells produced ex vivo.

The compounds according to the present invention or pharmaceutical compositions thereof may be useful for treating or preventing, in particular treating, of infectious diseases, such as viral, bacterial, fungal, and parasitic infections. The compounds according to the present invention or pharmaceutical compositions thereof may be useful for treating or preventing, in particular treating, of chronic infections. The compounds according to the present invention or pharmaceutical compositions thereof may be useful for treating or preventing, in particular treating, of chronic viral infections.

The invention relates to compounds of Formula (I) and pharmaceutically acceptable addition salts, N-oxides, and solvates thereof, for use as a medicament.

The invention relates to compounds of Formula (I) and pharmaceutically acceptable addition salts, N-oxides, and solvates thereof, for use in the inhibition of HPK1 activity.

The compounds of the present invention can be "anti-cancer agents", which term also encompasses "anti-tumor cell growth agents" and "anti-neoplastic agents".

The invention relates to compounds of Formula (I) and pharmaceutically acceptable addition salts, N-oxides, and solvates thereof, for use in the treatment of diseases mentioned above.

The invention relates to compounds of Formula (I) and pharmaceutically acceptable addition salts, N-oxides, and solvates thereof, for the treatment or prevention, in particular for the treatment, of said diseases.

The invention relates to compounds of Formula (I) and pharmaceutically acceptable addition salts, N-oxides, and solvates thereof, for the treatment or prevention, in particular in the treatment, of HPK1 mediated diseases or conditions.

The invention relates to compounds of Formula (I) and pharmaceutically acceptable addition salts, N-oxides, and solvates thereof, for the manufacture of a medicament.

The invention relates to compounds of Formula (I) and pharmaceutically acceptable addition salts, N-oxides, and solvates thereof, for the manufacture of a medicament for the inhibition of HPK1.

The invention relates to compounds of Formula (I) and pharmaceutically acceptable addition salts, N-oxides, and solvates thereof, for the manufacture of a medicament for the treatment or prevention, in particular for the treatment, of any one of the disease conditions mentioned hereinbefore.

The invention relates to compounds of Formula (I) and pharmaceutically acceptable addition salts, N-oxides, and solvates thereof, for the manufacture of a medicament for the treatment of any one of the disease conditions mentioned hereinbefore.

The invention relates to compounds of Formula (I) and pharmaceutically acceptable addition salts, N-oxides, and solvates thereof, can be administered to mammals, preferably humans, for the treatment or prevention of any one of the diseases mentioned hereinbefore.

In view of the utility of the compounds of Formula (I) and pharmaceutically acceptable addition salts, N-oxides, and solvates thereof, there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I) or a pharmaceutically acceptable addition salt, an N-oxide, or a solvate thereof, to warm-blooded animals, including humans.

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. An effective therapeutic daily amount would be from about 0.005 mg/kg to 100 mg/kg. In particular, an effective therapeutic daily amount would be 25 mg/kg BID (twice a day) or 50 mg/kg BID. In particular, an effective therapeutic daily amount would be 50 mg/kg QD (once a day) or 100 mg/kg QD. The amount of a compound according to the present invention, also referred to herein as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to administration.

The present invention also provides compositions for preventing or treating the disorders referred to herein. Said compositions comprising a therapeutically effective amount of a compound of Formula (I), or a pharmaceutically acceptable addition salt, an N-oxide, or a solvate thereof, and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions may be prepared by any methods well known in the art of pharmacy, for example, using methods such as those described in Gennaro et al. Remington's Pharmaceutical Sciences ($18^{th}$ ed., Mack Publishing Company, 1990, see especially Part 8: Pharmaceutical preparations and their Manufacture).

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation.

Therefore, an embodiment of the present invention relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular condition, in particular tumour, being treated and the particular host being treated.

The following examples further illustrate the present invention.

EXAMPLES

Several methods for preparing the compounds of this invention are illustrated in the following examples. Unless otherwise noted, all starting materials were obtained from commercial suppliers and used without further purification, or alternatively can be synthesized by a skilled person by using well-known methods.

Hereinafter, "DCM" means dichloromethane; "DME" means 1,2-dimethoxyethane; "DMF-DMA" means N,N-dimethylformamide dimethyl acetal; "ACN" means acetonitrile; "Ac" means acetyl; "LAH" means lithium aluminium hydride; "sol." means solution; "prep." means preparative; "aq." means aqueous; "Int." Means Intermediate; "Co." means compound; "r.t." means room temperature; "r.m." means reaction mixture; "KOAc" means potassium acetate; "$AcONH_4$" means ammonium acetate; "BisPin" means bis (pinacolato)diboron; "DCE" means 1,2-dichloroethane; "AcOEt" or "EtOAc" means ethylacetate; "DIPE" means diisopropyl ether; "Boc" means tert-butoxycarbonyl; "DMA" means dimethylacetamide; "HBr" means hydrogen bromide; "MeCN" means acetonitrile; "HOBT" means 1-hydroxy-1H-benzotriazole; "TMS" means trimethylsilyl; "DIPE" means diisopropylether; ""DMAP" means 4-(dimethylamino)pyridine; "MeOH" means methanol; "LC" means liquid chromatography; "LCMS" means Liquid Chromatography/Mass spectrometry; "HPLC" means high-performance liquid chromatography; "$NH_4Cl$" means ammonium chloride; "$H_2O$" means water "TFA" means trifluoroacetic acid; "m.p." means melting point; "$N_2$" means nitrogen; "$Na_2SO_4$" means sodium sulfate; "AcOH" means acetic acid; "MeOD" means deuterated methanol; "$D_2$" means deuterium; "RP" means reversed phase; "min" means minute(s); "EtOAc" means ethyl acetate; "$Et_3N$" means triethylamine; "EtOH" means ethanol; "THF" means tetrahydrofuran; "$MnO_2$" means manganese dioxide; Celite® means diatomaceous earth; "$MgSO_4$" means magnesium sulfate; "$NH_4OH$" means ammonium hydroxide; "$K_2CO_3$" means potassium carbonate; "DMF" means N,N-dimethyl formamide; "$Na_2SO_3$" means sodium sulfite; "$NaHCO_3$" means sodium bicarbonate; "$Na_2CO_3$" means sodium carbonate; "HCl" means hydrogen chloride "NaOH" means sodium hydroxide; "HCOOH" means formic acid; "DMSO" means dimethyl sulfoxide; 'iPrOH" means 2-propanol; "$iPrNH_2$" means isopropylamine; "SFC" means Supercritical Fluid Chromatography; "$CO_2$" means carbon dioxide; "$Et_3N$" means triethylamine; "DIPEA" means N,N-diisopropylethylamine; "$Pd(PPh_3)_4$" means tetrakis(triphenylphosphine)palladium; "w/v" means weight/volume; "[Ir(dtbbpy)$(ppy)_2$] $PF_6$" means (4,4'-Di-t-butyl-2,2'-bipyridine)bis[2-(2-pyridinyl-kN)phenyl-kC]iridium(III) hexafluorophosphate, "SLAP™" means 2-(((Trimethylsilyl) methyl)thio)ethanamine; "SLAP" means silicon amine protocol; "SLAP hydropyridopyrazine" means (1-((trimethylsilyl)methyl)piperidin-2-yl)methanamine; "m-CPBA" means 3-chloroperbenzoic acid "$PPh_3$" means triphenylphosphine; "$Et_2O$" means diethyl ether; "Pd/C" means palladium on carbon; "Et" means ethyl; "Me" means methyl; "h" means hours; "$PdCl_2$(dppf)" means [1,1'-bis (diphenylphosphino-κP)ferrocene]dichloropalladium; and "quant." means quantitative.

When a stereocentre is indicated with 'RS' this means that a racemic mixture was obtained at the indicated centre, unless otherwise indicated.

Preparation of the Intermediates and the Final Compounds

Synthesis of Intermediate 1

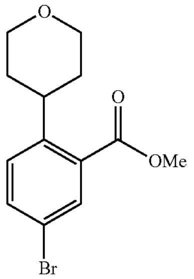 [SMILES: COC(=O)c1cc(Br)ccc1C1CCOCC1]

To a mixture of Zn (69.9 g, 1.07 mol) in DMA (500 mL) was added ethylene dibromide (16.5 g, 88 mmol, 6.64 mL) in one portion under $N_2$. Then TMSCl (6.83 g, 62.9 mmol, 8.0 mL) was added slowly and the mixture was stirred for 30 min at 25° C. A solution of 4-iodotetrahydropyran (200 g, 943 mmol) in DMA (500 mL) was added dropwise slowly (30 min) to maintain temperature below 50° C., the resulting mixture was stirred at 25° C. for 1.5 h and then added via a cannula to a solution of methyl 5-bromo-2-iodobenzoate (214.4 g, 629 mmol), $Pd(dppf)Cl_2 \cdot CH_2Cl_2$ (25.7 g, 31.4 mmol) and CuI (12.0 g, 62.9 mmol) in DMA (2400 mL) under $N_2$, the color of the mixture turned brown, then the mixture was heated and stirred at 80° C. for 14 h under $N_2$. Six batches were combined together. The mixture was cooled to rt and diluted with EtOAc (10 L). A saturated aqueous solution of $NH_4Cl$ (18 L) and $H_2O$ (10 L) were added and the mixture was stirred for 30 mins, then filtered through a pad of Celite®. The cake was washed with EtOAc (5 L*2), the filtrate was extracted with EtOAc (8 L*4), the combined organic phase was washed with brine (15 L*2), dried with anhydrous $Na_2SO_4$, filtered and concentrated in vacuum to give the crude product. The crude product was purified by silica gel chromatography eluted with Petroleum ether:EtOAc=100:0-93:7 to give intermediate 1 (700 g, 61% yield) as a yellow solid.

The following intermediate was prepared via an analogous procedure:

| Intermediate | Structure | Quantity | Yield |
|---|---|---|---|
| Intermediate 2 Starting from iodocyclohexane | 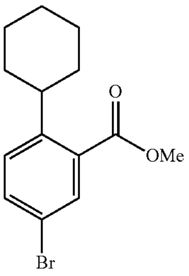 [SMILES: COC(=O)c1cc(Br)ccc1C1CCCCC1] | 0.7 g | 40% |

Synthesis of Intermediate 3

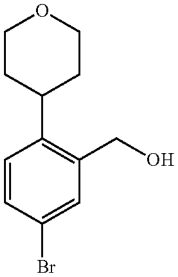 [SMILES: OCc1cc(Br)ccc1C1CCOCC1]

To a mixture of intermediate 1 (220 g, 735 mmol) in THF (2200 mL) was added portionwise LAH (27.9 g, 735 mmol) at 0-10° C. over 30 min. The grey suspension was stirred at 0-30° C. for 1 h. The mixture was cooled to 0° C. and $H_2O$ (800 mL) was added dropwise and then the mixture was stirred for 30 min. The three batches were worked together. The mixture was filtered and the cake was washed with EtOAc (3 L*3), the filtrated was extracted with EtOAc (2 L*3), the combined organic phase was washed with brine (2 L*2), dried with $Na_2SO_4$, filtered and concentrated in vacuum. The crude product was used for next step without purification to give intermediate 3 (576 g, 87% yield) as a yellow oil.

The following intermediate was prepared via an analogous procedure:

| Intermediate | Structure | Quantity | Yield |
|---|---|---|---|
| Intermediate 4 Starting from intermediate 2 | 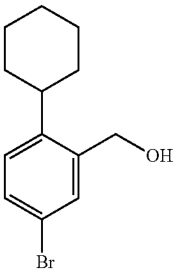 [SMILES: OCc1cc(Br)ccc1C1CCCCC1] | 0.53 g | 84% |

Synthesis of Intermediate 5

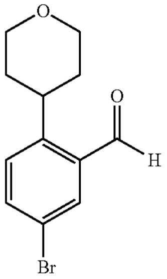 [SMILES: O=Cc1cc(Br)ccc1C1CCOCC1]

To a mixture of intermediate 3 (325 g, 1.2 mol) in $CH_2Cl_2$ (3200 mL) was added $MnO_2$ (834 g, 9.6 mol) in one portion. The black mixture was stirred at 30° C. for 34 h. The two batches were worked together. The mixture was filtered through Celite and the cake was washed with $CH_2Cl_2$ (2 L*3), the filtrate was concentrated in vacuum. The crude product was purified by silica gel column chromatography (Petroleum ether/Ethyl acetate=100:0-85:15) to give 560 g as a crude product which was stirred with Petroleum ether (800 mL) at 30° C. for 4 h, filtered and the cake was washed with Petroleum ether (200 mL*2) and concentrated in high vacuum to give intermediate 5 (502 g, 1.85 mol, 77% yield) as a white solid.

The following intermediate was prepared via an analogous procedure:

| Intermediate | Structure | Quantity | Yield |
|---|---|---|---|
| Intermediate 6 Starting from intermediate 4 | 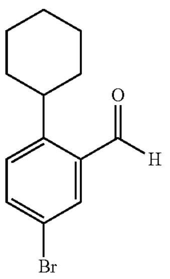 [SMILES: O=Cc1cc(Br)ccc1C1CCCCC1] | 0.35 g | 67% |

Synthesis of Intermediate 7

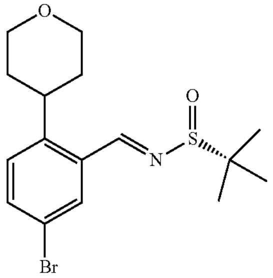

Titanium (IV) ethoxide (64.5 mL, 0.308 mol) was added dropwise to a solution of intermediate 5 (20.7 g, 77 mmol) and (S)-(−)-t-butylsulfinamide (18.06 g, 0.149 mol). The solution was stirred at rt overnight and the mixture was poured into brine and Ethyl acetate was added. The organic layer was separated, dried over $MgSO_4$, filtered and evaporated until dryness. The residue was purified br preparative LC (330 g of irregular SiOH 35-40 μm GraceResolv, mobile phase:gradient from 100% DCM to DCM 95%/MeOH 5%/$NH_4OH$ 0.1%. The pure fractions were collected and the solvent evaporated until dryness to give intermediate 7 (30 g, y=quant.)

The following intermediates were prepared via an analogous procedure:

| Intermediate | Structure | Quantity | Yield |
|---|---|---|---|
| Intermediate 8 Starting from intermediate 6 | 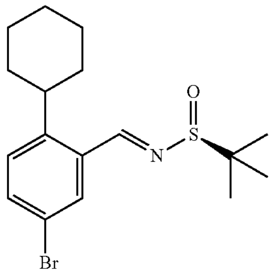 [SMILES: CC(C)(C)[S@](=O)/N=C/c1cc(Br)ccc1C1CCCCC1] | 0.32 g | 66% |
| Intermediate 9 Starting from 5-bromo-2-(N-morpholino)-benzaldehyde | 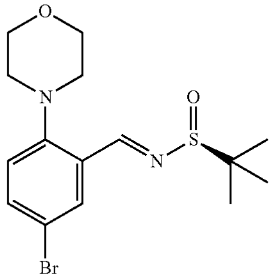 [SMILES: CC(C)(C)[S@](=O)/N=C/c1cc(Br)ccc1N1CCOCC1] | 3.2 g | 76% |
| Intermediate 10 Starting from intermediate 5 | 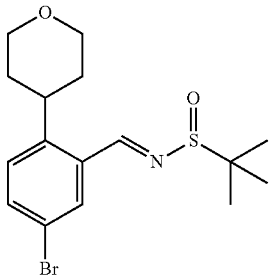 [SMILES: CC(C)(C)S(=O)/N=C/c1cc(Br)ccc1C1CCOCC1] | 9.5 g | 94% |

Synthesis of Intermediate 11

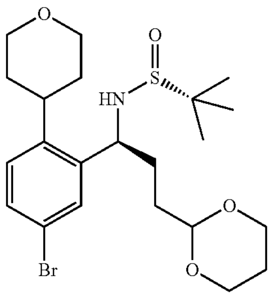

A solution of intermediate 7 (41 g, 0.11 mol) in THF (500 mL) was added dropwise at −78° C. to a solution of (1,3-dioxan-2-ylethyl)magnesium bromide (96.6 g, 0.44 mol) in THF (550 mL) The reaction mixture was stirred at −78° C. for 0.5 h. A saturated solution of $NH_4C_1$ was added and the reaction mixture was extracted with ethyl acetate, the organic layer was separated, dried over $MgSO_4$, filtered and evaporated until dryness to give intermediate 11 (60 g, y=quant.)

The following intermediates were prepared via an analogous procedure:

| Intermediate | Structure | Quantity | Yield |
|---|---|---|---|
| Intermediate 12 Starting from intermediate 8 | 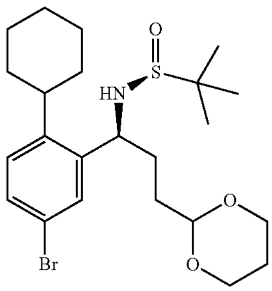 [SMILES: CC(C)(C)[S@](=O)N[C@@H](CCC1OCCCO1)c1cc(Br)ccc1C1CCCCC1] | 0.28 g | 67% |
| Intermediate 13 Starting from intermediate 9 | 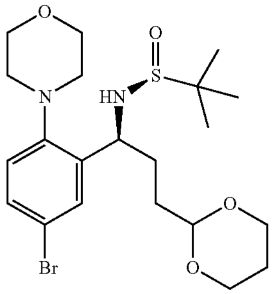 [SMILES: CC(C)(C)[S@](=O)N[C@@H](CCC1OCCCO1)c1cc(Br)ccc1N1CCOCC1] | 1.23 g | 93% |

Synthesis of Intermediate 14

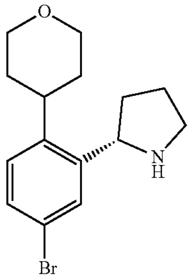 [SMILES: Brc1ccc(C2CCOCC2)c([C@@H]2CCCN2)c1]

Intermediate 11 (66.4 g, 0.135 mol) was slowly added to a mixture of TFA (597 mL) and water (33 mL) to maintain temperature below 25° C. The reaction mixture was stirred at rt for 40 min. Triethylsilane (221 mL, 1.38 mol) was added and the reaction mixture vigorously stirred at rt overnight. The reaction mixture was evaporated till dryness. A purification was performed via preparative LC (stationary phase: irregular SiOH 35-40 μM 220+330 g, GraceResolv, mobile phase: from DCM 100% to DCM 80%/MeOH/20%/$NH_4OH$ 0.1%). The pure fractions were evaporated and taken up in DCM and water, basified with $K_2CO_3$. The organic layer was separated, dried over $MgSO_4$, filtered and evaporated to give intermediate 14 (33.2 g, 79%). $[\alpha]_d$: −47.5° (589 nm, c 0.36 w/v %, DMF, 20° C.)

The following intermediates were prepared via an analogous procedure:

| Intermediate | Structure | Quantity | Yield |
|---|---|---|---|
| Intermediate 15 Starting from intermediate 12 | 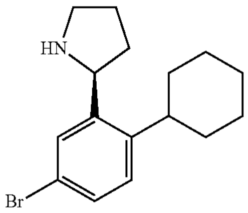 [SMILES: Brc1ccc(C2CCCCC2)c([C@@H]2CCCN2)c1] | 0.13 g | 73% |
| Intermediate 16 Starting from intermediate 13 | 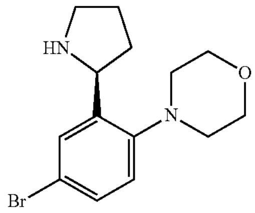 [SMILES: Brc1ccc(N2CCOCC2)c([C@@H]2CCCN2)c1] | 0.18 g | 23% |

Synthesis of Intermediate 17

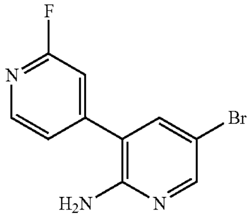 [SMILES: Nc1ncc(Br)cc1-c1ccnc(F)c1]

A solution of 2-amino-3-iodo-5-bromopyridine (25.12 g, 84.0 mmol), 2-fluoropyridine-4-boronic acid pinacol ester (18.75 g, 84.0 mmol) and sodium carbonate (17.81 g, 168 mmol) in 1,4-dioxane (240 mL) and water (35 mL) in a sealed tube was degassed during 10 min. After addition of $PdCl_2$(dppf) (3.44 g, 4.2 mmol), the reaction mixture was stirred at 90° C. overnight. Water, potassium carbonate and ethyl acetate were added. The organic layer was separated, dried over $MgSO_4$, filtered and evaporated until dryness. DCM was added to the residue, the insoluble was filtered, washed with DCM and dried yielding 13.6 g (60.4%) of intermediate 17. The filtrate was purified by preparative LC (SiOH 30 μm Interchim, from 100% DCM to DCM 90%/MeOH 10%/$NH_4OH$ 0.1%). The pure fractions were collected and evaporated until dryness to give intermediate 17 (6 g, 26.6%).

Synthesis of Intermediate 18

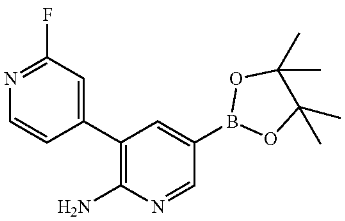 [SMILES: CC1(C)OB(c2cnc(N)c(-c3ccnc(F)c3)c2)OC1(C)C]

To a solution of intermediate 17 (13.6 g, 50.7 mmol), bis(pinacolato)diboron (14.2 g, 55.8 mmol) and potassium acetate (14.94 g, 152 mmol) in 1,4-dioxane (490 mL) was added under nitrogen atmosphere PdCl2(dppf) (1.66 g, 2.03 mmol). The reaction mixture was heated at 80° C. for 20 hours, cooled to room temperature. Ethyl acetate was added and the mixture was filtered through a pad of celite and the filtrate was evaporated until dryness. Water and Ethyl acetate were added, the insoluble was filtered, taken up into diethtlether then filtered and dried to give 9.13 g of intermediate 18 (57.1%). The organic layer was separated, dried over $MgSO_4$, filtered and evaporated until dryness. The residue was taken up into diethylether, stirred for 30 min then filtered and dried to give 6 g of intermediate 18 (37.7%).

The following intermediates were prepared via an analogous procedure as for intermediate 18:

| Intermediate | Structure | Quantity | Yield |
|---|---|---|---|
| Intermediate 23 Starting from 5-bromo-3-(pyrimidin-5-yl)pyridine-2-amine | 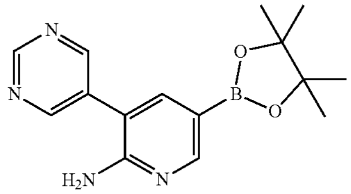 [SMILES: CC1(C)OB(c2cnc(N)c(-c3cncnc3)c2)OC1(C)C] | 0.527 g | 56% (80% purity) |
| Intermediate 24 Starting from 5-bromo-3-(pyridin-3-yl)pyridin-2-amine | 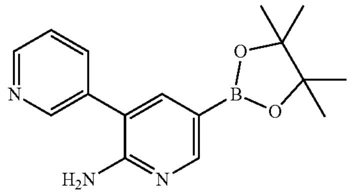 [SMILES: CC1(C)OB(c2cnc(N)c(-c3cccnc3)c2)OC1(C)C] | 0.263 g | 29% |
| Intermediate 25 Starting from 5-bromo-3-(1-methyl-1H-pyrazol-4-yl)pyridin-2-amine | 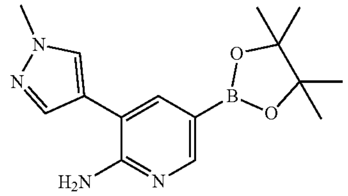 [SMILES: Cn1cc(-c2cc(B3OC(C)(C)C(C)(C)O3)cnc2N)cn1] | 0.465 g | 24% |
| Intermediate 26 Starting from 5-bromo-[3,4'-Bipyridin]-2-amine | 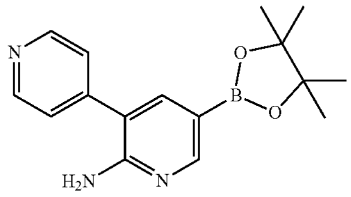 | 2.2 g | 38% |

Synthesis of Intermediate 19

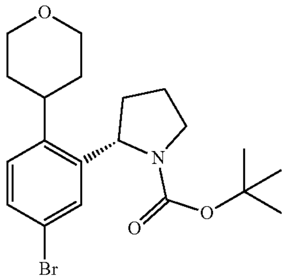 [SMILES: CC(C)(C)OC(=O)N1CCC[C@H]1c1cc(Br)ccc1C1CCOCC1]

Di-tert-butyl dicarbonate (44.3 g, 0.203 mol) was added to a solution of intermediate 14 (21 g, 67.7 mmol) and 4-dimethylaminopyridine (1.65 g 13.5 mmol) in DCM (680 mL). The reaction mixture was stirred at rt for 24 h. Water and DCM were added, the organic layer was separated, dried over $MgSO_4$, filtered and evaporated until dryness. The residue was crystallized in diethylether, filtered and dried to give 22.2 g of intermediate 19 (80%).

The following intermediates were prepared via an analogous procedure:

| Intermediate | Structure | Quantity | Yield |
|---|---|---|---|
| Intermediate 20 Starting from intermediate 15 | 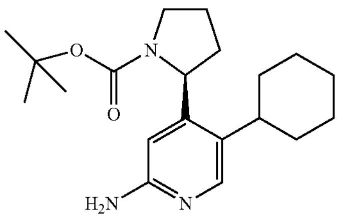 [SMILES: CC(C)(C)OC(=O)N1CCC[C@H]1c1cc(N)ncc1C1CCCCC1] | 0.2 g | Quant. |
| Intermediate 21 Starting from Pyrrolidine,2-(2-bromo-5-iodophenyl), (2S) | 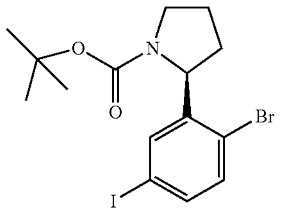 [SMILES: CC(C)(C)OC(=O)N1CCC[C@H]1c1cc(I)ccc1Br] | 27.5 g | 58% |

Synthesis of Intermediate 22

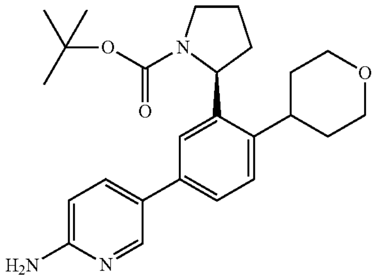 [SMILES: CC(C)(C)OC(=O)N1CCC[C@H]1c1cc(-c2ccc(N)nc2)ccc1C1CCOCC1]

A mixture of 2-aminopyridine-5-boronic acid pinacol ester (5.92 g, 26.9 mmol), intermediate 19 (9.2 g, 22.4 mmol), $Pd(PPh_3)_4$ (2.6 g, 2.25 mmol) and sodium carbonate (7.1 g, 67.2 mmol) in 2-methyltetrahydrofuran (250 mL) and water (25 mL) was stirred under $N_2$ in a sealed tube at 85° C. for 15 hours. The reaction mixture was cooled down; water, potassium carbonate and ethyl acetate were added. The organic layer was separated, dried over $MgSO_4$, filtered and evaporated until dryness. The residue was purified by preparative LC (SiOH 30 μm Interchim, from 100% DCM to DCM 90%/MeOH 10%/$NH_4OH$ 0.1%). The fractions were collected and evaporated until dryness to give 11.6 g of a residue which was purified again via preparative LC (Stationary phase: irregular SiOH 40 μm 220 g, Mobile phase: 60% Heptane, 5% MeOH (+5% $NH_4OH$), 35% AcOEt). The pure fractions were collected and evaporated until dryness to give 6 g of intermediate 22 (63%).

Synthesis of Intermediate 27

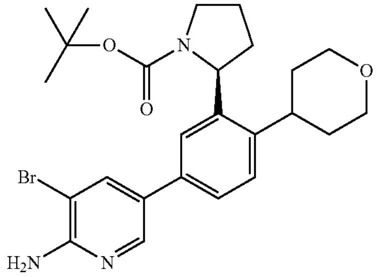 [SMILES: CC(C)(C)OC(=O)N1CCC[C@H]1c1cc(-c2cnc(N)c(Br)c2)ccc1C1CCOCC1]

Bromine (0.73 mL, 14.2 mmol) was added dropwise to a solution of intermediate 22 (6 g, 14.2 mmol) in acetic acid (90 mL) at rt. After 20 min, water and potassium carbonate were added. The aqueous phase was extracted with ethyl acetate and the organic layer was dried over $MgSO_4$, filtered and evaporated until dryness. The residue was purified by preparative LC (SiOH 30 μm Interchim, from 100% DCM to DCM 90%/MeOH 10%/$NH_4OH$ 0.1%). The pure fractions were collected and evaporated until dryness to give 5.8 g of intermediate 27 (81%).

Synthesis of intermediate 28

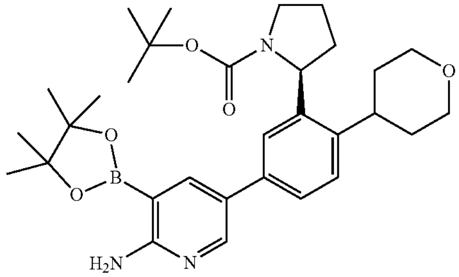 [SMILES: CC(C)(C)OC(=O)N1CCC[C@H]1c1cc(-c2cnc(N)c(B3OC(C)(C)C(C)(C)O3)c2)ccc1C1CCOCC1]

To a solution of intermediate 27 (0.51 g, 1 mmol), bis(pinacolato)diboron (0.3 g, 1.2 mmol) and potassium acetate (0.31 g, 3.1 mmol) in 1,4-dioxane (11 mL) was added under nitrogen atmosphere $PdCl_2(dppf)$ (0.084 g, 0.1 mmol) in a schlenk. The reaction mixture was stirred and heated at 110° C. for 20 hours, cooled at room temperature, then DCM was added and the mixture was filtered through a cellite pad and the filtrate was evaporated until dryness and the residue was used without purification for the next step.

Synthesis of Intermediate 29

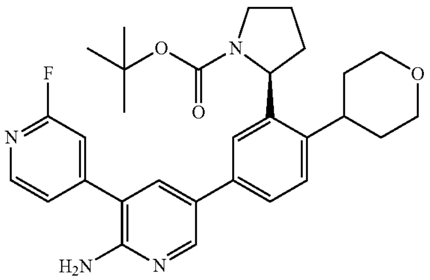 [SMILES: CC(C)(C)OC(=O)N1CCC[C@H]1c1cc(-c2cnc(N)c(-c3ccnc(F)c3)c2)ccc1C1CCOCC1]

A mixture of intermediate 27 (6 g, 22.4 mmol),), 2-fluoropyridine-4-boronic acid pinacol ester (3.2 g, 14.3 mmol), $PdCl_2(dppf)$ (0.61 g, 0.75 mmol) and sodium carbonate (2.5 g, 23.9 mmol) in 1,4-dioxane (115 mL) and water (11.5 mL) was stirred under $N_2$ in a sealed tube at 90° C. for 6 hours. The reaction mixture was cooled down, poured into water and potassium carbonate and the aqueous phase was extracted with ethyl acetate. The organic layer was separated, dried over $MgSO_4$, filtered and evaporated until dryness. The residue was purified by preparative LC (220 g SiOH 30 μm Interchim, from 100% DCM to DCM 90%/MeOH 10%/$NH_4OH$ 0.1%). The pure fractions were collected and evaporated until dryness to give 6.8 g of intermediate 29 (quant.).

The following intermediates were prepared via an analogous procedure:

| Intermediate | Structure | Quantity | Yield |
|---|---|---|---|
| Intermediate 30 Starting from 2-Chloropyridine-4-boronic acid pinacol ester | 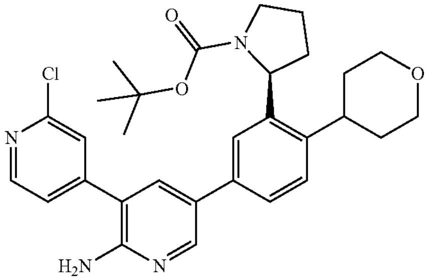 | 0.75 g | 71% |
| Intermediate 31 Starting from (4,5,6,7-TETRAHYDROPYRAZOLO[1,5-A]PYRIDIN-3-YL)BORONIC ACID PINACOL ESTER | 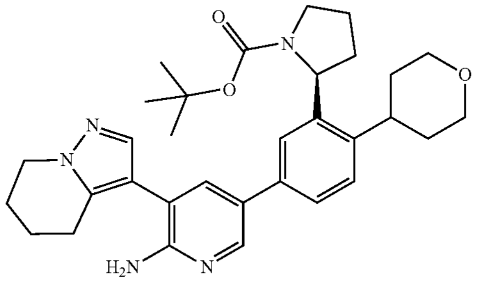 [SMILES: CC(C)(C)OC(=O)N1CCC[C@H]1c1cc(-c2cnc(N)c(-c3cnn4c3CCCC4)c2)ccc1C1CCOCC1] | 0.16 g | 59% |
| Intermediate 32 Starting from 1-(Methylsulfonyl) pyrazole-4-boronic acid pinacol ester | 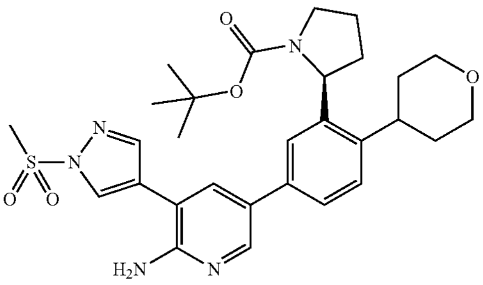 [SMILES: CC(C)(C)OC(=O)N1CCC[C@H]1c1cc(-c2cnc(N)c(-c3cnn(S(C)(=O)=O)c3)c2)ccc1C1CCOCC1] | 0.102 g | 58% |

-continued

| Intermediate | Structure | Quantity | Yield |
|---|---|---|---|
| Intermediate 33 Starting from 2-(Tributylstannyl) thiazole | 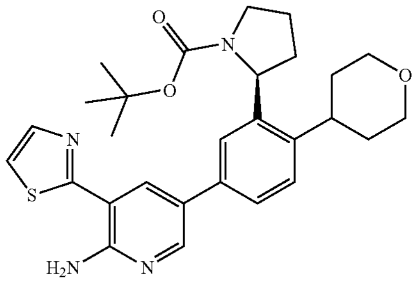 [SMILES: CC(C)(C)OC(=O)N1CCC[C@H]1c1cc(-c2cnc(N)c(-c3nccs3)c2)ccc1C1CCOCC1] | 0.042 g | 42% |
| Intermediate 34 Starting from 1-(2-{[tert-butyl(dimethyl) silyl]oxy}ethyl)-4-(4,4-5,5-tetramethyl-1,3,2-dioxaborolan-2-yl)-1H-pyrazole | 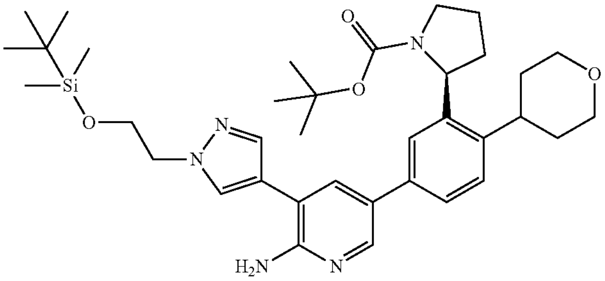 [SMILES: CC(C)(C)OC(=O)N1CCC[C@H]1c1cc(-c2cnc(N)c(-c3cnn(CCO[Si](C)(C)C(C)(C)C)c3)c2)ccc1C1CCOCC1] | 0.079 g | 41% |
| Intermediate 35 Starting from 1-Isopropyl-1H-pyrazole-4-boronic acid pinacol ester | 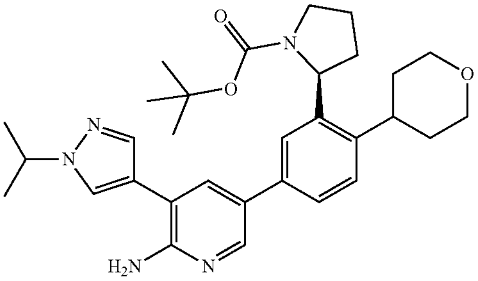 [SMILES: CC(C)n1cc(-c2cc(-c3ccc(C4CCOCC4)c([C@@H]4CCCN4C(=O)OC(C)(C)C)c3)cnc2N)cn1] | 0.058 g | 36% |
| Intermediate 36 Starting from 1-Boc-pyrazole-4-boronic acid pinacol ester | 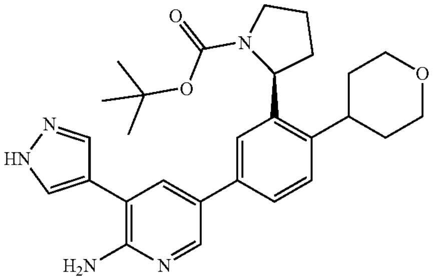 [SMILES: CC(C)(C)OC(=O)N1CCC[C@H]1c1cc(-c2cnc(N)c(-c3cn[nH]c3)c2)ccc1C1CCOCC1] | 0.086 g | 59% |
| Intermediate 37 Starting from 3-Methoxy-4-pyridineboronic acid pinacol ester | 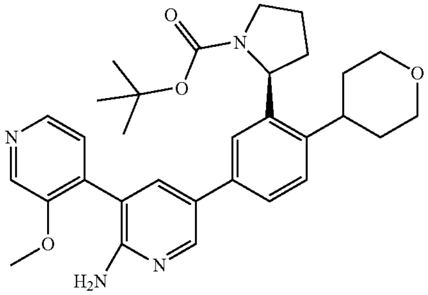 [SMILES: COc1cnccc1-c1cc(-c2ccc(C3CCOCC3)c([C@@H]3CCCN3C(=O)OC(C)(C)C)c2)cnc1N] | 0.073 g | 99% |

-continued

| Intermediate | Structure | Quantity | Yield |
|---|---|---|---|
| Intermediate 38 Starting from Pyridine-4-boronic acid pinacol ester | 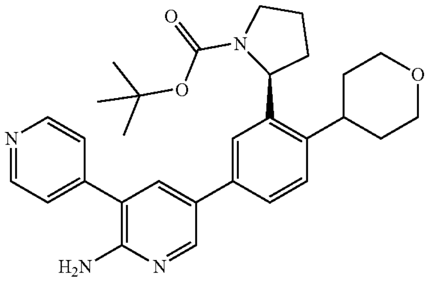 [SMILES: CC(C)(C)OC(=O)N1CCC[C@H]1c1cc(-c2cnc(N)c(-c3ccncc3)c2)ccc1C1CCOCC1] | 0.127 g | 69% |
| Intermediate 39 Starting from 4-(4,4,5-5-Tetramethyl-1,3,2-dioxaborolan-2-yl)-3,6-dihydro-2H-thiopyran 1,1-dioxide | 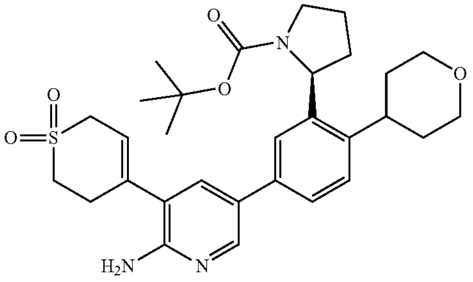 [SMILES: CC(C)(C)OC(=O)N1CCC[C@H]1c1cc(-c2cnc(N)c(C3=CCS(=O)(=O)CC3)c2)ccc1C1CCOCC1] | 0.38 g | Quant. |
| Intermediate 40 Starting from 6-hydroxypyridine-3-boronic acid pincol ester | 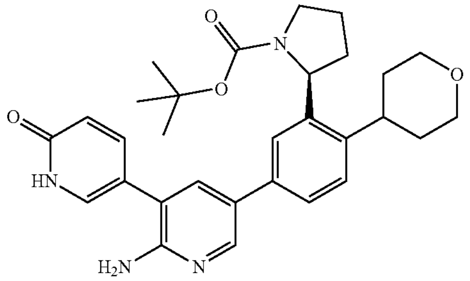 [SMILES: CC(C)(C)OC(=O)N1CCC[C@H]1c1cc(-c2cnc(N)c(-c3ccc(=O)[nH]c3)c2)ccc1C1CCOCC1] | 0.086 g | 38% |
| Intermediate 41 Starting from 2-Hydroxypyridine-4-boronic acid pinacol ester | 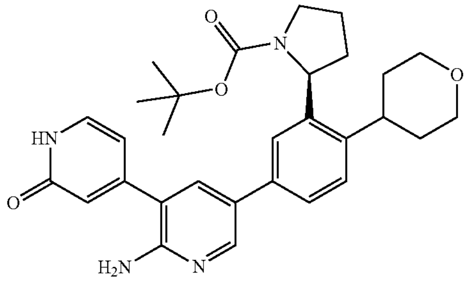 [SMILES: CC(C)(C)OC(=O)N1CCC[C@H]1c1cc(-c2cnc(N)c(-c3cc[nH]c(=O)c3)c2)ccc1C1CCOCC1] | 0.092 g | 40% |
| Intermediate 42 Starting from 2-Cyanopyridine-4-boronic acid pinacol ester | 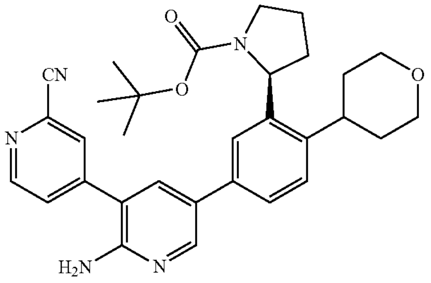 [SMILES: CC(C)(C)OC(=O)N1CCC[C@H]1c1cc(-c2cnc(N)c(-c3ccnc(C#N)c3)c2)ccc1C1CCOCC1] | 0.23 g | 88% |

-continued

| Intermediate | Structure | Quantity | Yield |
|---|---|---|---|
| Intermediate 43 Starting from 4-Fluorophenylboronic acid, pinacol ester | 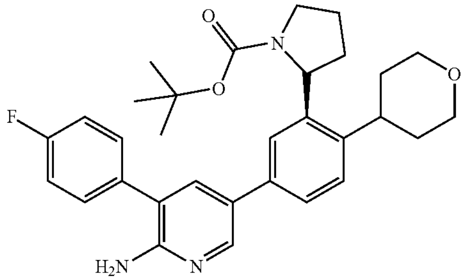 | 0.24 g | 94% |
| Intermediate 44 Starting 2-Trifluoromethyl-4-pyridineboronic acid pinazol ester | 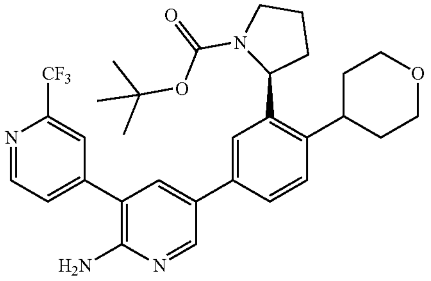 [SMILES: CC(C)(C)OC(=O)N1CCC[C@H]1c1cc(-c2cnc(N)c(-c3ccnc(C(F)(F)F)c3)c2)ccc1C1CCOCC1] | 0.22 g | 78% |

The following intermediates were prepared via an analogous procedure as for intermediate 17:

| Intermediate | Structure | Quantity | Yield |
|---|---|---|---|
| Intermediate 45 Starting from 2,3-difluoropyridine-4-boronic acid | 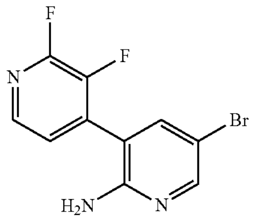 [SMILES: Nc1ncc(Br)cc1-c1ccnc(F)c1F] | 0.09 g | 31% |
| Intermediate 46 Starting from 3-fluoropyridin-4-boronic acid | 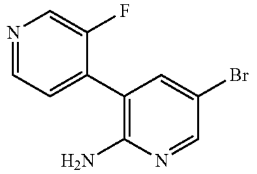 | 0.257 g | 20% |
| Intermediate 47 Starting from (2-(2-CYANOPROPAN-2-YL) PYRIDIN-4-YL)BORONIC ACID PINACOL ESTER | 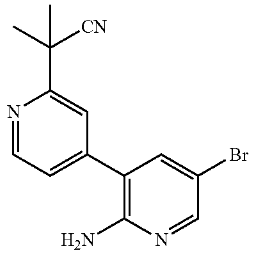 [SMILES: CC(C)(C#N)c1cc(-c2cc(Br)cnc2N)ccn1] | 0.234 g | 70% |
| Intermediate 48 Starting from 3-chloropyridine-4-boronic acid | 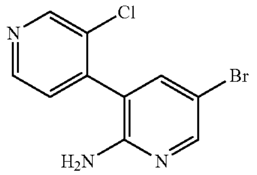 [SMILES: Nc1ncc(Br)cc1-c1ccncc1Cl] | 0.139 g | 23% |

-continued

| Intermediate | Structure | Quantity | Yield |
| --- | --- | --- | --- |
| Intermediate 49 Starting from 2,5-difluoropyridine-4-boronic acid | 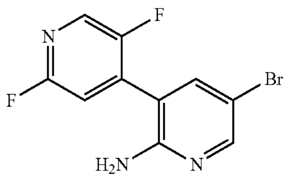 [SMILES: Nc1ncc(Br)cc1-c1cc(F)ncc1F] | 0.103 g | 28% |
| Intermediate 50 Starting from 5-chloro-2-fluoropyridine-4-yl) boronic acid | 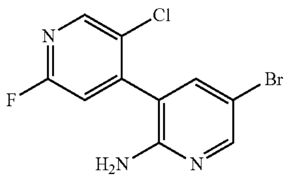 [SMILES: Nc1ncc(Br)cc1-c1cc(F)ncc1Cl] | 0.179 g | 26% |
| Intermediate 51 Starting from 4-(tributylstannyl)-pyridazine | 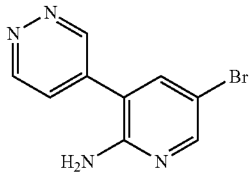 [SMILES: Nc1ncc(Br)cc1-c1ccnnc1] | 0.294 g | 69% |
| Intermediate 52 | 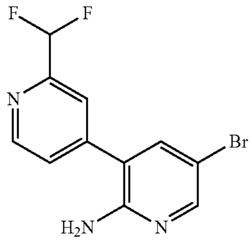 [SMILES: Nc1ncc(Br)cc1-c1ccnc(C(F)F)c1] | 0.04 g | 31% |
| Intermediate 53 Starting from 3-chloro-2-fluoropyridine-4-boronic acid | 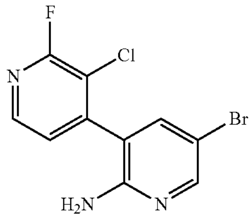 [SMILES: Nc1ncc(Br)cc1-c1ccnc(F)c1Cl] | 0.09 g | 30% |
| Intermediate 54 Starting from 4-Cyanophenylboronic acid | 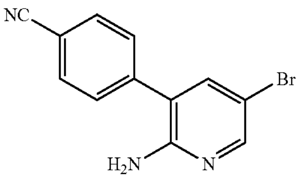 [SMILES: N#Cc1ccc(-c2cc(Br)cnc2N)cc1] | 0.097 g | 52% |
| Intermediate 55 Starting from 4-(tributylstannyl)-pyrimidine | 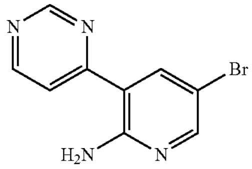 [SMILES: Nc1ncc(Br)cc1-c1ccncn1] | 0.268 g | 41% |

-continued

| Intermediate | Structure | Quantity | Yield |
|---|---|---|---|
| Intermediate 56 Starting from intermediate 65 | 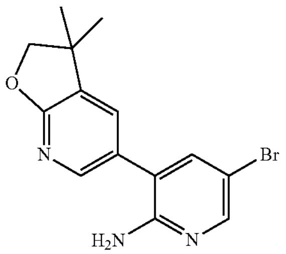 [SMILES: CC1(C)COc2ncc(-c3cc(Br)cnc3N)cc21] | 0.3 g | 47% |
| Intermediate 57 Starting from 3,6-dihydro-2H-pyran-4-boronic acid pinacol ester | 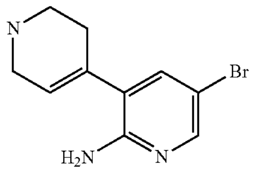 | 0.375 g | 99% |
| Intermediate 58 Starting from N-Boc-1,2,5,6-Tetrahydropyridine-4-Boronic Acid Pinacol Ester | 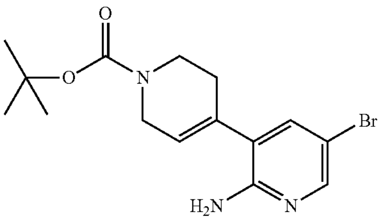 [SMILES: CC(C)(C)OC(=O)N1CC=C(c2cc(Br)cnc2N)CC1] | 0.520 g | 83% |

1) Synthesis of intermediate 59:

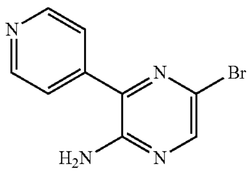 [SMILES: Nc1ncc(Br)nc1-c1ccncc1]

A mixture of 3,5-dibromopyrazin-2-amine (1.3 g, 5.14 mmol), 4-pyridinylboronic acid (0.948 g, 7.71 mmol) and sodium carbonate (1.09 g, 10.28 mmol) in 1,4-dioxane (50 mL) and water (12.5 mL) was degazed 10 min. After addition of $PdCl_2$(dppf) (0.21 g, 0.257 mmol) the reaction mixture was heated at 90° C. for 12 h. The reaction mixture was filtered through a pad of Celite®, water was added and the aqueous phase was extracted with DCM. The organic layer was dried over $MgSO_4$, filtered and concentrated. The crude mixture was purified by flash chromatography using Heptane/Ethylacetate 0% to 100% as gradient. The desired fractions were collected and concentrated to give intermediate 59 (0.5 g, 38%).

2) The Following Intermediate was Prepared Via an Analogous Procedure

| Intermediate | Structure | Quantity | Yield |
|---|---|---|---|
| Intermediate 60 | 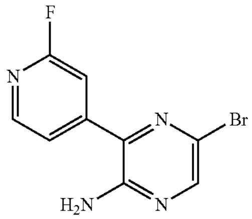 [SMILES: Nc1ncc(Br)nc1-c1ccnc(F)c1] | 0.3 g | 28% |

Synthesis of Intermediate 61

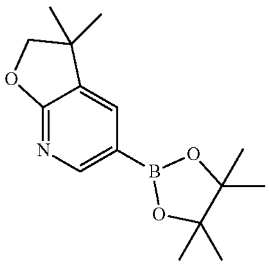 [SMILES: CC1(C)COc2ncc(B3OC(C)(C)C(C)(C)O3)cc21]

3) A mixture of 3,3-dimethyl-2,3-dihydrofuro[2,3-b]pyridine (2.8 g, 18.77 mmol), N-bromosuccinamide (10 g, 56.3 mmol) in acetonitrile (50 mL) was heated at 60° C. for 18 hours. The mixture was concentrated and diluted with ethyl acetate (100 mL). The organic layer was washed with 1M $Na_2SO_3$ (30 mL, twice) and 1M $NaHCO_3$ (30 mL, twice). The organic layer was separated, dried over $MgSO_4$, filtered and evaporated until dryness. The residue was purified by column chromatography over silica gel (petroleum ether/ethyl acetate: 100/0 to 4/1). The pure fractions were collected and evaporated until dryness to give 3.7 g of 5-bromo-3,3-dimethyl-2H-furo[2,3-b]pyridine (86%.).

4) A mixture of 5-bromo-3,3-dimethyl-2H-furo[2,3-b]pyridine (0.5 g, 2.19 mmol), bis(pinacolato)diboron (0.72 g, 2.85 mmol), $PdCl_2$(dppf) (0.143 g, 0.175 mmol) and potassium acetate (0.645 g, 6.58 mmol) in Me-THF (7.5 mL) was stirred at 85° C. under nitrogen atmosphere in a sealed tube overnight. The reaction mixture was cooled to rt, ethyl acetate was added and the reaction mixture was filtered through decalite. The filtrate was evaporated until dryness to give intermediate 61 used without purification for the next step.

Synthesis of Intermediate 62

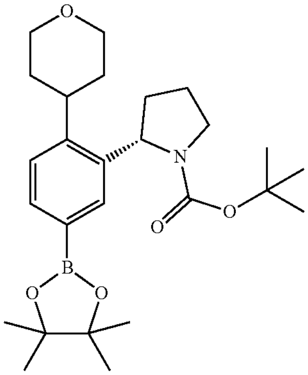 [SMILES: CC(C)(C)OC(=O)N1CCC[C@H]1c1cc(B2OC(C)(C)C(C)(C)O2)ccc1C1CCOCC1]

A mixture of intermediate 19 (4 g, 9.7 mmol), bis(pinacolato)diboron (3 g, 11.8 mmol), $PdCl_2$(dppf) (0.8 g, 0.98 mmol) and potassium acetate (2.87 g, 29.2 mmol) in 1,4-dioxane (90 mL) was stirred at 90° C. under nitrogen atmosphere in a schlenk flask for 15 hours. The reaction mixture was cooled to rt, water was added. The aqueous layer was extracted with ethyl acetate. The organic layer was dried over $MgSO_4$, filtered and evaporated until dryness. The residue was purified by preparative LC (SiOH 35-40 μm GraceResolv, from heptane/AcOEt 80/20 to 50/50). The fractions were collected and evaporated until dryness to give 5.3 g of intermediate 62 (quant.).

The following intermediate was prepared via an analogous procedure:

| Intermediate | Structure | Quantity | Yield |
|---|---|---|---|
| Intermediate 63 Starting from intermediate 51 | 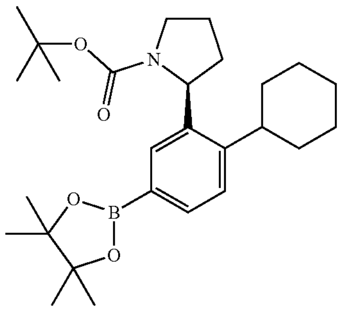 [SMILES: CC(C)(C)OC(=O)N1CCC[C@H]1c1cc(B2OC(C)(C)C(C)(C)O2)ccc1C1CCCCC1] | Used without purification in next step | |

Synthesis of Intermediate 64

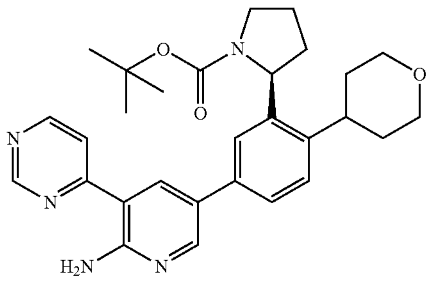 [SMILES: CC(C)(C)OC(=O)N1CCC[C@H]1c1cc(-c2cnc(N)c(-c3ccncn3)c2)ccc1C1CCOCC1]

Sodium carbonate (60 mg, 0.57 mmol) was added to a solution of intermediate 55 (71 mg, 0.28 mmol), intermediate 62 (130 mg, 0.28 mmol) in water (1 mL) and 1,4-dioxane (4 mL). The mixture was degassed with a stream of nitrogen for 5 min., then $PdCl_2$(dppf) (12 mg, 0.014 mmol) was added. The reaction mixture was stirred at 90° C. overnight. The reaction mixture was cooled to rt, water (15 mL) and AcOEt (20 mL) were added. The aqueous layer was extracted with ethyl acetate (3×25 mL). The organic layer was dried over $MgSO_4$, filtered and evaporated until dryness. The residue was purified by silicagel chromatography (Heptane/EtOAc: 0-100%). The fractions were collected and evaporated until dryness to give 98 mg of intermediate 64 (68%).

The following intermediates were prepared via an analogous procedure:

| Intermediate | Structure | Quantity | Yield |
|---|---|---|---|
| Intermediate 65 Starting from Intermediate 45 | 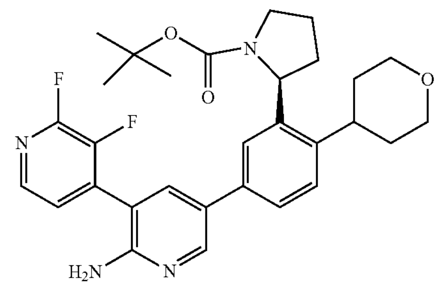 [SMILES: CC(C)(C)OC(=O)N1CCC[C@H]1c1cc(-c2cnc(N)c(-c3ccnc(F)c3F)c2)ccc1C1CCOCC1] | 0.1 g | 65% |
| Intermediate 66 Starting from Intermediate 46 | 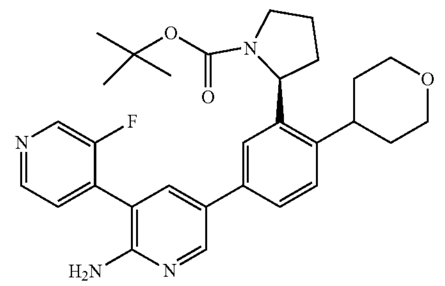 [SMILES: CC(C)(C)OC(=O)N1CCC[C@H]1c1cc(-c2cnc(N)c(-c3ccncc3F)c2)ccc1C1CCOCC1] | 0.14 g | 43% |
| Intermediate 67 Starting from Intermediate 47 | 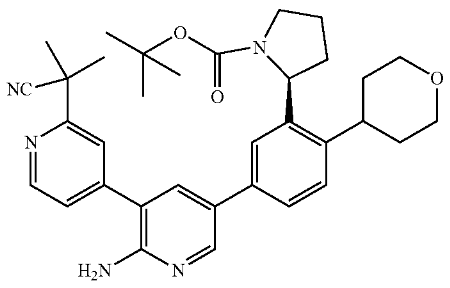 [SMILES: CC(C)(C)OC(=O)N1CCC[C@H]1c1cc(-c2cnc(N)c(-c3ccnc(C(C)(C)C#N)c3)c2)ccc1C1CCOCC1] | 0.194 g | 67% |
| Intermediate 68 Starting from Intermediate 48 | 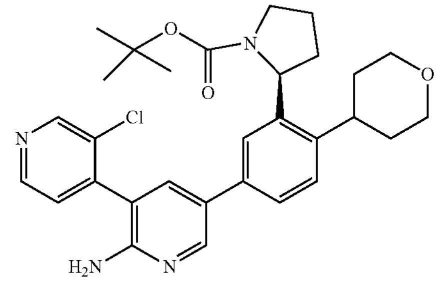 | 0.167 g | 57% |

-continued
| Intermediate | Structure | Quantity | Yield |
|---|---|---|---|
| Intermediate 69 Starting from Intermediate 49 | 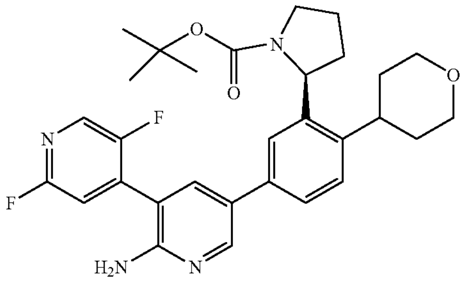 [SMILES: CC(C)(C)OC(=O)N1CCC[C@H]1c1cc(-c2cnc(N)c(-c3cc(F)ncc3F)c2)ccc1C1CCOCC1] | 0.15 g | 72% |
| Intermediate 70 Starting from intermediate 50 | 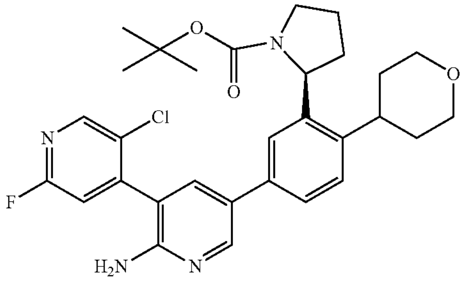 [SMILES: CC(C)(C)OC(=O)N1CCC[C@H]1c1cc(-c2cnc(N)c(-c3cc(F)ncc3Cl)c2)ccc1C1CCOCC1] | 0.229 g | 71% |
| Intermediate 71 Starting from Intermediate 51 | 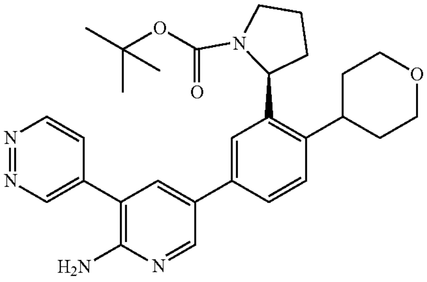 [SMILES: CC(C)(C)OC(=O)N1CCC[C@H]1c1cc(-c2cnc(N)c(-c3ccnnc3)c2)ccc1C1CCOCC1] | 0.109 g | 51% |
| Intermediate 72 Starting from intermediate 52 | 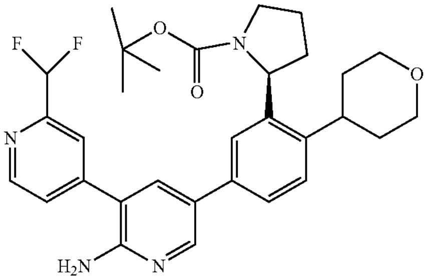 [SMILES: CC(C)(C)OC(=O)N1CCC[C@H]1c1cc(-c2cnc(N)c(-c3ccnc(C(F)F)c3)c2)ccc1C1CCOCC1] | 0.04 g | 73% |
| Intermediate 73 Starting from Intermediate 53 | 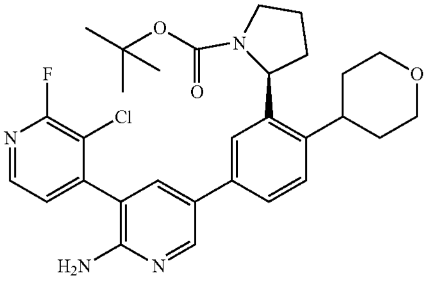 [SMILES: CC(C)(C)OC(=O)N1CCC[C@H]1c1cc(-c2cnc(N)c(-c3ccnc(F)c3Cl)c2)ccc1C1CCOCC1] | 0.072 g | 45% |

-continued
| Intermediate | Structure | Quantity | Yield |
|---|---|---|---|
| Intermediate 74 Starting from Intermediate 54 | 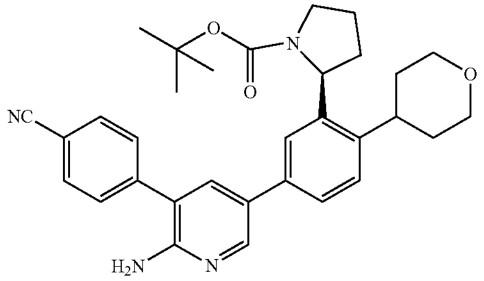 [SMILES: CC(C)(C)OC(=O)N1CCC[C@H]1c1cc(-c2cnc(N)c(-c3ccc(C#N)cc3)c2)ccc1C1CCOCC1] | 0.1 g | 66% |
| Intermediate 75 Starting from Intermediate 63 and 71 | 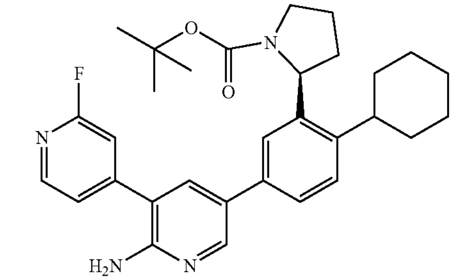 [SMILES: CC(C)(C)OC(=O)N1CCC[C@H]1c1cc(-c2cnc(N)c(-c3ccnc(F)c3)c2)ccc1C1CCCCC1] | 0.05 g | 20% |
| Intermediate 76 Starting from 5-bromo-3-(3-methyl-1,2-oxazol-5-yl)pyridin-2-amine | 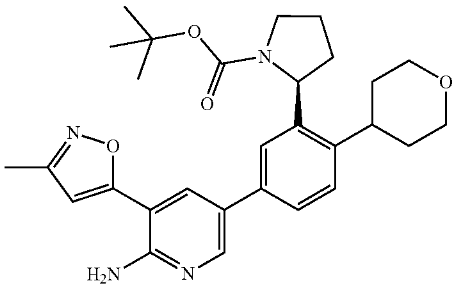 [SMILES: Cc1cc(-c2cc(-c3ccc(C4CCOCC4)c([C@@H]4CCCN4C(=O)OC(C)(C)C)c3)cnc2N)on1] | 0.147 g | 71% |
| Intermediate 77 Starting from Intermediate 56 | 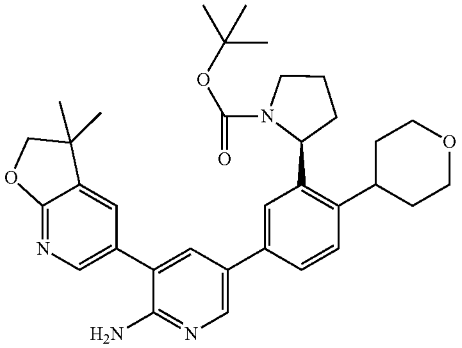 [SMILES: CC(C)(C)OC(=O)N1CCC[C@H]1c1cc(-c2cnc(N)c(-c3cnc4c(c3)C(C)(C)CO4)c2)ccc1C1CCOCC1] | 0.22 g | 41% |
| Intermediate 78 Starting from 2-pyrazinamine, 5-bromo-3-(1-methyl-1H-pyrazol-4-yl) | 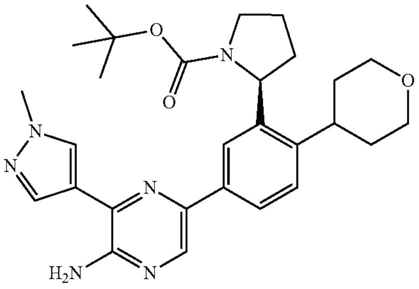 [SMILES: Cn1cc(-c2nc(-c3ccc(C4CCOCC4)c([C@@H]4CCCN4C(=O)OC(C)(C)C)c3)cnc2N)cn1] | 0.111 g | 31% |

-continued
| Intermediate | Structure | Quantity | Yield |
|---|---|---|---|
| Intermediate 79 Starting from Intermediate 59 | 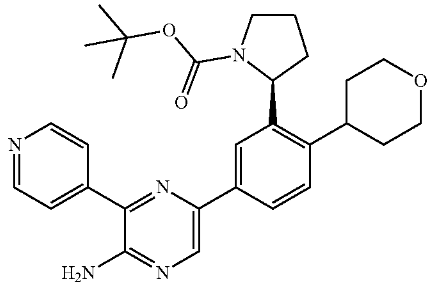 [SMILES: CC(C)(C)OC(=O)N1CCC[C@H]1c1cc(-c2cnc(N)c(-c3ccncc3)n2)ccc1C1CCOCC1] | 0.054 g | 51% |
| Intermediate 80 Starting from Intermediate 60 | 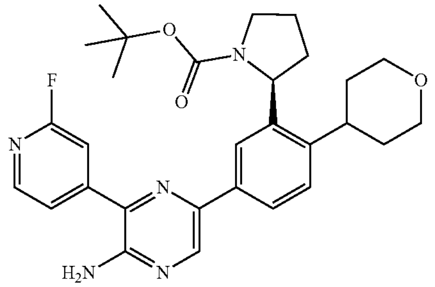 [SMILES: CC(C)(C)OC(=O)N1CCC[C@H]1c1cc(-c2cnc(N)c(-c3ccnc(F)c3)n2)ccc1C1CCOCC1] | 0.107 g | 65% |
| Intermediate 81 Starting from Intermediate 57 | 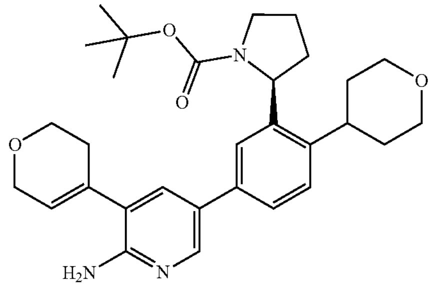 [SMILES: CC(C)(C)OC(=O)N1CCC[C@H]1c1cc(-c2cnc(N)c(C3=CCOCC3)c2)ccc1C1CCOCC1] | 0.250 g | 92% (70% purity) |
| Intermediate 82 Starting from 2-amino-5-bromonicotinonitrile | 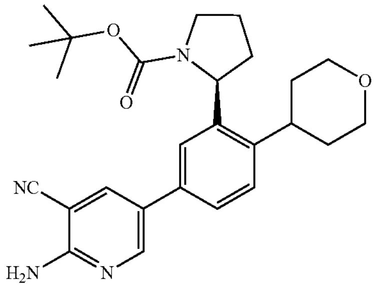 [SMILES: CC(C)(C)OC(=O)N1CCC[C@H]1c1cc(-c2cnc(N)c(C#N)c2)ccc1C1CCOCC1] | 1.92 g | 98% |
| Intermediate 83 Starting from 2-Amino-5-bromopyrazine | 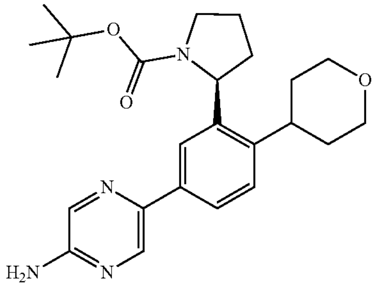 [SMILES: CC(C)(C)OC(=O)N1CCC[C@H]1c1cc(-c2cnc(N)cn2)ccc1C1CCOCC1] | 0.63 g | 86% |

Synthesis of Intermediate 84

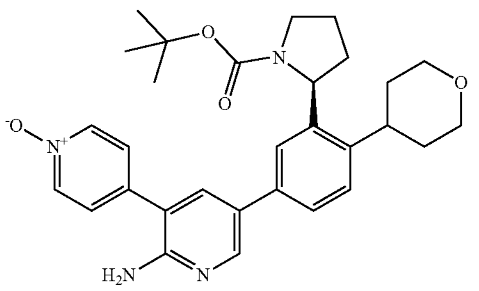

A mixture of intermediate 28 (0.55 g, 1 mmol), Pyridine, 4-bromo-, 1-oxide (0.174 g, 1 mmol), $PdCl_2$(dppf) (0.082 g, 0.1 mmol) and sodium carbonate (0.212 g, 2 mmol) in 1,4-dioxane (15 mL) and water (1.5 mL) was stirred under $N_2$ in a sealed tube at 90° C. for 5 hours. The reaction mixture was cooled down, poured into water and potassium carbonate and the aqueous phase was extracted with ethyl acetate. The organic layer was separated, dried over $MgSO_4$, filtered and evaporated until dryness. The residue was purified by preparative LC (12 g SiOH 30 μm Interchim, from 100% DCM to DCM 90%/MeOH 10%/$NH_4OH$ 0.1%). The pure fractions were collected and evaporated until dryness to give 0.274 g of intermediate 84 (53%).

Synthesis of Intermediate 85

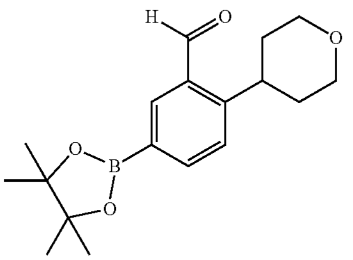 [SMILES: CC1(C)OB(c2ccc(C3CCOCC3)c(C=O)c2)OC1(C)C]

$PdCl_2$(dppf) (5.43 g, 7.43 mmol) was added to a solution of intermediate 5 (20 g, 74.3 mmol), bis(pinacolato)diboron (22.6 g, 89.2 mmol) and potassium acetate (21.88 g, 223 mmol) under a nitrogen atmosphere in 1,4-dioxane (600 mL). The reaction mixture was stirred at 100° C. for 18 h. The reaction mixture was cooled to rt, diluted with AcOEt (1800 mL) and filtered. The filtrate was washed with water (400 mL, three times). The organic layer was dried over $MgSO_4$, filtered and evaporated until dryness to give 23.5 g of intermediate 85 (100%).

Synthesis of Intermediate 86

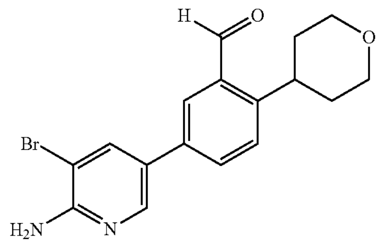 [SMILES: Nc1ncc(-c2ccc(C3CCOCC3)c(C=O)c2)cc1Br]

A solution of 2-amino-3-iodo-5-bromopyridine (42.92 g, 143.6 mmol), intermediate 85 (45.4 g, 143.6 mmol) and sodium carbonate (45.6 g, 430.7 mmol) in 1,4-dioxane (500 mL) and water (125 mL) was degassed during 10 min. After addition of $PdCl_2$(dppf) (11.72 g, 14.4 mmol), the reaction mixture was stirred at 75° C. overnight. The mixture was filtered through a pad of celite and rinsed with DCM/MeOH (10/1, 500 mL). The filtrate was evaporated until dryness and purified by column chromatography over silica gel (mobile phase: DCM/MeOH 100/0 to 90/10). The pure fractions were collected and evaporated until dryness, washed with acetonitrile (75 mL, twice) to give intermediate 86 as a brown solid (27.5 g, 51%).

Synthesis of Intermediate 87

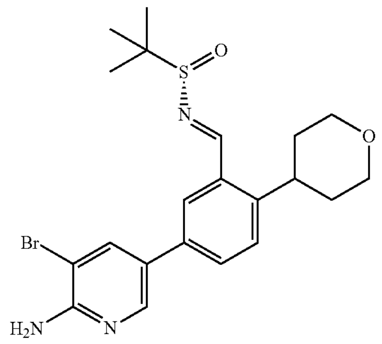 [SMILES: CC(C)(C)[S@](=O)/N=C/c1cc(-c2cnc(N)c(Br)c2)ccc1C1CCOCC1]

Titanium (IV) ethoxide (25.26 g, 110.7 mmol) was added dropwise to a solution of intermediate 86 (10 g, 27.7 mmol) and (S)-(−)-t-butylsulfinamide (6.71 g, 55.37 mmol). The solution was stirred at 45° C. overnight and the mixture was poured into brine (400 mL) and DCM (500 mL) was added. The mixture was filtered through a pad of celite which was washed with DCM (500 mL). The organic layer was separated, dried over $Na_2SO_4$, filtered and evaporated until dryness. The residue was purified by column chromatography over silica gel (mobile phase: DCM/MeOH 100/0 to 90/10). The pure fractions were collected and evaporated until dryness, washed with acetonitrile (20 mL, twice) to give intermediate 87 as a pale brown solid (12 g, 93%).

Synthesis of Intermediate 88

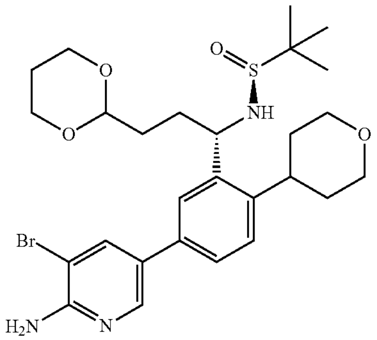 [SMILES: CC(C)(C)[S@](=O)N[C@@H](CCC1OCCCO1)c1cc(-c2cnc(N)c(Br)c2)ccc1C1CCOCC1]

To a mixture of magnesium (9.77 g, 406.96 mmol) in THF (170 mL) were added catalytic amounts of 12 under nitrogen atmosphere. (1,3-dioxan-2-ylethyl) bromide (31.75 g, 162.78 mmol) was added dropwise. The reaction mixture was periodically cooled in a room temperature water bath to prevent over-refluxing. The mixture was stirred at rt for 1 h and then cooled to −65° C. A solution of intermediate 87 (12.6 g, 27.13 mmol) in THF (80 mL) was added dropwise and the reaction mixture was stirred at −65° C. for 1 h and then at rt overnight. A saturated solution of $NH_4Cl$ (120 mL) and ethyl acetate (200 mL) were added. The mixture was filtered through a pad of celite which was washed with ethyl acetate (200 mL). The organic layer was separated, dried over $Na_2SO_4$, filtered and evaporated until dryness. The crude compound was washed with acetonitrile (20 mL, twice) and dried to give intermediate 88 as a brown solid (12.6 g, 80%).

Synthesis of Intermediate 89

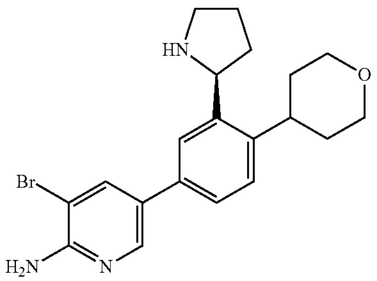 [SMILES: Nc1ncc(-c2ccc(C3CCOCC3)c([C@@H]3CCCN3)c2)cc1Br]

Intermediate 88 (0.35 g, 0.603 mmol) was slowly added to a mixture of TFA (2.66 mL, 34.8 mmol) and water (0.14 mL) to maintain temperature below 25° C. The reaction mixture was stirred at rt for 30 min. Triethylsilane (0.963 mL, 6.028 mmol) was added and the reaction mixture vigorously stirred at rt overnight. The reaction mixture was evaporated till dryness. A purification was performed via preparative LC (stationary phase: irregular SiOH 15-40 μM 4 g, Interchim, mobile phase: DCM/MeOH/$NH_4OH$ 95/5/1 to 90/10/1). The pure fractions were evaporated to give intermediate 89 (0.2 g, 82%).

Synthesis of Intermediate 90

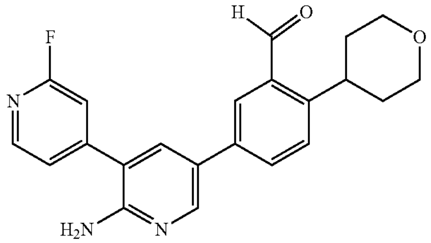 [SMILES: Nc1ncc(-c2ccc(C3CCOCC3)c(C=O)c2)cc1-c1ccnc(F)c1]

Sodium carbonate (0.41 g, 3.88 mmol) was added to a solution of intermediate 86 (1 g, 1.94 mmol), 2-fluoropyridine-4-boronic acid pinacol ester (0.52 g, 2.33 mmol) in water (1.75 mL) and 1,4-dioxane (18.7 mL). The mixture was degassed with a stream of nitrogen for 5 min., then $PdCl_2$(dppf) (0.158 g, 0.194 mmol) was added. The reaction mixture was stirred at 90° C. for 6 hours. The reaction mixture was cooled to rt, water and DCM were added. The aqueous layer was extracted DCM. The organic layer was dried over $MgSO_4$, filtered and evaporated until dryness. A purification was performed via preparative LC (stationary phase: irregular SiOH 15-40 μM 12 g, Grace, mobile phase: DCM/MeOH/$NH_4OH$ 100/0/0 to 90/10/1). The pure fractions were evaporated to give intermediate 90 (0.66 g, 90%).

The following intermediate was prepared via an analogous procedure:

| Intermediate | Structure | Quantity | Yield |
|---|---|---|---|
| Intermediate 91 Starting from intermediate 58 and [3,4'-Bipyridin]-2-amine, 5-bromo | 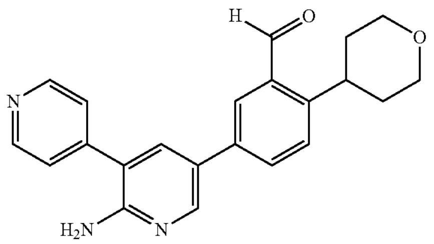 [SMILES: Nc1ncc(-c2ccc(C3CCOCC3)c(C=O)c2)cc1-c1ccncc1] | 0.1 g | 49% |

Synthesis of Intermediate 92

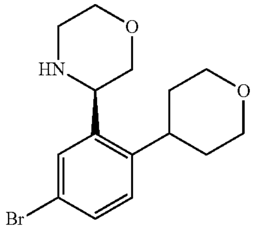

Intermediate 5 (7.39 g, 27.46 mmol) and molecular sieves 4 A (3.6 g) were added to [(2-aminoethoxy)methyl]tributyl stannane (10 g, 27.46 mmol) in DCM (95 mL). The reaction mixture was stirred at rt for 6 h, filtered over Celite® and the filtrate was evaporated till dryness to give the imine. (R,R)-2,2'-Isopropylidenebis(4-phenyl-2-oxazoline) (1.84 g, 5.5 mmol) was added in one portion to a suspension of copper (II) triflate in hexafluoroisopropanol (50 mL). To this mixture was added the imine in hexafluoroisopropanol (50 mL). The reaction mixture was stirred at rt overnight. 1N NaOH was added, the mixture was stirred and extracted with DCM, the organic layer was separated, dried over $MgSO_4$, filtered and evaporated till dryness. A purification was performed via preparative LC (Stationary phase: SiOH 35-40 μm. 330 g interchim, Mobile phase: 100% DCM to 50/50 DCM/AcOEt). The fractions were collected and evaporated until dryness (8.5 g, 95%). Both enantiomers were separated via chiral SFC (Stationary phase: CHIRALPAK AD-H 5 μm 250*30 mm, Mobile phase: 70% CO2, 30% iPrOH(0.3% $iPrNH_2$)) yielding 1.86 g of enantiomer A (20.8%, $[\alpha]_d$: +7.05° (589 nm, c 0.19 w/v %, DMF, 20° C.) and 4.63 g of enantiomer B (intermediate 92, 51.7%, $[\alpha]_d$: −76.67° (589 nm, c 0.27 w/v %, DMF, 20° C.).

The following intermediates were prepared via an analogous procedure:

| Intermediate | Structure | Quantity | Yield |
|---|---|---|---|
| Intermediate 93a Starting from intermediate 5 and {[(1-aminopropan-2-yl) oxy]methyl}tributylstannane | 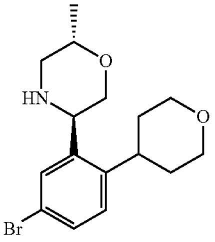 $[\alpha]_d$: −73.4° (589 nm, c 0.29 w/v %, DMF, 20° C.) | 2.6 g | 26% |
| Intermediate 93b Starting from intermediate 5 and {[(1-aminopropan-2-yl) oxy]methyl}tributylstannane | 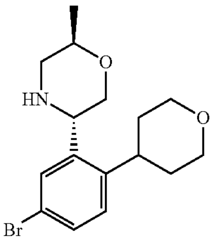 $[\alpha]_d$: +71.3° (589 nm, c 0.24 w/v %, DMF, 20° C.) | 2.8 g | 28% |

-continued

| Intermediate | Structure | Quantity | Yield |
|---|---|---|---|
| Intermediate 94 Starting from intermediate 5 and [(2-aminopropoxy) methyl]tributylstannane | 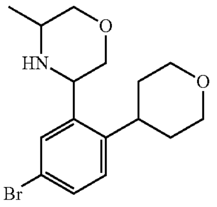 [SMILES: CC1COCC(c2cc(Br)ccc2C2CCOCC2)N1] | 0.8 g | 63% |
| Intermediate 95 Starting from intermediate 5 and 3-[(Tributylstannyl) methoxy]-1-propanamine | 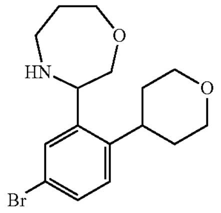 [SMILES: Brc1ccc(C2CCOCC2)c(C2COCCCN2)c1] | 0.54 g | 35% |

Synthesis of Intermediate 96

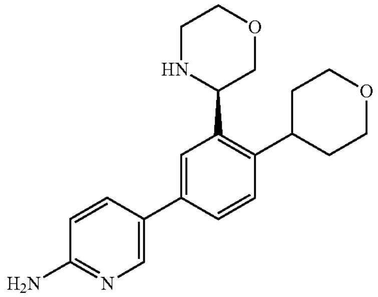 [SMILES: Nc1ccc(-c2ccc(C3CCOCC3)c([C@@H]3COCCN3)c2)cn1]

A mixture of 2-Aminopyridine-5-boronic acid pinacol ester (1.2 g, 5.45 mmol), intermediate 92 (1.44 g, 4.41 mmol), $Pd(PPh_3)_4$ (0.51 g, 0.44 mmol), $Na_2CO_3$ (1.4 g, 13.2 mmol) in Me-THF (50 mL) and water (5 mL) was heated under $N_2$ in a sealed tube at 85° C. for 15 hours. $H_2O$, $K_2CO_3$ and AcOEt were added; the organic layer was extracted, dried over $MgSO_4$, filtered and evaporated until dryness. The residue was purified by preparative LC (SiOH 30 μm Interchim, gradient from 100% DCM to 90% DCM 10% $CH_3OH$ 0.1% $NH_4OH$). The pure fractions were collected and evaporated until dryness yielding intermediate 96 (1.24 g, 83%).

The following intermediate was prepared via an analogous procedure:

| Intermediate | Structure | Quantity | Yield |
|---|---|---|---|
| Intermediate 97 Starting from intermediate 93a | 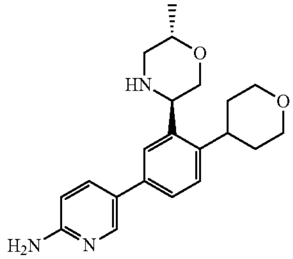 [SMILES: C[C@H]1CN[C@H](c2cc(-c3ccc(N)nc3)ccc2C2CCOCC2)CO1] | 2.3 g | 87% |

Synthesis of Intermediate 98

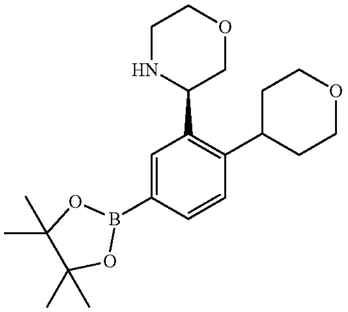 [SMILES: CC1(C)OB(c2ccc(C3CCOCC3)c([C@@H]3COCCN3)c2)OC1(C)C]

A mixture of intermediate 92 (0.28 g, 0.86 mmol), bis(pinacolato)diboron (0.261 g, 1 mmol), $PdCl_2$(dppf) (0.045 g, 0.05 mmol), potassium acetate (0.252 mg, 2.6 mmol) in 1,4-dioxane (8 mL) was stirred at 120° C. using one single mode microwave (Biotage Initiator EXP 60) with a power output ranging from 0 to 400 W for 45 min. The reaction mixture was filtered over Celite®, $H_2O$ was added to the filtrate, the filtrate was extracted with ethyl acetate, the organic layer was separated, dried over $MgSO_4$, filtered and evaporated. Compound 98 was used as it for next step.

The following intermediates were prepared via an analogous procedure:

| Intermediate | Structure | Quantity |
|---|---|---|
| Intermediate 99 Starting from intermediate 94 | 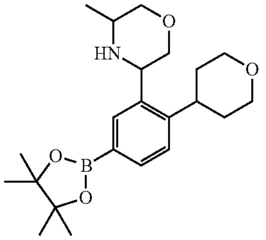 [SMILES: CC1COCC(c2cc(B3OC(C)(C)C(C)(C)O3)ccc2C2CCOCC2)N1] | Used without purification in next step |
| Intermediate 100a Starting from intermediate 93a | 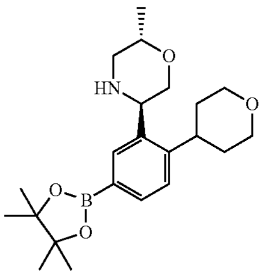 [SMILES: C[C@H]1CN[C@H](c2cc(B3OC(C)(C)C(C)(C)O3)ccc2C2CCOCC2)CO1] | Used without purification in next step |
| Intermediate 100b Starting from intermediate 93b | 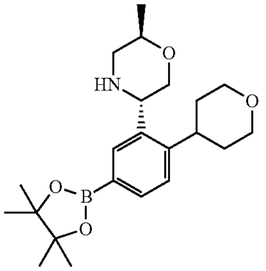 [SMILES: C[C@@H]1CN[C@@H](c2cc(B3OC(C)(C)C(C)(C)O3)ccc2C2CCOCC2)CO1] | Used without purification in next step |

-continued

| Intermediate | Structure | Quantity |
|---|---|---|
| Intermediate 101 Starting from intermediate 95 | 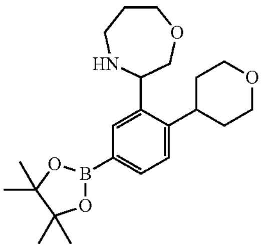 [SMILES: CC1(C)OB(c2ccc(C3CCOCC3)c(C3COCCCN3)c2)OC1(C)C] | Used without purification in next step |

Synthesis of Intermediate 102

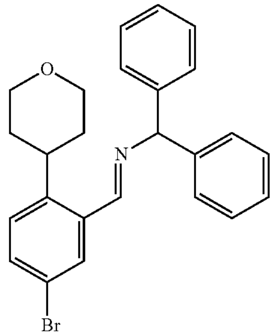 [SMILES: Brc1ccc(C2CCOCC2)c(/C=N/C(c2ccccc2)c2ccccc2)c1]

Magnesium sulfate (3.94 g, 32.7 mmol) and intermediate 5 (4 g, 14.86 mmol) were added successively to a stirred solution of Benhydrylamine (2.64 mL, 14.86 mmol) in DCM (52 mL). The resulting mixture was stirred at rt overnight, filtered. The filtrate was evaporated until dryness, dried under vacuum and used directly in the next step without further purification.

Synthesis of Intermediate 103

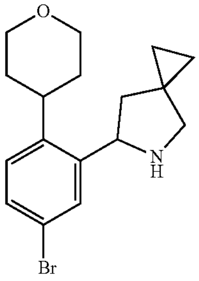 [SMILES: Brc1ccc(C2CCOCC2)c(C2CC3(CC3)CN2)c1]

Intermediate 102 (1.079 g, 2.48 mmol) was dissolved in THF (17 mL) under nitrogen atmosphere and cooled to −78° C. A 1M solution of Potassium tert-butoxide in dry THF (334.6 mg, 2.98 mmol) was added dropwise (changing of color to violet). After 30 min 1,1-bis(iodomethyl)cyclopropane (2.4 g, 7.45 mmol) was added rapidly. The mixture was stirred for 1 h at −78° C., then warmed to room temperature (after 5 min changing of color to grey) and stirred overnight. Water and DCM were added, the phases separated and the aqueous phase extracted with DCM (3×100 mL). The combined organic extracts were dried over $MgSO_4$, filtered, the solvent removed under reduced pressure and the residue obtained dried under high vacuum. This residue was dissolved in acetone (10 mL), 3M HCl (3.56 mL, 10.67 mmol) was added and the mixture stirred at room temperature overnight. The mixture was basified with sat. $Na_2CO_3$ aqueous solution and extracted with DCM. The layers were separated and the aqueous phase extracted with DCM (5×50 mL). The combined organic extracts were dried over $MgSO_4$, filtered and the solvent removed under reduced pressure. The crude mixture was purified by silicagel column chromatography (DCM/MeOH: 0-15%). The pure fractions were collected and evaporated until dryness to give intermediate 103 (425 mg, 51%)

The following intermediate was prepared via an analogous procedure:

| Intermediate | Structure | Quantity | Yield |
|---|---|---|---|
| Intermediate 104 Starting from intermediate 102 and 1,1-Bis(iodomethyl) cyclobutane | 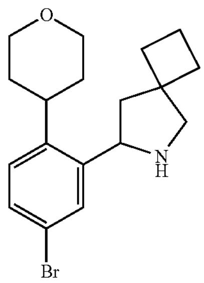 [SMILES: Brc1ccc(C2CCOCC2)c(C2CC3(CCC3)CN2)c1] | 0.128 g | 15% |

Synthesis of Intermediate 105

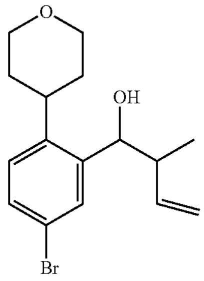 [SMILES: C=CC(C)C(O)c1cc(Br)ccc1C1CCOCC1]

Zinc dust (1.21 g, 18.58 mmol) and crotyl bromide (0.9 mL, 7.43 mmol) were added to a solution of intermediate 5 (1 g, 3.42 mmol) in THF (75 mL). A saturated aqueous solution of $NH_4Cl$ (37.5 mL) was added dropwise to the previous mixture and the reaction stirred at room temperature for 50 min. The mixture was filtered through a pad of celite. The filtrate was acidified with 2N HCl and extracted with EtOAc (3x50 mL). The combined organic extracts were washed with brine, dried over $MgSO_4$, filtered and concentrated. The crude mixture was purified by silicagel column chromatography (Heptane:EtOAc; 0-40%). The pure fractions were collected and evaporated until dryness to give intermediate 105 (1.16 g, 94%).

Synthesis of Intermediate 106

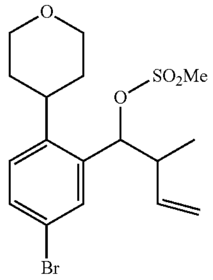 [SMILES: C=CC(C)C(OS(C)(=O)=O)c1cc(Br)ccc1C1CCOCC1]

Triethylamine (0.944 mL, 6.8 mmol) was added at 0° C. to a solution of intermediate 105 (1.16 g, 3.57 mmol) in DCM (35 mL) under argon atmosphere. Then methane sulfonyl chloride (0.414 mL, 5.35 mmol) was added slowly to the previous solution and the mixture warmed to room temperature and stirred for 20 h. The mixture was diluted with water and the layers separated and the aqueous phase was extracted with DCM (3×40 mL). The combined organic extracts were dried over $MgSO_4$, filtered and the solvent removed under reduced pressure. The crude intermediate 106 obtained was dried under high vacuum and used directly in the next step without further purification.

Synthesis of Intermediate 107

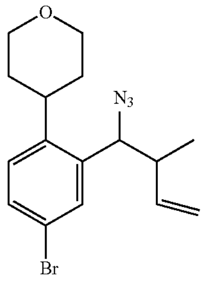 [SMILES: C=CC(C)C(N=[N+]=[N-])c1cc(Br)ccc1C1CCOCC1]

Sodium azide (0.616 g, 9.48 mmol) was added carefully to a solution of intermediate 106 (1.53 g, 3.79 mmol) in dry DMF (35 mL) and the mixture stirred at 45° C. overnight. The mixture was diluted with water (200 mL) and extracted with EtOAc (3x40 mL). The combined organic extracts were washed with brine (25 mL), dried over $MgSO_4$, filtered and the solvent removed under reduced pressure. The crude mixture was purified by silicagel column chromatography (Heptane:EtOAc; 0-10%). The pure fractions were collected and evaporated until dryness to give intermediate 107 (0.929 g, 67%).

Synthesis of Intermediate 108 and 109

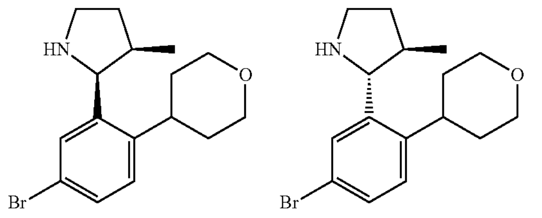 [SMILES: C[C@@H]1CCN[C@@H]1c1cc(Br)ccc1C1CCOCC1 ; C[C@@H]1CCN[C@H]1c1cc(Br)ccc1C1CCOCC1]

A solution of Borane dimethyl sulphide complex (0.550 mL, 5.8 mmol) in 2.9 mL of dry THF (2 M solution) was added dropwise at 0° C. to a solution of cyclohexene (1.18 mL, 11.6 mmol) in 1.7 mL of dry THF. The resulting white suspension was stirred at 0° C. for 1 h, then cooled to −15° C. and a solution of intermediate 107 (0.677 g, 1.93 mmol) in dry THF (5.4 mL) was added dropwise to it. The reaction was allowed to warm to room temperature, stirred at this temperature for 3 h. The reaction was quenched with MeOH at 0° C. and evaporated to dryness. The crude mixture was dissolved in EtOAc and washed with 1M HCl aqueous solution. The layers were separated and the aqueous phase extracted with EtOAc (10×20 mL). The combined organic extracts were dried over $MgSO_4$, filtered and the solvent removed under reduced pressure. The crude mixture was purified by silicagel column chromatography (DCM:MeOH; 0-15%). All fractions containing product were combined and concentrated to afford a mixture of intermediates 108 and 109 (0.421 g, 67%) which was separated by reverse phase using a GILSON Semi-Preparative System, operated by Trilution software, equipped with a Phenomenex Gemini C18 100A column (100 mm long×30 mm I.D.; 5 μm particles) at 25° C., with a flow rate of 20 or 40 mL/min. A gradient elution (method ISO15-AF): [start: 85% $H_2O$ (0.1% HCOOH)−15% ACN-MeOH; finish: 85% $H_2O$ (0.1% HCOOH)−15% ACN-MeOH]. The desired fractions were collected and partially concentrated to removed the organic solvents. Then the fractions were basified with saturated $Na_2CO_3$ aqueous solution and extracted with EtOAc. The combined organic extracts were dried over $MgSO_4$, filtered, the solvent removed under reduced pressure and dried under high vacuum to afford intermediate 108 (0.079 g, 12.6%) and intermediate 109 (0.180 g, 28.7%).

Synthesis of Intermediate 110

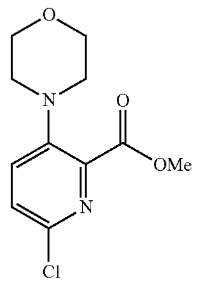 [SMILES: COC(=O)c1nc(Cl)ccc1N1CCOCC1]

To a solution of Methyl 6-chloro-3-fluoropicolinate (1.64 g, 8.65 mmol) in DMSO (10 mL) were added morpholine (0.908 mL, 10.38 mmol) and N,N-diisopropylethylamine (4.52 mL, 25.9 mmol). The reaction mixture was stirred at rt over the week-end. The mixture was diluted with AcOEt. The organic phase was washed with water and the aqueous phase extracted with AcOEt. The combined organic extracts were dried over $MgSO_4$, filtered and the solvent removed under reduced pressure. The crude mixture was purified by silicagel column chromatography (Heptane:EtOAc; 0-20%). The pure fractions were collected and evaporated until dryness to give intermediate 110 (1.82 g, 82%).

Synthesis of Intermediate 111

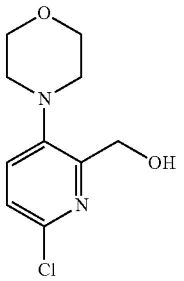 [SMILES: OCc1nc(Cl)ccc1N1CCOCC1]

To a mixture of intermediate 110 (1.7 g, 6.62 mmol) and calcium chloride (1.47 g, 13.25 mmol) in ethanol (17 mL) was added sodium borohydride (0.751 g, 19.9 mmol) at 0° C. The reaction mixture was stirred for 2 h at 0° C. and 4 h at rt. Then water was added to the reaction mixture, and it was extracted with DCM. The organic layer was dried over anhydrous magnesium sulfate and filtered. The crude mixture was purified by flash column chromatography eluting with a mixture of Heptane/AcOEt (40%) to give intermediate 111 (1.37 g, 90%).

Synthesis of Intermediate 112

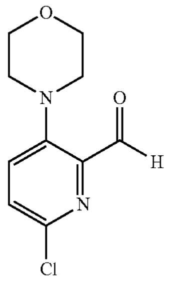 [SMILES: O=Cc1nc(Cl)ccc1N1CCOCC1]

To a solution of intermediate 111 (1.37 g, 5.99 mmol) in dry DCM (30 mL) was added Dess-Martin Periodinane (3.81 g, 8.99 mmol). The reaction mixture was stirred at rt for 3 h. The reaction was quenched with $Na_2S_2O_3$ and $Na_2CO_3$ was added until basic pH. Then it was extracted with DCM, the organic phase was dried over $MgSO_4$, filtered and the solvent was concentrated in vacuo. The crude mixture was purified by flash column chromatography eluting with a mixture of Heptane/AcOEt (50%) to yield intermediate 112 (1.34 g, 99%).

Synthesis of Intermediate 113

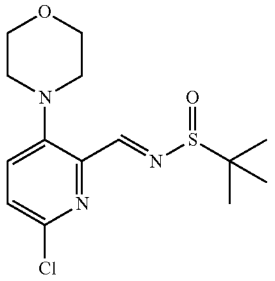 [SMILES: CC(C)(C)S(=O)/N=C/c1nc(Cl)ccc1N1CCOCC1]

Titanium (IV) ethoxide (4.96 mL, 23.65 mmol) was added dropwise under nitrogen atmosphere to a solution of intermediate 112 (1.34 g, 5.91 mmol) and 2-methyl-2-propanesulfinamide in dry THF (17 mL). The mixture was stirred at room temperature for 16 h. The reaction mixture was diluted with DCM and brine. The resulting precipitate was removed by filtration through celite and washed with DCM. The layers were separated and the aqueous phase extracted with DCM. The combined organic extracts were dried over $MgSO_4$, filtered and the solvent removed under reduced pressure. The crude mixture was purified by flash column chromatography eluting with a mixture of Heptane/AcOEt (50%) to afford intermediate 113 (1.3 g, 67%).

Synthesis of Intermediate 114

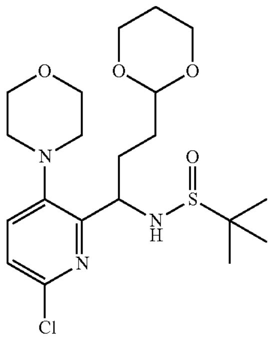 [SMILES: CC(C)(C)S(=O)NC(CCC1OCCCO1)c1nc(Cl)ccc1N1CCOCC1]

(1,3-dioxan-2-ylethyl)magnesium bromide (28.7 mL, 14.37 mmol) was added dropwise at −78° C. to a solution of intermediate 113 (1.58 g, 4.79 mmol) in dry THF (49 mL). The mixture was stirred at −78° C. for 1 h, quenched with a saturated $NH_4C_1$ aqueous solution and slowly warmed to room temperature. The mixture was diluted with EtOAc and the aqueous phase was extracted with EtOAc. The combined organic extracts were dried over $MgSO_4$, filtered and the solvent removed under reduced pressure. The crude mixture was purified by flash column chromatography over silica gel, eluting with a mixture of Heptane/AcOEt (60%) to yield intermediate 114 (1.82 g, 85%).

Synthesis of Intermediate 115

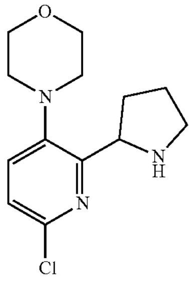 [SMILES: Clc1ccc(N2CCOCC2)c(C2CCCN2)n1]

Intermediate 114 (2 g, 4.48 mmol) was slowly added to a mixture of TFA (19.8 mL, 259 mmol) and water (1.3 mL) to maintain temperature below 25° C. The reaction mixture was stirred at rt for 30 min. Triethylsilane (7.16 mL, 44.8 mmol) was added and the reaction mixture vigorously stirred at rt overnight. The reaction mixture was evaporated till dryness. The crude mixture was purified by silicagel column chromatography, gradient in DCM/DCM:MeOH (9:1) (50%) to yield intermediate 115 (1.09 g, 88%).

Synthesis of Intermediate 116

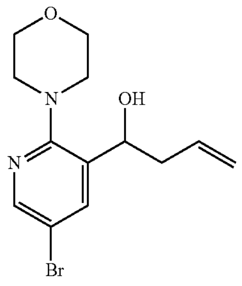 [SMILES: C=CCC(O)c1cc(Br)cnc1N1CCOCC1]

Zinc dust (1.27 g, 19.4 mmol) and allyl bromide (0.67 mL, 7.75 mmol) were added to a solution of 5-bromo-2-(morpholin-4-yl)pyridine-3-carbaldehyde (1.05 g, 3.9 mmol) in THF (75 mL). $NH_4Cl$ (sat. aq. Solution, 39 mL) was added dropwise to the previous mixture and the reaction stirred at room temperature for 1 h. The mixture was filtered through a pad of celite. The filtrate was acidified with 2N HCl and extracted with EtOAc (3×50 mL). The combined organic extracts were washed with brine, dried over $MgSO_4$, filtered and concentrated. The crude mixture was purified by silicagel column chromatography (Heptane:EtOAc; 0-40%) to yield intermediate 116 (1.09 g, 89%).

Synthesis of Intermediate 117

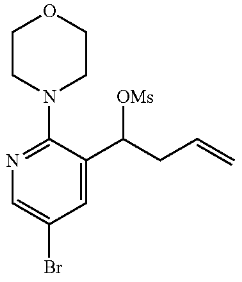 [SMILES: C=CCC(OS(C)(=O)=O)c1cc(Br)cnc1N1CCOCC1]

Triethylamine (0.922 mL, 6.6 mmol) was added at 0° C. to a solution of intermediate 116 (1.09 g, 3.48 mmol) in DCM (35 mL) under argon atmosphere. Then methanesulfonyl chloride (0.404 mL, 5.2 mmol) was added slowly to the previous solution and the mixture warmed to room temperature and stirred for 2 h. The mixture was diluted with water and the layers separated and the aqueous phase was extracted with DCM (3x40 mL). The combined organic extracts were dried over $MgSO_4$, filtered and the solvent removed under reduced pressure. The yellow oil obtained was dried under high vacuum and used directly in the next step without further purification.

Synthesis of Intermediate 118

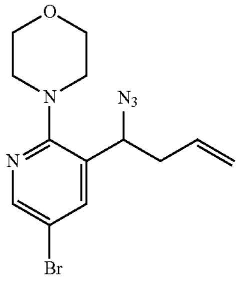 [SMILES: C=CCC(N=[N+]=[N-])c1cc(Br)cnc1N1CCOCC1]

Sodium azide (0.429 g, 6.6 mmol) was added carefully to a solution of intermediate 117 (1.29 g, 3.3 mmol) in dry DMF (25 mL) and the mixture stirred at 60° C. for 5 hours. The mixture was diluted with water (100 mL) and extracted with EtOAc (3x30 mL). The combined organic extracts were washed with brine (25 mL), dried over $MgSO_4$, filtered and the solvent removed under reduced pressure. The crude mixture was purified by silicagel column chromatography (Heptane:EtOAc; 0-10%) yielding intermediate 118 (0.72 g, 64%).

Synthesis of Intermediate 119

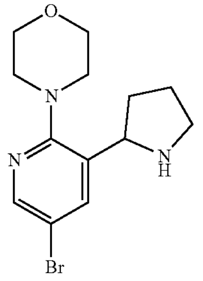 [SMILES: Brc1cnc(N2CCOCC2)c(C2CCCN2)c1]

A solution of Borane dimethyl sulfide complex (0.6 mL, 6.1 mmol) in dry THF (2M solution, 3 mL) was added dropwise at 0° C. to a solution of cyclohexene (1.2 mL, 12.2 mmol) in dry THF (2 mL). The resulting white suspension was stirred at 0° C. for 1 h, then cooled to −15° C. and a solution of intermediate 118 (0.691 g, 2.04 mmol) in dry THF (6 mL) was added dropwise. The reaction was allowed to warm to room temperature and stirred overnight at this temperature. The reaction was quenched with MeOH at 0° C., the mixture was evaporated to dryness and the crude mixture was purified by silicagel column chromatography (DCM:MeOH; 0-15%) yielding intermediate 119 (0.47 g, 71%).

Synthesis of Intermediate 120

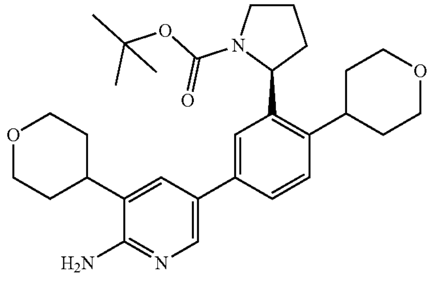 [SMILES: CC(C)(C)OC(=O)N1CCC[C@H]1c1cc(-c2cnc(N)c(C3CCOCC3)c2)ccc1C1CCOCC1]

To a solution of intermediate 81 (0.335 g, 0.53 mmol, 80% purity) in methanol (20 mL) was added Pd/C 10% under nitrogen atmosphere. The resulting reaction mixture was stirred at room temperature under hydrogen atmosphere for 3 hours. After completion of the reaction, the catalyst was filtered off on Celite® and washed with methanol. The filtrate was concentrated under reduced pressure to yield intermediate 120 (0.232 g, 60%, 70% purity)

Synthesis of Intermediate 121

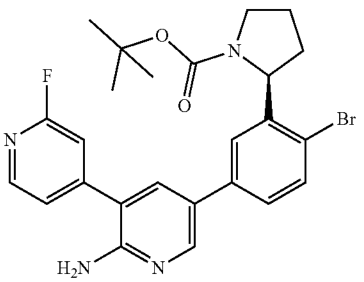 [SMILES: CC(C)(C)OC(=O)N1CCC[C@H]1c1cc(-c2cnc(N)c(-c3ccnc(F)c3)c2)ccc1Br]

A mixture of intermediate 18 (13.45 g, 42.7 mmol), intermediate 21 (19.3 g, 42.7 mmol), $PdCl_2$(dppf) (3.49 g, 4.27 mmol) and sodium carbonate (13.6 g, 128.1 mmol) in 1,4-dioxane (386 mL) and water (64 mL) under $N_2$ was heated at 90° C. for 3 hours. The reaction mixture was cooled to rt, diluted with ethyl acetate (1000 mL) and filtered. The filtrate was washed with water (3*300 mL), the aqueous layer was extracted with ethyl acetate. The organic layer was dried over $MgSO_4$, filtered and evaporated until dryness. The residue was purified by chromatography over silica gel (petroleum ether/ethyl acetate: from 100/0 to/100). The fractions were collected and evaporated until dryness to give intermediate 121 (15.7 g, 70%).

Synthesis of Intermediate 122

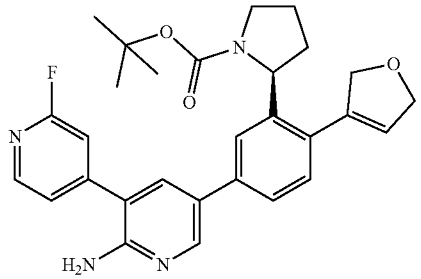 [SMILES: CC(C)(C)OC(=O)N1CCC[C@H]1c1cc(-c2cnc(N)c(-c3ccnc(F)c3)c2)ccc1C1=CCOC1]

A mixture of intermediate 121 (0.846 g, 1.59 mmol), 2,5-dihydrofuran-3-ylboronic acid pinacol ester (2.43 g, 3.18 mmol), $PdCl_2$(dppf) (0.130 g, 0.159 mmol) and sodium carbonate (0.506 g, 4.77 mmol) in 1,4-dioxane (42 mL) and water (8 mL) under $N_2$ was heated at 95° C. for 18 hours. The reaction mixture was cooled to rt, diluted with ethyl acetate (200 mL) and filtered. The filtrate was washed with water (3*50 mL), the aqueous layer was extracted with ethyl acetate. The organic layer was dried over $MgSO_4$, filtered and evaporated until dryness. The residue was purified by chromatography over silica gel (petroleum ether/ethyl acetate: from 100/0 to/100) followed by preparative HPLC (Phenomenex Gemini 150*25 mm*10 μm; water (0.05% ammonia hydroxide v/v) and MeCN: from 55/45 to 25/75). The fractions were collected and evaporated until dryness to give intermediate 122 (0.39 g, 47%).

The following intermediates were prepared via an analogous procedure:

| Intermediate | Structure | Quantity | Yield |
|---|---|---|---|
| Intermediate 123 Starting from intermediates 121 and 1-Methanesulfonyl-4-(tetramethyl-1,3,2-dioxaborolan-2-yl)-1,2,3,6-tetrahydropyridine | 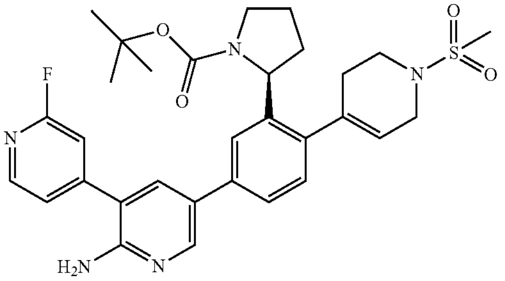 [SMILES: CC(C)(C)OC(=O)N1CCC[C@H]1c1cc(-c2cnc(N)c(-c3ccnc(F)c3)c2)ccc1C1=CCN(S(C)(=O)=O)CC1] | 0.75 g | 98% |
| Intermediate 124 Starting from intermediates 121 and 1-Acetyl-5,6-dihydro-2H-pyridine-4-boronic acid, pinacol ester | 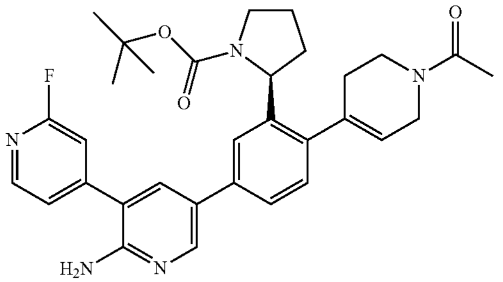 [SMILES: CC(=O)N1CC=C(c2ccc(-c3cnc(N)c(-c4ccnc(F)c4)c3)cc2[C@@H]2CCCN2C(=O)OC(C)(C)C)CC1] | 0.56 g | 78% |

-continued

| Intermediate | Structure | Quantity | Yield |
|---|---|---|---|
| Intermediate 125 Starting from intermediates 121 and 3,6-Dihydro-2H-thiopyran-4-ylboronic acid pinacol ester | 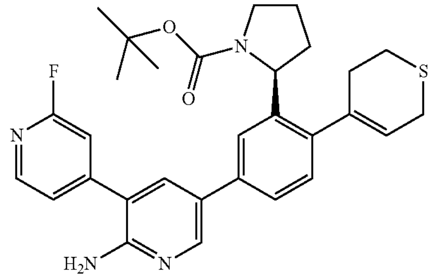 [SMILES: CC(C)(C)OC(=O)N1CCC[C@H]1c1cc(-c2cnc(N)c(-c3ccnc(F)c3)c2)ccc1C1=CCSCC1] | 0.53 g | 75% |
| Intermediate 126 Starting from intermediates 121 and 1,1-Dioxo-1,2,3,6-tetrahydro-2H-thiopyran-4-yl-boronic acid pinacol ester | 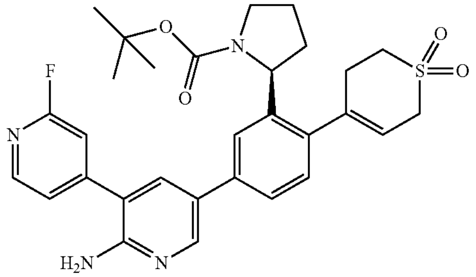 [SMILES: CC(C)(C)OC(=O)N1CCC[C@H]1c1cc(-c2cnc(N)c(-c3ccnc(F)c3)c2)ccc1C1=CCS(=O)(=O)CC1] | 0.28 g | Quant. |
| Intermediate 127 Starting from intermediates 121 and 4-Methoxycyclohexene-1-boronic acid pinacol ester | 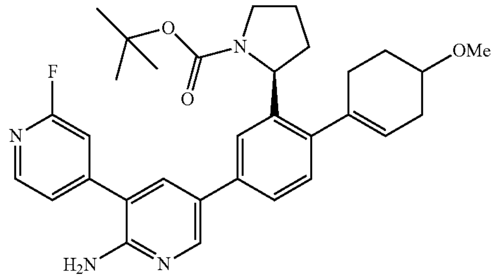 [SMILES: COC1CC=C(c2ccc(-c3cnc(N)c(-c4ccnc(F)c4)c3)cc2[C@@H]2CCCN2C(=O)OC(C)(C)C)CC1] | 0.45 g | Quant. |
| Intermediate 128 Starting from intermediates 121 and 4,4-Difluoro-1-cyclohexene-1-boronic acid pinacol ester | 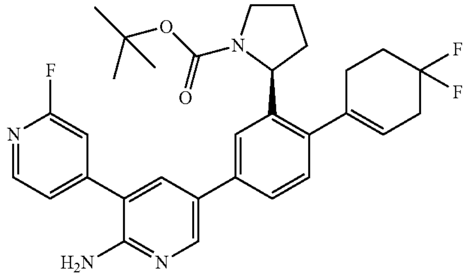 [SMILES: CC(C)(C)OC(=O)N1CCC[C@H]1c1cc(-c2cnc(N)c(-c3ccnc(F)c3)c2)ccc1C1=CCC(F)(F)CC1] | 0.22 g | 67% |

Synthesis of Intermediate 129

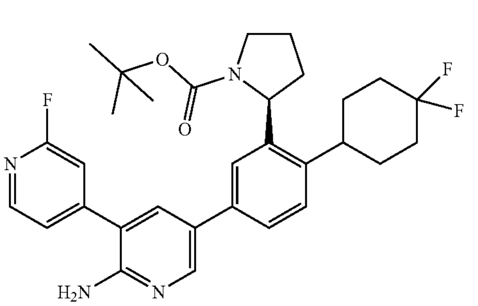 [SMILES: CC(C)(C)OC(=O)N1CCC[C@H]1c1cc(-c2cnc(N)c(-c3ccnc(F)c3)c2)ccc1C1CCC(F)(F)CC1]

A mixture of intermediate 128 (0.15 g, 0.272 mmol), Pd/C 10% (0.15 g, 0.272 mmol) in MeOH (3 mL) was hydrogenated under 5 bars pressure at 80° C. overnight. The reaction mixture was filtered over celite, washed with DCM/MeOH and the filtrate was evaporated. The residue was purified by preparative LC (12 g SiOH 40 μm irregular, mobile phase: DCM/MeOH/$NH_4OH$ 98/2/0 to 90/10/0.1) The pure fractions were collected and evaporated until dryness yielding 0.017 g of intermediate in (11%).

The following intermediate was prepared via an analogous procedure:

| Intermediate | Structure | Quantity | Yield |
| --- | --- | --- | --- |
| Intermediate 130 Starting from intermediate 127 | 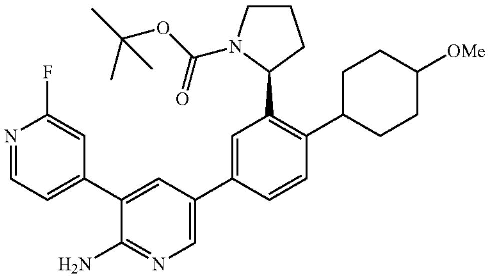 [SMILES: COC1CCC(c2ccc(-c3cnc(N)c(-c4ccnc(F)c4)c3)cc2[C@@H]2CCCN2C(=O)OC(C)(C)C)CC1] | 0.045 g | 10% |

Synthesis of Intermediate 131

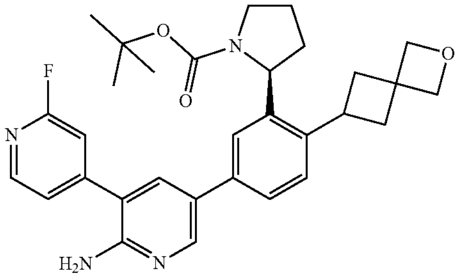 [SMILES: CC(C)(C)OC(=O)N1CCC[C@H]1c1cc(-c2cnc(N)c(-c3ccnc(F)c3)c2)ccc1C1CC2(COC2)C1]

To a solution of intermediate 121 (0.2 g, 0.39 mmol), tris(trimethylsilyl)silane (0.145 g, 0.584 mmol), [Ir(dtbbpy)(ppy)$_2$]$PF_6$ (0.035 g, 0.039 mmol), sodium carbonate (0.124 g, 1.17 mmol), 6-Bromo-2-oxaspiro[3.3]heptane (0.138 g, 0.779 mmol) in DME (3.5 mL) was added a solution of Nickel (II) chloride ethylene glycol dimethyl ether complex (4.3 mg, 0.02 mmol) and 4'-di-tert-butyl-2, 2'-bipyridine (5.3 mg, 0.02 mmol) in DME (1.5 mL). The reaction mixture was degassed with nitrogen and irradiated under blue light in a Hepatochem device for 20 hours (Hepatochem photoreactor—irradiated with a Cree lamp 18 W). Water and ethyl acetate were added, the organic layer was separated, dried over $MgSO_4$, filtered and evaporated until dryness. The residue was purified by preparative LC (irregular SiOH 40 µm 12 g, from 100% DCM to DCM 95%/MeOH 5%/$NH_4OH$ 0.1%). The fractions were collected and evaporated until dryness to give intermediate 131 (0.094 g, 45%).

The following intermediates were prepared via an analogous procedure:

| Intermediate | Structure | Quantity | Yield |
| --- | --- | --- | --- |
| Intermediate 132 Starting from intermediate 121 | 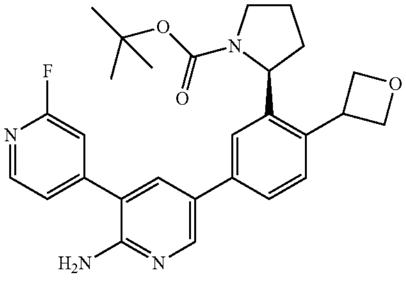 [SMILES: CC(C)(C)OC(=O)N1CCC[C@H]1c1cc(-c2cnc(N)c(-c3ccnc(F)c3)c2)ccc1C1COC1] | 0.2 g | 70% |
| Intermediate 132b Starting from intermediate 121 | 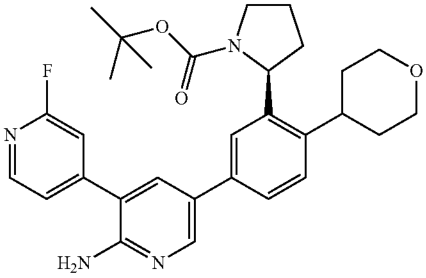 [SMILES: CC(C)(C)OC(=O)N1CCC[C@H]1c1cc(-c2cnc(N)c(-c3ccnc(F)c3)c2)ccc1C1CCOCC1] | 0.053 g | 26% |

Synthesis of Intermediate 133

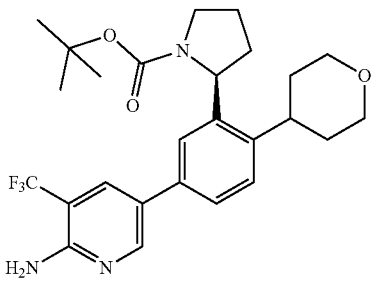 [SMILES: CC(C)(C)OC(=O)N1CCC[C@H]1c1cc(-c2cnc(N)c(C(F)(F)F)c2)ccc1C1CCOCC1]

A mixture of intermediate 83 (0.25 g, 0.589 mmol), ammonium persulfate (0.205 g, 0.898 mmol), (Ir[dF($CF_3$)ppy]2(dtbpy))$PF_6$ (10 mg, 0.009 mmol) and sodium trifluoromethanesulfinate (0.14 g, 0.897 mmol) in DMSO (12.5 mL) was irradiated with a Kessil lamp for 5 hours. The solution was poured into $H_2O$ then extracted with DCM. The organic layer was dried over $MgSO_4$, filtered and evaporated until dryness. The residue was purified by preparative LC (12 g of SiOH 40 μm Buchi, gradient from 100% DCM to 90% DCM 10% $CH_3OH$ 0.1% $NH_4OH$). The fractions were collected and evaporated until dryness. Another purification was performed by preparative LC (12 g of SiOH 15 μm Buchi, gradient from 100% DCM to 90% DCM 10% MeOH 0.1% $NH_4OH$). The fractions were collected and evaporated until dryness yielding intermediate 133 (0.064 g, 22%).

Synthesis of Intermediate 134

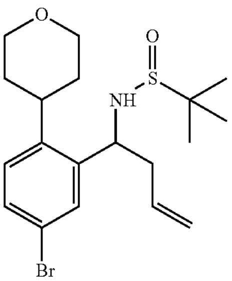 [SMILES: C=CCC(NS(=O)C(C)(C)C)c1cc(Br)ccc1C1CCOCC1]

Allylmagnesium chloride (12 mL, 20.5 mmol) was added dropwise to a solution of intermediate 10 (1.9 g, 5.1 mmol) in THF (55 mL) at −70° C. under $N_2$. The reaction mixture was stirred for 1 hour, poured into $H_2O$ and $NH_4Cl$. The aqueous phase was extracted with AcOEt. The organic layer was dried over $MgSO_4$, filtered and evaporated until dryness yielding intermediate 134 (2.07 g, 98%).

Synthesis of Intermediate 135

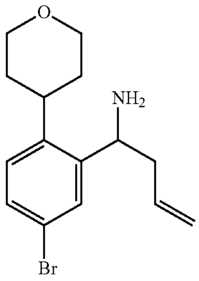 [SMILES: C=CCC(N)c1cc(Br)ccc1C1CCOCC1]

HCl 3M (35 mL) was added slowly to a solution of intermediate 134 (2.07 g, 5 mmol) in THF (18 mL) at 5° C. The reaction mixture was stirred for 20 hours at room temperature. Water was added and the aqueous phase was basified by addition of potassium carbonate, then extracted with AcOEt. The organic layer was dried over $MgSO_4$, filtered and evaporated until dryness yielding intermediate 135 (1.6 g, Quant.).

Synthesis of Intermediate 136

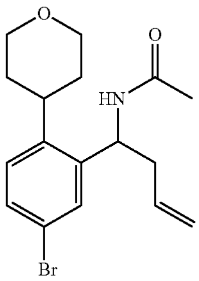 [SMILES: C=CCC(NC(C)=O)c1cc(Br)ccc1C1CCOCC1]

A mixture of intermediate 135 (1.6 g, 5.2 mmol) and $Et_3N$ (2.9 mL, 20.9 mmol) in DCM (25 mL) was cooled at 5° C.; Acetic anhydride (1.45 mL, 15.5 mmol) was added and the reaction mixture was stirred for 3 hours. Water and potassium carbonate were added and the organic layer was extracted, dried over $MgSO_4$, filtered and evaporated until dryness. The residue was purified by preparative LC (12 g of SiOH 15 μm Interchim, gradient from 100% DCM to 90% DCM 10% MeOH 0.1% $NH_4OH$). The fractions were collected and evaporated until dryness yielding intermediate 136 (1.55 g, 85%).

Synthesis of Intermediate 137

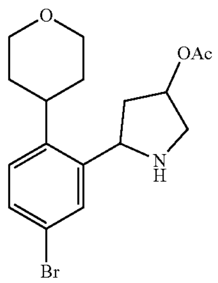 [SMILES: CC(=O)OC1CNC(c2cc(Br)ccc2C2CCOCC2)C1]

Iodine (10.8 g, 42.6 mmol) was added to a solution of intermediate 136 (5 g, 14.2 mmol) in THF (40 mL) and water (10 mL) at room temperature. The reaction mixture was heated at 50° C. for 1 hour, then poured into a saturated solution of $NaHCO_3$. The aqueous phase was extracted with AcOEt. The organic layer was washed with a saturated solution of $Na_2S_2O_3$, dried over $MgSO_4$, filtered and evaporated until dryness. The residue was purified by preparative LC (80 g of SiOH 35-40 μm GraceResolv, gradient from 100% DCM to 90% DCM 10% $CH_3OH$ 0.1% $NH_4OH$. The fractions were collected and evaporated until dryness yielding intermediate 137 (2.21 g, 42%).

Synthesis of Intermediate 138

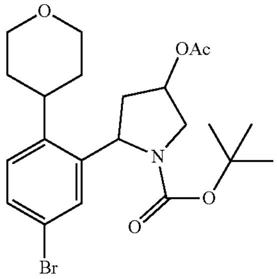 [SMILES: CC(=O)OC1CC(c2cc(Br)ccc2C2CCOCC2)N(C(=O)OC(C)(C)C)C1]

Di-tert-butyl dicarbonate (3.56 g, 16.3 mmol) was added to a solution of intermediate 137 (2 g, 5.43 mmol), 4-Dimethylaminopyridine (0.133 g, 1.09 mmol) in DCM (60 mL) at room temperature. The reaction mixture was stirred for 2 days, poured into water. The organic layer was extracted, dried over $MgSO_4$, filtered and evaporated until dryness. The residue was purified by preparative LC (12 g of SiOH 35-40 μm GraceResolv, gradient from 100% DCM to 95% DCM 5% $CH_3OH$). The fractions were collected and evaporated until dryness yielding intermediate 138 (2.19 g, 86%).

Synthesis of Intermediate 139

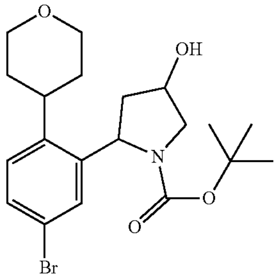 [SMILES: CC(C)(C)OC(=O)N1CC(O)CC1c1cc(Br)ccc1C1CCOCC1]

NaOH 1M (5 mL, 5 mmol) was slowly added to a mixture of intermediate 138 (2.1 g, 4.5 mmol) in MeOH (25 mL) at 5° C. The reaction mixture was stirred for 2 hours. MeOH was evaporated at room temperature and the residue was taken up with water then neutralized with HCl 1N. The insoluble was filtered and dried yielding intermediate 139 (1.92 g, Quantitatif).

Synthesis of Intermediate 140

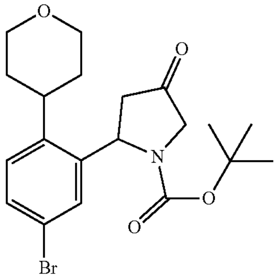 [SMILES: CC(C)(C)OC(=O)N1CC(=O)CC1c1cc(Br)ccc1C1CCOCC1]

DMSO (0.5 mL, 7 mmol) was added dropwise to oxalyl chloride (1.76 mL, 3.52 mmol) in DCM (5 mL) at −78° C., the solution was stirred for 10 min then intermediate 139 (0.5 g, 1.17 mmol) in DCM (5 mL) was added dropwise and the reaction was stirred at −50° C. for 30 min. After dropwise addition of $Et_3N$ (1.5 mL, 10.8 mmol), the reaction mixture was allowed to warm to room temperature over 30 min. The mixture was poured into $NH_4Cl$ and $H_2O$. The organic layer was extracted, dried over $MgSO_4$, filtered and evaporated until dryness. The residue was purified by preparative LC (24 g of SiOH 35-40 μm GraceResolv, gradient from 100% DCM to 95% DCM 5% $CH_3OH$). The fractions were collected and evaporated until dryness yielding intermediate 140 (0.312 g, 63%).

Synthesis of Intermediate 141

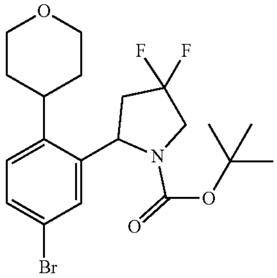 [SMILES: CC(C)(C)OC(=O)N1CC(F)(F)CC1c1cc(Br)ccc1C1CCOCC1]

Diethylaminosulfur trifluoride (0.31 mL, 2.19 mmol) was added dropwise to a solution of intermediate 140 (0.31 g, 0.73 mmol) in DCM (6 mL) at −70° C. under $N_2$. The mixture was stirred for 15 hours at room temperature, cooled at −70° C. then diethylaminosulfur trifluoride (0.31 mL, 2.19 mmol) was added dropwise. The reaction mixture was stirred for 2.5 hours at room temperature. Water was added and the aqueous phase was basified potassium carbonate. The organic layer was extracted, dried over $MgSO_4$, filtered and evaporated until dryness. The residue was purified by preparative LC (12 g of SiOH 35-40 μm GraceResolv, gradient from 100% DCM to 95% DCM 5% $CH_3OH$). The fractions were collected and evaporated until dryness yielding intermediate 141 (0.3 g, 92%).

Synthesis of Intermediate 142

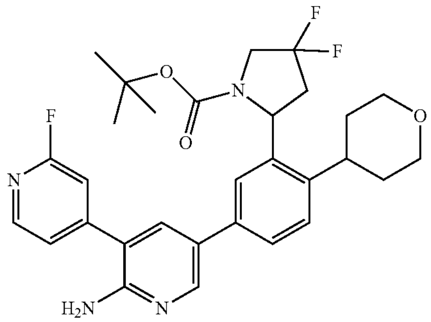 [SMILES: CC(C)(C)OC(=O)N1CC(F)(F)CC1c1cc(-c2cnc(N)c(-c3ccnc(F)c3)c2)ccc1C1CCOCC1]

A mixture of intermediate 18 (0.233 g, 0.74 mmol), intermediate 141 (0.3 g, 0.67 mmol), $PdCl_2$(dppf) (0.071 g, 0.087 mmol) and sodium carbonate (0.143 g, 1.34 mmol) in 1,4-dioxane (10 mL) and water (1 mL) under $N_2$ was heated at 90° C. for 8 hours. Water and potassium carbonate were added. The aqueous layer was extracted with ethyl acetate. The organic layer was dried over $MgSO_4$, filtered and evaporated until dryness. The residue was purified by preparative LC (24 g of SiOH 35-40 μm GraceResolv, graduent from 100% DCM to 90% DCM 10% $CH_3OH$ 0.1% $NH_4OH$). The fractions were collected and evaporated until dryness yielding intermediate 142 (0.225 g, 92%).

Synthesis of Intermediate 143

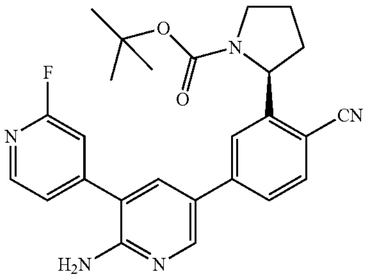 [SMILES: CC(C)(C)OC(=O)N1CCC[C@H]1c1cc(-c2cnc(N)c(-c3ccnc(F)c3)c2)ccc1C#N]

A mixture of intermediate 121 (300 mg, 0.58 mmol), Zinc cyanide (316 mg, 2.7 mmol), Pd $(PPh_3)_4$ (67.5 mg, 0.06 mmol) in DMF (2.9 mL) was stirred in a Biotage apparatus at 140° C. for 45 min. Water and AcOEt were added, the organic layer was separated, dried over MgSO4, filtered and evaporated. A purification was performed via preparative LC (Stationary phase: irregular SiOH 40 μm 25 g, Mobile phase: 98/2 to 90% DCM 10% $CH_3OH$ 0.1% $NH_4OH$) yielding intermediate 143 (0.2 g, 74%).

Synthesis of Intermediate 144

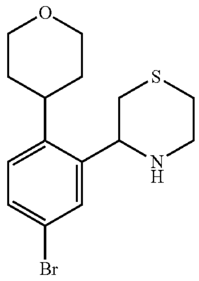 [SMILES: Brc1ccc(C2CCOCC2)c(C2CSCCN2)c1]

Intermediate 5 (0.5 g, 1.86 mmol) and molecular sieves 4A (0.1 g) were added to SLAP™ (0.38 g, 2.32 mmol) in DCM (8 mL). The reaction mixture was stirred at rt 5 h, filtered over Celite©, the filtrate was evaporated till dryness to afford the imine which was added to a solution of $[Ir(dtbbpy)(ppy)_2]PF_6$ (17 mg, 0.0186 mmol), Copper (II) trifluoromethanesulfonate (0.67 g, 1.86 mmol) and Bismuth (III) trifluoromethane sulfonate (0.612 g, 0.93 mmol) in MeCN (10 mL). The reaction mixture was stirred at rt for 16 h under blue light (34 W—Hepatochem photoreactor—irraditated with a Kessil lamp). The reaction mixture was poured into $H_2O$ and $K_2CO_3$ and extracted with AcOEt. The organic layer was dried over MgSO4, filtered and evaporated until dryness. The residue was purified by preparative LC (Stationary phase: irregular SiOH 15-40 μm 40 g GraceResolv, graduent from 100% heptane to 50% heptane 50% AcOEt). The fractions were collected and evaporated until dryness yielding intermediate 144 (0.4 g, 63%).

Synthesis of Intermediate 145

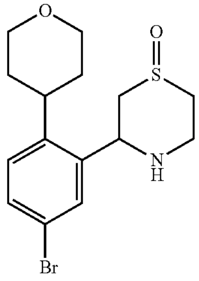 [SMILES: O=S1CCNC(c2cc(Br)ccc2C2CCOCC2)C1]

m-CPBA (0.221 g, 0.85 mmol) was added portionwise to intermediate 144 (0.291 g, 0.85 mmol) in DCM (12 mL) at 0° C. The reaction mixture was stirred at room temperature for 15 hours. $H_2O$ and $K_2CO_3$ were added and the mixture was stirred for 1 hour. The organic layer was extracted, dried over $MgSO_4$, filtered and evaporated until dryness yielding intermediate 145 (0.3 g, 98%).

Synthesis of Intermediate 146

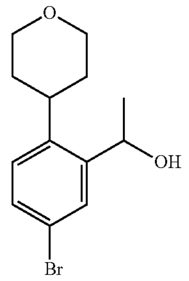 [SMILES: CC(O)c1cc(Br)ccc1C1CCOCC1]

Methylmagnesium bromide (1.4 M in THF, 3.8 mL, 5.35 mmol) was added at 0° C. to a solution of intermediate 5 (1.2 g, 4.46 mmol) in dry THF (8 mL) under nitrogen atmosphere. The reaction was stirred at 0° C. for 30 min and then warmed to room temperature for 1.5 h. The reaction was quenched with a saturated $NH_4C_1$ aqueous solution. The aqueous phase was extracted with EtOAc (5x15 mL). The combined organic extracts were dried over $MgSO_4$, filtered and the solvent removed under reduced pressure. The crude mixture was purified by silica gel column chromatography gradient n-heptane/Ethyl Acetate from 100/0 to 65/35. The desired fractions were collected and evaporated in vacuo to afford intermediate 146 (1.18 g, 93%).

Synthesis of Intermediate 147

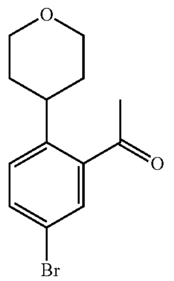 [SMILES: CC(=O)c1cc(Br)ccc1C1CCOCC1]

Manganese oxide (8.45 g, 86.6 mmol) was added to a solution of intermediate 146 (1.18 g, 4.13 mmol) in DCM (20 mL). The resulting suspension was stirred at room temperature overnight. The mixture was filtered through a pad of celite and was washed with DCM and MeOH. The solvents were evaporated under reduced pressure and the crude mixture was purified by flash silicagel column chromatography (Heptane:EtOAc; 0-50%). The fractions were collected and concentrated to afford intermediate 147 (0.51 g, 44%).

Synthesis of Intermediate 148

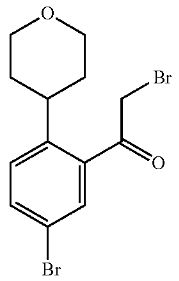 [SMILES: O=C(CBr)c1cc(Br)ccc1C1CCOCC1]

Tetra-n-butylammonium tribromide (1.6 g, 3.31 mmol) was added to a solution of intermediate 147 (0.94 g, 3.31 mmol) in acetonitrile (10 mL). The reaction was stirred at rt for 2 h. The solvent was concentrated under reduced pressure, and the residue was re-dissolved in EtOAc. The solution was washed with saturated aqueous $NaHCO_3$, dried over $MgSO_4$, and concentrated under reduced pressure. The crude mixture was purified by silicagel column chromatography (Heptane:EtOAc; 0-35%). All fractions were combined and concentrated to afford intermediate 148 (1.14 g, 95%).

Synthesis of Intermediate 149

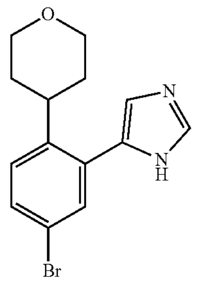 [SMILES: Brc1ccc(C2CCOCC2)c(-c2cnc[nH]2)c1]

Intermediate 148 (0.6 g, 1.66 mmol) was dissolved in formamide (3 mL) and the reaction was stirred for 11 h at 165° C. The mixture obtained was diluted with EtOAc, washed with saturated $NaHCO_3$ and the layers were separated. The aqueous phase was extracted with DCM (3x20 mL), the combined organic extracts dried over $MgSO_4$, filtered and concentrated under reduced pressure. The crude mixture was purified by silicagel column chromatography with Heptane/EtOAc (gradient: 0-70% EtOAc). All fractions were combined and concentrated to afford intermediate 149 (0.250 g, 49%).

Synthesis of Intermediate 150

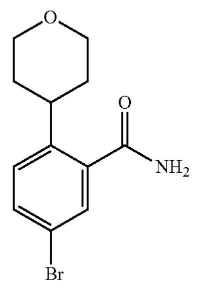 [SMILES: NC(=O)c1cc(Br)ccc1C1CCOCC1]

To a solution of intermediate 5 (0.6 g, 2.23 mmol) in DMF (20 mL) was added oxone (0.75 g, 2.45 mmol). The reaction mixture was stirred at rt for 48 hours. 1N HCl was used to dissolve the salts and the aqueous phase was extracted with ethyl acetate. The organic layer was washed with 1N HCl (×3) and brine, dried over $Na_2SO_4$ and the solvent was reduced under pressure. The crude mixture was purified by flash chromatography using Heptane/Ethyl acetate 0% to 100% as gradient. The desired fractions were collected and concentrated yielding intermediate 150 (0.46 g, 66%).

Synthesis of Intermediate 151

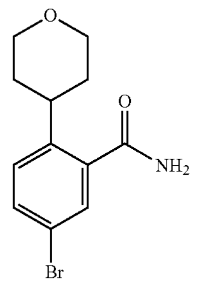 [SMILES: NC(=O)c1cc(Br)ccc1C1CCOCC1]

To a solution of intermediate 150 (0.46 g, 1.48 mmol) in dry THF (20 mL) was added portionwise 1,1-carbonylimidazole (0.36 g, 2.22 mmol). The mixture was stirred at rt for 2 h. An ammonium hydroxide solution (0.91 g/mL, 11.4 mL, 74 mmol) was added and the reaction was stirred at rt overnight. The reaction mixture was diluted with ethyl acetate (50 ml) and washed with water. The phases were separated and the aqueous layer was extracted with Ethyl acetate (5×30 mL). The organic layer was dried over MgSO4, filtered and evaporated until dryness. The residue was purified by flash chromatography using Heptane/Ethyl acetate 0% to 100% as gradient. The desired fractions were collected and concentrated to afford intermediate 151 (0.349 g, 82%).

Synthesis of Intermediate 152

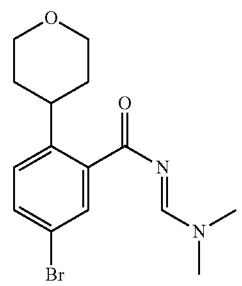 [SMILES: CN(C)/C=N/C(=O)c1cc(Br)ccc1C1CCOCC1]

A solution of intermediate 151 (0.27 g, 0.95 mmol) in DMF-DMA (3.4 mL, 25.6 mmol) was stirred and heated at 110° C. overnight. The reaction mixture was concentrated and used directly in the next reaction.

Synthesis of Intermediate 153

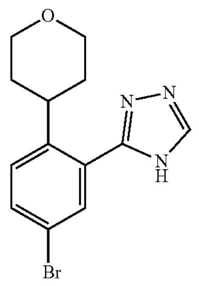 [SMILES: Brc1ccc(C2CCOCC2)c(-c2nnc[nH]2)c1]

To a solution of intermediate 152 (0.32 g, 0.95 mmol) in AcOH (1.68 mL) was added hydrazine monohydrate (0.101 mL, 2.08 mmol). The reaction mixture was stirred and heated at 120° C. for 1 hour. The reaction mixture was concentrated and was triturated with diethyl ether, filtered and the solid was dried under high vacuum yielding intermediate 150 (0.3 g, Quant.).

Synthesis of Intermediate 154

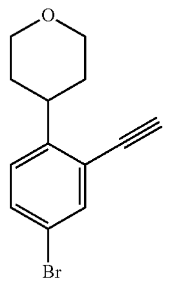

Dimethyl(1-diazo-2-oxopropyl)phosphonate (0.4 mL, 2.68 mmol) was added to a mixture of intermediate 5 (0.6 g, 2.23 mmol) and potassium carbonate (0.62 g, 4.46 mmol) in methanol (30 mL). The mixture was stirred at r.t. for 4 h. Methanol was evaporated in vacuo. Half saturated aqueous solution of $NaHCO_3$ was added and the aqueous phase was extracted with dichloromethane (×4). The combined organic extracts were dried over $MgSO_4$, filtered and concentrated. The residue was purified by flash column chromatography (Heptane/EtOAc gradient from 100:0 to 80:20) yielding intermediate 154 (0.45 g, 76%).

Synthesis of Intermediate 155

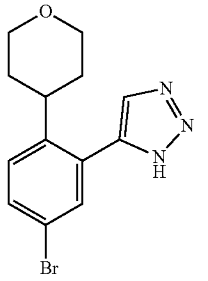 [SMILES: Brc1ccc(C2CCOCC2)c(-c2cnn[nH]2)c1]

Intermediate 154 (0.25 g, 0.943 mmol) and copper iodide (9 mg, 0.047 mmol) were added in a vial which was sealed with a screw-cap septum. It was backfilled with nitrogen (3 times), then trimethylsilyl azide (0.19 mL, 1.41 mmol) was added via syringe, followed by addition of DMF/MeOH (4/1) (2 mL). The mixture was stirred at 80° C. for 10 h. The solvents were evaporated and the mixture was diluted with water and AcOEt. The layers were separated and the aqueous phase extracted with AcOEt. The combined organic extracts were dried over $MgSO_4$, filtered and concentrated. The residue was purified by flash column chromatography (Heptane/AcOEt gradient from 100:0 to 85:15) yielding intermediate 155 (0.15 g, 52%).

Synthesis of Intermediate 156

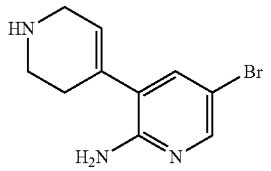 [SMILES: Nc1ncc(Br)cc1C1=CCNCC1]

A mixture of intermediate 58 (0.52 g) and a hydrogen chloride solution (4 M in dioxane, 8 mL) in dioxane was stirred at rt overnight. The solvents were evaporated in vacuo and the crude mixture was used in the next step without further purification.

Synthesis of Intermediate 157

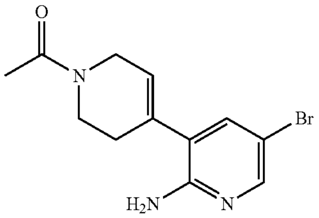 [SMILES: CC(=O)N1CC=C(c2cc(Br)cnc2N)CC1]

Triethylamine (0.51 mL, 3.67 mmol) was added to a mixture of intermediate 156 (0.427 g, 1.47 mmol), acetic anhydride (0.15 mL, 1.62 mmol) in DCM (15 mL) at room temperature. The mixture was stirred overnight. The solvents were evaporated and the crude mixture was purified by flash column chromatography over silica gel, gradient: DCM/DCM-MeOH (9:1) from 100/0 to 0/100% yielding intermediate 157 (0.41 g, 90%).

Synthesis of Intermediate 158

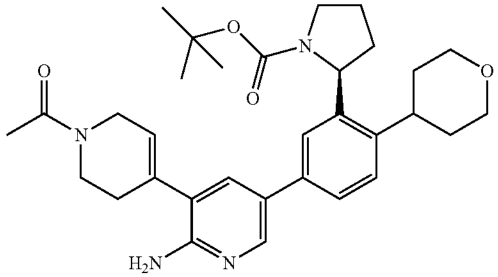 [SMILES: CC(=O)N1CC=C(c2cc(-c3ccc(C4CCOCC4)c([C@@H]4CCCN4C(=O)OC(C)(C)C)c3)cnc2N)CC1]

Sodium carbonate (139 mg, 1.31 mmol) was added to a solution of intermediate 157 (0.243 g, 0.66 mmol), intermediate 62 (0.3 g, 0.66 mmol) in water (2 mL) and 1,4-dioxane (12 mL). The mixture was degassed with a stream of nitrogen for 5 min., then $PdCl_2$(dppf) (27 mg, 0.033 mmol) was added. The reaction mixture was stirred at 90° C. overnight. The reaction mixture was cooled to rt, water and AcOEt were added. The aqueous layer was extracted with ethyl acetate. The organic layer was dried over $MgSO_4$, filtered and evaporated until dryness. The residue was purified by silicagel chromatography (DCM/DCM:MeOH (4:1) from 100/0 to 0/100. The fractions were collected and evaporated until dryness to give 0.252 g of intermediate 158 (53%, purity 75%).

Synthesis of Intermediate 159

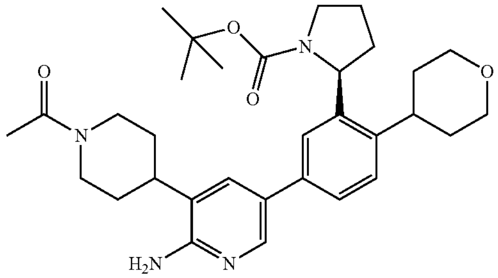 [SMILES: CC(=O)N1CCC(c2cc(-c3ccc(C4CCOCC4)c([C@@H]4CCCN4C(=O)OC(C)(C)C)c3)cnc2N)CC1]

To a solution of intermediate 158 (0.252 g, 0.35 mmol, 75% purity) in methanol (15 mL) was added Pd/C 10% under nitrogen atmosphere. The resulting reaction mixture was stirred at room temperature under hydrogen atmosphere for 3 hours. After completion of the reaction, the catalyst was filtered off on celite and washed with methanol. The filtrate was concentrated under reduced pressure to get intermediate 159 (0.205 g, 97%, 90% purity).

Synthesis of Intermediate 160

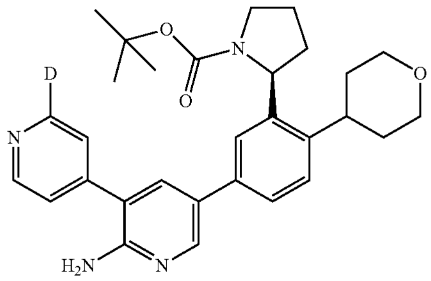

A mixture of intermediate 30 (0.1 g, 0.187 mmol), Pd/C (10 mg, 0.094 mmol) in MeOD (10 mL) was deuterated with D2 (1 atm) at room temperature in a round bottom flask and stirred for 20 hours. The mixture was filtered through a pad of Celite® and the filtrate was evaporated until dryness. The residue was purified by preparative LC (12 g of SiOH 30 μm Interchim, gradient from 100% DCM to 90% DCM 10% $CH_3OH$ 0.1% $NH_4OH$). The fractions were collected and evaporated until dryness yielding intermediate 160 (0.067 g, 71%).

Synthesis of Intermediate 161

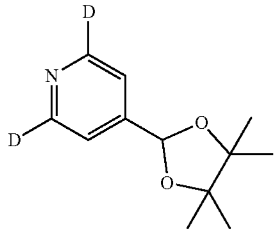 [SMILES: [2H]c1cc(C2OC(C)(C)C(C)(C)O2)cc([2H])n1]

A mixture of 2,6-Dichloropyridine-4-boronic acid, pinacol ester (1 g, 3.65 mmol), Pd/C (0.194 g, 1.82 mmol) in MeOD (20 mL) was deuterated with D2 (1 atm) at room temperature in a round bottom flask and stirred for 20 hours. The mixture was filtered through a pad of Celite® and the filtrate was evaporated until dryness used directly in the next step.

Synthesis of Intermediate 162

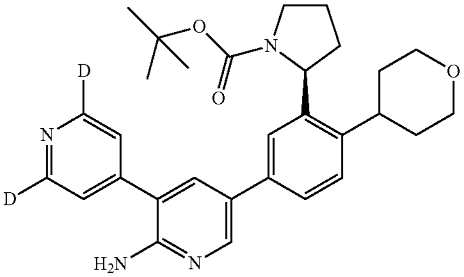 [SMILES: [2H]c1cc(-c2cc(-c3ccc(C4CCOCC4)c([C@@H]4CCCN4C(=O)OC(C)(C)C)c3)cnc2N)cc([2H])n1]

A mixture of intermediate 27 (0.5 g, 1 mmol), intermediate 161 (0.516 g, 2.5 mmol), sodium carbonate (0.21 g, 2 mmol), $PdCl_2$(dppf) (0.04 g, 0.05 mmol) in 1,4-dioxane (10 mL) and water (1 mL) was heated at 90° C. under $N_2$ for 3 hours in a sealed tube. The reaction mixture was poured into water and potassium carbonate and extracted with ethyl acetate. The organic layer was dried over MgSO4, filtered and evaporated until dryness. The residue was purified by preparative LC (12 g of SiOH 35-40 μm GraceResolv, graduent from 100% DCM to 88% DCM 12% CH3OH 0.1% $NH_4OH$) yielding intermediate 162 (0.204 g, 41%).

Synthesis of Intermediate 163

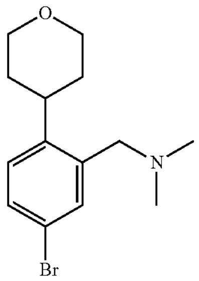 [SMILES: CN(C)Cc1cc(Br)ccc1C1CCOCC1]

To a solution of Benzenemethanamine, 5-amino-N,N-dimethyl-2-(tetrahydro-2H-pyran-4-yl) (6.82 g, 26.75 mmol) in HBr (48% in water, 2 mL) cooled in an ice bath, was added dropwise sodium nitrite (2.03 g, 29.42 mmol) in water. The mixture was stirred for 30 min at 0-4° C. Then this mixture was added dropwise to a solution of copper bromide (2.12 g, 14.71 mmol) in HBr (48% in water, 5.5 mL) cooled in an ice bath. The reaction mixture was stirred at 100° C. for 2 hours, then poured into aqueous NaOH (10 mol/L, 200 mL) and was extracted with ethyl acetate (100 mL*5). The organic layer was dried over $MgSO_4$, filtered and evaporated until dryness. The residue was purified by column chromatography over silica gel (eluent: petrol/ethyl acetate=100:0-2:1) yielding intermediate 163 (6.02 g, 76.6%) as a white solid.

Synthesis of Intermediate 164

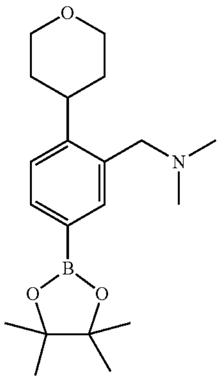

A mixture of intermediate 163 (1.5 g, 5.1 mmol), bis (pinacolato)diboron (1.5 g, 6.1 mmol), $PdCl_2$(dppf) (0.267 g, 0.3 mmol) and potassium acetate (1.5 g, 15.3 mmol) in 1,4-dioxane (20 mL) was stirred at 120° C. using one single mode microwave (Biotage Initiator EXP 60) with a power output ranging from 0 to 400 W for 45 min. The reaction mixture was cooled to rt, filtered over celite and water was added. The organic layer was dried over $MgSO_4$, filtered and evaporated until dryness. The residue was cristallized in DIPE/pentane, the precipitate was filtered off (catalyst derivatives) and the filtrate was evaporated and used as it for next step.

Synthesis of Intermediate 165

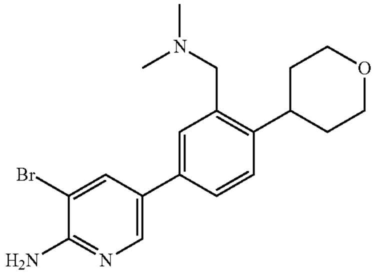 [SMILES: CN(C)Cc1cc(-c2cnc(N)c(Br)c2)ccc1C1CCOCC1]

In a sealed tube, a mixture of intermediate 164 (1.75 g, 5.1 mmol), 3-Bromo-5-iodopyridin-2-amine (1.5 g, 5.1 mmol), sodium carbonate (1.6 g, 15.2 mmol), $PdCl_2$(dppf) (0.415 g, 0.51 mmol) in 1,4-dioxane (22.6 mL) and water (5.3 mL) was stirred at 90° C. for 16 h. The mixture was poured into $H_2O$ and potassium carbonate and extracted with AcOEt. The organic layer was dried over $MgSO_4$, filtered and evaporated until dryness. The residue was purified by preparative LC (Stationary phase: irregular 15-40 μm 80 g Merck, Mobile phase: 0.4% $NH_4OH$, 96% DCM, 4% MeOH) yielding intermediate 165 (0.685 g, 35%).

Intermediate 166 was prepared starting from intermediate 165 and following an analogous reaction protocol as was used for intermediate 158.

| Intermediate | Structure | Quantity | Yield |
|---|---|---|---|
| Intermediate 166 Starting from intermediate 165 and 2-(4-tert-Butoxycarbonylpiperazin-1-yl)pyridine-4-boronic acid, pinacol ester | 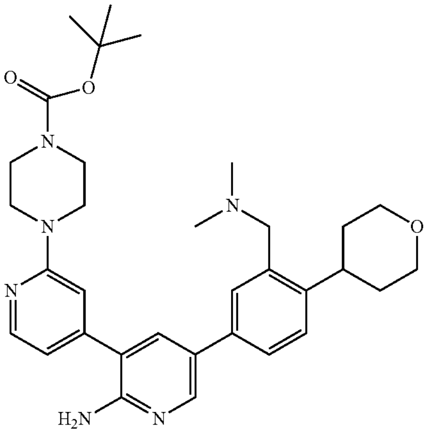 [SMILES: CN(C)Cc1cc(-c2cnc(N)c(-c3ccnc(N4CCN(C(=O)OC(C)(C)C)CC4)c3)c2)ccc1C1CCOCC1] | 0.128 g | 87% |

Synthesis of Intermediate 167

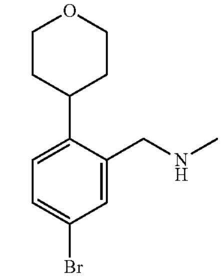 [SMILES: CNCc1cc(Br)ccc1C1CCOCC1]

A mixture of intermediate 5 (0.4 g, 1.49 mmol) and methylamine (aqueous solution, 0.129 mL, 1.49 mmol) in MeOH (5 mL) and acetic acid (five drops) was stirred at room temperature for 15 min. Sodiumtriacetoxyborohydride (0.945 g, 4.46 mmol) was added to the resulting mixture and the mixture was stirred at room temperature for 2 h. 1 eq of methylamine (0.130 ml) and 1.5 eq of sodiumtriacetoxyborohydride (470 mg) were added to the reaction mixture which was stirred at room temperature overnight. The mixture was evaporated under vacuo and diluted with water, extracted with dichloromethane three times. The combined organic phases were dried over $MgSO_4$, filtered and concentrated under reduced pressure. The residue was purified by flash chromatography (dichloromethane/(dichloromethane/methanol 9:1) gradient 100:0 to 0:100). The desired fractions were collected and the solvent removed under reduced pressure to afford 0.15 g of intermediate 167 (0.15 g, 35%).

Synthesis of Intermediate 168

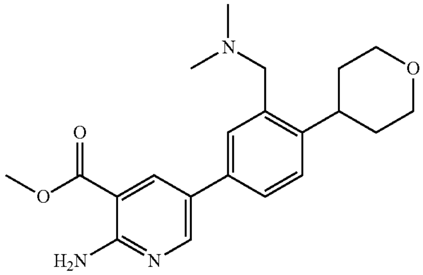 [SMILES: COC(=O)c1cc(-c2ccc(C3CCOCC3)c(CN(C)C)c2)cnc1N]

Sodium carbonate (2.36 g, 22.24 mmol) was added to a solution of intermediate 163 (3.35 g, 11.12 mmol) and methyl 2-amino-5-(4,4,5,5-tetramethyl-1,3,2-dioxaborolan-2-yl) nicotinate (4.02 g, 14.5 mmol) in 1,4-dioxane (60 mL) and water (12 mL). The mixture was degassed with a stream of nitrogen for 5 min, then $PdCl_2$(dppf) (0.455 g, 0.56 mmol) was added. The reaction mixture was stirred at 90° C. overnight. The reaction was diluted with water (20 mL). The layers were separated and the aqueous phase extracted with DCM (3×20 mL). The combined organic extracts were dried over $MgSO_4$, filtered and the solvent removed under reduced pressure. The crude mixture was purified by silica-gel column chromatography (Heptane/EtOAc: 0-40%). The desired fractions were collected and the solvent removed under reduced pressure to afford intermediate 168 (3.3 g, 79%).

Synthesis of Intermediate 169

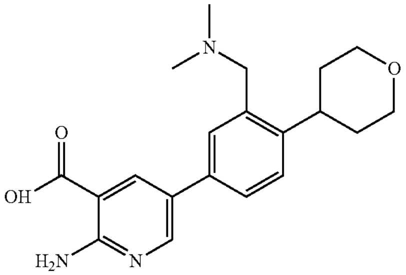 [SMILES: CN(C)Cc1cc(-c2cnc(N)c(C(=O)O)c2)ccc1C1CCOCC1]

Lithium hydroxide (1.09 g, 17.9 mmol) was added to a solution of intermediate 168 in methanol (12 mL) and water (3 mL). The reaction mixture was stirred at 55° C. for 14 h. Methanol was evaporated under reduced pressure and the residue obtained was diluted with EtOAc and water. Organic layer was discarded, the aqueous layer was acidified with HCl 6N and extracted with EtOAc (10×20 mL). The organic layer and aqueous layer were filtrated under reduce pressure to obtain a brown solid washed with DCM and dried to yield intermediate 169 (1.05 g, 65%).

Synthesis of Final Compounds

Preparation of Co. 1 ($1^{st}$ Approach)

Synthesis of Co.1

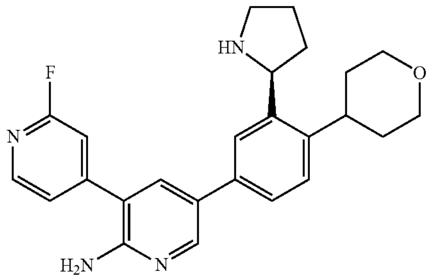 [SMILES: Nc1ncc(-c2ccc(C3CCOCC3)c([C@@H]3CCCN3)c2)cc1-c1ccnc(F)c1]

A mixture of intermediate 18 (21.7 g, 67.4 mmol), intermediate 14 (16.04 g, 51.7 mmol), $PdCl_2$(dppf) (6.78 g, 8.3 mmol) and sodium carbonate (11 g, 103.4 mmol) in 1,4-dioxane (800 mL) and water (80 mL) under $N_2$ was heated at 80° C. for 4 hours. The reaction mixture was cooled to rt, water and potassium carbonate were added. The aqueous layer was extracted with ethyl acetate. The organic layer was dried over $MgSO_4$, filtered and evaporated until dryness. The residue was purified by preparative LC (SiOH 30-40 μm GraceResolv, from 100% DCM to DCM 80%/MeOH 20%/$NH_4OH$ 1%). The fractions were collected and evaporated until dryness to give Co.1 which was further purified in multiple batches via preparative LC (Stationary phase: irregular SiOH 40 μm 300 g, mobile phase: DCM 96%/MeOH 4%/$NH_4OH$ 0.5%). The pure fractions were collected and evaporated until dryness to give Co.1 (15.3 g, 71%). Co.1 was taken up in acetonitrile, heated at 50° C. 15 min, cooled down. The compound was filtered off and dried yielding 11.5 g of Co.1 (53%) as an off-white powder.$[\alpha]_d$: −42.22° (589 nm, c 0.27 w/v %, DMF, 20° C.); m.p.=218° C. (DSC).

The following compound was prepared via an analogous procedure:

| Compound | Structure | Quantity | Yield |
|---|---|---|---|
| Co. 1b | 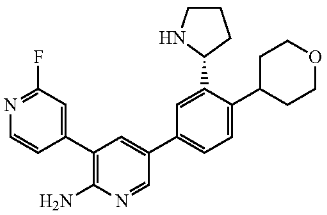 $[\alpha]_d$: +20.3° (589 nm, c 0.093, w/v %, MeOH, 23° C.) | 0.085 g | 54% |

Preparation of Co. 1 (2nd Approach)

Synthesis of Co.1

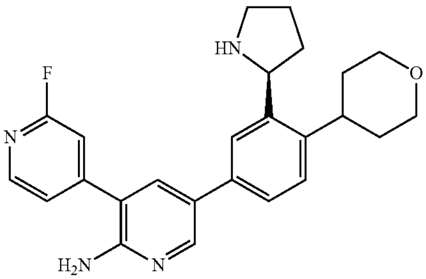 [SMILES: Nc1ncc(-c2ccc(C3CCOCC3)c([C@@H]3CCCN3)c2)cc1-c1ccnc(F)c1]

Trifluoroacetic acid (13 mL, 0.17 mol) was added dropwise to a solution of intermediate 29 (3.1 g, 6 mmol) in DCM (80 mL). The mixture was stirred at rt for 15 h, poured into water, basified with potassium carbonate. The aqueous phase was extracted with ethyl acetate. The organic layer was separated, dried over $MgSO_4$, filtered and evaporated until dryness. The residue was purified by preparative LC (40 g SiOH 30 μm Interchim, from 100% DCM to DCM 80%/MeOH 20%/$NH_4OH$ 1%). Two fractions were obtained: F1=2 g and F2=0.5 g. F1 was crystallized in acetonitrile, filtered, washed with diethylether and dried to give F3. The filtrate and F2 were combined and purified by preparative LC (40 g SiOH 30 μm Interchim, from 100% DCM to DCM 80%/MeOH 20%/$NH_4OH$ 1%). The fractions were collected and evaporated until dryness to give F4=0.75 g. F4 and F3 were combined, taken up in DCM and a solution of potassium carbonate 10%. The organic layer was separated, dried over $MgSO_4$, filtered and evaporated until dryness. The compound was crystallized in acetonitrile, filtered and dried to give 1.54 g of Co. 1 (62%).[α]d: −35.95° (589 nm, c 0.194 w/v %, DMF, 20° C.); m.p.=218° C. (DSC).

The compounds listed in the table below have been prepared by an analogous reaction protocol as was used for the synthesis of Co. 1 (1st approach).

| Compound | Structure | Quantity | Yield |
|---|---|---|---|
| Co. 2 Starting from Intermediate 16 | 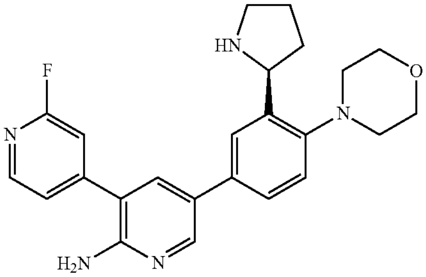 [α]d: −26.5° (589 nm, c 0.43 w/v %, MeOH, 23° C.); m.p. >300 °C. (Mettler Toledo MP50) | 0.197 g | 95% |
| Co. 3 Starting from Intermediate 23 | 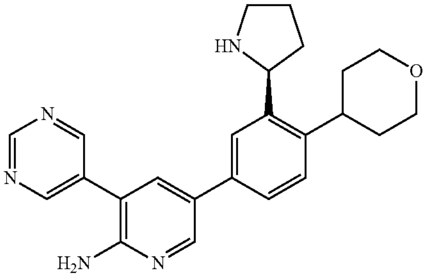 [α]d: −34° (589 nm, c 0.11 w/v %, MeOH, 23° C.); m.p. = 245° C. (Mettler Toledo MP50) | 0.105 g | 80% |

-continued
| Compound | Structure | Quantity | Yield |
|---|---|---|---|
| Co. 4 Starting from Intermediate 24 | 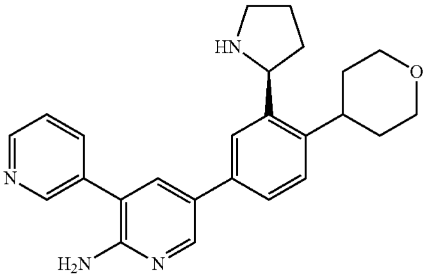 [α]$_d$: −11.9° (589 nm, c 0.186 w/v %, MeOH, 23° C.); m.p. = 257° C. (Mettler Toledo MP50) | 0.12 g | 92% |
| Co. 5a Starting from Intermediate 103 | 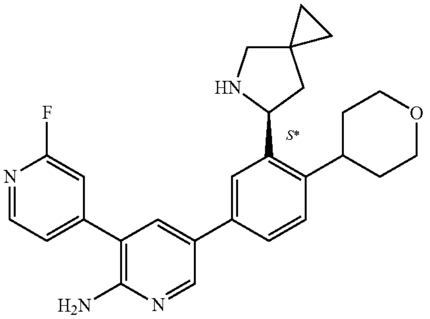 [α]$_d$: −7.42° (589 nm, c 0.31 w/v %, DMF, 20° C.) | 0.064 g | 35% |
| Co. 5b Starting from Intermediate 103 | 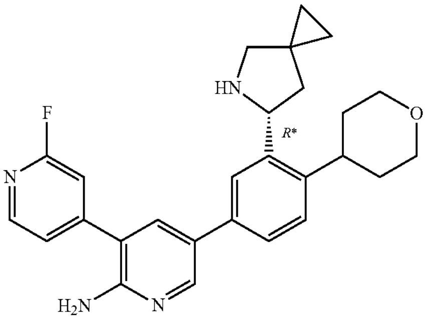 [α]$_d$: +7.2° (589 nm, c 0.25 w/v %, DMF, 20° C.) | 0.055 g | 30% |
| Co. 6 Starting from Intermediate 103 & 25 | 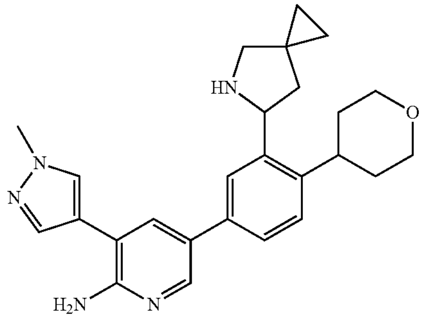 m.p. = 196.5° C. (Mettler Toledo MP50) | 0.088 g | 32% |

-continued
| Compound | Structure | Quantity | Yield |
|---|---|---|---|
| Co. 7a Starting from Intermediate 104 & 18 | 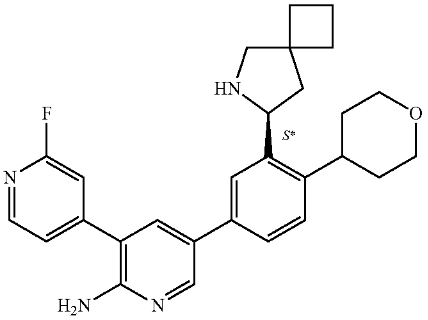 [α]$_d$: +7.78° (589 nm, c 0.18 w/v %, DMF, 20° C.) | 0.024 g | 28% |
| Co. 7b Starting from Intermediate 104 & 18 | 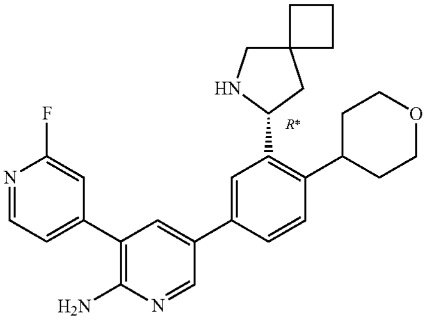 [α]$_d$: −10.43° (589 nm, c 0.23 w/v %, DMF, 20° C.) | 0.024 g | 28% |
| Co. 8a Starting from Intermediate 103 & 26 | 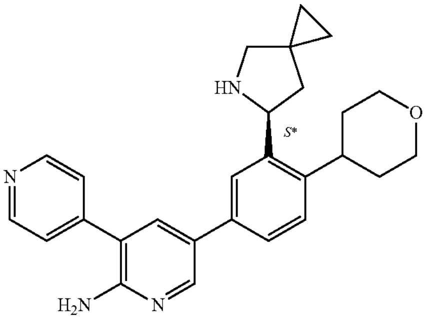 [α]$_d$: +6.32° (589 nm, c 0.19 w/v %, DMF, 20° C.) | 0.024 g | 17% |
| Co. 8b Starting from Intermediate 103 & 26 | 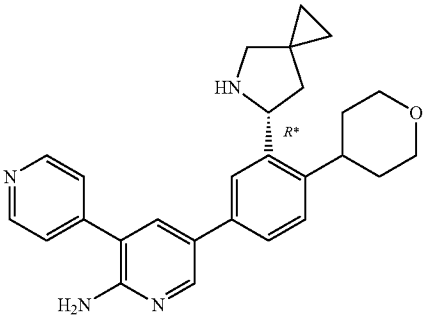 [α]$_d$: −6.09° (589 nm, c 0.23 w/v %, DMF, 20° C.) | 0.035 g | 25% |

-continued
| Compound | Structure | Quantity | Yield |
|---|---|---|---|
| Co. 9 Starting from Intermediate 104 & 109 | Racemic mixture of 2 trans forms 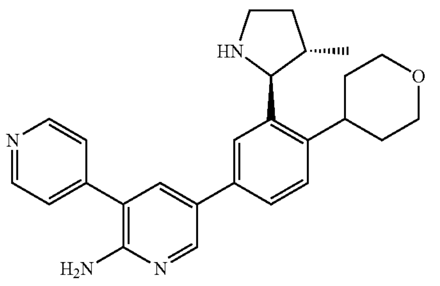 and 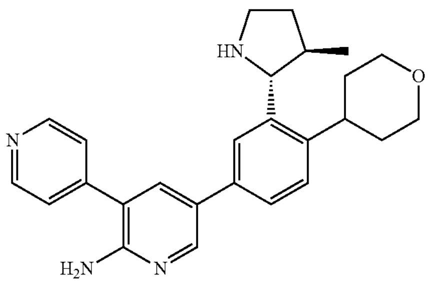 m.p. = 218.3° C. (Mettler Toledo MP50) | 0.080 g | 36% |
| Co. 10 Starting from Intermediate 104 & 108 | Racemic mixture of 2 cis forms 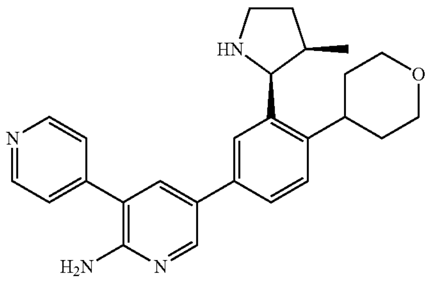 and 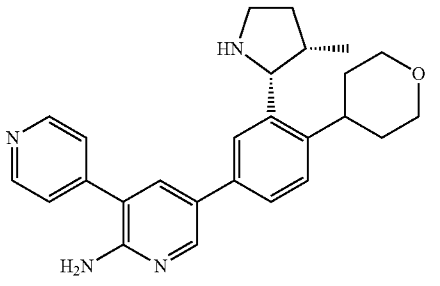 [SMILES: C[C@H]1CCN[C@H]1c1cc(-c2cnc(N)c(-c3ccncc3)c2)ccc1C1CCOCC1] | 0.014 g | 14% |

-continued
| Compound | Structure | Quantity | Yield |
| --- | --- | --- | --- |
| Co. 11 Starting from Intermediate 104 & 115 | 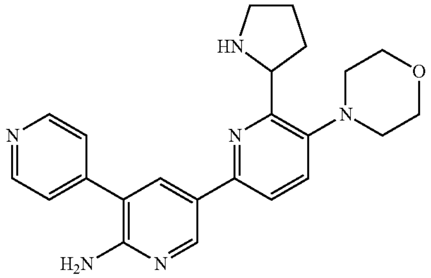 m.p. = 245° C. (Mettler Toledo MP50) | 0.163 g | 43% |
| Co. 12 Starting from Intermediate 104 & 119 | 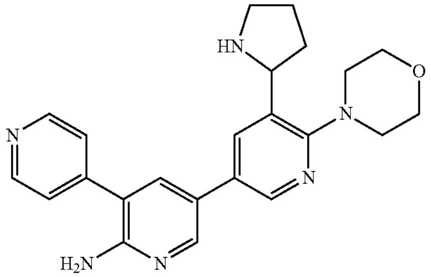 m.p. = 196° C. (Mettler Toledo MP50) | 0.21 g | 36% |
| Co. 13 Starting from Intermediate 149 and 104 | 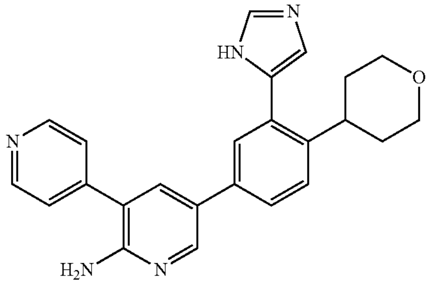 m.p. = 257° C. (Mettler Toledo MP50) | 0.07 g | 21% |
| Co. 14 Starting from Intermediate 153 and 104 | 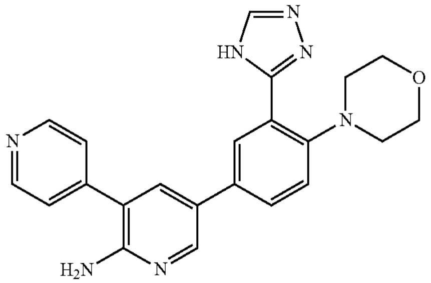 m.p. = 263° C. (Mettler Toledo MP50) | 0.14 g | 54% |

-continued
| Compound | Structure | Quantity | Yield |
|---|---|---|---|
| Co. 15 Starting from Intermediate 155 and 104 | 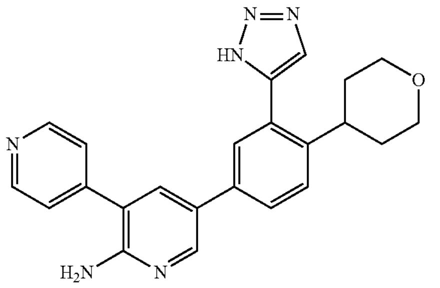 m.p. >300° C. (Mettler Toledo MP50) | 0.03 g | 16% |
| Co. 15a Starting from intermediates 145 and 18 | 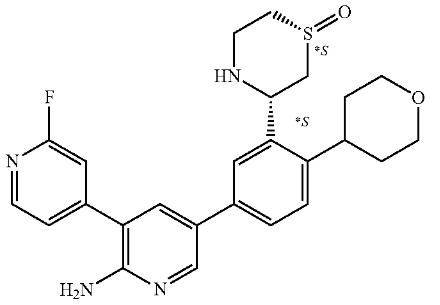 [α]$_d$: +29.6° (589 nm, c 0.22, w/v %, DMF, 20° C.) | 0.039 g | 10% |
| Co. 15b Starting from intermediates 145 and 18 | 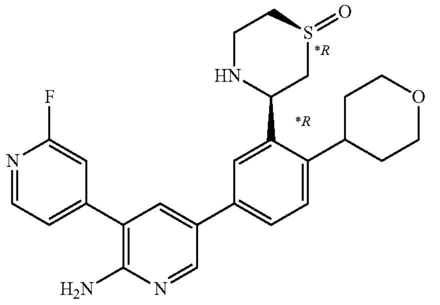 [α]$_d$: −9° (589 nm, c 0.2, w/v %, DMF, 20° C.) | 0.037 g | 9.5% |
| Co. 15c Starting from intermediates 145 and 18 | 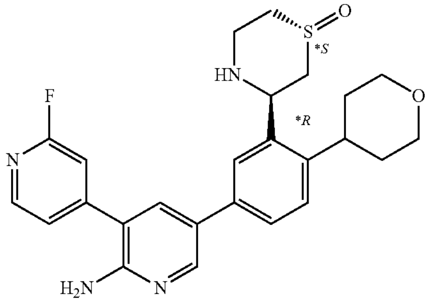 [α]$_d$: −4.4° (589 nm, c 0.23, w/v %, DMF, 20° C.) | 0.026 g | 6.7% |

-continued

| Compound | Structure | Quantity | Yield |
|---|---|---|---|
| Co. 15d Starting from intermediates 145 and 18 | 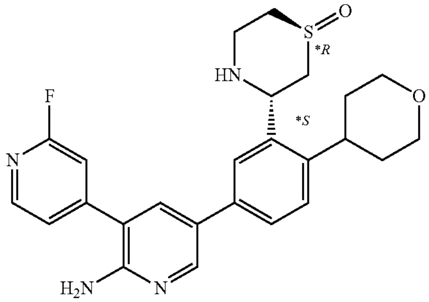 [α]$_d$: +9° (589 nm, c 0.19, w/v %, DMF, 20° C.) | 0.028 g | 7.2% |
| Co. 16 Starting from intermediate 167 and 104 | 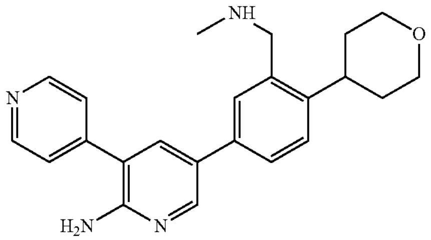 m.p. = 265° C. (Mettler Toledo MP50) | 0.065 g | 32% |

The compounds listed in the table below have been prepared by an analogous reaction protocol as was used for the synthesis of Co. 1 (2$^{nd}$ approach).

| Compound | Structure | Quantity | Yield |
|---|---|---|---|
| Co. 17 Starting from Intermediate 30 | 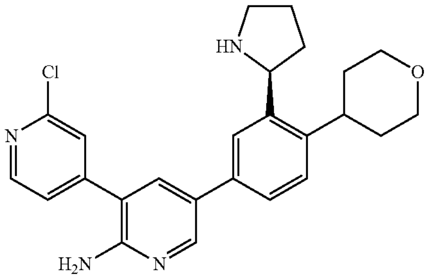 [α]$_d$: −36.4° (589 nm, c 0.25 w/v %, DMF, 20° C.) | 0.241 g | 70% |
| Co. 18 Starting from Intermediate 31 | 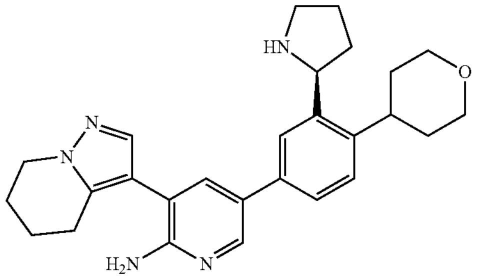 [α]$_d$: −45° (589 nm, c 0.24 w/v %, DMF, 20° C.) | 0.052 g | 40% |

-continued
| Compound | Structure | Quantity | Yield |
|---|---|---|---|
| Co. 19 Starting from Intermediate 32 | 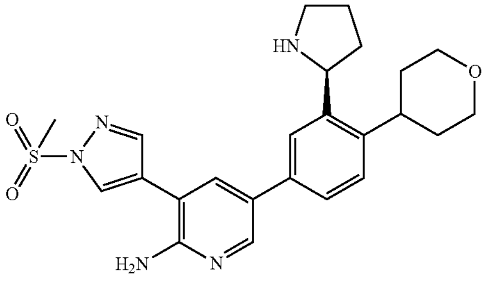 [α]$_d$: −55° (589 nm, c 0.18 w/v %, DMF, 20° C.) | 0.019 g | 23% |
| Co. 20 Starting from Intermediate 33 | 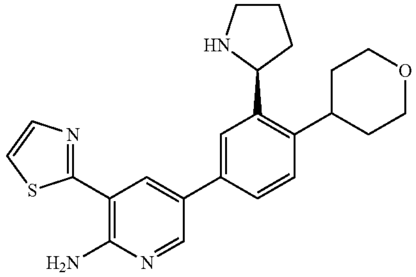 [α]$_d$: −39.6° (589 nm, c 0.23 w/v %, DMF, 20° C.) | 0.026 g | 77% |
| Co. 21 Starting from Intermediate 34 | 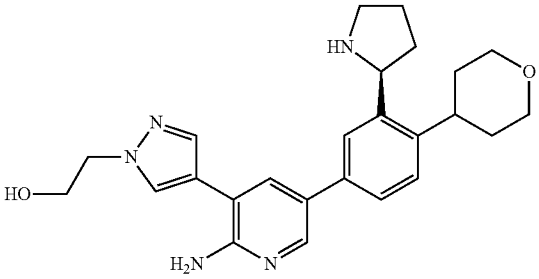 [α]$_d$: −41.8° (589 nm, c 0.22 w/v %, DMF, 20° C.) | 0.024 g | 45% |
| Co. 22 Starting from intermediate 35 | 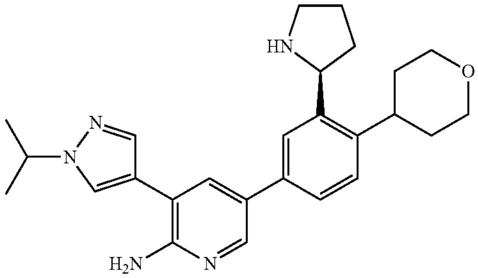 [α]$_d$: −40.9° (589 nm, c 0.22 w/v %, DMF, 20° C.); m.p. = 191.7° C. (DSC) | 0.026 g | 55% |

-continued
| Compound | Structure | Quantity | Yield |
|---|---|---|---|
| Co. 23 Starting from Intermediate 36 | 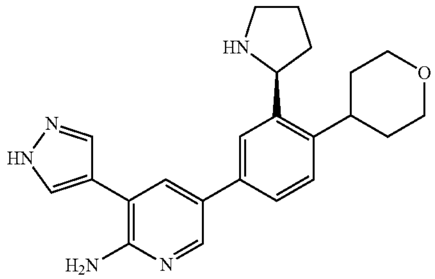 $[\alpha]_d$: −46.5° (589 nm, c 0.2 w/v %, DMF, 20° C.); m.p. = 223.4° C. (DSC) | 0.026 g | 38% |
| Co. 24 Starting from intermediate 37 | 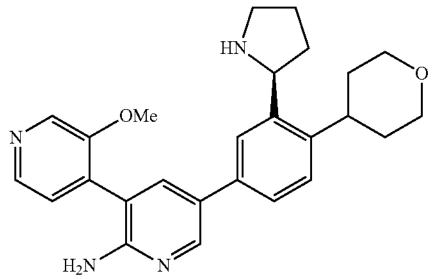 $[\alpha]_d$: −36.1° (589 nm, c 0.31 w/v %, DMF, 20° C.); m.p. = 217.5° C. (DSC) | 0.025 g | 42% |
| Co. 25 Starting from Intermediate 38 | 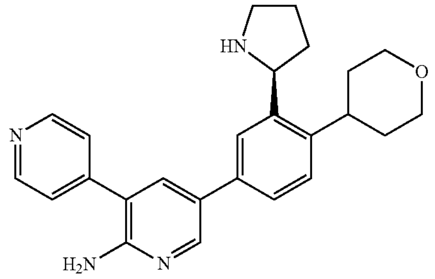 $[\alpha]_d$: −44.4° (589 nm, c 0.25 w/v %, DMF, 20° C.); m.p. = 238.1° C. (DSC) | 0.057 g | 56% |
| Co. 25b | 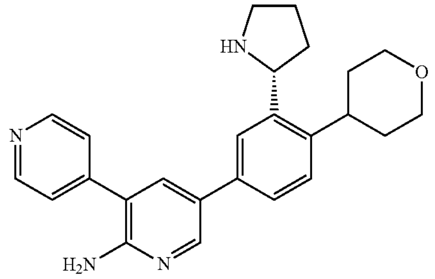 $[\alpha]_d$: +36° (589 nm, c 0.28 w/v %, DMF, 20° C.) | 0.033 g | 26% |

-continued

| Compound | Structure | Quantity | Yield |
|---|---|---|---|
| Co. 26 Starting from Intermediate 64 | 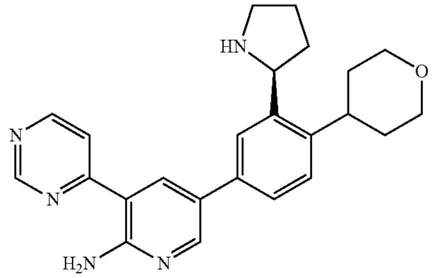 [α]$_d$: −21.7° (589 nm, c 0.12 w/v %, MeOH, 23° C.); m.p. = 201° C. (Mettler Toledo MP50) | 0.065 g | 85% |
| Co. 27 Starting from Intermediate 65 | 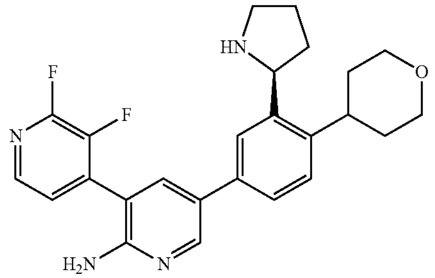 [α]$_d$: −94.8° (589 nm, c 0.25 w/v %, DMF, 20° C.); m.p. >300° C. (Mettler Toledo MP50) | 0.068 g | 83% |
| Co. 28 Starting from Intermediate 66 | 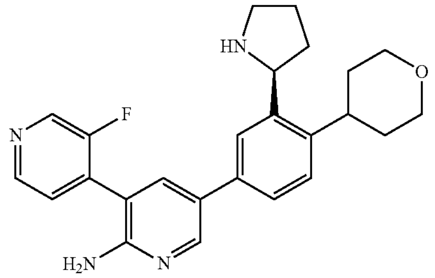 [α]$_d$: −29.6° (589 nm, c 0.36 w/v %, MeOH, 23° C.); m.p. = 230° C. (Mettler Toledo MP50) | 0.052 g | 46% |
| Co. 29 Starting from Intermediate 67 | 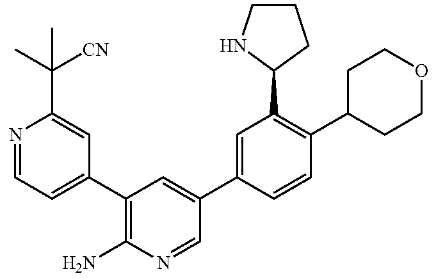 [α]$_d$: −18.2° (589 nm, c 0.39 w/v %, MeOH, 23° C.); m.p. = 228° C. (Mettler Toledo MP50) | 0.11 g | 68% |

-continued

| Compound | Structure | Quantity | Yield |
|---|---|---|---|
| Co. 30 Starting from Intermediate 68 | 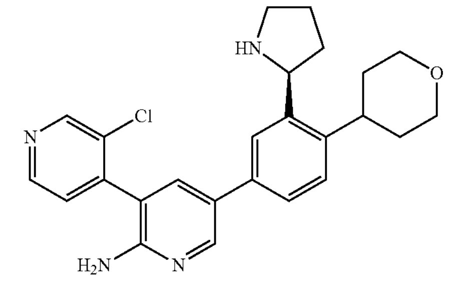 [α]$_d$: −23.9° (589 nm, c 0.27 w/v %, MeOH, 23° C.); m.p. >300° C. (Mettler Toledo MP50) | 0.088 g | 71% |
| Co. 31 Starting from Intermediate 69 | 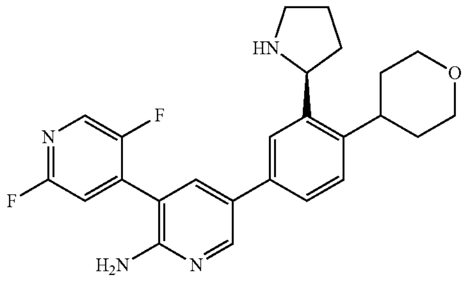 [α]$_d$: −25.5° (589 nm, c 0.093 w/v %, MeOH, 23° C.); m.p. = 225° C. (Mettler Toledo MP50) | 0.085 g | 68% |
| Co. 32 Starting from Intermediate 70 | 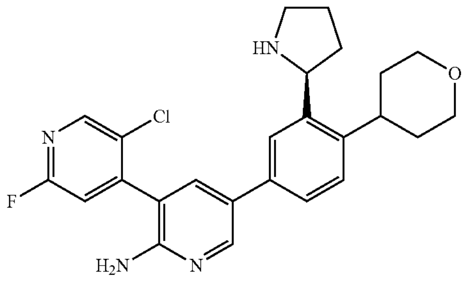 [α]$_d$: −28.1° (589 nm, c 0.73 w/v %, MeOH, 23° C.); m.p. = 221.6° C. (Mettler Toledo MP50) | 0.093 g | 49% |
| Co. 33 Starting from Intermediate 71 | 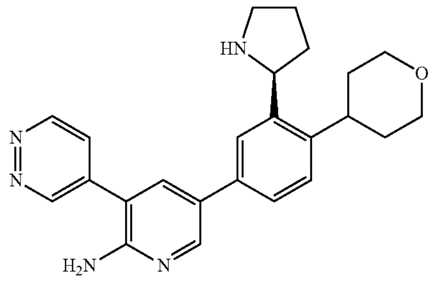 [α]$_d$: −23.1° (589 nm, c 0.73 w/v %, MeOH, 23° C.); m.p. = 240° C. (Mettler Toledo MP50) | 0.071 g | 39% |

-continued
| Compound | Structure | Quantity | Yield |
|---|---|---|---|
| Co. 34 Starting from Intermediate 72 | 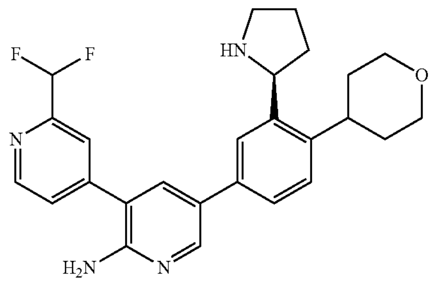 [SMILES: Nc1ncc(-c2ccc(C3CCOCC3)c([C@@H]3CCCN3)c2)cc1-c1ccnc(C(F)F)c1] | 0.007 g | 21% |
| Co. 35 Starting from Intermediate 73 | 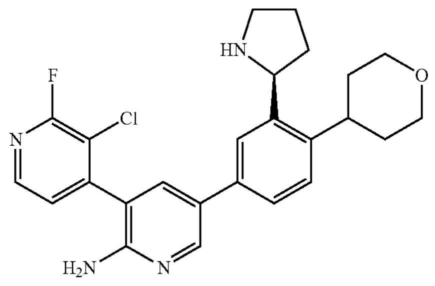 [α]$_d$: −16.6° (589 nm, c 0.53 w/v %, MeOH, 23° C.); m.p. = 218° C. (Mettler Toledo MP50) | 0.049 g | 82% |
| Co. 36 Starting from Intermediate 74 | 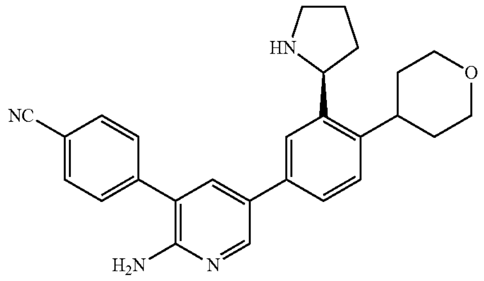 [α]$_d$: −22.6° (589 nm, c 0.1 w/v %, MeOH, 23° C.); m.p. = 231.6° C. (Mettler Toledo MP50) | 0.049 g | 82% |
| Co. 37 Starting from Intermediate 27 | 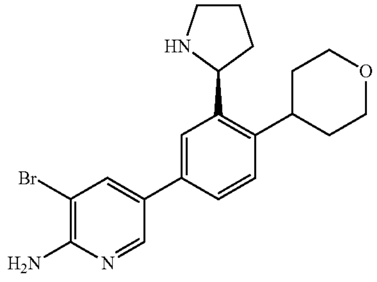 [α]$_d$: −42.1° (589 nm, c 0.24 w/v %, DMF, 20° C.); m.p. = 173° C. (Mettler Toledo MP50) | 0.052 g | 65% |

-continued
| Compound | Structure | Quantity | Yield |
|---|---|---|---|
| Co. 38 Starting from Intermediate 75 | 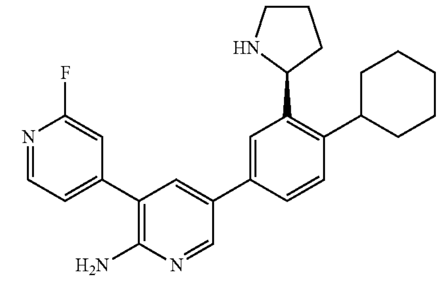 [SMILES: Nc1ncc(-c2ccc(C3CCCCC3)c([C@@H]3CCCN3)c2)cc1-c1ccnc(F)c1] | 0.015 g | 37% |
| Co. 39 Starting from Intermediate 76 | 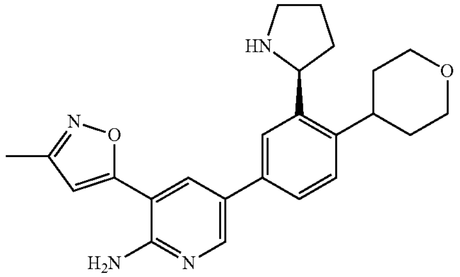 [α]$_d$: −18.7° (589 nm, c 0.13 w/v %, MeOH, 23° C.); m.p. = 184.8° C. (Mettler Toledo MP50) | 0.075 g | 64% |
| Co. 40 Starting from Intermediate 77 | 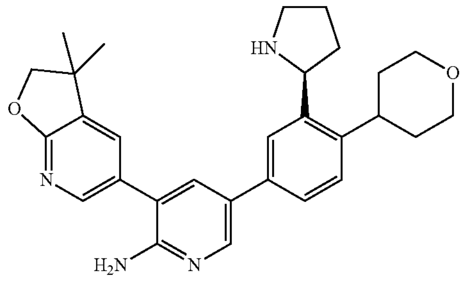 [SMILES: CC1(C)COc2ncc(-c3cc(-c4ccc(C5CCOCC5)c([C@@H]5CCCN5)c4)cnc3N)cc21] | 0.04 g | 22% |
| Co. 41 Starting from Intermediate 78 | 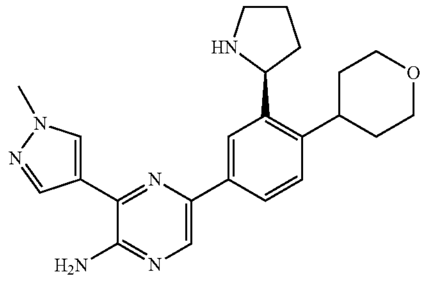 [α]$_d$: −33.9° (589 nm, c 0.1 w/v %, MeOH, 23° C.); m.p. = 216.5° C. (Mettler Toledo MP50) | 0.1 g | 49% |

-continued
| Compound | Structure | Quantity | Yield |
|---|---|---|---|
| Co. 42 Starting from Intermediate 79 | 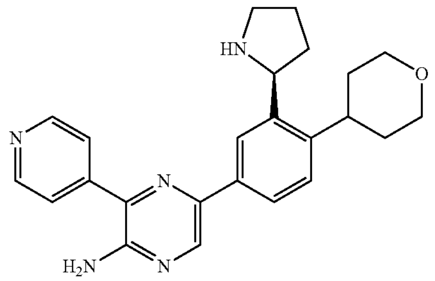 [α]$_d$: −37.47° (589 nm, c 0.13 w/v %, MeOH, 23° C.); m.p. = 262° C. (Mettler Toledo MP50) | 0.03 g | 68% |
| Co. 43 Starting from Intermediate 80 | 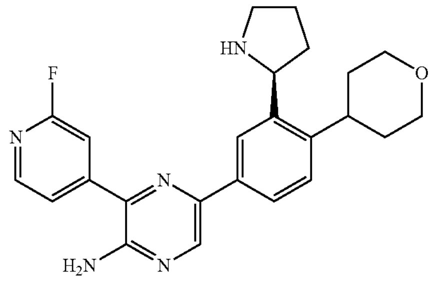 [α]$_d$: −24.8° (589 nm, c 0.08 w/v %, MeOH, 23° C.); m.p. = 217° C. (Mettler Toledo MP50) | 0.063 g | 80% |
| Co. 44 Starting from Intermediate 82 | 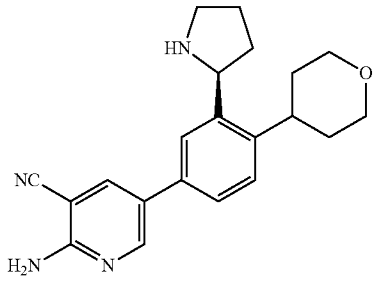 [α]$_d$: −56.8° (589 nm, c 0.19 w/v %, DMF, 20° C.); m.p. = 206° C. (DSC) | 0.404 g | 27% |
| Co. 45 Starting from intermediate 122 | 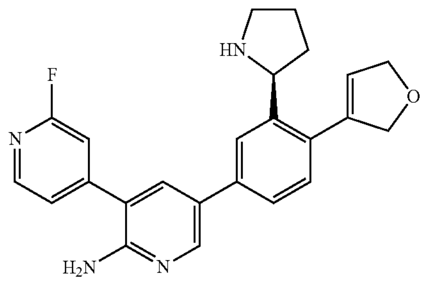 [α]$_d$: −50.4° (589 nm, c 0.28 w/v %, DMF, 20° C.); m.p. = 206.7° C. (DSC) | 0.25 g | 95% |

-continued
| Compound | Structure | Quantity | Yield |
|---|---|---|---|
| Co. 46 Starting from intermediate 123 | 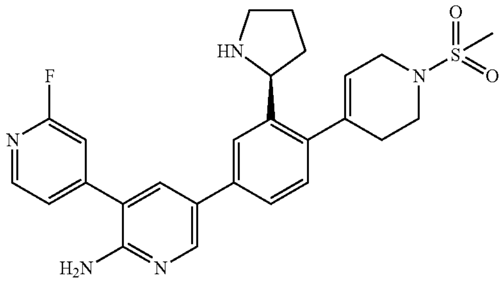 m.p. = 224° C. (DSC) | 0.33 g | 53% |
| Co. 47 Starting from intermediate 124 | 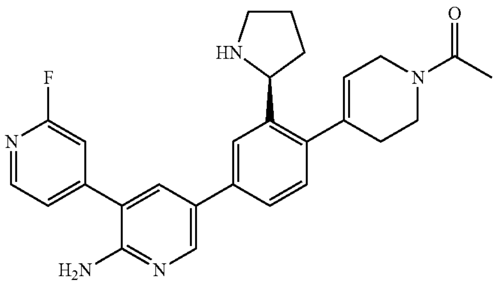 [SMILES: CC(=O)N1CC=C(c2ccc(-c3cnc(N)c(-c4ccnc(F)c4)c3)cc2[C@@H]2CCCN2)CC1] | 0.1 g | 22% |
| Co. 48 Starting from intermediate 125 | 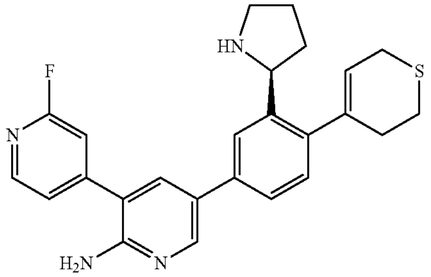 m.p. = 208° C. (DSC) | 0.41 g | 97% |
| Co. 49 Starting from intermediate 126 | 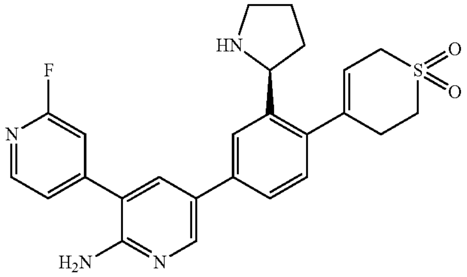 [SMILES: Nc1ncc(-c2ccc(C3=CCS(=O)(=O)CC3)c([C@@H]3CCCN3)c2)cc1-c1ccnc(F)c1] | 0.05 g | 29% |
| Co. 50 Starting from intermediate 129 | 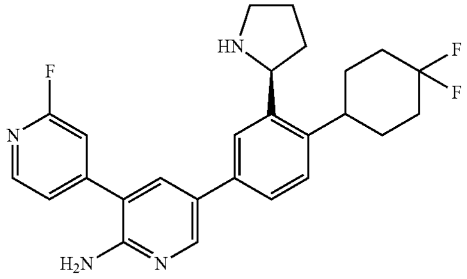 m.p. = 219° C. (DSC) | 0.036 g | 38% |

-continued
| Compound | Structure | Quantity | Yield |
|---|---|---|---|
| Co. 51 Starting from intermediate 130 | 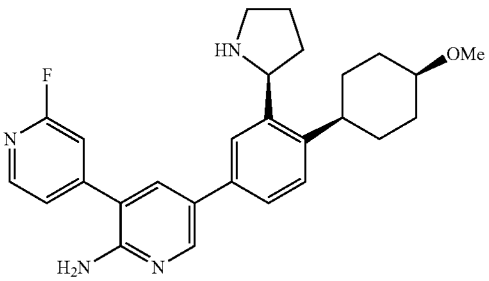 | 0.018 g | 49% |
| Co. 52 Starting from intermediate 131 | 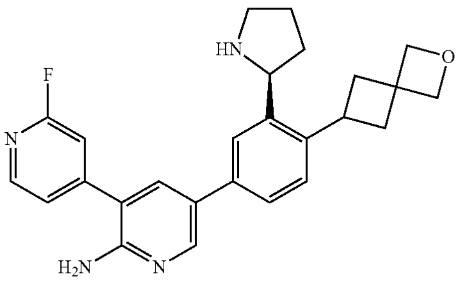 [α]$_d$: −26.2° (589 nm, c 0.29 w/v %, DMF, 20° C.); m.p. = 222° C. (DSC) | 0.016 g | 26% |
| Co. 53 Starting from intermediate 133 | 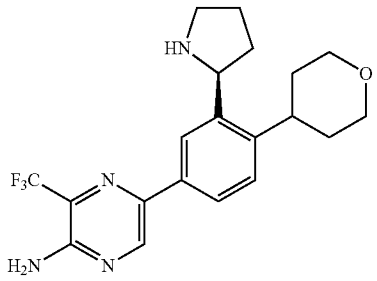 [α]$_d$: −44.55° (589 nm, c 0.11 w/v %, DMF, 20° C.) | 0.019 g | 40% |
| Co. 54 Starting from intermediate 132 | 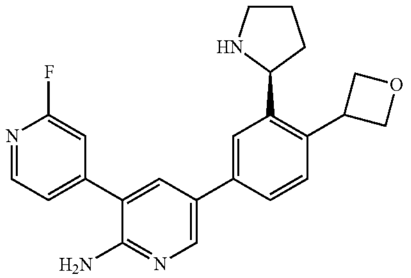 [α]$_d$: −90° (589 nm, c 0.42 w/v %, DMF, 20° C.) | 0.02 g | 13% |

-continued
| Compound | Structure | Quantity | Yield |
|---|---|---|---|
| Co. 55 Starting from intermediate 39 | 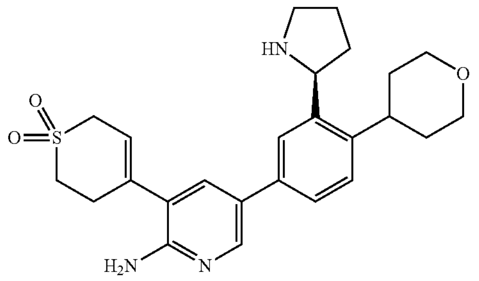 [α]$_d$: −33.7° (589 nm, c 0.27 w/v %, DMF, 20° C.) | 0.045 g | 20% |
| Co. 56 Starting from intermediate 40 | 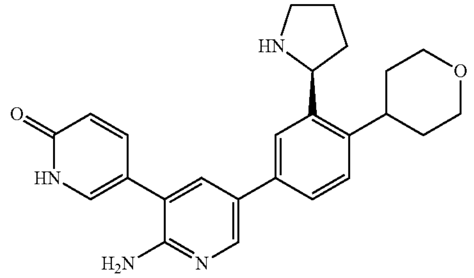 [SMILES: Nc1ncc(-c2ccc(C3CCOCC3)c([C@@H]3CCCN3)c2)cc1-c1ccc(=O)[nH]c1] | 0.019 g | 20% |
| Co. 57 Starting from intermediate 41 | 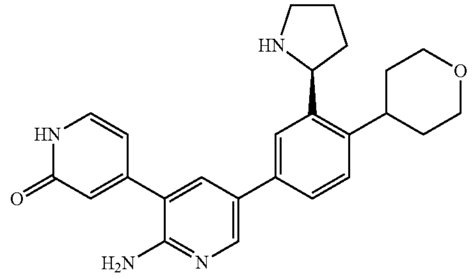 [α]$_d$: −30.5° (589 nm, c 0.22 w/v %, DMF, 20° C.) | 0.039 g | 40% |
| Co. 58 Starting from intermediate 142 | 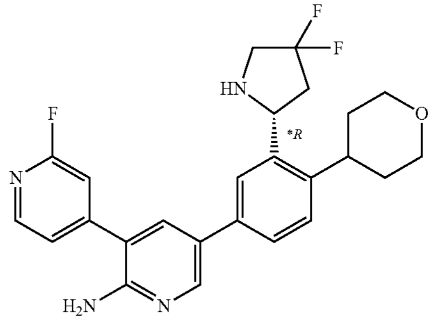 [α]$_d$: +26.8° (589 nm, c 0.22 w/v %, DMF, 20° C.); m.p. = 216° C. (DSC) | 0.039 g | 21% |

-continued
| Compound | Structure | Quantity | Yield |
|---|---|---|---|
| Co. 59 Starting from intermediate 142 | 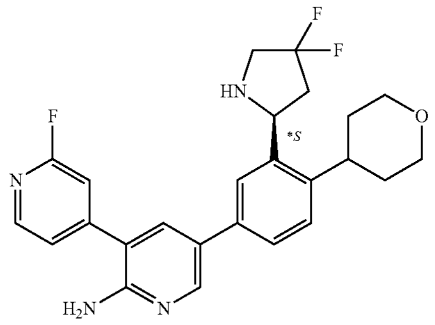 [α]$_d$: −23.9° (589 nm, c 0.26 w/v %, DMF, 20° C.); m.p. = 215° C. (DSC) | 0.045 g | 24% |
| Co. 60 Starting from intermediate 143 | 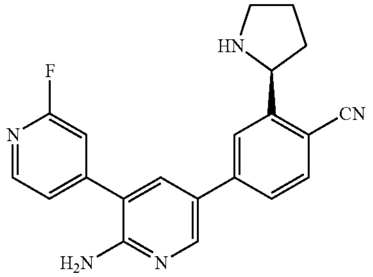 [SMILES: N#Cc1ccc(-c2cnc(N)c(-c3ccnc(F)c3)c2)cc1[C@@H]1CCCN1] | 0.076 g | 49% |
| Co. 61 Starting from intermediate 42 | 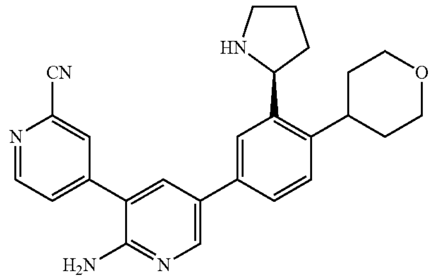 [α]$_d$: −29.3° (589 nm, c 0.15, w/v %, DMF, 20° C.) | 0.072 g | 39% |
| Co. 62 Starting from intermediate 43 | 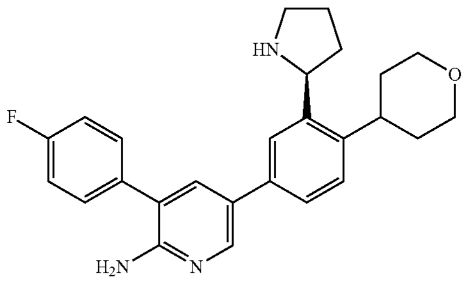 [α]$_d$: −35.83° (589 nm, c 0.26 w/v %, DMF, 20° C.); m.p. = 216° C. (DSC) | 0.102 g | 52% |

-continued
| Compound | Structure | Quantity | Yield |
|---|---|---|---|
| Co. 63 Starting from intermediate 44 | 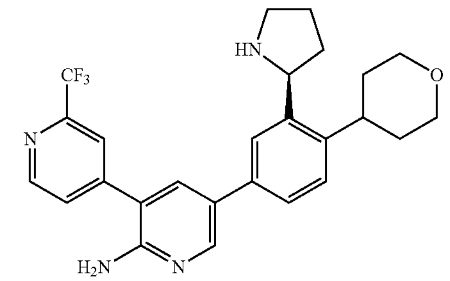 [α]$_d$: −40° (589 nm, c 0.1, w/v %, DMF, 20° C.); m.p. = 213° C. (DSC) | 0.084 g | 46% |
| Co. 64 Starting from intermediate 160 | 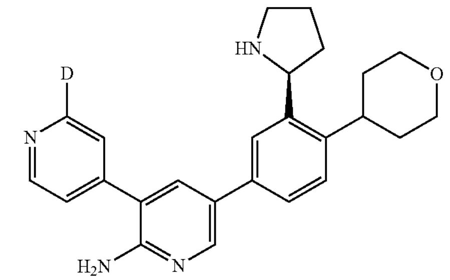 [SMILES: [2H]c1cc(-c2cc(-c3ccc(C4CCOCC4)c([C@@H]4CCCN4)c3)cnc2N)ccn1] | 0.04 g | 33% |
| Co. 65 Starting from intermediate 162 | 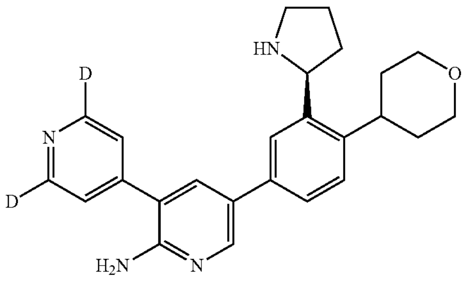 [SMILES: [2H]c1cc(-c2cc(-c3ccc(C4CCOCC4)c([C@@H]4CCCN4)c3)cnc2N)cc([2H])n1] | 0.106 g | 65% |
| Co. 66 Starting from intermediate 84 | 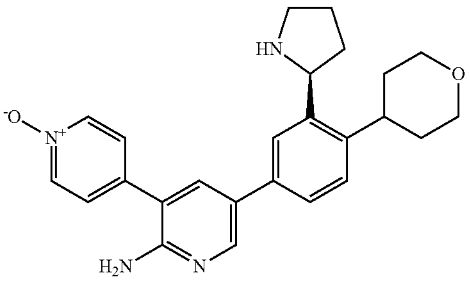 [α]$_d$: −32.2° (589 nm, c 0.27, w/v %, DMF, 20° C.); m.p. >260° C. (Kofler) | 0.110 g | 48% |

-continued

| Compound | Structure | Quantity | Yield |
|---|---|---|---|
| Co.67 Starting from intermediate 166 | 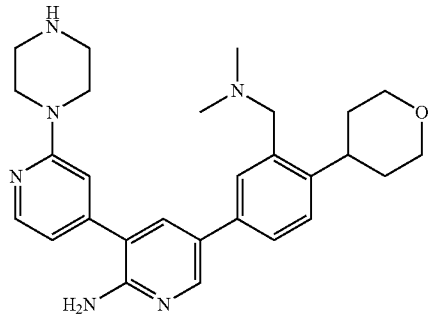 m.p. = 185° C. (Kofler) | 0.05 g | 48% |

Synthesis of Co.68

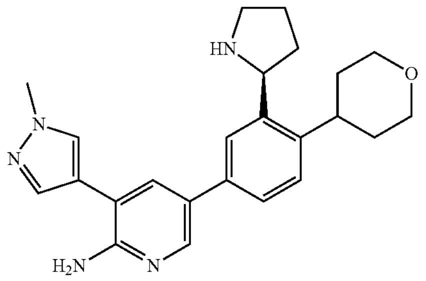 [SMILES: Cn1cc(-c2cc(-c3ccc(C4CCOCC4)c([C@@H]4CCCN4)c3)cnc2N)cn1]

Sodium carbonate (119 mg, 1.12 mmol) was added to a solution of intermediate 89 (200 mg, 0.497 mmol), 1-Methyl-1H-pyrazole-4-boronic acid pinacol ester (124 mg, 0.6 mmol) in water (1.16 mL) and 1,4-dioxane (5.8 mL). The mixture was degassed with a stream of nitrogen for 5 min., then $PdCl_2(dppf)$ (34 mg, 0.041 mmol) was added. The reaction mixture was stirred at 90° C. overnight in a sealed tube. The reaction mixture was cooled to rt, water and AcOEt were added. The aqueous layer was extracted with ethyl acetate. The organic layer was dried over $MgSO_4$, filtered and evaporated until dryness. The residue was purified by preparative LC (12 g SiOH 15-40 μm Interchim, mobile phase: DCM/MeOH/$NH_4OH$ 97/3/0 to 90/10/0.1) The pure fractions were collected and evaporated until dryness to give 80 mg of Co.68 (39%) which was taken up in $Et_2O$. The precipitate was filtered off and dried yielding 53 mg of Co.68 (26%).

The compounds listed in the table below have been prepared by an analogous reaction protocol:

| Compound | Structure | Quantity | Yield |
|---|---|---|---|
| Co. 69 Starting from Intermediate 165 | 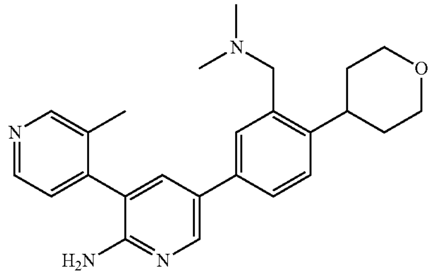 [SMILES: Cc1cnccc1-c1cc(-c2ccc(C3CCOCC3)c(CN(C)C)c2)cnc1N] m.p. = 236° C. (Kofler) | 0.023 g | 22% |
| Co. 70 Starting from Intermediate 165 | 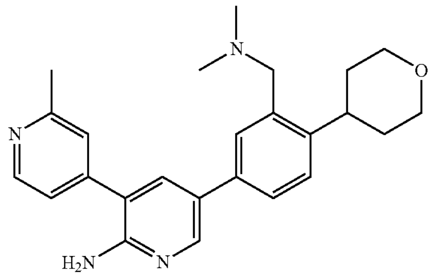 m.p. = 225° C. | 0.057 g | 55% |

-continued
| Compound | Structure | Quantity | Yield |
|---|---|---|---|
| Co. 71 Starting from Intermediate 165 | 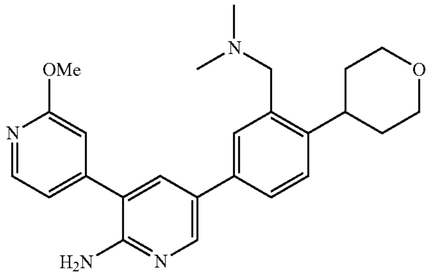 [SMILES: COc1cc(-c2cc(-c3ccc(C4CCOCC4)c(CN(C)C)c3)cnc2N)ccn1] m.p. = 222° C. (Kofler) | 0.056 g | 52% |
| Co. 72 Starting from Intermediate 165 | 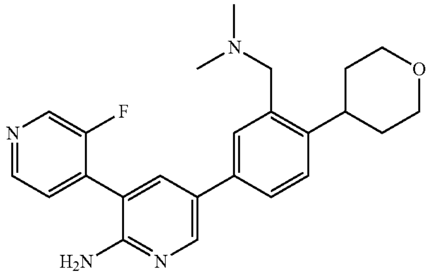 [SMILES: CN(C)Cc1cc(-c2cnc(N)c(-c3ccncc3F)c2)ccc1C1CCOCC1] m.p. = 234° C. (Kofler) | 0.063 g | 60% |
| Co. 73 Starting from Intermediate 165 | 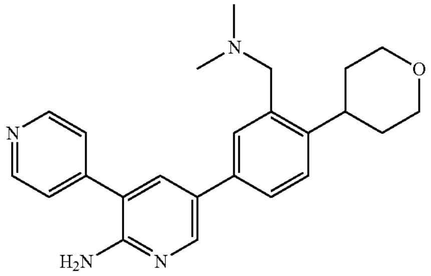 m.p. = 227° C. (DSC) | 0.064 g | 80% |
| Co. 74 Starting from intermediate 165 and 2-(4-(4,4,5,5-tetramethyl-1,3,2-dioxaborolan-2-yl) pyridin-2-ylamino) ethanol | 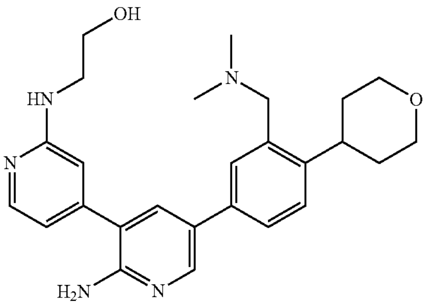 [SMILES: CN(C)Cc1cc(-c2cnc(N)c(-c3ccnc(NCCO)c3)c2)ccc1C1CCOCC1] | 0039 g | 34% |

-continued

| Compound | Structure | Quantity | Yield |
|---|---|---|---|
| Co. 75 Starting from intermediate 165 and 3-(4-(4,4,5,5-tetramethyl-1,3,2-dioxaborolan-2-yl) pyridin-2-ylamino) propan-1-ol | 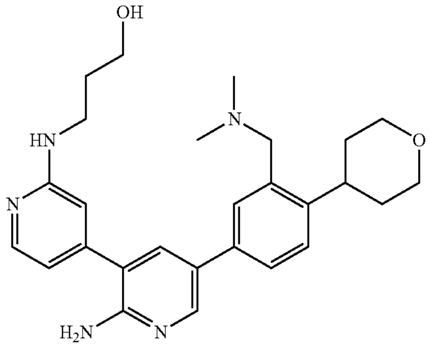 [SMILES: CN(C)Cc1cc(-c2cnc(N)c(-c3ccnc(NCCCO)c3)c2)ccc1C1CCOCC1] m.p. = 170° C. (Kofler) | 0.071 g | 60% |

Synthesis of Co.76

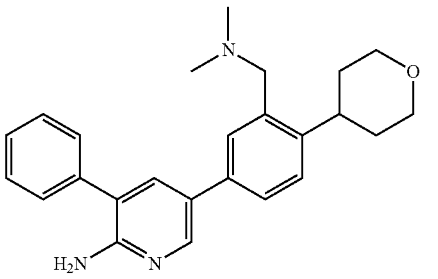

A mixture of intermediate 164 (0.119 g, 0.345 mmol), 5-bromo-3phenylpyridine-2-amine (0.08 g, 0.321 mmol), $PdCl_2$(dppf) (0.028 g, 0.0345 mmol) and sodium carbonate (0.11 g, 1.034 mmol) in 1,4-dioxane (1.5 mL) and water (0.4 mL) in a sealed tube was stirred at 120° C. using one single mode microwave (Biotage Initiator EXP 60) with a power output ranging from 0 to 400 W for 30 min. The reaction mixture was poured into water and potassium carbonate, extracted with AcOEt. The organic layer was dried over $MgSO_4$, filtered and evaporated until dryness. The residue was purified by preparative LC (24 g of SiOH 30 μm Interchim, graduent from 100% DCM to 90% DCM 10% $CH_3OH$ 0.1% $NH_4OH$). The fractions were collected and evaporated until dryness and the residue was cristallized in DIPE. The precipitate was filtered off and dried yielding Co.76 (0.028 g, 21%). m.p.=173° C. (Kofler).

Synthesis of Co.77

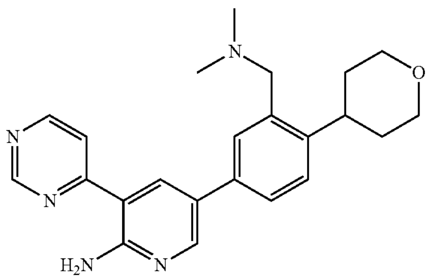 [SMILES: CN(C)Cc1cc(-c2cnc(N)c(-c3ccncn3)c2)ccc1C1CCOCC1]

A mixture of intermediate 165 (0.100 g, 0.26 mmol), 4-(tributylstannyl)pyrimidine (0.114 g, 0.307 mmol), Copperiodide (11.7 mg, 0.062 mmol), $Pd(PPh_3)_4$ (0.021 g, 0.018 mmol) and lithiumchloride (0.016 g, 0.384 mmol) in 1,4-dioxane (5 mL) was stirred at 130° C. in a Biotage Microwave for 20 minutes. The reaction mixture was poured into water, extracted with AcOEt. The organic layer was dried over $MgSO_4$, filtered and evaporated until dryness. The residue was purified by preparative LC (40 g of SiOH, 95% DCM 5% $CH_3OH$ 0.1% $NH_4OH$). The fractions were collected and evaporated until dryness yielding Co.77 (0.051 g, 51%).

The compounds listed in the table below have been prepared by an analogous reaction protocol as described for the preparation of intermediate 27:

| Compound | Structure | Quantity | Yield |
|---|---|---|---|
| Co. 78 Starting from Intermediate 96 | 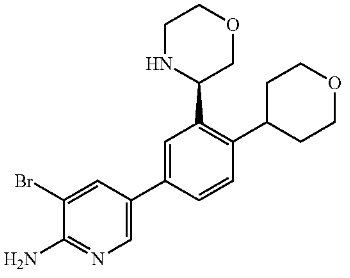 $[\alpha]_d$: −77.8° (589 nm, c 0.27 w/v %, DMF, 20° C.); m.p. = 208° C. (DSC) | 0.5 g | 56% |
| Co. 79 Starting from Intermediate 97 | 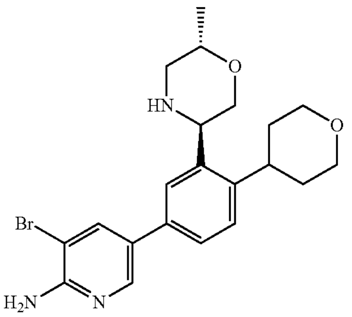 [SMILES: C[C@H]1CN[C@H](c2cc(-c3cnc(N)c(Br)c3)ccc2C2CCOCC2)CO1] | 1.85 g | 66% |

The compounds listed in the table below have been prepared by an analogous reaction protocol as for preparation of intermediate 64:

| Compound | Structure | Quantity | Yield |
|---|---|---|---|
| Co. 80a Starting from Intermediate 98 and 5-bromo-[3,4'-bipyridin]-2-amine | 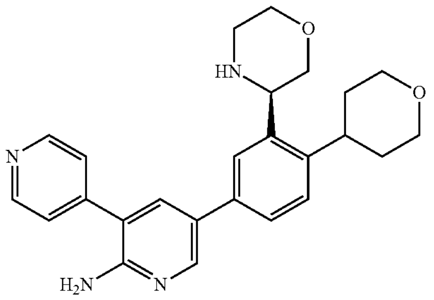 [α]d: −28.4° (589 nm, c 0.26 w/v %, DMF, 20° C.) | 0.07 g | 24% |
| Co. 80b | 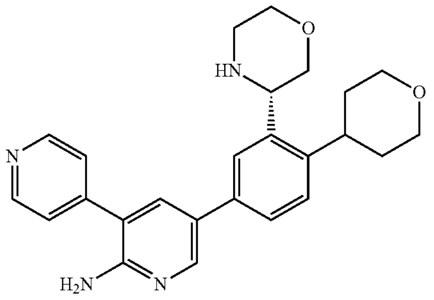 [α]d: +48° (589 nm, c 0.11 w/v %, DMF, 20° C.) | 0.022 g | 17% |
| Co. 81 Starting from Intermediate 98 and 5-bromo-3-(1-methyl-1H-pyrazol-4-yl) pyridin-2-amine | 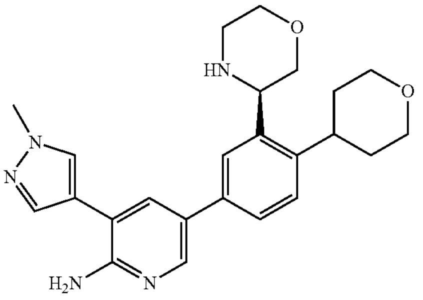 [α]d: −70° (589 nm, c 0.21 w/v %, DMF, 20° C.) | 0.025 g | 10% |
| Co. 82 Starting from Intermediate 98 and 17 | 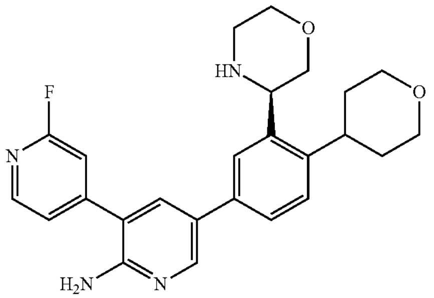 [α]d: −73.25° (589 nm, c 0.24 w/v %, DMF, 20° C.) | 0.072 g | 36% |

-continued
| Compound | Structure | Quantity | Yield |
|---|---|---|---|
| Co. 83a Starting from Intermediate 99 and 5-bromo-[3,4'-bipyridin]-2-amine | 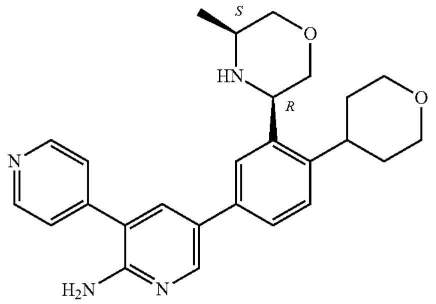 or 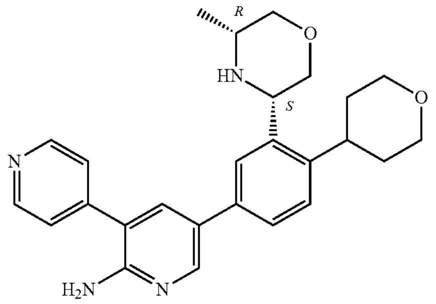 [α]$_d$: −84.9° (589 nm, c 0.35 w/v %, DMF, 20° C.) | 0.04 g | 5% |
| Co. 83b | 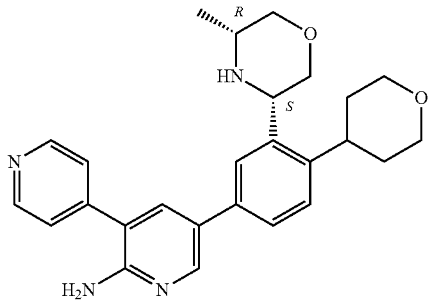 or 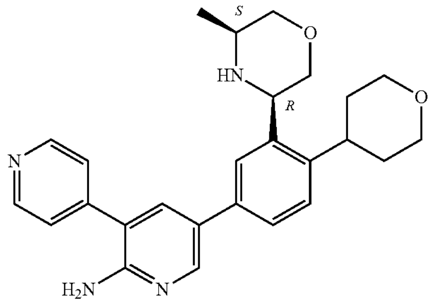 [α]$_d$: +82.2° (589 nm, c 0.35 w/v %, DMF, 20° C.) | 0.036 g | 4% |

-continued
| Compound | Structure | Quantity | Yield |
|---|---|---|---|
| Co. 84 Starting from Intermediate 98 and 2-pyrazinamine, 5-bromo-3-(1-methyl-1H-pyrazol-4-yl) | 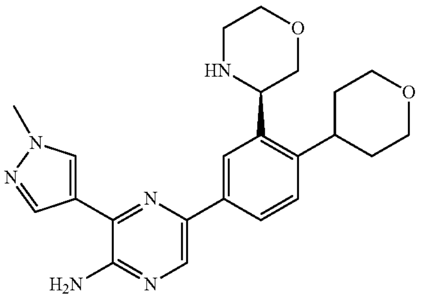 [α]$_d$: −79.6° (589 nm, c 0.26 w/v %, DMF, 20° C.) m.p. = 243° C. (DSC) | 0.06 g | 23% |
| Co. 85 Starting from Intermediate 98 and 2-pyridineamine, 5-bromo-3-chloro | 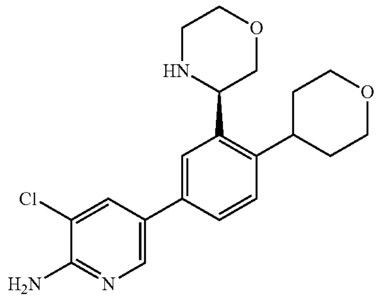 [α]$_d$: −82.4° (589 nm, c 0.25 w/v %, DMF, 20° C.) m.p. = 213° C. (DSC) | 0.148 g | 52% |
| Co. 86 Starting from Intermediate 98 and 2-Amino-5-bromo-3-methylpyridine | 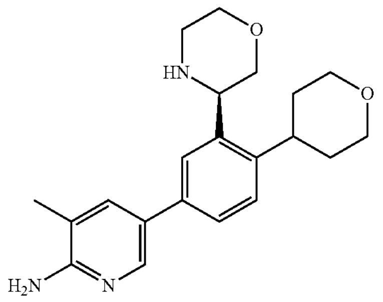 [α]$_d$: −22.3° (589 nm, c 0.22 w/v %, DMF, 20° C.) m.p. = 266° C. (DSC) | 0.069 g | 32% |

-continued
| Compound | Structure | Quantity | Yield |
|---|---|---|---|
| Co. 87 Starting from Intermediate 98 and 5-bromo-3-methoxypyridin-2-amine | 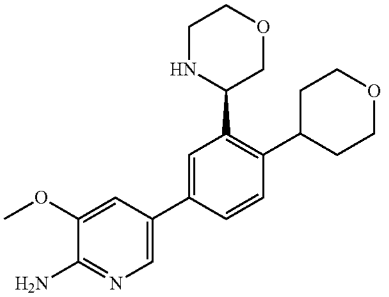 $[\alpha]_d$: −78.9° (589 nm, c 0.19 w/v %, DMF, 20° C.) m.p. = 239° C. (DSC) | 0.053 g | 23% |
| Co. 88 Starting from Intermediate 98 and 5-bromo-3-fluoropyridin-2-amine | 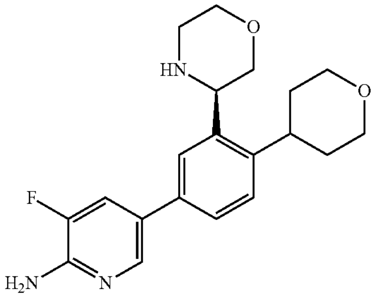 $[\alpha]_d$: −83.5° (589 nm, c 0.2 w/v %, DMF, 20° C.) m.p. = 225° C. (DSC) | 0.089 g | 41% |
| Co. 89 Starting from Intermediate 98 and 2-Amino-5-bromonicotinonitrile | 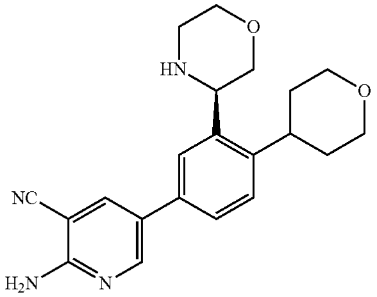 $[\alpha]_d$: −108.3° (589 nm, c 0.24 w/v %, DMF, 20° C.) m.p. = 258° C. (DSC) | 0.086 g | 39% |

-continued

| Compound | Structure | Quantity | Yield |
|---|---|---|---|
| Co. 90 Starting from Intermediate 100a and 5-bromo-3-(1-methyl-1H-pyrazol-4-yl)pyrazin-2-amine | 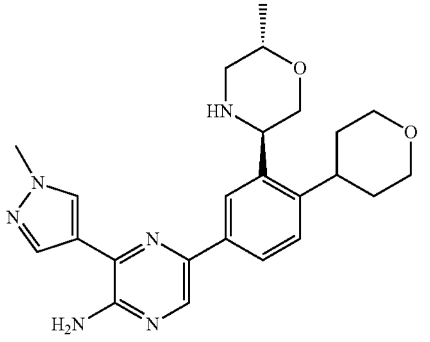 [α]$_d$: −45.6° (589 nm, c 0.16 w/v %, DMF, 20° C.) m.p. = 246° C. (DSC) | 0.195 g | 61% |
| Co. 91 Starting from Intermediate 98 and 5-bromo-3-(1-methyl-1H-pyrazol-4-yl) pyrazin-2-amine | 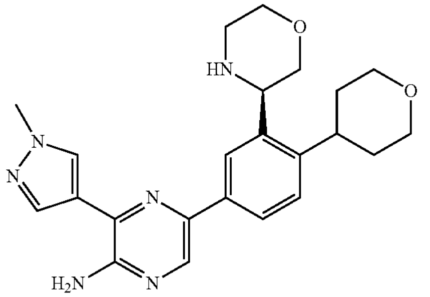 [α]$_d$: −73.2° (589 nm, c 0.25 w/v %, DMF, 20° C.) m.p. = 242° C. (DSC) | 0.76 g | 46% |
| Co. 92 Starting from Intermediate 100b and 17 | 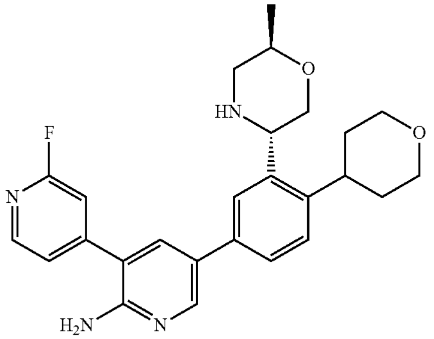 [α]$_d$: +60.6° (589 nm, c 0.17 w/v %, DMF, 20° C.) m.p. = 209° C. (DSC) | 0.052 g | 19% |
| Co. 93a Starting from Intermediate 101 and 5-bromo-[3,4'-bipyridin]-2-amine | 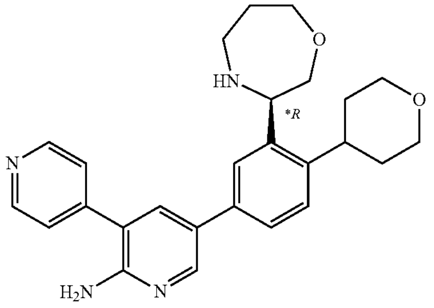 [SMILES: Nc1ncc(-c2ccc(C3CCOCC3)c([C@@H]3COCCCN3)c2)cc1-c1ccncc1] | 0.02 g | 3.5% |

-continued

| Compound | Structure | Quantity | Yield |
|---|---|---|---|
| Co. 93b Starting from Intermediate 101 and 5-bromo-[3,4'-bipyridin]-2-amine | 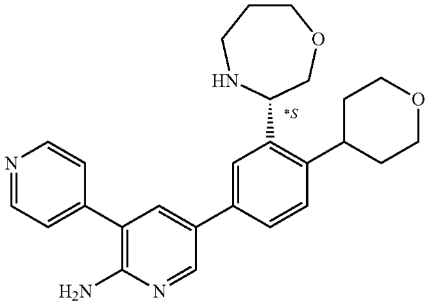 [SMILES: Nc1ncc(-c2ccc(C3CCOCC3)c([C@H]3COCCCN3)c2)cc1-c1ccncc1] | 0.028 g | 5% |

Synthesis of Co.94

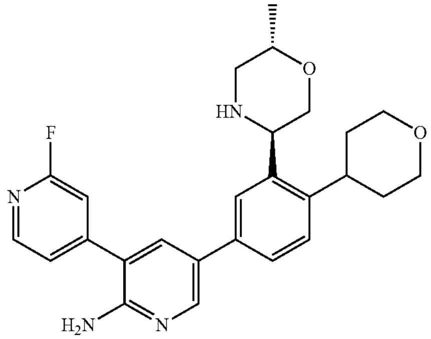 [SMILES: C[C@H]1CN[C@H](c2cc(-c3cnc(N)c(-c4ccnc(F)c4)c3)ccc2C2CCOCC2)CO1]

Sodium carbonate (0.402 g, 3.79 mmol) was added to a solution of Co.79 (0.82 g, 1.90 mmol), 2-Fluoropyridine-4-boronic acid pinacol ester (0.508 g, 2.28 mmol) in water (1.8 mL) and 1,4-dioxane (18 mL). The mixture was degassed with a stream of nitrogen for 5 min., then $PdCl_2$(dppf) (0.085 g, 0.104 mmol) was added. The reaction mixture was stirred at 90° C. for 6 hours in a sealed tube. The reaction mixture was cooled to rt, poured into water and $K_2CO_3$. The aqueous layer was extracted with ethyl acetate. The organic layer was dried over $MgSO_4$, filtered and evaporated until dryness. The residue was purified by preparative LC (40 g SiOH 15 μm Interchim, mobile phase: DCM/MeOH/$NH_4OH$ 100/0/0 to 90/10/0.1) The pure fractions were collected and evaporated until dryness. The compound was taken up in diisopropylether, stirred, filtered and dried yielding Co.94 (0.735 g, 85%). $[\alpha]_d$: −82.7° (589 nm, c 0.22 w/v %, DMF, 20° C.).

Synthesis of Co.95

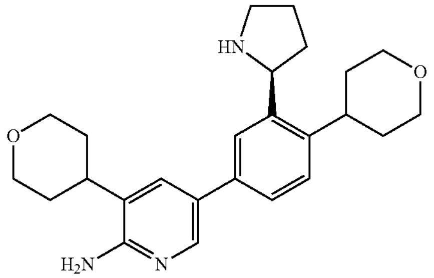 [SMILES: Nc1ncc(-c2ccc(C3CCOCC3)c([C@@H]3CCCN3)c2)cc1C1CCOCC1]

To a solution of intermediate 120 (0.240 g, 0.331 mmol) in DCM (5 mL) was added trifluoroacetic acid (2.54 mL) dropwise under an ice bath. The resulting reaction mixture was stirred at room temperature for 3 hours. The mixture was evaporated in vacuo and the crude mixture was neutralized with $NaHCO_3$ until basic-pH. The solvents were evaporated in vacuo and the crude was purified by reverse phase: Column: Brand Phenomenex; Type Gemini; I.D. (mm) 100×21.2; Particle size 5 um (C18). Method: From 81% of $H_2O$ (25 mM $NH_4HCO_3$)−19% (ACN: MeOH 1:1) until 45% of $H_2O$ (25 mM $NH_4HCO_3$)−55% (ACN: MeOH 1:1). The desired fractions were collected and the solvents were evaporated in vacuo. The solid was washed with acetonitrile and evaporated under high vacuum three times at 60° C. until a white solid appeared to give pure Co.95 (0.062 g, 45%). $[\alpha]_d$: −19.3° (589 nm, c 0.13 w/v %, methanol, 23° C.). m.p.=223° C. (Mettler Toledo MP50)

The compound listed in the table below was prepared by an analogous reaction protocol:

| Compound | Structure | Quantity | Yield |
|---|---|---|---|
| Co. 96 Starting from intermediate 159 | 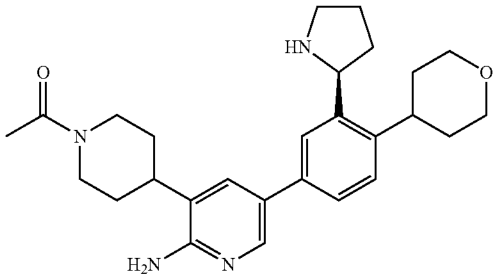 [α]$_d$: −44.6° (589 nm, c 0.12 w/v %, MeOH, 23° C.) m.p. = 237° C. (Mettler Toledo MP50)) | 0.115 g | 75% |

Synthesis of Co.97

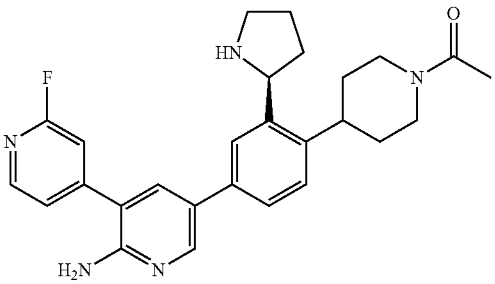

A mixture of Co.47 (0.324 g, 0.709 mmol), Pd/C 10% (0.3 g, 0.282 mmol) in THF (10 mL) was hydrogenated under 10 bars pressure at 55° C. overnight. The reaction mixture was filtered over celite, washed with DCM and the filtrate was evaporated. The residue was purified by preparative LC (12 g SiOH 40 μm irregular, mobile phase: DCM/MeOH/$NH_4OH$ 95/5/1 to 90/10/1) The pure fractions were collected and evaporated until dryness. The compound was taken up in diisopropylether, stirred, filtered and dried yielding Co.97 (0.08 g, 25%). [α]$_d$: −30.71° (589 nm, c 0.28 w/v %, DMF, 20° C.).

The compounds listed in the table below have been prepared by an analogous reaction protocol:

| Compound | Structure | Quantity | Yield |
|---|---|---|---|
| Co. 98 Starting from Co. 46 | 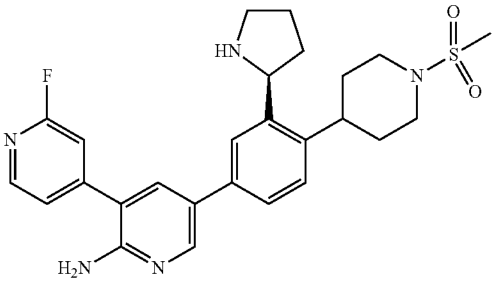 [α]$_d$: −16.8° (589 nm, c 0.28 w/v %, DMF, 20° C.) | 0.1 g | 35% |
| Co. 99 Starting from Co. 48 | 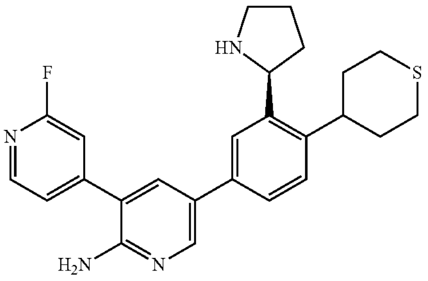 m.p. = 222° C. (DSC) | 0.097 g | 27% |

-continued

| Compound | Structure | Quantity | Yield |
|---|---|---|---|
| Co. 100 Starting from Co. 49 | 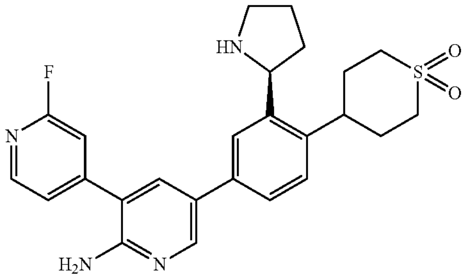 [SMILES: Nc1ncc(-c2ccc(C3CCS(=O)(=O)CC3)c([C@@H]3CCCN3)c2)cc1-c1ccnc(F)c1] | 0.15 g | 45% |
| Co. 101 Starting from Co. 45 | 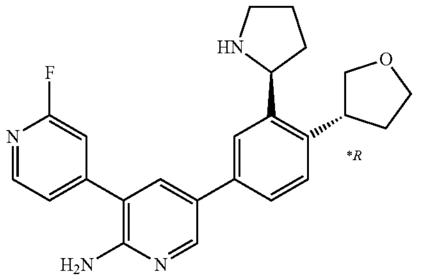 [SMILES: Nc1ncc(-c2ccc([C@H]3CCOC3)c([C@@H]3CCCN3)c2)cc1-c1ccnc(F)c1] | 0.05 g | 20% |
| Co. 102 Starting from Co. 55 | 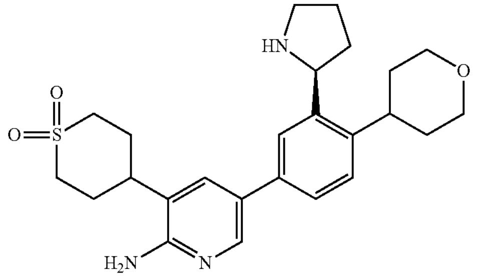 [α]d: −33.7° (589 nm, c 0.27 w/v %, DMF, 20° C.) | 0.024 g | 28% |

Synthesis of Co.103

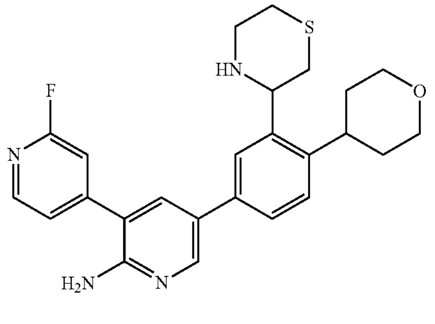 [SMILES: Nc1ncc(-c2ccc(C3CCOCC3)c(C3CSCCN3)c2)cc1-c1ccnc(F)c1]

Intermediate 90 (1.45 g, 3.84 mmol) and molecular sieves 4A (0.2 g) were added to SLAP™ (0.78 g, 4.8 mmol) in DCM (16 mL). The reaction mixture was stirred at rt 5 h, filtered over Celite©. The filtrate was evaporated till dryness to afford the imine which was added to a solution of $[Ir(dtbbpy)(ppy)_2]PF_6$ (35 mg, 0.0384 mmol), Copper (II) trifluoromethanesulfonate (1.39 g, 3.85 mmol) and Bismuth (III) trifluoromethane sulfonate (1.26 g, 1.93 mmol) in MeCN (80 mL). The reaction mixture was stirred at rt for 16 h under blue light (34 W—Hepatochem photoreactor—irraditated with a Kessil lamp). The reaction mixture was poured into $H_2O$ and $K_2CO_3$ and extracted with DCM. The organic layer was dried over $MgSO_4$, filtered and evaporated until dryness. The residue was purified by preparative LC twice (Stationary phase: irregular SiOH 15-40 μm 80 and 40 g GraceResolv, gradient from $DCM/MeOH/NH_4OH$ 98/2/0 to 95/5/0.1). The fractions were collected and evaporated until dryness yielding Co.103 (1.09 g, 63%).

The compounds listed in the table below have been prepared by an analogous reaction protocol as was described for preparation of Co.103:

| Compound | Structure |
|---|---|
| Co. 103a | 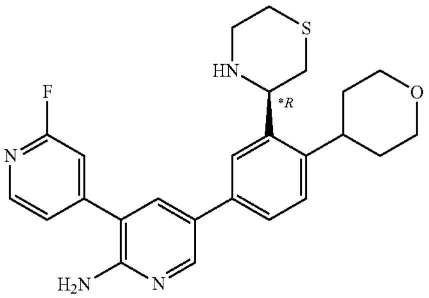 [α]d: −40.8° (589 nm, c 0.26 w/v %, DMF, 20° C.) |
| Co. 103b | 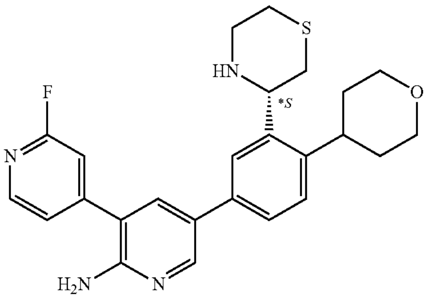 [α]d: +77.7° (589 nm, c 0.26 w/v %, DMF, 20° C.) |

Synthesis of Co.104

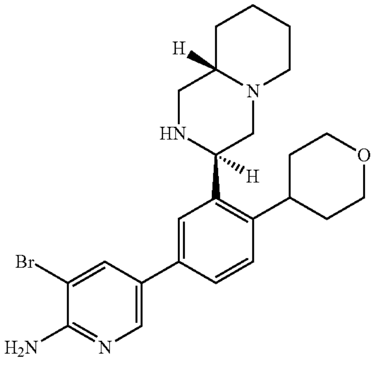 [SMILES: Nc1ncc(-c2ccc(C3CCOCC3)c([C@@H]3CN4CCCC[C@H]4CN3)c2)cc1Br]

A mixture of intermediate 86 (100 mg, 0.28 mmol), SLAP hydropyridopyrazine (55 mg, 0.28 mmol), molecular sieves (30 mg) in DCM (7 mL) was stirred at rt for 5 h. The imine was filtered off over celite, the filtrate was evaporated. Acetonitrile (4 mL), trifluoromethanol (1 mL) and DCM (3 mL) were added and then the photocalyst [Ir(dtbbpy)(ppy)$_2$]$PF_6$ (2.5 mg). The reaction mixture was stirred at rt for 16 h under blue light (34 W—Hepatochem photoreactor—irraditated with a Kessil lamp). Water and AcOEt were added, the aqueous phase was extracted, the organic layer was separated, dried over $MgSO_4$, filtered and evaporated. A first purification was performed via preparative LC (Stationary phase: irregular SiOH 40 μm 4 g, Mobile phase: 98/2 to 90/10/1 DCM/MeOH/$NH_4OH$) followed by a second one via reverse phase (Stationary phase: YMC-actus Triart C18 10 μm 30*150 mm, Mobile phase: Gradient from 65% $NH_4HCO_3$ 0.2%, 35% ACN to 25% NH4HCO3 0.2%, 75% ACN) yielding Co. 104 (15 mg, 11%).

Synthesis of Co.105

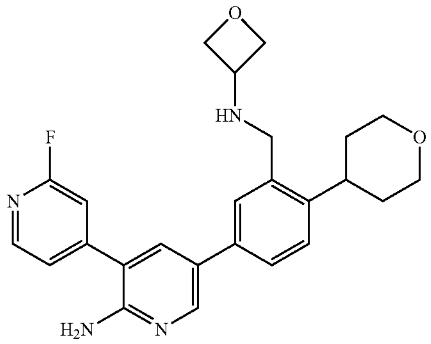 [SMILES: Nc1ncc(-c2ccc(C3CCOCC3)c(CNC3COC3)c2)cc1-c1ccnc(F)c1]

Sodium triacetoxyborohydride (0.168 g, 0.8 mmol) was added portionwise to a mixture of intermediate 90 (0.150 g, 0.4 mmol), 3-Oxetanamine (0.090 g, 1.2 mmol) in DCM (3 mL) at room temperature. The reaction mixture was stirred for 15 hours. Water was added and the mixture was basified with potassium carbonate. The organic layer was extracted, dried over $MgSO_4$, filtered and evaporated until dryness. The residue was purified by preparative LC (12 g of SiOH 15 μm Interchim, graduent from 100% DCM to 90% DCM 10% $CH_3OH$ 0.1% $NH_4OH$). The fractions were collected and evaporated until dryness and the compound was cristallized in diisopropylether, filtered and dried to give of Co.105 (0.085 g, 49%).

The compounds listed in the table below have been prepared by an analogous reaction protocol:

| Compound | Structure | Quantity | Yield |
| --- | --- | --- | --- |
| Co. 106 Starting from intermediate 91 | 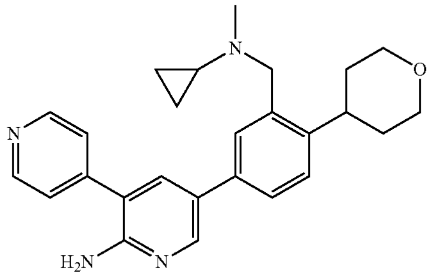 m.p. = 245° C. (DSC) | 0.023 g | 13% |
| Co. 107 Starting from intermediate 91 | 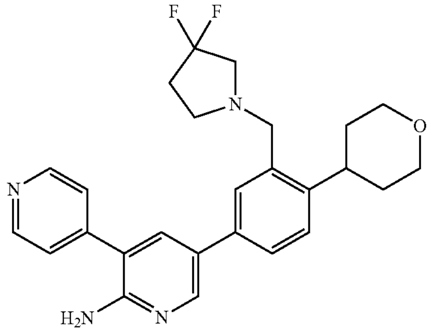 [SMILES: Nc1ncc(-c2ccc(C3CCOCC3)c(CN3CCC(F)(F)C3)c2)cc1-c1ccncc1] | 0.02 g | 11% |
| Co. 108 Starting from intermediate 91 | 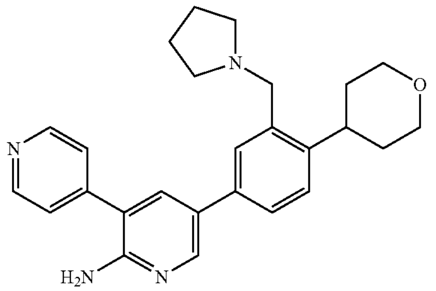 [SMILES: Nc1ncc(-c2ccc(C3CCOCC3)c(CN3CCCC3)c2)cc1-c1ccncc1] | 0.026 g | 26% |

Synthesis of Co.109

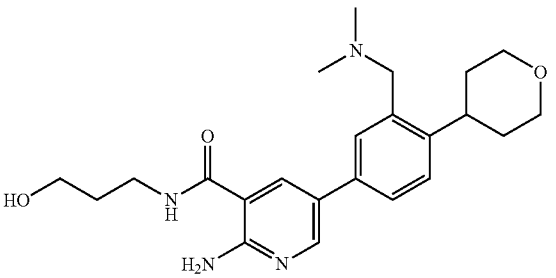 [SMILES: CN(C)Cc1cc(-c2cnc(N)c(C(=O)NCCCO)c2)ccc1C1CCOCC1]

Aminopropanol (0.045 mL, 0.59 mmol) was added to a stirring solution of intermediate 169 (0.15 g, 0.422 mmol), DIPEA (0.147 mL, 0.84 mmol), 1-Ethyl-3-(3-dimethylaminopropyl) carbodiimide hydrochloride (0.121 g, 0.63 mmol), HOBt (0.086 g, 0.63 mmol) in DCM (3.2 mL) and DMSO (1.5 mL). The reaction mixture was stirred at rt overnight. To complete the reaction, 1.5 eq of 1-Ethyl-3-(3-dimethylaminopropyl) carbodiimide hydrochloride, 1.5 eq of HOBt, 1.4 eq of aminopropanol, 2 eq of DIPEA were added. After 14 h at rt, the reaction mixture was diluted with water (5 mL) and DCM (20 mL). The layers were separated and the aqueous phase extracted with DCM (3×5 mL). The organic layer was dried over $MgSO_4$, filtered and evaporated until dryness. The residue was purified by flash chromatography (silica, gradient: 0-100% DCM-DCM/MeOH (4/1)). The desired fractions were collected and evaporated yielding Co. 109 (0.092 g, 52%). m.p.=203° C.

The compounds listed in the table below have been prepared by an analogous reaction protocol:

| Compound | Structure | Quantity | Yield |
|---|---|---|---|
| Co. 110 Starting from intermediate 169 | 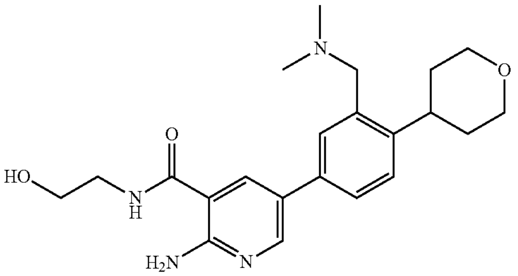 m.p. = 272° C. (MP50 Mettler Toledo) | 0.060 g | 35% |
| Co. 111 Starting from intermediate 169 | 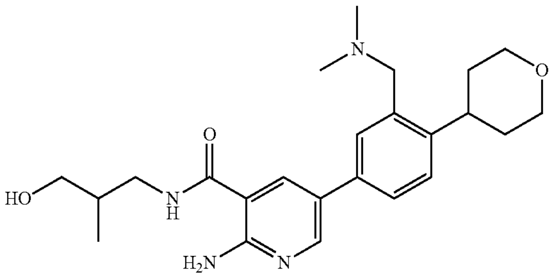 m.p. = 228° C. (MP50 Mettler Toledo) | 0.075 g | 41% |

Analytical Part

Optical Rotation (OR)

Optical rotations were measured at 20° C. or 23° C. on a Perkin Elmer 341 digital polarimeter at λ=589 nm (i.e., sodium D line), using a 0.2 mL cell (1=1 dm), and are given as $[\alpha]_D$ (concentration in g/100 mL solvent).

LCMS (Liquid Chromatography/Mass Spectrometry)

LCMS General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl.), the reported value is the one obtained for the lowest isotope mass. All results were obtained with experimental uncertainties that are commonly associated with the method used.

Hereinafter, "MSD" means Mass Selective Detector, "DAD" Diode Array Detector.

TABLE

LCMS Method codes (Flow expressed in mL/min; column temperature (T) in ° C.; Run time in minutes).

| Method code | Instrument | Column | Mobile phase | gradient | Flow Column T | Run time |
|---|---|---|---|---|---|---|
| 1 | Agilent: 1100-DAD and MSD | YMC: Pack ODS-AQ (3 μm, 4.6 x 50 mm) | A: HCOOH 0.1% in water, B: $CH_3CN$ | 95% A to 5% A in 4.8 min, held for 1 min, back to 95% A in 0.2 min. | 2.6<br>35<br>60 | 6 |
| 2 | Agilent 1290 Infinity DAD TOF-LC/MS G6224A | YMC-pack ODS-AQ C18 (50 x 4.6 mm, 3 μm) | A: 0.1% HCOOH in $H_2O$<br>B: $CH_3CN$ | ISET 2V1.0 Emulated Agilent Pump G1312A V1.0<br>From 94.51% A to 5% A in 4.8 min, held for 1.0 min, to 95% A in 0.2 min | 2.6<br>35 | 6 |

TABLE-continued

| LCMS Method codes (Flow expressed in mL/min; column temperature (T) in ° C.; Run time in minutes). | | | | | | |
|---|---|---|---|---|---|---|
| Method code | Instrument | Column | Mobile phase | gradient | Flow Column T | Run time |
| 3 | Waters: Acquity UPLC ® - DAD and Quattro Micro ™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 40 | 6.2 |
| 4 | Waters: Acquity ® H-Class - DAD and SQD2 ™ | Waters: BEH C18 (1.7 μm, 2.1 × 100 mm) | A: 95% $CH_3COONH_4$ 7 mM/5% $CH_3CN$, B: $CH_3CN$ | 84.2% A to 10.5% A in 2.18 min, held for 1.96 min, back to 84.2% A in 0.73 min, held for 0.73 min. | 0.343 40 | 6.1 |
| 5 | Waters: Acquity ® UPLC - DAD and Quattro ™ | Waters HSS ® T3 (1.8 μm, 2.1 × 100 mm) | A: $CH_3COONH_4$ 7 mM 95%/ CH3CN 5%, B: $CH_3CN$ | 99% A/1% B for 0.5 min, to 15% A in 3.5 min, held for 2 min, back to 99% A/1% B in 0.5 min, held for 1.5 min. | 0.35 40 40 | 8 |

Melting Points

For a number of compounds, melting points (m.p.) were determined with a DSC 1 STAR' System from Mettler Toledo (method 1) or a Mettler Toledo MP50 (method 2) or a Kofler bench (method 3). Melting points were measured with a temperature gradient of 10° C./minute up to 350° C. Melting points are given by peak values.

The results of the analytical measurements are shown in table 3.

TABLE 3

| Retention time ($R_t$) in min., $[M + H]^+$ peak (protonated molecule), LCMS method and m.p. (melting point in ° C.) (n.d. means not determined). | | | | | |
|---|---|---|---|---|---|
| Co. No. | $R_t$ | $[M + H]^+$ | LCMS Method | m.p. (° C.) | m.p. method |
| 1 | 2.03 | 419.3 | 3 | 218 | 1 |
| 2 | 2.02 | 420.3 | 3 | >300 | 2 |
| 6 | 1.53 | 430.2 | 1 | 196 | 2 |
| 9 | 1.44 | 415.2 | 1 | 218 | 2 |
| 10 | 1.42 | 415.2 | 1 | n.d. | |
| 11 | 1.79 | 403.3 | 3 | 245 | 2 |
| 12 | 1.59 | 403.3 | 3 | 196 | 2 |
| 13 | 1.20 | 398.1 | 1 | 257 | 2 |
| 14 | 1.46 | 399.1 | 1 | 263 | 2 |
| 15 | 1.60 | 399.1 | 1 | >300 | 2 |
| 16 | 1.35 | 375.1 | 1 | 265 | 2 |
| 17 | 2.10 | 435.2 | 3 | n.d. | |
| 18 | 2.09 | 444.2 | 3 | n.d. | |
| 19 | 2.08 | 468.2 | 3 | n.d. | |
| 20 | 2.34 | 407.2 | 3 | n.d. | |
| 21 | 1.76 | 434.2 | 3 | n.d. | |
| 22 | 2.16 | 432.2 | 3 | 192 | 1 |
| 23 | 1.78 | 390.1 | 3 | 223 | 1 |
| 24 | 1.92 | 431.2 | 3 | 218 | 1 |
| 25 | 1.90 | 401.2 | 3 | 238 | 1 |
| 26 | 1.90 | 402.3 | 3 | 201 | 2 |
| 27 | 1.82 | 437.2 | 1 | >300 | 2 |
| 28 | n.d. | 419.2 | 1 | 230 | 2 |
| 29 | 1.79 | 468.2 | 1 | 228 | 2 |
| 31 | 1.79 | 437.2 | 1 | 225 | 2 |
| 32 | 1.86 | 453.1 | 1 | 222 | 2 |
| 33 | 1.37 | 402.2 | 1 | 240 | 2 |
| 34 | 2.17 | 451.2 | 3 | n.d. | |
| 35 | 1.88 | 453.1 | 1 | 218 | 2 |
| 36 | 1.74 | 425.1 | 1 | 232 | 2 |

TABLE 3-continued

| Retention time ($R_t$) in min., $[M + H]^+$ peak (protonated molecule), LCMS method and m.p. (melting point in ° C.) (n.d. means not determined). | | | | | |
|---|---|---|---|---|---|
| Co. No. | $R_t$ | $[M + H]^+$ | LCMS Method | m.p. (° C.) | m.p. method |
| 37 | 2.16 | 404.0 | 3 | 173 | 1 |
| 38 | 2.84 | 417.2 | 3 | n.d. | |
| 39 | 2.07 | 405.3 | 3 | 185 | |
| 40 | 2.13 | 471.6 | 4 | n.d. | |
| 41 | 1.82 | 405.2 | 1 | 217 | 2 |
| 43 | 2.03 | 420 | 1 | 217 | 2 |
| 44 | 1.90 | 349.2 | 3 | 206 | 1 |
| 45 | 2.05 | 403.1 | 3 | 207 | 1 |
| 46 | 2.11 | 494.2 | 3 | 224 | 1 |
| 47 | 1.96 | 458.2 | 3 | 227 | 1 |
| 48 | 2.37 | 433.1 | 3 | 208 | 1 |
| 49 | 1.94 | 465.1 | 3 | n.d. | |
| 50 | 2.49 | 453.2 | 3 | 219 | 1 |
| 51 | 2.34 | 447.3 | 3 | n.d. | |
| 52 | 2.07 | 472.2 $[M + CH_3CN]^+$ | 3 | 222 | 1 |
| 53 | 2.21 | 393.1 | 3 | 219 | 1 |
| 54 | 1.86 | 391 | 3 | n.d. | |
| 55 | 1.67 | 454.5 | 4 | n.d. | |
| 56 | 1.44 | 417.5 | 4 | n.d. | |
| 57 | 1.47 | 417.5 | 4 | n.d. | |
| 58 | 2.57 | 455.5 | 4 | 216 | 1 |
| 59 | 2.55 | 455.5 | 4 | 215 | 1 |
| 60 | 1.85 | 360.1 | 3 | n.d. | |
| 61 | 2.06 | 426.3 | 3 | n.d. | |
| 62 | 2.33 | 418.2 | 3 | 216 | 1 |
| 63 | 2.27 | 469.3 | 3 | 213 | 1 |
| 64 | 1.91 | 402.2 | 3 | n.d. | |
| 65 | 1.78 | 403 | 4 | n.d. | |
| 66 | 2.56 | 417.4 | 5 | >260 | 3 |
| 67 | 1.79 | 473.6 | 4 | 185 | 3 |
| 68 | 1.73 | 404.6 | 4 | n.d. | |
| 69 | 2.02 | 403.6 | 4 | 236 | 3 |
| 70 | 2.19 | 403.1 | 3 | 225 | 3 |
| 71 | 2.45 | 419.1 | 3 | 222 | 3 |
| 72 | 2.04 | 407.5 | 4 | 234 | 3 |
| 73 | 2.04 | 389.1 | 3 | 227 | 1 |
| 74 | 1.81 | 448.6 | 4 | n.d. | |
| 75 | 2.00 | 462.2 | 3 | 170 | 3 |
| 76 | 2.67 | 388 | 3 | 173 | 3 |
| 77 | 2.12 | 390.1 | 3 | n.d. | |
| 78 | 2.32 | 418.1 | 3 | 208 | 1 |

TABLE 3-continued

Retention time ($R_t$) in min., $[M + H]^+$ peak (protonated molecule), LCMS method and m.p. (melting point in ° C.) (n.d. means not determined).

| Co. No. | $R_t$ | $[M + H]^+$ | LCMS Method | m.p. (° C.) | m.p. method |
|---|---|---|---|---|---|
| 79 | 2.45 | 474.9 $[M + CH_3CN]^+$ | 3 | 176 | 1 |
| 81 | 2.05 | 420.1 | 3 | n.d. | |
| 82 | 2.30 | 435.2 | 3 | n.d. | |
| 84 | 1.98 | 421.2 | 3 | 243 | 1 |
| 85 | 2.25 | 374 | 3 | 213 | 1 |
| 86 | 2.05 | 354 | 3 | 266 | 1 |
| 87 | 2.03 | 370 | 3 | 239 | 1 |
| 88 | 2.08 | 358 | 3 | 225 | 1 |
| 89 | 2.10 | 406.0 $[M + CH_3CN]^+$ | 3 | 258 | 1 |
| 90 | 2.11 | 435.2 | 3 | 246 | 1 |
| 92 | 2.46 | 449.2 | 3 | 209 | 1 |
| 94 | 2.46 | 449.2 | 3 | 205 | 1 |
| 95 | 1.91 | 408.4 | 3 | 223 | 2 |
| 96 | 1.37 | 449.4 | 1 | 237 | 2 |
| 98 | 2.11 | 496.4 | 3 | n.d. | |
| 99 | 2.41 | 435.1 | 3 | 222 | 1 |
| 100 | 1.94 | 467.1 | 3 | n.d. | |
| 101 | 1.99 | 405.1 | 3 | n.d. | |
| 102 | 1.80 | 456.2 | 3 | n.d. | |
| 105 | 2.25 | 435.2 | 3 | n.d. | |
| 106 | 2.91 | 415.2 | 3 | 245 | 1 |
| 107 | 2.75-2.79 | 451.2 | 3 | nd | |
| 108 | 2.06 | 415.2 | 3 | n.d. | |
| 109 | 1.16 | 413.3 | 2 | 203 | 2 |
| 110 | 1.05 | 399.2 | 2 | 272 | 2 |
| 111 | 1.26 | 427.3 | 2 | 228 | 2 |
| 103a | 2.55 | 451.3 | 3 | n.d. | |
| 103b | 2.55 | 451.3 | 3 | n.d. | |
| 15a | 1.97 | 508.3 $[M + CH_3CN]^+$ | 3 | n.d. | |
| 15b | 1.97 | 467.2 | 3 | n.d. | |
| 15c | 2.02 | 467.2 | 3 | n.d. | |
| 15d | 2.02 | 467.2 | 3 | n.d. | |
| 1b | 1.63 | 419 | 1 | n.d. | |
| 25b | 1.89 | 401.2 | 3 | n.d. | |
| 5a | 2.32 | 445.2 | 3 | n.d. | |
| 5b | 2.32 | 445.1 | 3 | n.d. | |
| 7a | 2.47 | 459.2 | 3 | n.d. | |
| 7b | 2.46 | 459.2 | 3 | n.d. | |
| 80a | 2.05 | 417.2 | 3 | n.d. | |
| 80b | 2.05 | 417.3 | 3 | n.d. | |
| 83a | 2.17 | 431.4 | 3 | n.d. | |
| 83b | 2.20 | 431.3 | 3 | n.d. | |
| 8a | 2.09 | 427.2 | 3 | n.d. | |
| 8b | 2.08 | 427.2 | 3 | n.d. | |
| 93a | 1.88 | 431.6 | 4 | n.d. | |
| 93b | 1.89 | 431.6 | 4 | n.d. | |

NMR

Some NMR experiments were carried out using a Bruker Avance 500 spectrometer equipped with a Bruker 5 mm BBFO probe head with z gradients and operating at 500 MHz for the proton and 125 MHz for carbon. Chemical shifts (d) are reported in parts per million (ppm). J values are expressed in Hz.

Some NMR experiments were carried out using a Bruker Avance III 400 spectrometer at ambient temperature (298.6 K), using internal deuterium lock and equipped with reverse double-resonance ($^{C}$H, $^{13}$C, SEI) probe head with z gradients and operating at 400 MHz for the proton. Chemical shifts (d) are reported in parts per million (ppm). J values are expressed in Hz.

TABLE 4

$^1$H NMR results

| Co. No. | $^1$H NMR result |
|---|---|
| 1 | $^1$H NMR (500 MHz, DMSO-$d_6$) δ 8.28-8.37 (m, 2 H), 7.76 (d, J = 1.98 Hz, 1 H), 7.68 (d, J = 2.44 Hz, 1 H), 7.52 (td, J = 1.56, 5.11 Hz, 1 H), 7.44 (dd, J = 2.06, 8.01 Hz, 1 H), 7.35 (s, 1 H), 7.29 (d, J = 8.09 Hz, 1 H), 6.08 (s, 2 H), 4.32 (t, J = 7.78 Hz, 1 H), 3.91-4.02 (m, 2 H), 3.43-3.54 (m, 2 H), 3.33 (br s, 2 H), 3.05-3.19 (m, 2 H), 2.88 (td, J = 7.67, 9.54 Hz, 1 H), 2.71 (br s, 1 H), 2.10-2.20 (m, 1 H), 1.66-1.88 (m, 4 H), 1.51-1.65 (m, 2 H), 1.34-1.49 (m, 1 H) |
| 25 | $^1$H NMR (400 MHz, DMSO-$d_6$) δ ppm 8.63-8.68 (m, 2 H), 8.36 (d, J = 2.3 Hz, 1 H), 7.77 (d, J = 1.8 Hz, 1 H), 7.70 (d, J = 2.3 Hz, 1 H), 7.52-7.59 (m, 3 H), 7.36 (d, J = 8.2 Hz, 1 H), 6.00 (s, 2 H), 4.62 (t, J = 8.2 Hz, 1 H), 3.96 (br d, J = 11.1 Hz, 2 H), 3.45-3.55 (m, 2 H), 3.20-3.30 (m, 1 H), 3.07-3.18 (m, 2 H), 2.19-2.30 (m, 1 H) 1.85-2.03 (m, 2 H) 1.61-1.82 (m, 4 H) 1.56 (br d, J = 12.7 Hz 1 H) |
| 41 | $^1$H NMR (500 MHz, DMSO-$d_6$) δ ppm 8.37 (s, 1 H), 8.32 (s, 1 H), 8.12 (s, 1 H), 8.04 (s, 1 H), 7.80 (br d, J = 7.9 Hz, 1 H), 7.32 (br d, J = 8.2 Hz, 1 H), 6.12 (br s, 2 H), 4.39 (br t, J = 7.6 Hz, 1 H), 3.88-4.02 (m, 5 H), 3.49 (br t, J = 11.3 Hz, 2 H), 3.09-3.21 (m, 2 H), 2.89-3.02 (m, 1 H), 2.11-2.23 (m, 1 H), 1.68-1.96 (m, 4 H), 1.54-1.68 (m, 2 H) 1.43-1.54 (m, 1 H) |
| 44 | $^1$H NMR (500 MHz, DMSO-$d_6$) δ ppm 8.50 (d, J = 2.5 Hz, 1 H), 8.14 (d, J = 2.5 Hz, 1 H), 7.73 (d, J = 1.9 Hz, 1 H), 7.42 (dd, J = 7.9, 1.9 Hz, 1 H), 7.30 (d, J = 8.2 Hz, 1 H), 6.92 (s, 2 H), 4.33 (t, J = 7.7 Hz, 1 H), 3.89-4.00 (m, 2 H), 3.43-3.53 (m, 2 H), 3.06-3.20 (m, 2 H), 2.83-2.94 (m, 1 H), 2.70 (br s, 1 H), 2.08-2.22 (m, 1 H) 1.66-1.90 (m, 4 H) 1.50-1.65 (m, 2 H) 1.44 (dq, J = 11.7, 8.4 Hz, 1 H) |
| 73 | $^1$H NMR (500 MHz, DMSO-$d_6$) δ ppm 8.65 (d, J = 5.7 Hz, 2 H), 8.32 (d, J = 2.2 Hz, 1 H), 7.66 (d, J = 1.9 Hz, 1 H), 7.57 (d, J = 5.7 Hz, 2 H), 7.52 (dd, J = 7.9, 1.3 Hz, 1 H), 7.47 (s, 1 H), 7.33 (d, J = 8.2 Hz, 1 H), 5.92 (s, 2 H), 3.96 (br dd, J = 11.0, 3.5 Hz, 2 H), 3.38-3.52 (m, 4 H), 3.12-3.26 (m, 1 H), 2.17 (s, 6 H), 1.70 (qd, J = 12.3, 3.8 Hz, 2 H), 1.58-1.64 (m, 2 H) |
| 78 | $^1$H NMR (500 MHz, DMSO-$d_6$) δ ppm 8.25 (d, J = 1.9 Hz, 1 H), 7.99 (d, J = 1.9 Hz, 1 H), 7.75 (d, J = 1.9 Hz, 1 H), 7.46 (dd, J = 8.2, 1.9 Hz, 1 H), 7.32 (d, J = 8.2 Hz, 1 H), 6.28 (s, 2 H), 4.12 (dd, J = 9.9, 2.7 Hz, 1 H), 3.96 (td, J = 10.7, 3.8 Hz, 2 H), 3.76 (br d, J = 9.5 Hz, 1 H), 3.65 (dd, J = 10.9, 2.7 Hz, 1 H), 3.46-3.56 (m, 3 H), 3.25 (d, J = 10.4 Hz 1 H), 3.10-3.19 (m, 1 H), 2.97 (td, J = 12, 2.8 Hz, 1 H), 2.91 (d, |

TABLE 4-continued

| $^1H$ NMR results | |
|---|---|
| Co. No. | $^1H$ NMR result |
| | J = 11 Hz, 1 H), 2.77 (br s, 1 H), 1.79 (qd, J = 12.3, 4.3 Hz, 1 H), 1.60-1.73 (m, 2 H), 1.56 (br d, J = 12.6 Hz 1 H) |
| 84 | $^1H$ NMR (500 MHz, DMSO-$d_6$) δ ppm 8.37 (s, 1 H), 8.32 (s, 1 H), 8.14 (d, J = 1.6 Hz, 1 H), 8.04 (s, 1 H), 7.85 (dd, J = 8.0, 1.7 Hz, 1 H), 7.35 (d, J = 8.2 Hz, 1 H), 6.15 (s, 2 H), 4.14 (br dd, J = 9.8, 2.2 Hz, 1 H), 3.89-4.02 (m, 5 H), 3.78 (br d, J = 10.7 Hz, 1 H), 3.67 (dd, J = 10.7, 2.5 Hz, 1 H), 3.46-3.59 (m, 3 H), 3.25-3.35 (m, 1 H, partially obscured by solvent peak), 3.15-3.23 (m, 1 H), 2.88-3.02 (m, 2 H), 2.72 (br s, 1 H), 1.81 (qd, J = 12.3, 4.3 Hz, 1 H), 1.62-1.74 (m, 2 H), 1.58 (br d, J = 12.9 Hz, 1 H) |
| 94 | $^1H$ NMR (400 MHz, DMSO-$d_6$) δ ppm 8.28-8.34 (m, 2 H), 7.78 (d, J = 1.7 Hz, 1 H), 7.69 (d, J = 2.3 Hz, 1 H), 7.52 (br d, J = 6.4 Hz, 2 H), 7.31-7.37 (m, 2 H), 6.11 (s, 2 H), 4.10 (br d, J = 8.7 Hz, 1 H), 3.91-4.01 (m, 2 H), 3.68 (br dd, J = 11.0, 2.4 Hz, 1 H), 3.56-3.64 (m, 1 H), 3.51 (br t, J = 11.1 Hz, 2 H), 3.26-3.26 (m, 1 H, partially obscured by solvent peak), 3.07-3.21 (m, 1 H), 2.98 (br d, J = 11.2 Hz, 1 H), 2.56-2.65 (m, 1 H), 1.60-1.85 (m, 3 H), 1.55 (br d, J = 12.6 Hz, 1 H), 1.09 (d, J = 6.2 Hz, 3 H) |

Pharmacological Part

HPK1 Kinase Assay

A recombinant fusion protein consisting of full-length human Hpk1 with an N-terminal Glutatione S-transferase (GST) tag was produced in a baculovirus/insect cell expression system. GST-Hpk1 protein was purified from cell lysates by glutathione sepharose affinity chromatography. Kinase inhibition was determined using the ADP Glo™ Kinase Assay kit (Promega, V9101). Test compounds were prepared by serial dilution in dimethyl sulfoxide (DMSO) and 0.1 μl of each dilution was spotted onto a 384-well white Proxiplate (Perkin Elmer, 6008289). 8 μl of kinase assay buffer (40 mM Tris pH 7.5, 2 mM dithiothreitol (DTT), 0.05% Bovine Serum Albumin, 5 mM $MgCl_2$) containing Hpk1 protein was transferred to each well and incubated for 30-45 minutes at room temperature. The enzymatic reaction was started by adding 2 μl of kinase assay buffer containing 75 μM ATP. After 120 minutes, the reaction was stopped by adding 3 μl of ADP Glo™ reagent (Promega, V9101) and incubating 45 minutes at room temperature. After adding 6 μl Kinase Detection Reagent (Promega, V9101) and incubating for at least 20 minutes at room temperature, the plate was transferred to an EnVision Plate Reader (Perkin Elmer) for luminescence detection and $IC_{50}$ values were determined.

SLP76 Phosphorylation Assay

Hpk1 inhibition in cells was determined by detection of SLP76 phosphorylation at S376 in lysates from HEK293 cells engineered to express Hpk1 and SLP76. Serial dilutions of test compounds were prepared in cell culture medium and 20 μl was transferred into each well of a 96-well plate containing HEK293 cells in 180 μl of culture medium. After incubation for 4 hours at 37° C./5% $CO_2$, the culture medium was removed, plates were put on ice and cells washed with cold Minimal Essential Medium before lysing in 90 μl of cold Mammalian Protein Extraction Reagent (Thermo Scientific, 78501) for 30 minutes on ice. The cell lysates were transferred to another 96-well plate, centrifuged 10 minutes at 3000 rcf (4° C.) and 30 μl transferred to a 96-well High-bind plate (MSD, L15XB-3). After coating overnight at 4° C., the cell lysate was removed, wells were washed with base buffer (TBS, 0.2% Tween-20), and blocking solution (base buffer containing 3% MSD blocker A) was added to each well for 1 hour at room temperature. The blocking solution was removed, the wells were washed with base buffer, and detection antibody (SLP76 pS376) was added in 25 μl base buffer containing 1% MSD blocker A to each well. After a 2 h incubation at room temperature, the detection antibody was removed, wells were washed four times with base buffer, 25 μl SULFO-TAG labeled goat anti-rabbit secondary antibody (MSD, R32AB-1) in base buffer containing 1% MSD blocker A was added to each well and left for 1 hour at room temperature. Wells were washed 4 times with base buffer, 150 μl Read Buffer T was added to each well, and the plates were read in a Mesoscale plate reader (MSD). $IC_{50}$ values were determined by curve-fitting the electrochemiluminescent signals obtained from the lysates of HEK293 cells expressing Hpk1 and SLP76 treated with test compounds at various concentrations minus the signal obtained from HEK293 cells expressing SLP76 only.

TABLE

Data of the HPK1 kinase assay and the SLP76 phosphorylation assay.

| Co. No. | Hpk1 biochemical ($pIC_{50}$) | pSLP76 (HEK293) ($pIC_{50}$) | Co. No. | Hpk1 biochemical ($pIC_{50}$) | pSLP76 (HEK293) ($pIC_{50}$) |
|---|---|---|---|---|---|
| 1 | 8.12 | 6.42 | 15a | 5.03 | <5 |
| 2 | 7.38 | 6.06 | 15b | 6.7 | <5 |
| 3 | 7.27 | 5.25 | 15c | 6.2 | <5 |
| 4 | 7.37 | 5.43 | 15d | 5.16 | <5 |
| 5a | 7.99 | 6.11 | 17 | 7.8 | 5.8 |
| 5b | 6.04 | n.d. | 18 | 7.75 | 5.81 |
| 7a | 7.92 | 6.87 | 19 | 8.37 | 6.01 |
| 7b | 5.71 | 5.14 | 20 | 8.5 | 6.77 |
| 8a | 8.2 | 6.46 | 21 | 7.73 | 5.16 |
| 8b | 6.87 | 5.16 | 22 | 8.56 | 6.47 |
| 9 | 7.37 | 5.67 | 23 | 8.99 | 6.52 |
| 10 | 8.18 | 6.55 | 24 | 7.88 | 6.05 |
| 11 | 7.45 | 5.3 | 25 | 8.01 | 6.37 |
| 12 | 6.95 | 5.13 | 25b | 6.02 | <5 |
| 13 | 6.73 | 5.05 | 26 | 8.69 | 6.61 |
| 14 | 6.08 | <5 | 27 | 8.24 | 6.62 |
| 15 | 6.24 | <5 | 28 | 7.99 | 6.5 |
| 29 | 7.42 | 5.22 | 73 | 7.37 | 5.81 |
| 30 | 7.55 | 6.31 | 74 | 7.25 | 5.73 |
| 31 | 7.69 | 5.98 | 75 | 7.38 | 5.64 |
| 32 | 7.55 | 5.73 | 76 | 7.46 | 5.71 |
| 33 | 7.84 | 5.64 | 77 | 7.85 | 5.59 |
| 34 | 7.76 | 5.74 | 78 | 8.09 | 6.04 |
| 35 | 8.09 | 6.17 | 79 | 7.59 | 6.1 |
| 36 | 8.1 | 6.16 | 80a | 7.84 | 6.07 |
| 37 | 8.14 | 6.19 | 80b | 5.43 | <5 |
| 38 | 8.12 | 5.89 | 81 | 7.81 | 6.09 |
| 39 | 8.63 | 6.56 | 82 | 8.06 | 6.9 |
| 40 | 8.05 | 5.96 | 83a | 7.35 | 5.87 |

TABLE-continued

Data of the HPK1 kinase assay and the SLP76 phosphorylation assay.

| Co. No. | Hpk1 biochemical ($pIC_{50}$) | pSLP76 (HEK293) ($pIC_{50}$) | Co. No. | Hpk1 biochemical ($pIC_{50}$) | pSLP76 (HEK293) ($pIC_{50}$) |
|---|---|---|---|---|---|
| 41 | 8.34 | 6.21 | 83b | 5.24 | n.d. |
| 42 | 7.61 | 5.7 | 84 | 7.6 | 6.32 |
| 43 | 7.67 | <5 | 85 | 7.42 | 5.94 |
| 44 | 8.03 | 6.47 | 86 | 6.92 | 5.4 |
| 45 | 7.38 | 5.95 | 87 | 7.32 | 5.96 |
| 46 | 7.45 | 5.99 | 88 | 6.95 | 5.38 |
| 47 | 7.61 | 5.87 | 89 | 7.67 | 6.07 |
| 48 | 7.6 | 5.88 | 90 | 7.45 | 5.91 |
| 49 | 7.62 | 5.6 | 92 | 5.71 | <5 |
| 50 | 7.7 | 5.61 | 93a | 6.79 | 5.34 |
| 51 | 7.74 | 6.26 | 93b | 7.73 | 5.91 |
| 52 | 7.41 | 6.07 | 94 | 7.89 | 6.24 |
| 53 | 7.8 | 6.01 | 95 | 7.36 | 5.65 |
| 54 | 6.34 | <5 | 96 | 6.84 | 5.1 |
| 55 | 7.02 | <5 | 98 | 7.58 | 6.14 |
| 56 | 7.45 | <5 | 99 | 7.67 | 6.19 |
| 57 | 7.58 | <5 | 100 | 7.71 | 5.73 |
| 58 | 5.06 | <5 | 101 | 8.43 | 6.16 |
| 59 | 7.11 | 5.25 | 102 | 6.53 | <5 |
| 60 | 6.6 | <5 | 103a | 8.11 | 5.71 |
| 61 | 7.46 | 5.4 | 103b | 6.22 | <5 |
| 62 | 7.5 | 5.97 | 104 | 7.23 | 5.1 |
| 63 | 7.23 | 5.27 | 105 | 6.42 | <5 |
| 64 | 7.77 | 6.42 | 106 | 6.75 | 5.13 |
| 65 | 7.57 | 5.92 | 107 | 6.08 | n.d. |
| 66 | 7.07 | <5 | 108 | 6.93 | 5.12 |
| 67 | 7.33 | 5.78 | 110 | 7.05 | 5.33 |
| 68 | 8.2 | 5.85 | 111 | 6.96 | 5.23 |
| 69 | 6.5 | n.d. | | | |
| 70 | 6.94 | 5.36 | | | |
| 71 | 7.38 | 5.69 | | | |
| 72 | 7.39 | 5.64 | | | |

Co. No. means Compound Number.

The invention claimed is:

1. A compound of Formula (I)

(I)

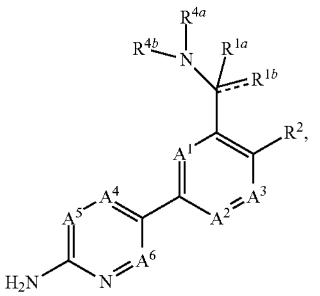

or a tautomer or a stereoisomeric form thereof, wherein the dotted bond towards $R^{1b}$ is an optional bond that may be present when $R^{1b}$ and $R^{4b}$ are taken together to form a monocyclic or bicyclic aromatic heterocyclyl as defined herein;

$A^1$ represents CH or N; $A^2$ represents CH; $A^3$ represents CH or N;

provided that only one of $A^1$ and $A^3$ represents N;

$A^4$ represents CH or N; $A^5$ represents $CR^{3a}$; $A^6$ represents CH;

$R^{1a}$ represents hydrogen;

$R^{1b}$ represents hydrogen or $CH_3$;

$R^{4a}$ represents hydrogen, $C_{1-4}$alkyl, or $C_{3-6}$cycloalkyl;

$R^{4b}$ represents hydrogen, $C_{1-4}$alkyl, $C_{3-6}$cycloalkyl, or a carbon linked monocyclic 4-, 5-, 6- or 7-membered non-aromatic heterocyclyl containing 1, 2 or 3 heteroatoms each independently selected from the group consisting of N, O, and S; wherein said S-atom might be substituted to form S(=O), $S(=O)_2$, or $S(=O)(=NR^x)$;

or $R^{1b}$ and $R^{4b}$ are taken together to form together with the atoms to which they are attached a monocyclic 5-membered aromatic heterocyclyl or a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(=O), $S(=O)_2$, or $S(=O)(=NR^x)$; or a bicyclic 6- to 12-membered aromatic or fully saturated heterocyclyl containing 1 N-atom and optionally 1 or 2 additional heteroatoms each independently selected from the group consisting of N, O, S; wherein said optional S-atom might be substituted to form S(=O), $S(=O)_2$, or $S(=O)(=NR^x)$;

wherein said monocyclic or bicyclic, aromatic or fully saturated heterocyclyl might be substituted on one or more of the carbon atoms with in total 1, 2 or 3 substituents each independently selected from the group consisting of —OH, CN, halo, $R^7$, —O—$R^7$, —$S(=O)_2$—$R^7$, —C(=O)—$R^7$, —$NR^{6c}R^{6d}$, —C(=O)-$NR^{6a}R^{6b}$, and $Het^c$;

wherein said monocyclic or bicyclic, aromatic or fully saturated heterocyclyl might be substituted on the optional additional nitrogen atoms with in total 1 or 2 substituents each independently selected from the group consisting of $R^7$, —$S(=O)_2$—$R^7$, —C(=O)—$R^7$, —C(=O)—$NR^{6a}R^{6b}$, and $Het^d$, provided that in case $R^{1b}$ and $R^{4b}$ are taken together, $R^{4a}$ represents hydrogen; and $R^{1a}$ represents hydrogen or $R^{1a}$ is absent when the dotted bond towards $R^{1b}$ is a bond;

or $R^{4a}$ and $R^{4b}$ are taken together to form together with the N-atom to which they are attached a monocyclic 5-membered aromatic heterocyclyl or a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(=O), $S(=O)_2$, or $S(=O)(=NR^x)$; or a bicyclic 6- to 12-membered aromatic or fully saturated heterocyclyl containing 1 N-atom and optionally 1 or 2 additional heteroatoms each independently selected from the group consisting of N, O, S; wherein said optional S-atom might be substituted to form S(=O), $S(=O)_2$, or $S(=O)(=NR^x)$;

wherein said monocyclic or bicyclic, aromatic or fully saturated heterocyclyl might be substituted on one or more of the carbon atoms with in total 1, 2 or 3 substituents each independently selected from the group consisting of —OH, CN, halo, $R^7$, —O—$R^7$, —$S(=O)_2$—$R^7$, —C(=O)—$R^7$, —$NR^{6c}R^{6d}$, —C(=O)—$NR^{6a}R^{6b}$, and $Het^c$;

wherein said monocyclic or bicyclic, aromatic or fully saturated heterocyclyl might be substituted on the nitrogen atoms with in total 1 or 2 substituents each independently selected from the group consisting of $R^7$, —S(═O)$_2$—$R^7$, —C(═O)—$R^7$, —C(═O)—$NR^{6a}R^{6b}$, and $Het^d$;

in case $R^{4a}$ and $R^{4b}$ are taken together, $R^{1a}$ represents hydrogen, and $R^{1b}$ represents hydrogen;

$R^2$ is selected from the group consisting of cyano; halo; —C(═O)—$NR^{8a}R^{8b}$;

—$CH_2$—$NR^{8c}R^{8d}$, $Het^b$; —P(═O)—($C_{1-4}$alkyl)$_2$; —S(═O)$_2$—$C_{1-4}$alkyl; —S(═O)(═$NR^x$)—$C_{1-4}$alkyl;

$C_{1-6}$alkyl optionally substituted with 1 or 2 substituents each independently selected from the group consisting of halo, —OH, cyano, and —O—$C_{1-4}$alkyl;

$C_{3-6}$cycloalkyl optionally substituted with 1 or 2 substituents each independently selected from the group consisting of halo, —OH, cyano and —O—$C_{1-4}$ alkyl; and $C_{3-6}$cycloalkenyl optionally substituted with 1 or 2 substituents each independently selected from the group consisting of halo, —OH, cyano and —O—$C_{1-4}$alkyl;

$R^{3a}$ represents hydrogen, halo, $R^7$,—O—$R^7$, cyano, —C(═O)—$NR^{6e}R^{6f}$, $Het^a$, or phenyl optionally substituted with 1, 2 or 3 substituents each independently selected from the group consisting of halo, cyano, $C_{1-4}$alkyl, —O—$C_{1-4}$alkyl, $C_{1-4}$alkyl substituted with one cyano, and $C_{1-4}$alkyl substituted with 1, 2 or 3 halo atoms;

$Het^a$ represents a carbon linked monocyclic 5-, 6- or 7-membered aromatic heterocyclyl or carbon linked monocyclic 4-, 5-, 6- or 7-membered non-aromatic heterocyclyl, each containing 1, 2 or 3 heteroatoms each independently selected from the group consisting of N, O or S; wherein said S-atom might be substituted to form S(═O), S(═O)$_2$, or S(═O)(═$NR^x$); or a carbon linked bicyclic 6- to 12-membered aromatic or non-aromatic heterocyclyl containing 1, 2 or 3 heteroatoms each independently selected from the group consisting of N, O or S; wherein said S-atom might be substituted to form S(═O), S(═O)$_2$, or S(═O)(═$NR^x$);

wherein said monocyclic or bicyclic, aromatic or non-aromatic heterocyclyl might be substituted on one or more of the carbon atoms with in total 1, 2 or 3 substituents each independently selected from the group consisting of —OH, CN, halo, $R^7$,—O—$R^7$, —S(═O)$_2$—$R^7$, —C(═O)—$R^7$, —$NR^{6c}R^{6d}$, —C(═O)—$NR^{6a}R^{6b}$, and $Het^c$;

wherein said monocyclic or bicyclic, aromatic or non-aromatic heterocyclyl might be substituted on the nitrogen atoms with in total 1 or 2 substituents each independently selected from the group consisting of $R^7$, —S(═O)$_2$—$R^7$, —C(═O)—$R^7$, —C(═O)-$NR^{6a}R^{6b}$ and $Het^d$;

$R^{6a}$, $R^{6b}$, $R^{6c}$, $R^{6d}$, $R^{6e}$, and $R^{6f}$ are each independently selected from the group consisting of hydrogen; $C_{3-6}$cycloalkyl optionally substituted with one —$OR^5$; and $C_{1-4}$alkyl optionally substituted with one —$OR^5$, wherein two hydrogen atoms on the same carbon atom of said $C_{1-4}$alkyl might be taken together to form $C_{3-6}$cycloalkyl;

$R^5$ represents hydrogen or $C_{1-4}$alkyl;

$R^{8a}$, $R^{8c}$C, and $R^{8d}$ are each independently selected from the group consisting of hydrogen; $C_{1-4}$alkyl optionally substituted with one —OH or —O—$C_{1-4}$alkyl; and $C_3$-6cycloalkyl optionally substituted with one —OH or —O—$C_{1-4}$alkyl;

$R^{8b}$ is selected from the group consisting $C_{1-4}$alkyl optionally substituted with one —OH or —O—$C_{1-4}$ alkyl; and $C_{3-6}$cycloalkyl optionally substituted with one —OH or —O—$C_{1-4}$alkyl;

or $R^{8a}$ and $R^{8b}$, or $R^{8c}$ and $R^{8d}$ are taken together to form together with the N-atom to which they are attached a monocyclic fully saturated heterocyclyl containing 1 N-atom and optionally 1 or 2 additional heteroatoms each independently selected from the group consisting of N, O, S; wherein said optional S-atom might be substituted to form S(═O), S(═O)$_2$, or S(═O)(═$NR^x$);

wherein said monocyclic 4-, 5-, 6- or 7-membered fully saturated heterocyclyl might be substituted on one or more of the carbon atoms with in total 1, 2 or 3 substituents each independently selected from the group consisting of —OH, CN, halo, $R^7$, —O—$R^7$, —S(═O)$_2$—$R^7$, —C(═O)—$R^7$, —$NR^{6c}R^{6d}$, and —C(═O)—$NR^{6a}R^{6b}$;

wherein said monocyclic fully saturated heterocyclyl might be substituted on the nitrogen atoms with in total 1 or 2 substituents each independently selected from the group consisting of $R^7$, —S(═O)$_2$—$R^7$, —C(═O)—$R^7$, and —C(═O)—$NR^{6a}R^{6b}$;

each $Het^c$ independently represents a monocyclic 4-, 5-, 6- or 7-membered fully saturated heterocyclyl containing 1, 2 or 3 heteroatoms each independently selected from the group consisting of N, O or S; wherein said S-atom might be substituted to form S(═O), S(═O)$_2$, or S(═O)(═$NR^x$);

each $Het^d$ independently represents a carbon linked monocyclic 4-, 5-, 6- or 7-membered fully saturated heterocyclyl containing 1, 2 or 3 heteroatoms each independently selected from the group consisting of N, O or S; wherein said S-atom might be substituted to form S(═O), S(═O)$_2$, or S(═O)(═$NR^x$);

$Het^b$ represents a monocyclic 4-, 5-, 6- or 7-membered non-aromatic heterocyclyl containing 1, 2 or 3 heteroatoms each independently selected from the group consisting of N, O, S; wherein said S-atom might be substituted to form S(═O), S(═O)$_2$, or S(═O)(═$NR^x$); or a bicyclic 6- to 12-membered non-aromatic heterocyclyl containing 1, 2 or 3 heteroatoms each independently selected from the group consisting of N, O, S; wherein said S-atom might be substituted to form S(═O), S(═O)$_2$, or S(═O)(═$NR^x$);

wherein said monocyclic or bicyclic non-aromatic heterocyclyl might be substituted on one or more of the carbon atoms with in total 1, 2 or 3 substituents each independently selected from the group consisting of —OH, CN, halo, $R^7$,—O—$R^7$, —S(═O)$_2$—$R^7$, —C(═O)—$R^7$, —$NR^{6c}R^{6d}$, and —C(═O)—$NR^{6a}R^{6b}$, wherein said monocyclic or bicyclic non-aromatic heterocyclyl might be substituted on the nitrogen atoms with in total 1 or 2 substituents each independently selected from the group consisting of $R^7$, —S(═O)$_2$ —$R^7$, —C(═O)—$R^7$, and —C(═O)—$NR^{6a}R^{6b}$;

each $R^7$ independently represents $C_{3-6}$cycloalkyl optionally substituted with 1, 2 or 3 substituents each independently selected from the group consisting of halo, —OH, —O—$C_{1-4}$alkyl and cyano; or $C_{1-4}$alkyl optionally substituted with 1, 2 or 3 substituents each independently selected from the group consisting of halo, —OH, —O—$C_{1-4}$alkyl and cyano; each Rx independently represents hydrogen or $C_{1-4}$alkyl;

or a pharmaceutically acceptable addition salt, an N-oxide, or a solvate thereof.

2. The compound according to claim 1, wherein the dotted bond towards $R^{1b}$ is an optional bond that may be present when $R^{1b}$ and $R^{4b}$ are taken together to form a monocyclic aromatic heterocyclyl as defined herein;

$A^1$ represents CH or N; $A^2$ represents CH; $A^3$ represents CH or N;

provided that only one of $A^1$ and $A^3$ represents N;

$A^4$ represents CH; $A^5$ represents $CR^{3a}$; $A^6$ represents CH;

$R^{1a}$ represents hydrogen;

$R^{1b}$ represents hydrogen;

$R^{4a}$ represents hydrogen, or $C_{1-4}$alkyl;

$R^{4b}$ represents $C_{1-4}$alkyl, $C_{3-6}$cycloalkyl, or a carbon linked monocyclic 4-, 5-, 6- or 7-membered non-aromatic heterocyclyl containing 1, 2 or 3 oxygen atoms;

or $R^{1b}$ and $R^{4b}$ are taken together to form together with the atoms to which they are attached a monocyclic 5-membered aromatic heterocyclyl or a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(═O); or a bicyclic 6- to 12-membered fully saturated heterocyclyl containing 1 N-atom and optionally 1 or 2 additional heteroatoms each independently selected from the group consisting of N, O, S; wherein said optional S-atom might be substituted to form S(═O);

wherein said monocyclic or bicyclic, aromatic or fully saturated heterocyclyl might be substituted on one or more of the carbon atoms with in total 1, 2 or 3 substituents each independently selected from the group consisting of halo and $R^7$;

provided that in case $R^{1b}$ and $R^{4b}$ are taken together, $R^{4a}$ represents hydrogen; and $R^{1a}$ represents hydrogen or $R^{1a}$ is absent when the dotted bond towards $R^{1b}$ is a bond;

or $R^{4a}$ and $R^{4b}$ are taken together to form together with the N-atom to which they are attached a monocyclic 4-, 5-, 6- or 7-membered fully saturated heterocyclyl containing 1 N-atom;

wherein said monocyclic fully saturated heterocyclyl might be substituted on one or more of the carbon atoms with in total 1, 2 or 3 halo substituents;

in case $R^{4a}$ and $R^{4b}$ are taken together, $R^{1a}$ represents hydrogen, and $R^{1b}$ represents hydrogen;

$R^2$ is selected from the group consisting of cyano; $Het^b$; and $C_{3-6}$cycloalkyl optionally substituted with 1 or 2 substituents each independently selected from the group consisting of halo and —O—$C_{1-4}$alkyl;

$R^{3a}$ represents halo, $R^7$,—O—$R^7$, cyano, —C(═O)—$NR^{6e}R^{6f}$, $Het^a$, or phenyl optionally substituted with 1, 2 or 3 substituents each independently selected from the group consisting of halo and cyano;

$Het^a$ represents a carbon linked monocyclic 5-, 6- or 7-membered aromatic heterocyclyl or carbon linked monocyclic 4-, 5-, 6- or 7-membered non-aromatic heterocyclyl, each containing 1, 2 or 3 heteroatoms each independently selected from the group consisting of N, O or S; wherein said S-atom might be substituted to form S(═O) or S(═O)$_2$; or a carbon linked bicyclic 6- to 12-membered non-aromatic heterocyclyl containing 1, 2 or 3 heteroatoms each independently selected from the group consisting of N or O; wherein said monocyclic or bicyclic, aromatic or non-aromatic heterocyclyl might be substituted on one or more of the carbon atoms with in total 1, 2 or 3 substituents each independently selected from the group consisting of —OH, CN, halo, $R^7$, —O—$R^7$, —$NR^6CR^6$d and $Het^c$;

wherein said monocyclic or bicyclic, aromatic or non-aromatic heterocyclyl might be substituted on the nitrogen atoms with in total 1 or 2 substituents each independently selected from the group consisting of $R^7$, —S(═O)$_2$—$R^7$, and —C(═O)—$R^7$;

$R^{6c}$, $R^{6d}$, $R^{6e}$, and $R^{6f}$ are each independently selected from the group consisting of hydrogen; and $C_{1-4}$alkyl optionally substituted with one —$OR^5$;

$R^5$ represents hydrogen;

each Het independently represents a monocyclic 4-, 5-, 6- or 7-membered fully saturated heterocyclyl containing 1, 2 or 3 nitrogen atoms;

$Het^b$ represents a monocyclic 4-, 5-, 6- or 7-membered non-aromatic heterocyclyl containing 1, 2 or 3 heteroatoms each independently selected from the group consisting of N, O, S; wherein said S-atom might be substituted to form S(═O) or S(═O)$_2$; or a bicyclic 6- to 12-membered non-aromatic heterocyclyl containing 1, 2 or 3 heteroatoms each independently selected from the group consisting of N, O, S; wherein said S-atom might be substituted to form S(═O) or S(═O)$_2$;

wherein said monocyclic or bicyclic non-aromatic heterocyclyl might be substituted on the nitrogen atoms with in total 1 or 2 substituents each independently selected from the group consisting of —S(═O)$_2$—$R^7$, and —C(═O)—$R^7$;

each $R^7$ independently represents $C_{1-4}$alkyl optionally substituted with 1, 2 or 3 substituents each independently selected from the group consisting of halo, —OH, and cyano.

3. The compound according to claim 1, wherein the dotted bond towards $R^{1b}$ is absent;

$A^1$ represents CH or N; $A^2$ represents CH; $A^3$ represents CH;

$A^4$ represents CH; $A^5$ represents $CR^{3a}$; $A^6$ represents CH;

$R^{1b}$ and $R^{4b}$ are taken together to form together with the atoms to which they are attached a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(═O);

wherein said monocyclic fully saturated heterocyclyl might be substituted on one of the carbon atoms with 1 substituent selected from the group consisting of halo and $R^7$;

provided that $R^{4a}$ represents hydrogen; and $R^{1a}$ represents hydrogen;

$R^2$ represents $Het^b$;

$R^{3a}$ represents halo, cyano, or $Het^a$;

$Het^a$ represents a carbon linked monocyclic 5-, 6- or 7-membered aromatic heterocyclyl containing 1, 2 or 3 heteroatoms each independently selected from the group consisting of N, O or S; wherein said S-atom might be substituted to form S(═O) or S(═O)$_2$;

wherein said monocyclic aromatic heterocyclyl might be substituted on one of the carbon atoms with a halo substituent;

wherein said monocyclic aromatic heterocyclyl might be substituted on one nitrogen atom with $R^7$;

$Het^b$ represents a monocyclic 4-, 5-, 6- or 7-membered non-aromatic heterocyclyl containing 1 oxygen atom;

each $R^7$ represents CI-4alkyl.

4. The compound according to claim 1, wherein $R^{1b}$ and $R^{4b}$ are taken together to form together with the atoms to which they are attached a monocyclic 5-membered aromatic heterocyclyl or a monocyclic 4-, 5-, 6- or 7-membered fully saturated heterocyclyl, each containing 1 N-atom and optionally 1 or 2 additional heteroatoms each independently selected from the group consisting of N, O, S; wherein said optional S-atom might be substituted to form S(═O), $S(═O)_2$, or S(═O)(═$NR^x$); or a bicyclic 6- to 12-membered aromatic or fully saturated heterocyclyl containing 1 N-atom and optionally 1 or 2 additional heteroatoms each independently selected from the group consisting of N, O, S; wherein said optional S-atom might be substituted to form S(═O), $S(═O)_2$, or S(═O)(═$NR^x$);

wherein said monocyclic or bicyclic, aromatic or fully saturated heterocyclyl might be substituted on one or more of the carbon atoms with in total 1, 2 or 3 substituents each independently selected from the group consisting of —OH, CN, halo, $R^7$, —O—$R^7$, —$S(═O)_2$—$R^7$, —C(═O)—$R^7$, —$NR^{6c}R^{6d}$, —C(═O)—$NR^{6a}R^{6b}$, and $Het^c$;

wherein said monocyclic or bicyclic, aromatic or fully saturated heterocyclyl might be substituted on the optional additional nitrogen atoms with in total 1 or 2 substituents each independently selected from the group consisting of $R^7$, —$S(═O)_2$—$R^7$, —C(═O)—$R^7$, —C(═O)—$NR^{6a}R^{6b}$, and $Het^d$, provided that $R^{4a}$ represents hydrogen; and $R^{1a}$ represents hydrogen or $R^{1a}$ is absent when the dotted bond towards $R^{1b}$ is a bond.

5. The compound according to claim 1, wherein the compound is selected from compounds 1-111, tautomers and stereoisomeric forms thereof, and pharmaceutically acceptable addition salts, N-oxides, and solvates thereof.

6. A pharmaceutical composition comprising a compound as claimed in claim 1 and a pharmaceutically acceptable carrier or diluent.

7. A process for preparing a pharmaceutical composition as defined in claim 6 comprising mixing a pharmaceutically acceptable carrier with a therapeutically effective amount of a compound according to claim 1.

8. A compound as claimed in claim 1 for use as a medicament.

9. A compound as claimed in claim 1 use in the prevention or treatment of cancer and viral infection.

10. The compound or a pharmaceutical composition for use according to claim 9 in the prevention or treatment of cancer wherein cancer is selected from lung cancer, melanoma, head and neck cancer, esophageal cancer, bladder and urothelial cancer, liver cancer, kidney cancer, prostate cancer and hematopoietic cancer.

11. The compound or a pharmaceutical composition for use according to claim 9 in the prevention or treatment of a chronic viral infection.

12. A pharmaceutical composition as claimed in claim 6 for use as a medicament.

13. A pharmaceutical composition as claimed in claim 6 for use in the prevention or treatment of cancer and viral infection.

14. The compound according to claim 1, wherein the compound is selected from the following compounds, and tautomers and stereoisomeric forms thereof, and pharmaceutically acceptable addition salts, N-oxides, and solvates thereof:

Co. 1

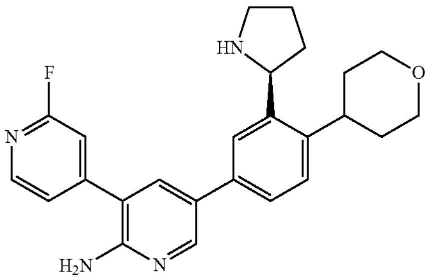

Co. 2

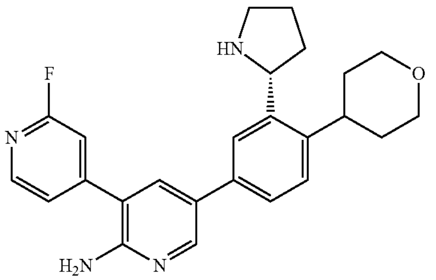

Co. 2

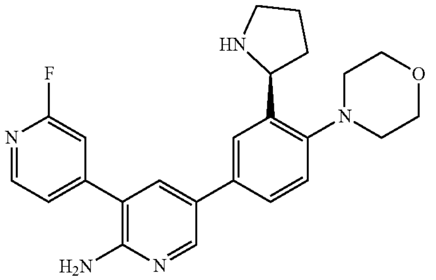

Co. 3

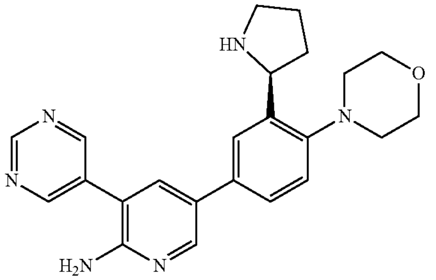

Co. 4

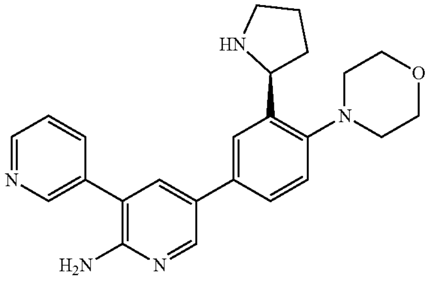

-continued
Co. 5a
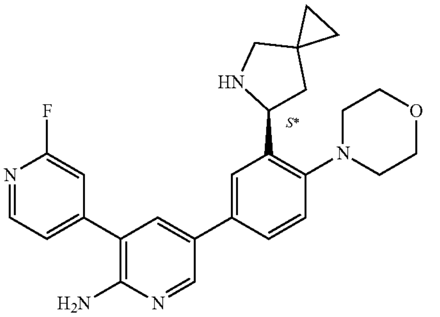
Co. 5b3
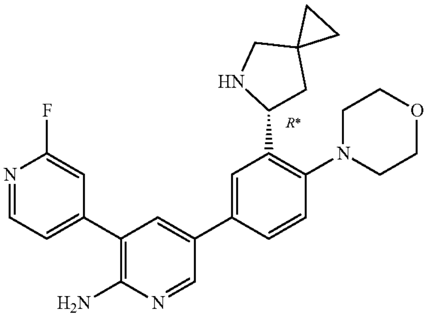
Co. 6
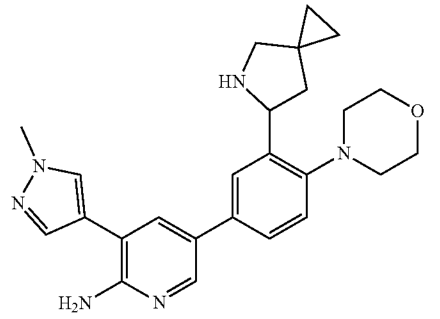
Co. 7a
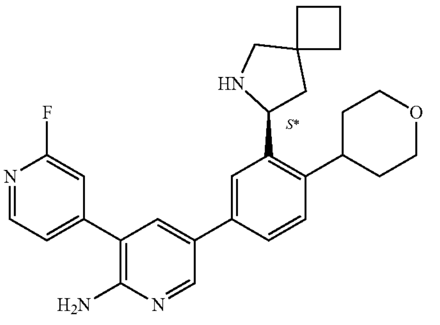
Co. 7b
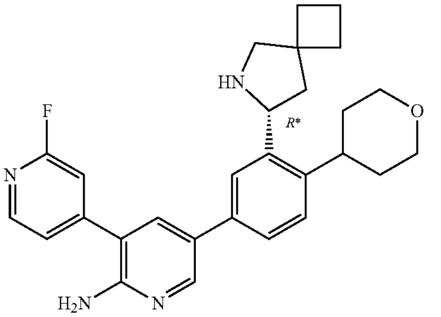
-continued
Co. 8a
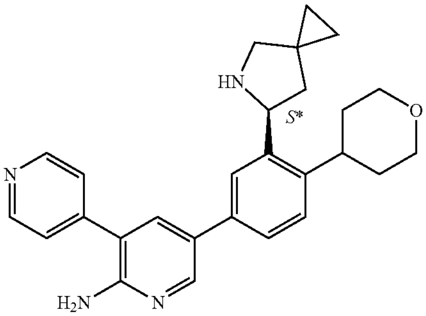
Co. 8b
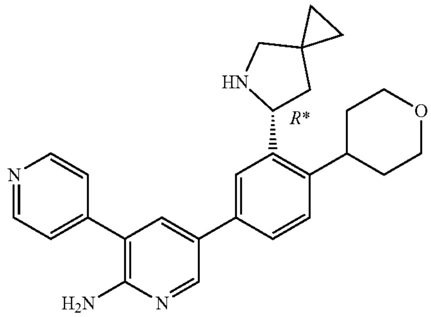
Racemic texture of 2 trans forms
Co. 9
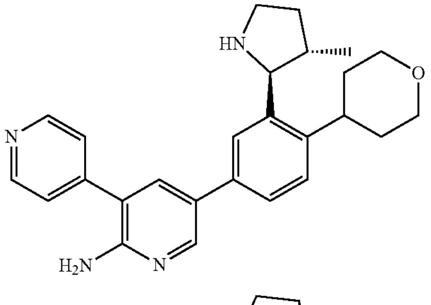
and
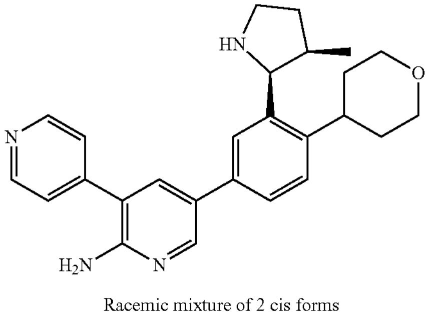
Racemic mixture of 2 cis forms -continued
Co. 10
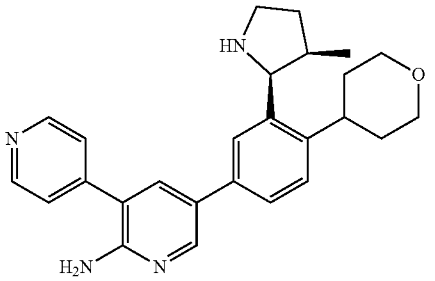
and
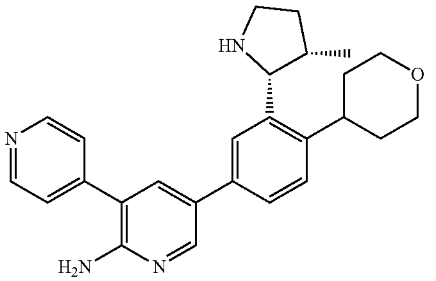
Co. 11
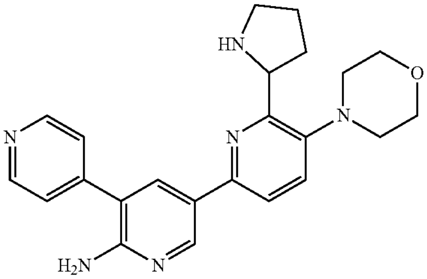
Co. 12
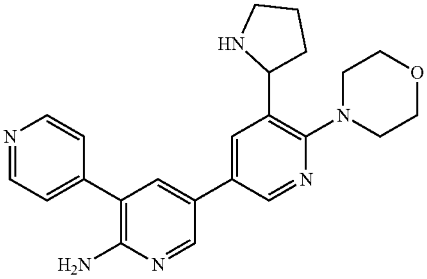
Co. 13
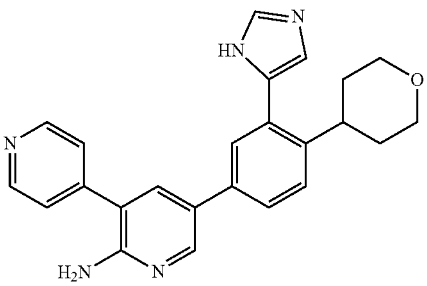
-continued
Co. 14
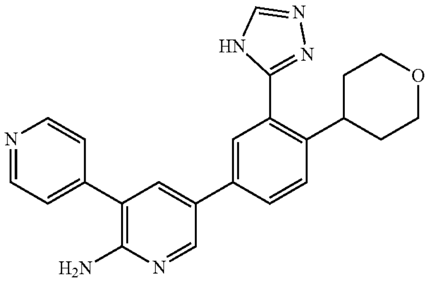
Co. 15
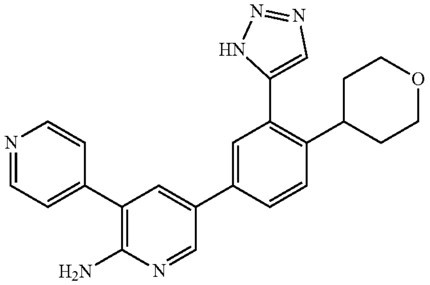
Co. 15a
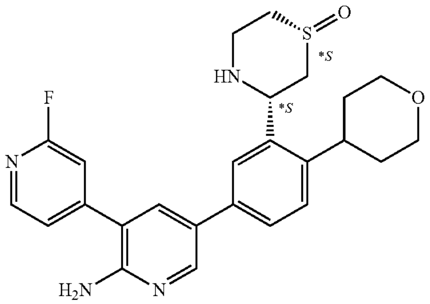
Co. 15b
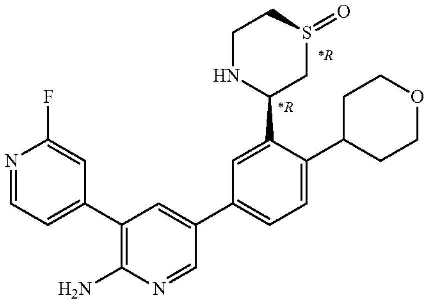
Co. 15c
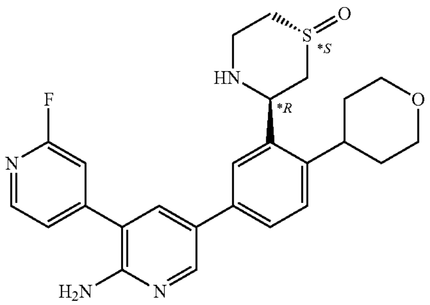

Co. 15d
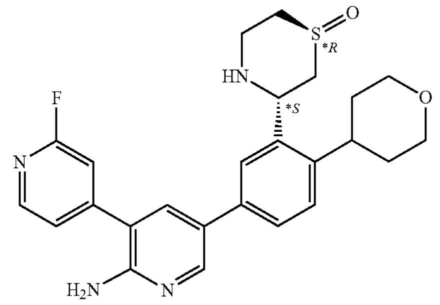
Co. 16
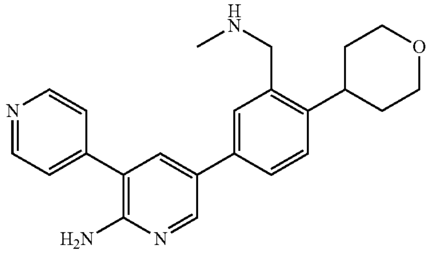
Co. 17
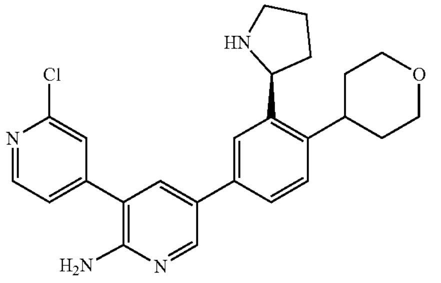
Co. 18
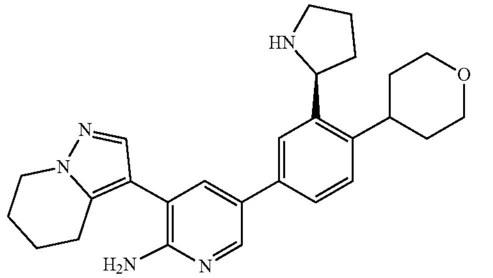
Co. 19
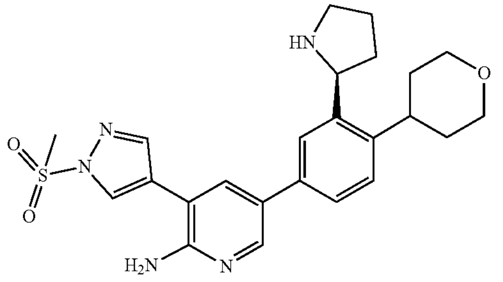
Co. 20
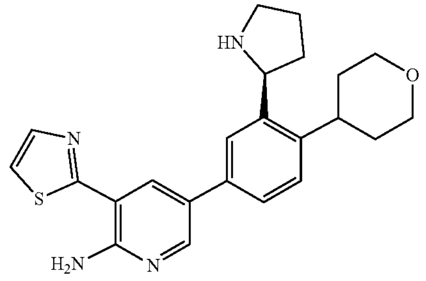
Co. 21
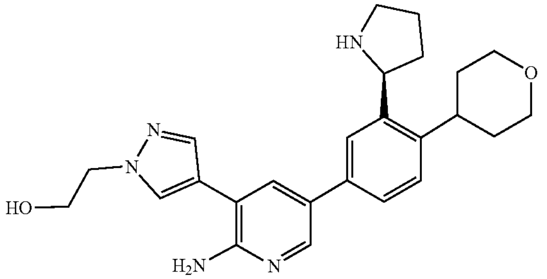
Co. 22
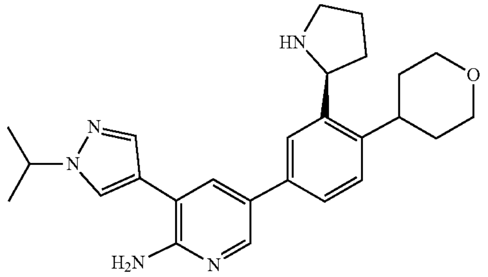
Co. 23
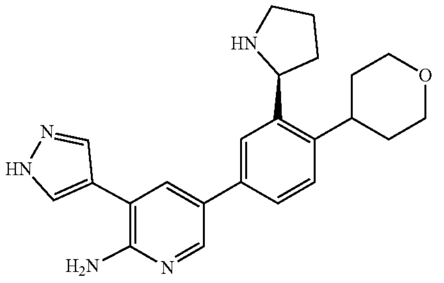
Co. 24
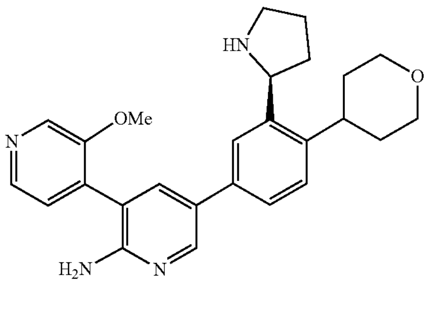

-continued
Co. 25
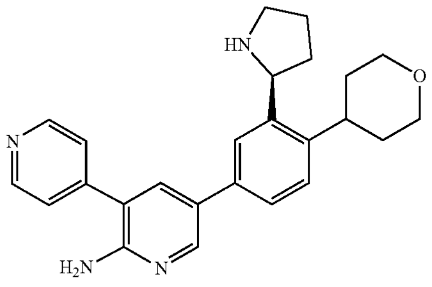
Co. 25b
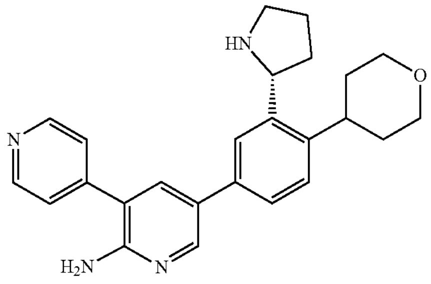
Co. 26
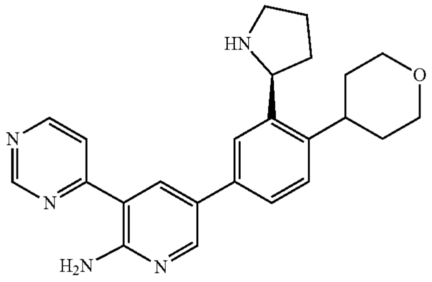
Co. 27
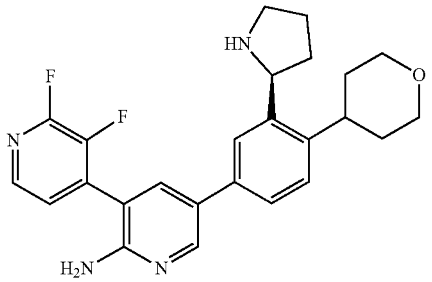
Co. 28
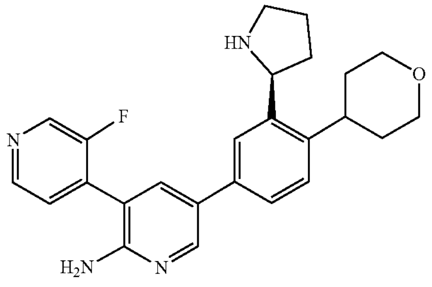
-continued
Co. 29
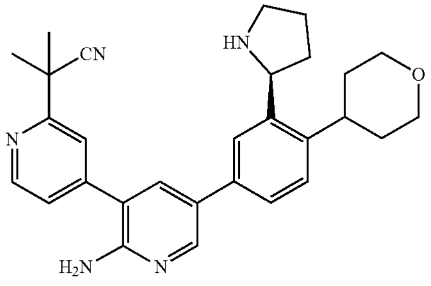
Co. 30
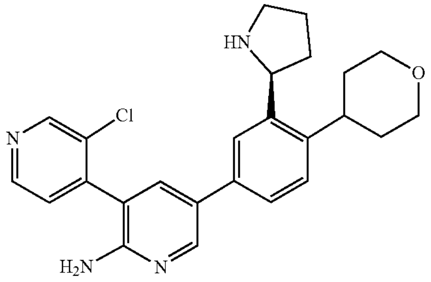
Co. 31
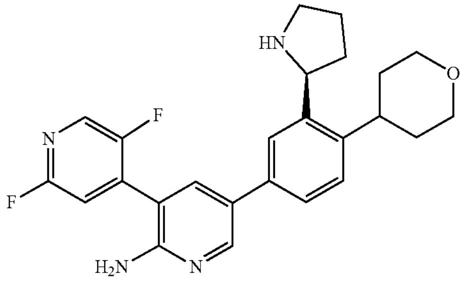
Co. 32
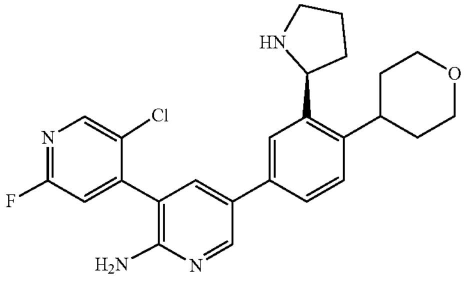
Co. 33
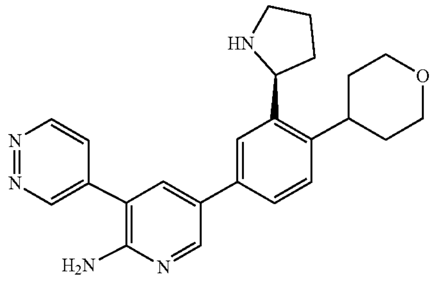

-continued
Co. 34
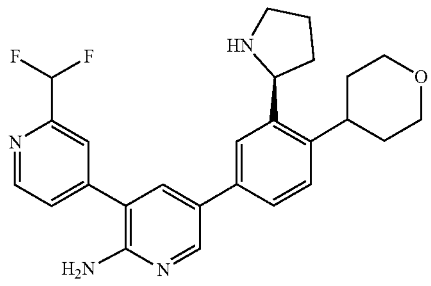
Co. 35
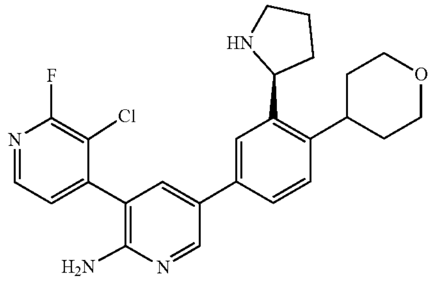
Co. 36
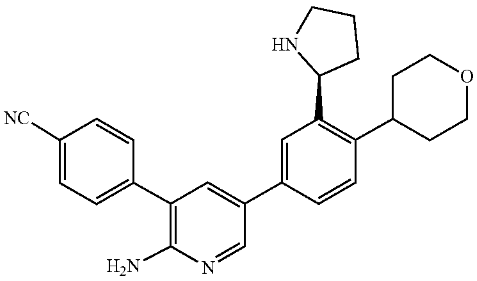
Co. 37
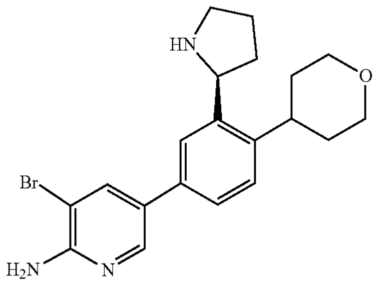
Co. 38
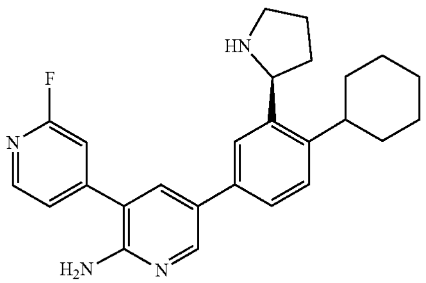
-continued
Co. 39
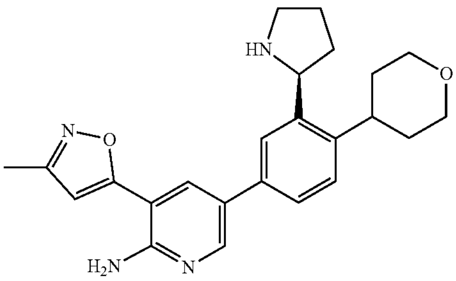
Co. 40
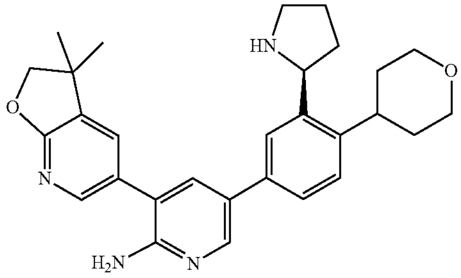
Co. 41
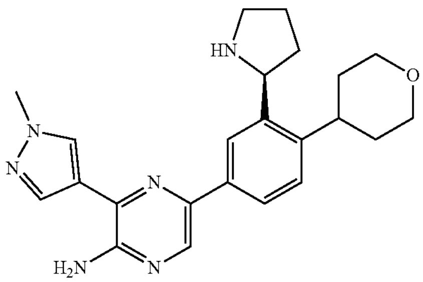
Co. 42
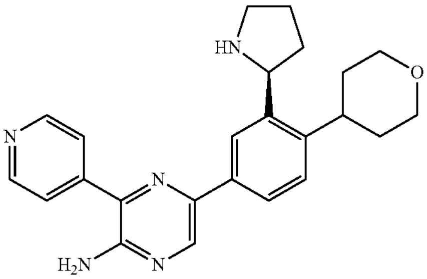
Co. 43
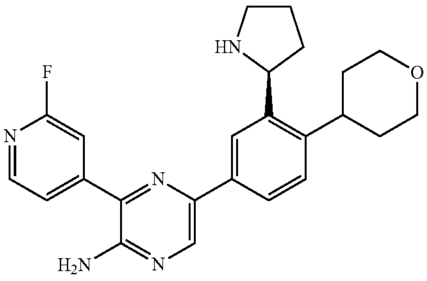

Co. 44
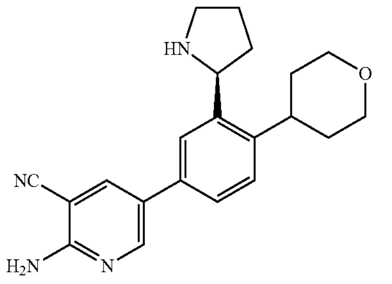
Co. 45
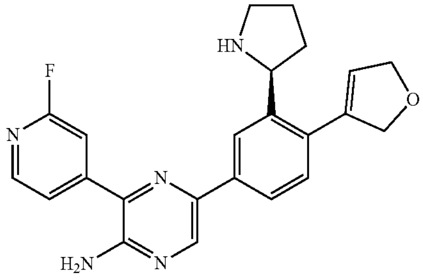
Co. 46
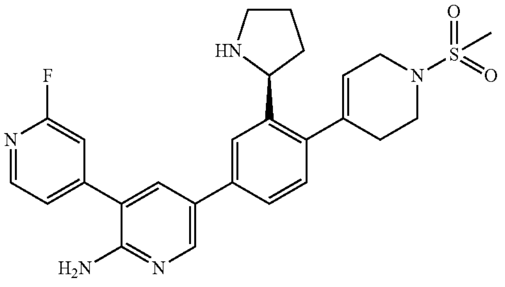
Co. 47
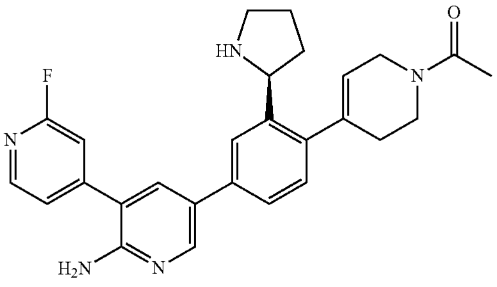
Co. 48
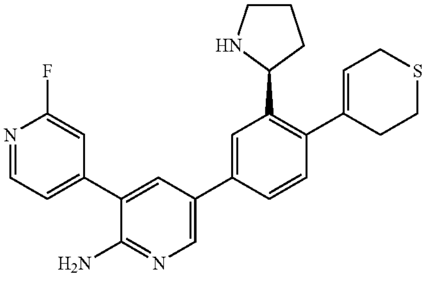
Co. 49
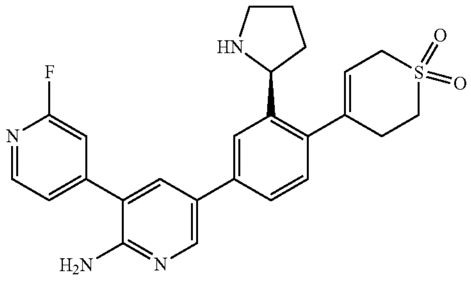
Co. 50
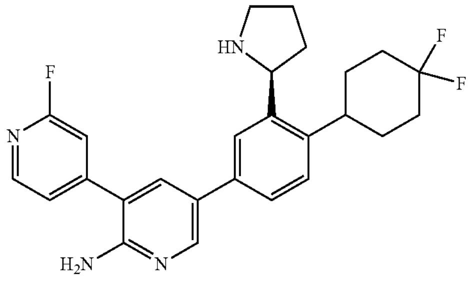
Co. 51
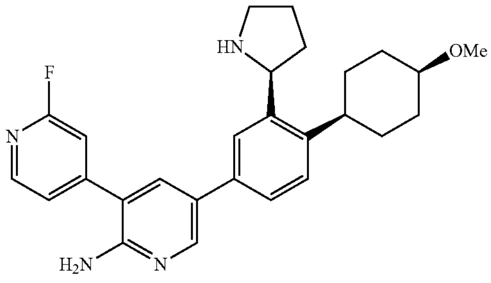
Co. 52
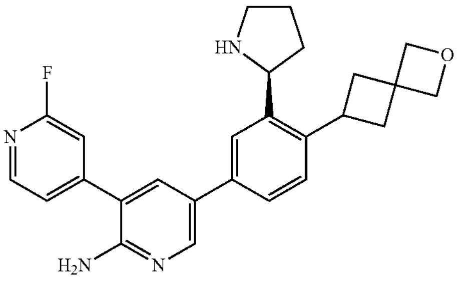
Co. 53
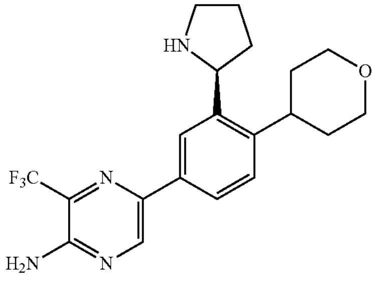

-continued
Co. 54
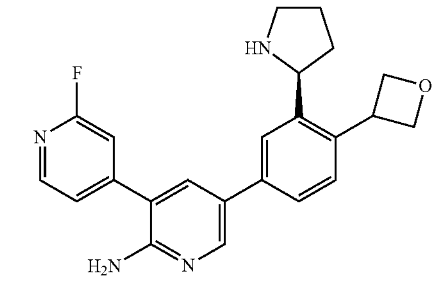
Co. 55
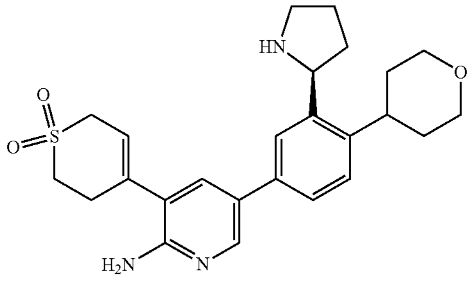
Co. 56
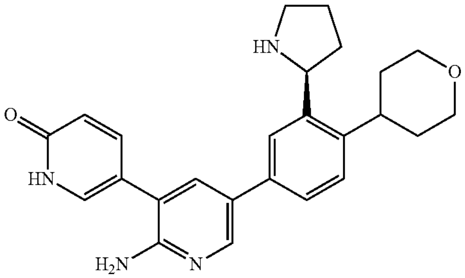
Co. 57
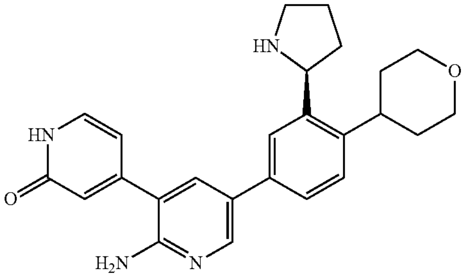
Co. 58
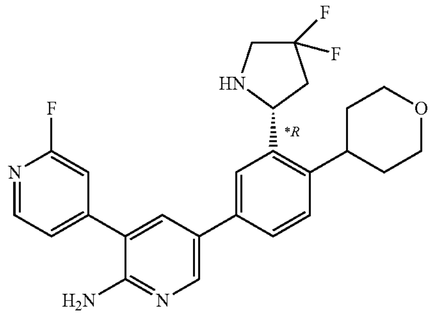
-continued
Co. 59
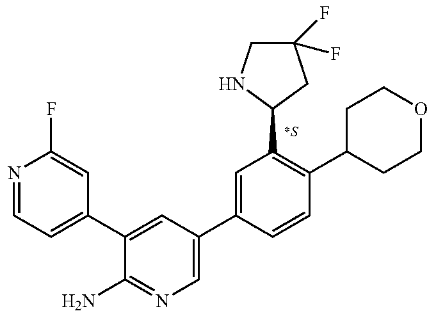
Co. 60
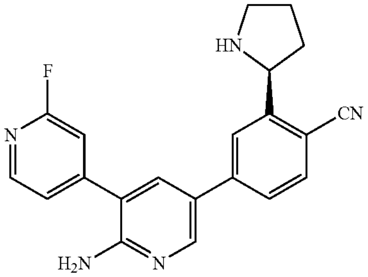
Co. 61
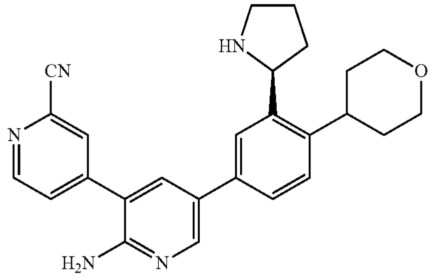
Co. 62
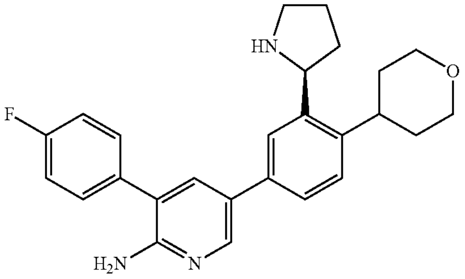
Co. 63
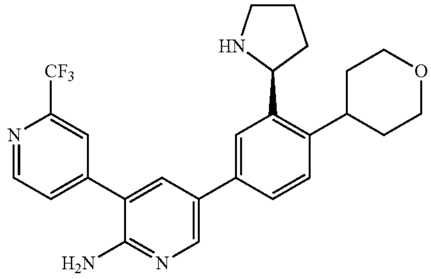

-continued
Co. 64
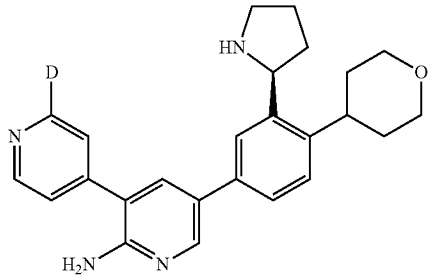
Co. 65
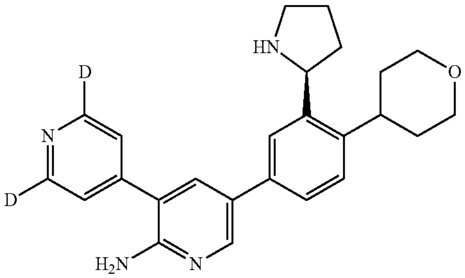
Co. 66
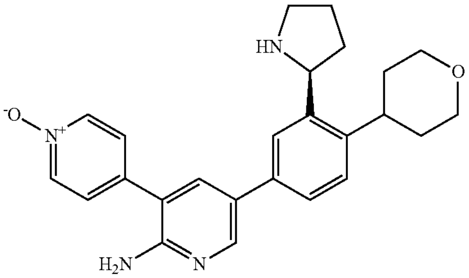
Co. 67
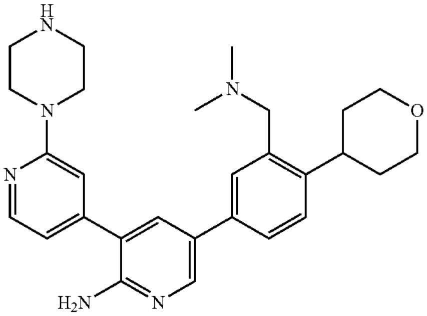
Co. 68
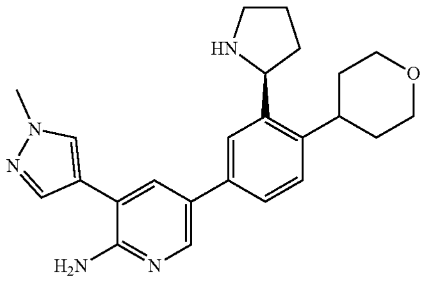
-continued
Co. 69
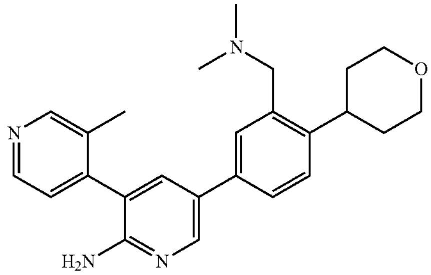
Co. 70
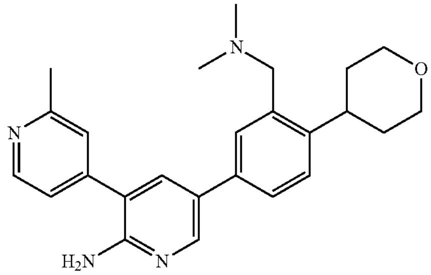
Co. 71
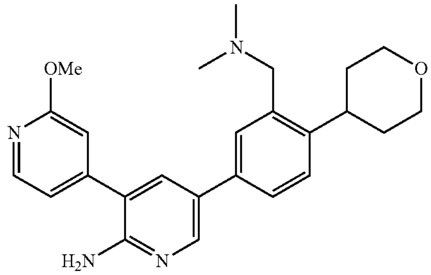
Co. 72
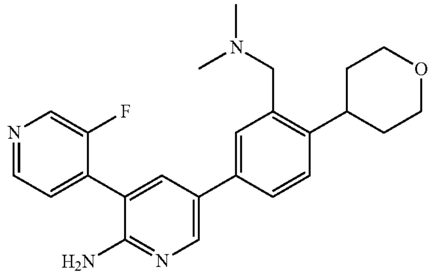
Co. 73
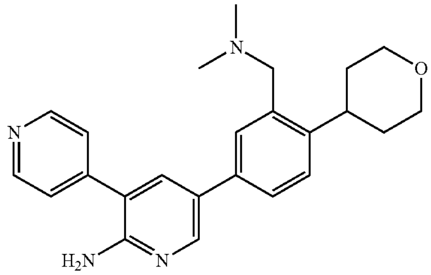

-continued
Co. 74
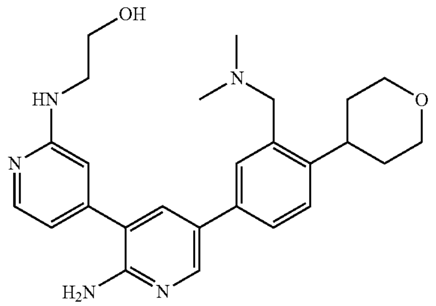
Co. 75
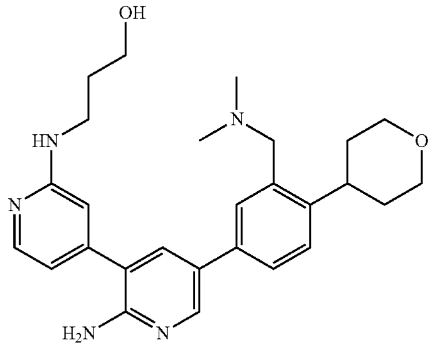
Co. 76
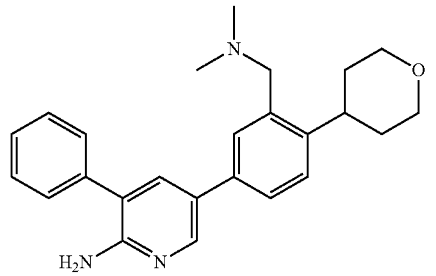
Co. 77
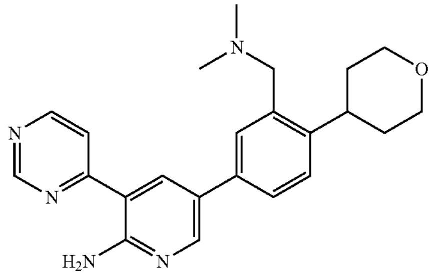
Co. 78
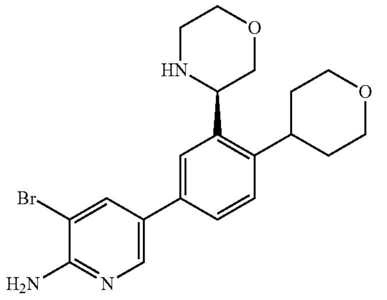
-continued
Co. 79
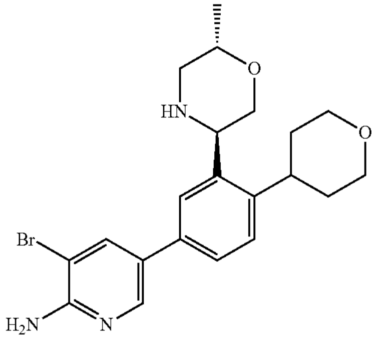
Co. 80a
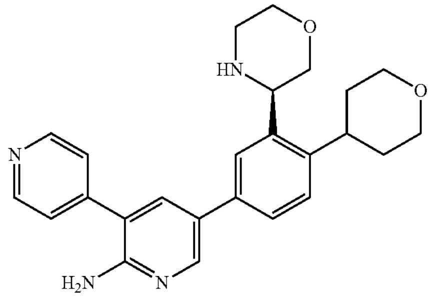
Co. 80b
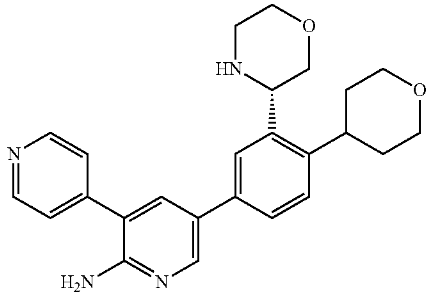
Co. 81
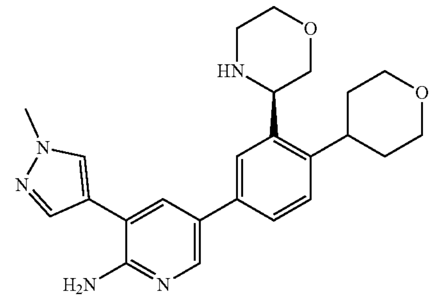
Co. 82
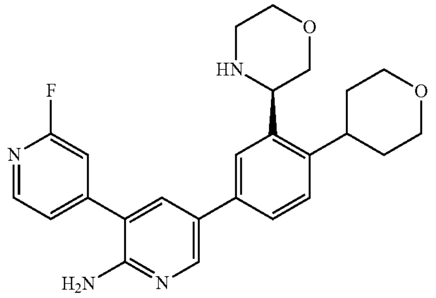

-continued
Co. 83a
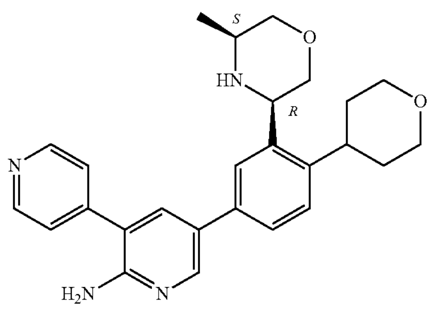
or
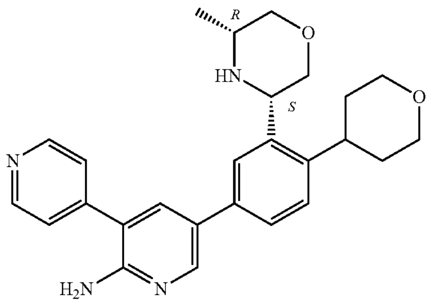
Co. 83b
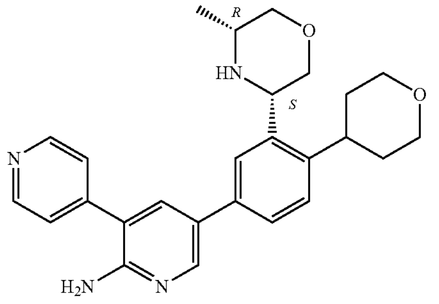
or
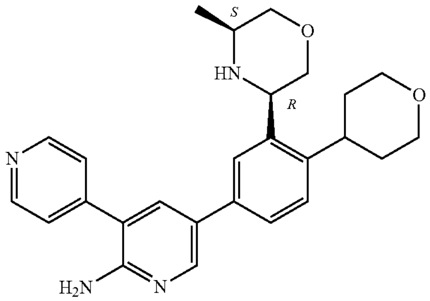
Co. 84
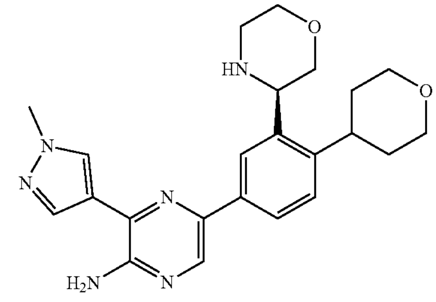
-continued
Co. 85
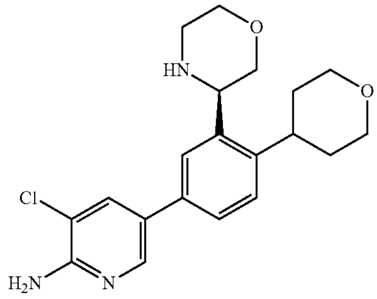
Co. 86
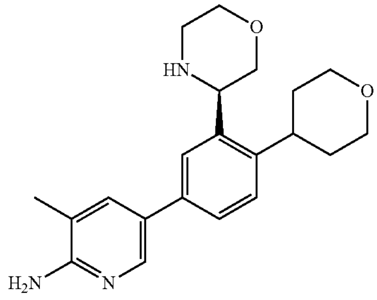
Co. 87
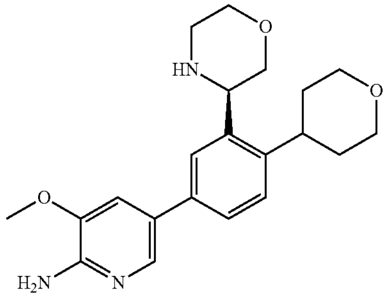
Co. 88
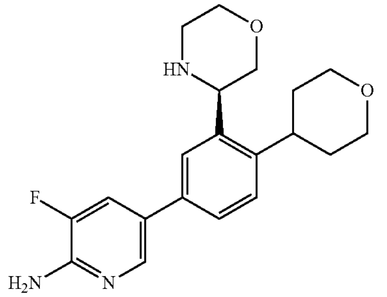
Co. 89
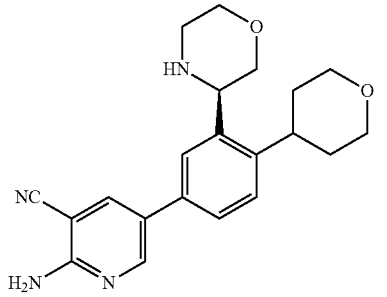

Co. 90
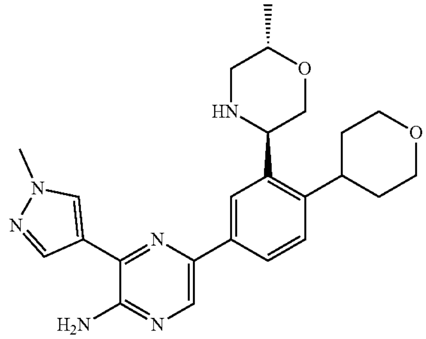
Co. 91
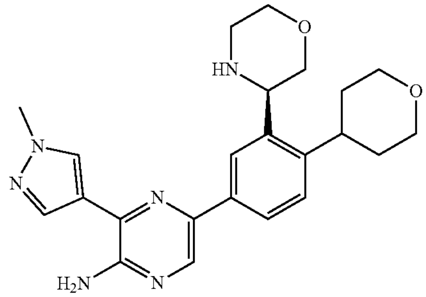
Co. 92
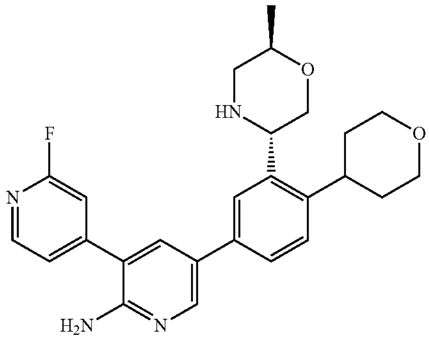
Co. 93a
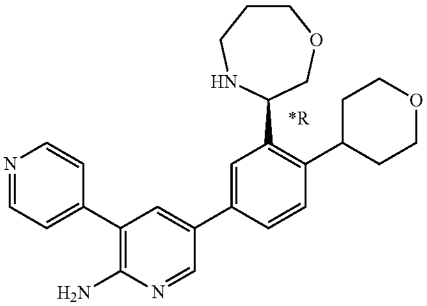
Co. 93b
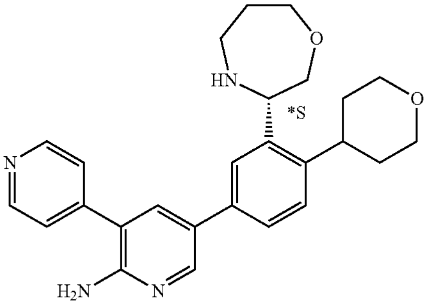
-continued
Co. 94
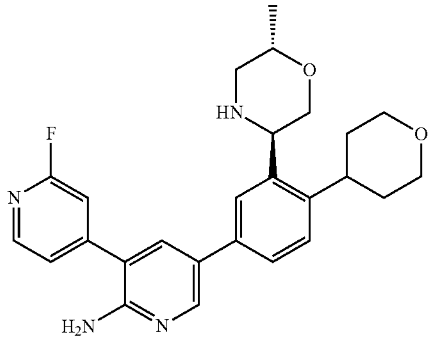
Co. 95
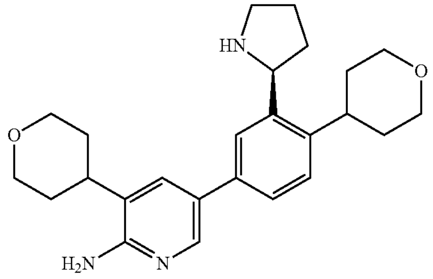
Co. 96
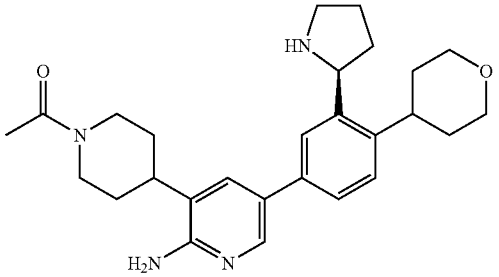
Co. 97
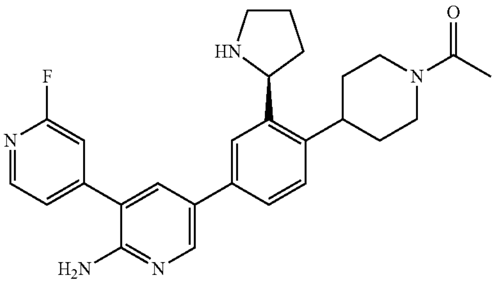
Co. 98
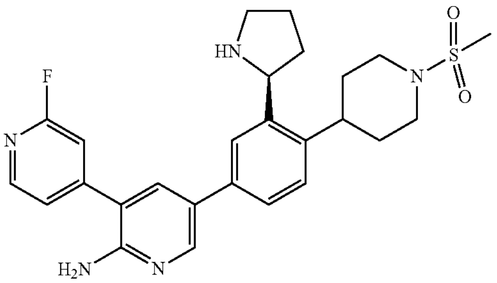

-continued
Co. 99
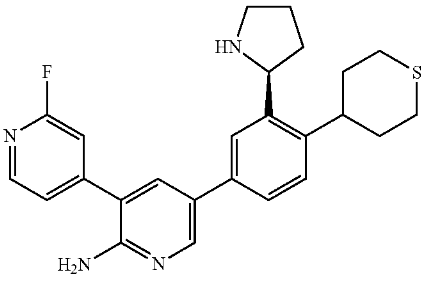
Co. 100
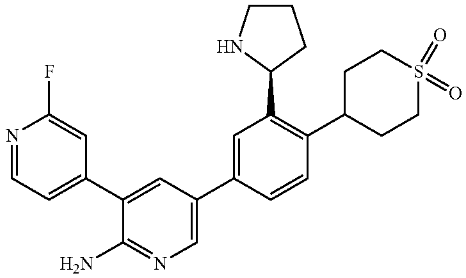
Co. 101
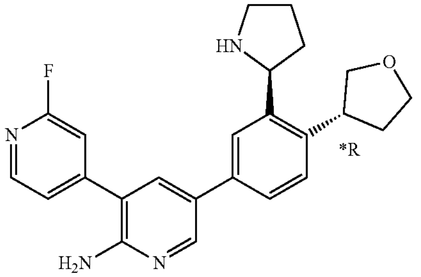
Co. 102
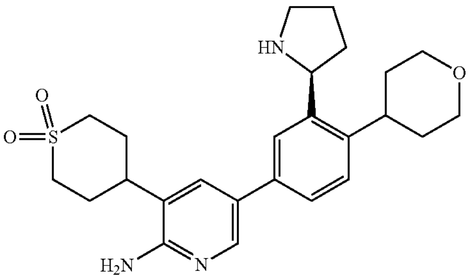
Co. 103
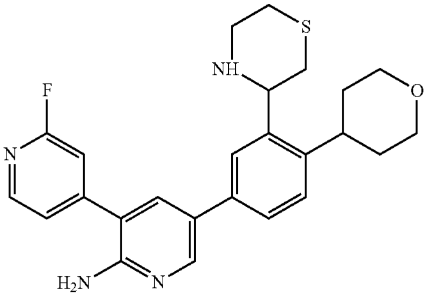
-continued
Co. 104
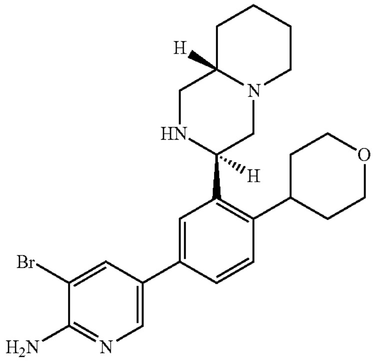
Co. 105
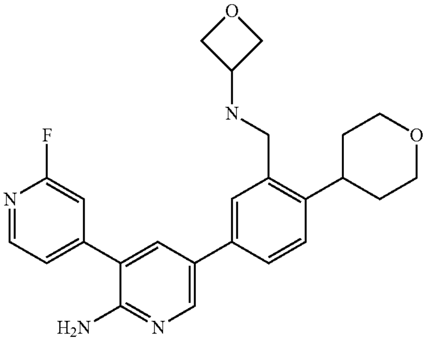
Co. 106
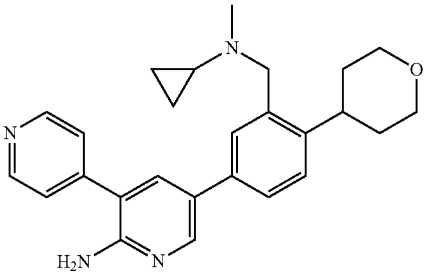
Co. 107
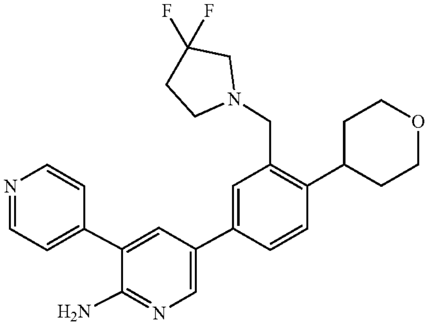
Co. 108
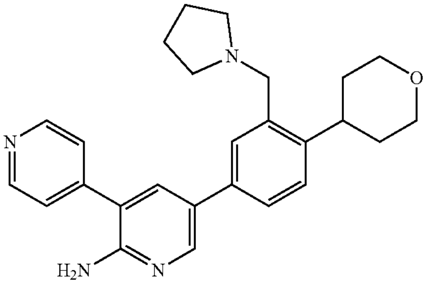

-continued
Co. 109
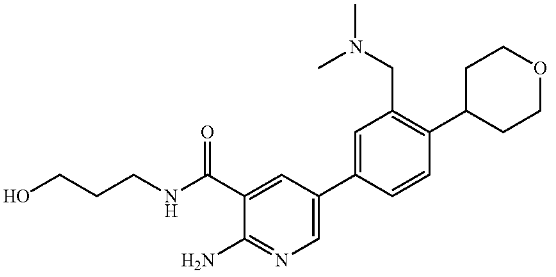
Co. 110
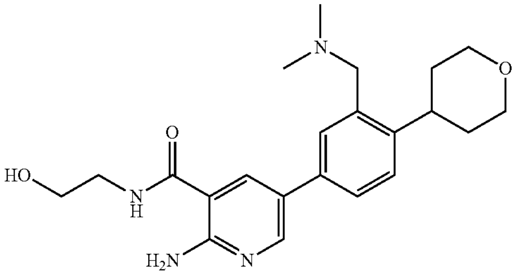
-continued
Co. 111
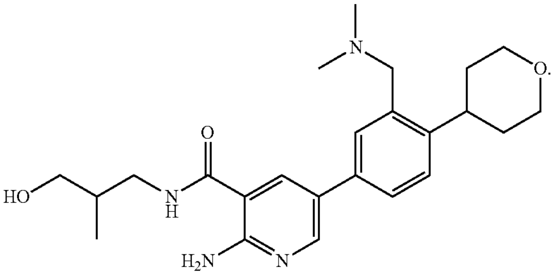
15. The compound according to claim 1, wherein the compound has the structure:
(Co. 84)
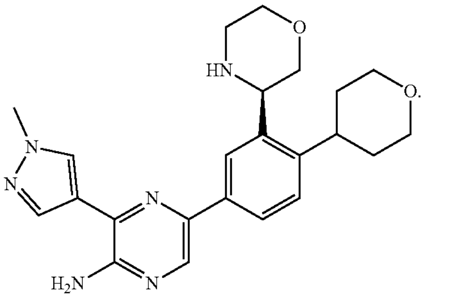
* * * * *